United States Patent
Song et al.

(10) Patent No.: US 12,102,004 B2
(45) Date of Patent: Sep. 24, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Hyun Ju Song, Cheonan-si (KR); Hyo Min Jin, Cheonan-si (KR); Junggeun Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/413,635

(22) Filed: Jan. 16, 2024

(65) Prior Publication Data

US 2024/0206334 A1 Jun. 20, 2024

Related U.S. Application Data

(63) Continuation-in-part of application No. 18/180,625, filed on Mar. 8, 2023, which is a continuation-in-part
(Continued)

(30) Foreign Application Priority Data

Oct. 26, 2020 (KR) ........................ 10-2020-0139441

(51) Int. Cl.
*H10K 85/60* (2023.01)
*C07D 251/24* (2006.01)
(Continued)

(52) U.S. Cl.
CPC ....... *H10K 85/6574* (2023.02); *C07D 251/24* (2013.01); *C09K 11/06* (2013.01);
(Continued)

(58) Field of Classification Search
CPC .. C07D 251/24; H10K 85/654; H10K 85/631; H10K 85/633; H10K 85/636;
(Continued)

(56) References Cited

U.S. PATENT DOCUMENTS 10,950,801 B2 * 3/2021 Huh .................... H10K 85/615
2014/0367654 A1 12/2014 Kim et al.
(Continued)

FOREIGN PATENT DOCUMENTS

CN 106831313 A * 6/2017 ............. C07C 15/24
KR 10-2009-0079134 A 7/2009
(Continued)

OTHER PUBLICATIONS

SciFinder Search, 4 pages, Apr. 7, 2021.
STN Search, 351 pages, Apr. 7, 2021.

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound of Formula (1) that improves the luminous efficiency, stability, and lifespan of an organic electronic element using the same, the element, and an electronic device thereof,
(Continued)

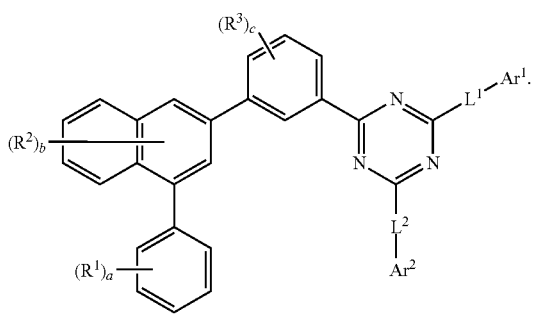

Formula (1)

14 Claims, 2 Drawing Sheets

Related U.S. Application Data of application No. 17/212,886, filed on Mar. 25, 2021, now Pat. No. 11,678,577, which is a continuation of application No. 17/096,790, filed on Nov. 12, 2020, now Pat. No. 11,063,226.

(51) Int. Cl.
| | |
|---|---|
| *C09K 11/06* | (2006.01) |
| *H10K 50/11* | (2023.01) |
| *H10K 50/15* | (2023.01) |
| *H10K 50/16* | (2023.01) |
| *H10K 50/18* | (2023.01) |
| *H10K 101/00* | (2023.01) |
| *H10K 101/10* | (2023.01) |

(52) U.S. Cl.
CPC ......... *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01); *C09K 2211/1018* (2013.01); *H10K 50/11* (2023.02); *H10K 50/15* (2023.02); *H10K 50/16* (2023.02); *H10K 50/18* (2023.02); *H10K 2101/10* (2023.02); *H10K 2101/90* (2023.02)

(58) Field of Classification Search
CPC .......... H10K 85/6572; H10K 85/6574; H10K 85/6576; C07B 63/00
See application file for complete search history.

(56) References Cited

U.S. PATENT DOCUMENTS

| | | | |
|---|---|---|---|
| 2015/0303379 A1 | 10/2015 | Lee et al. | |
| 2016/0133674 A1 | 5/2016 | Lee et al. | |
| 2018/0072695 A1 | 3/2018 | Byun et al. | |
| 2018/0123048 A1 | 5/2018 | So et al. | |
| 2018/0151806 A2 | 5/2018 | Park et al. | |
| 2018/0261774 A1 | 9/2018 | Park et al. | |

FOREIGN PATENT DOCUMENTS

| | | | | |
|---|---|---|---|---|
| KR | 10-2016-0111780 A | | 9/2016 | |
| KR | 1966306 B1 | * | 4/2019 | ............ C09K 11/06 |
| WO | 2017/171420 A1 | | 10/2017 | |
| WO | 2019/124902 A1 | | 6/2019 | |
| WO | WO-2019/245160 A1 | * | 12/2019 | ............ C09K 11/06 |

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and it can be classified into a fluorescent material derived from a singlet excited state of an electron and a phosphorescent material derived from a triplet excited state of an electron according to the light emission mechanism. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. Here, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

That is, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic element has not yet been sufficiently made. Therefore, the development of new materials is continuously required, and in particular, the development of a host material for the emitting layer is urgently required.

DETAILED DESCRIPTION OF THE INVENTION

Summary

In order to solve the problems of the above-mentioned background technology, the present invention has discovered a compound with a novel structure, and also discovered that when the compound is applied to an organic electronic element, the luminous efficiency, stability, and lifespan of the element can be greatly improved.

Accordingly, the purpose of the present invention is to provide a novel compound, an organic electronic element using the same, and an electronic device thereof.

Technical Solution

The present invention provides a compound represented by Formula (1).

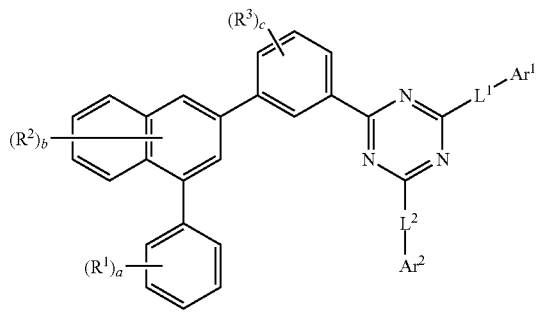

Formula (1)

In another aspect, the present invention provides a composition for an organic electronic element comprising a mixture of a compound represented by Formula (1) and a compound represented by Formula 4 or Formula 5.

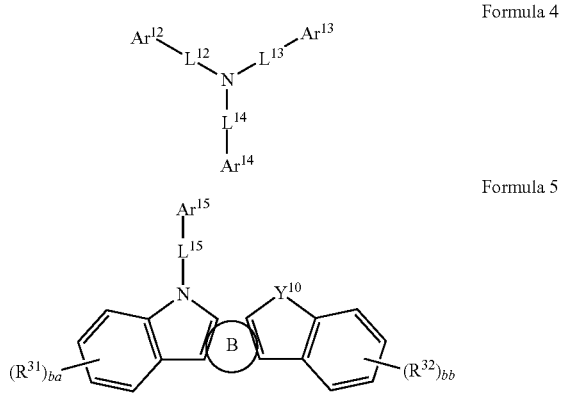

Formula 4

Formula 5

In another aspect, the present invention provides an organic electronic element comprising the compound represented by Formula (1) or the composition for an organic electronic element and an electronic device thereof.

Effects of the Invention

By using the compound according to the present invention, high luminous efficiency, low driving voltage and high heat resistance of the element can be achieved, and color purity and lifespan of the element can be greatly improved.

Figure 1:
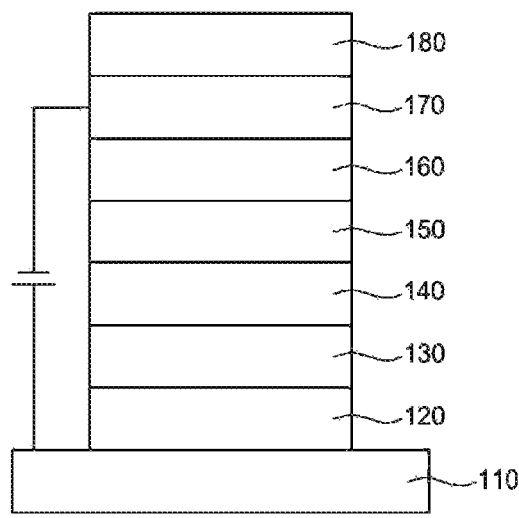
FIG. 1 to FIG. 3 are exemplary views of an organic electroluminescent device according to the present invention.

| Description of the numerals: | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected ",", coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an alkyl group bonded to oxygen radical, but is not limited thereto, and has 1 to 60 carbon atoms.

Unless otherwise stated, the term "aryloxyl group" or "aryloxy group", as used herein, means an aryl group bonded to oxygen radical, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including SO₂ instead of carbon consisting of cycle. For example, "heterocyclic group" includes the following compound.

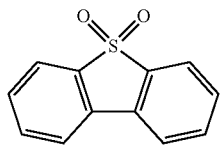 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

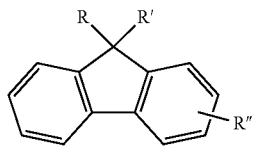

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

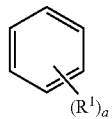

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

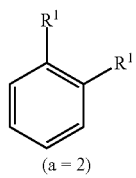

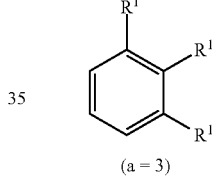

As used herein, the term "composition" is intended to be interpreted broadly, comprising compounds as well as solutions, dispersions, liquids and solid mixtures (mixture, admixture). The composition of the present invention may contain the compound of the present invention alone, or the compounds are contained in a combination of 2 or more different types, or the compounds may be contained in combinations of 2 or more types with other compounds. In other words, the composition may contain a compound corresponding to Formula (1) alone, a mixture of 2 or more compounds of Formula (1), and a mixture of a compound of Formula (1) and a compound not correspond to the present invention. Wherein, the compound not correspond to the present invention may be a single compound, or may be 2 or more types of compounds. Wherein, when the compound is contained in a combination of 2 or more types of other compounds, the other compounds may be already known compounds of each organic layer, or may be compounds to be developed in the future. Wherein, the compound contained in the organic layer may consist of only the same type of compound, but may also be a mixture of 2 or more types of heterogeneous compounds represented by Formula (1).

Hereinafter, a compound according to an aspect of the present invention, a composition for an organic electronic element, and an organic electronic element comprising the same will be described.

The present invention provides a compound represented by Formula (1).

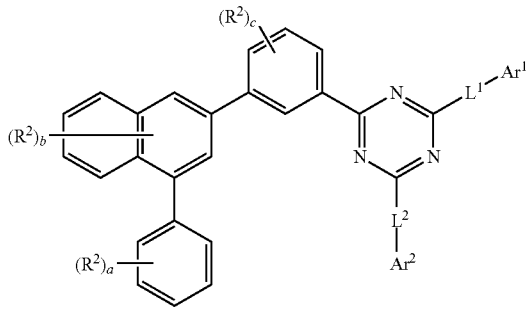

Formula (1)

Wherein:
$R^1$, $R^2$ and $R^3$ are each the same or different, and each independently hydrogen; or deuterium;
a is an integer of 0 to 5, b is an integer of 0 to 6, c is an integer of 0 to 4,
$L^1$ and $L^2$ are each independently selected from the group consisting of single bond; a $C_6$-$C_{60}$ arylene group; and a $C_2$-$C_{60}$ heterocyclic group including at least one heteroatom of O, N, S, Si or
When $L^1$ and $L^2$ are an arylene group, it is preferably an $C_6$-$C_{30}$ arylene group, more preferably an $C_6$-$C_{25}$ arylene group, for example, it may be phenylene, biphenylene, naphthylene, terphenylene, anthracenylene, and the like.
When $L^1$ and $L^2$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc.
$Ar^1$ and $Ar^2$ are each independently selected from the group consisting of an $C_6$-$C_{60}$ aryl group; a fluorenyl group; a $C_2$-$C_{60}$ heterocyclic group including at least one heteroatom of O, N, S, Si or P; a $C_3$-$C_{60}$ aliphatic ring; and a fused ring group of a $C_3$-$C_{60}$ aliphatic ring and a $C_6$-$C_{60}$ aromatic ring;
When $Ar^1$ and $Ar^2$ are an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene, triphenylene, and the like.
When $Ar^1$ and $Ar^2$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc.
When $Ar^1$ and $Ar^2$ are an aliphatic ring group, preferably a $C_3$-$C_{30}$ aliphatic ring group, more preferably a $C_3$-$C_{24}$ aliphatic ring group.
When $Ar^1$ and $Ar^2$ are a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

wherein the aryl group, arylene group, heterocyclic group, fluorenyl group, fluorenylene group, aliphatic ring group and fused ring group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; also the hydrogen of these substituents may be further substituted with one or more deuteriums, and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, $L^1$ and $L^2$ are a single bond or represented by any of the following formulas L-1 to L-20.

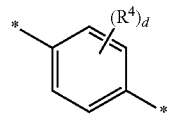

[Formula L-1]

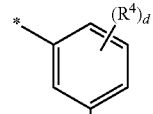

[Formula L-2]

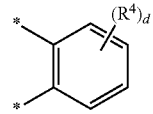

[Formula L-3]

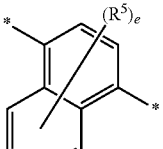

[Formula L-4]

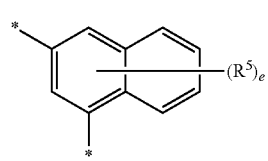

[Formula L-5]

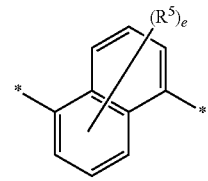

[Formula L-6]

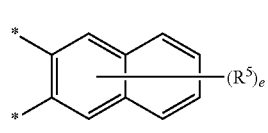

[Formula L-7]

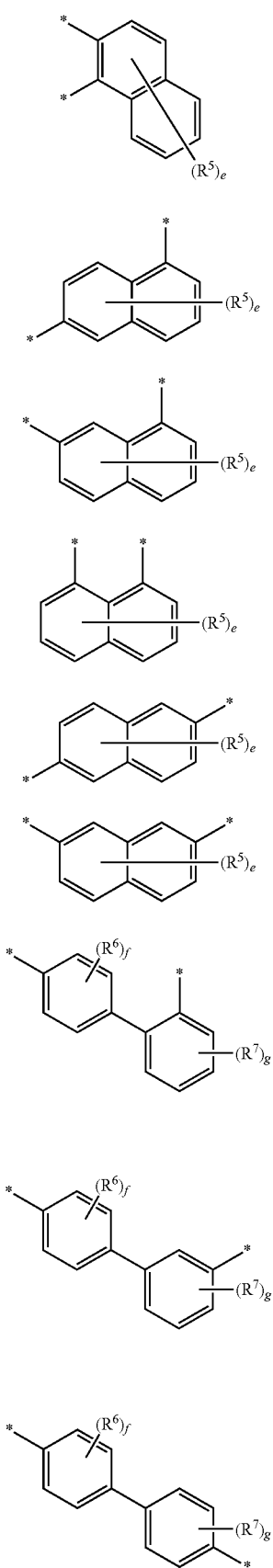

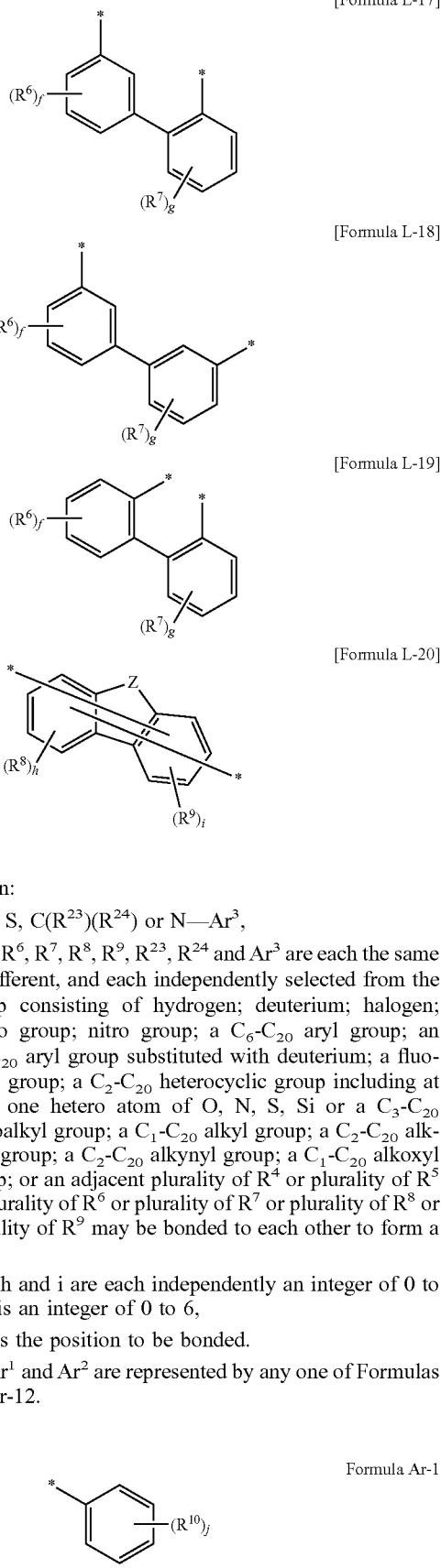

Wherein:

Z is O, S, C(R$^{23}$)(R$^{24}$) or N—Ar$^3$,

R$^4$, R$^5$, R$^6$, R$^7$, R$^8$, R$^9$, R$^{23}$, R$^{24}$ and Ar$^3$ are each the same or different, and each independently selected from the group consisting of hydrogen; deuterium; halogen; cyano group; nitro group; a C$_6$-C$_{20}$ aryl group; an C$_6$-C$_{20}$ aryl group substituted with deuterium; a fluorenyl group; a C$_2$-C$_{20}$ heterocyclic group including at least one hetero atom of O, N, S, Si or a C$_3$-C$_{20}$ cycloalkyl group; a C$_1$-C$_{20}$ alkyl group; a C$_2$-C$_{20}$ alkenyl group; a C$_2$-C$_{20}$ alkynyl group; a C$_1$-C$_{20}$ alkoxyl group; or an adjacent plurality of R$^4$ or plurality of R$^5$ or plurality of R$^6$ or plurality of R$^7$ or plurality of R$^8$ or plurality of R$^9$ may be bonded to each other to form a ring, d, f, g, h and i are each independently an integer of 0 to 4, e is an integer of 0 to 6,

* means the position to be bonded.

Also, Ar$^1$ and Ar$^2$ are represented by any one of Formulas Ar-1 to Ar-12.

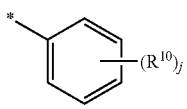

Formula Ar-1

Formula Ar-2

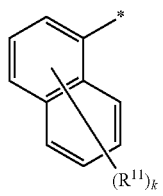

Formula Ar-3

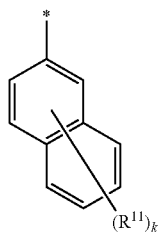

Formula Ar-4

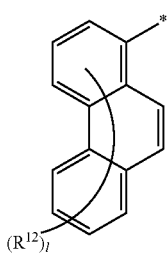

Formula Ar-5

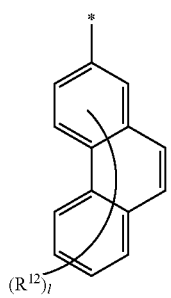

Formula Ar-6

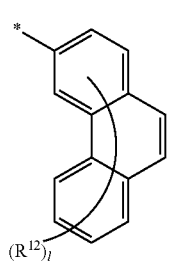

Formula Ar-7

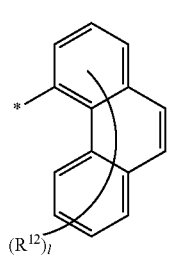

Formula Ar-8

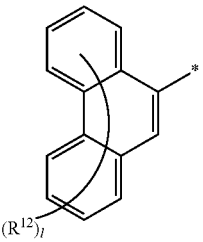

Formula Ar-9

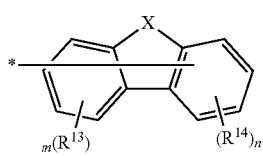

Formula Ar-10

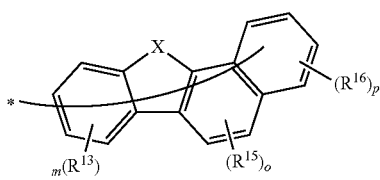

Formula Ar-11

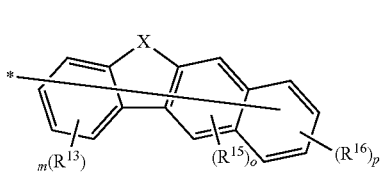

Formula Ar-12

Wherein:

X is O, S, CRaRb or NIRb, $R^a$, $R^b$, $R^c$, $R^{10}$, $R^{11}$, $R^{12}$, $R^{13}$, $R^{14}$, $R^{15}$ and $R^{16}$ are the same as the definition of $R^4$, or adjacent groups may be bonded to each other to form a ring, j is an integer of o to 5, k is an integer of 0 to 7, l is an integer of 0 to 9, m, n and p are each independently an integer of 0 to 4, o is an integer of 0 to 2,

* means the position to be bonded.

Specifically, the compound represented by Formula (1) may be a compound represented by any one of the following compounds P-1 to P-96, but is not limited thereto.

P-1
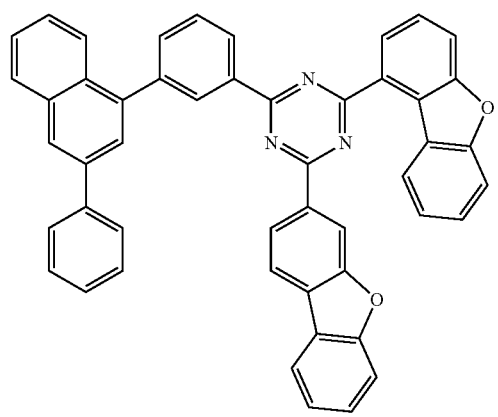
P-2
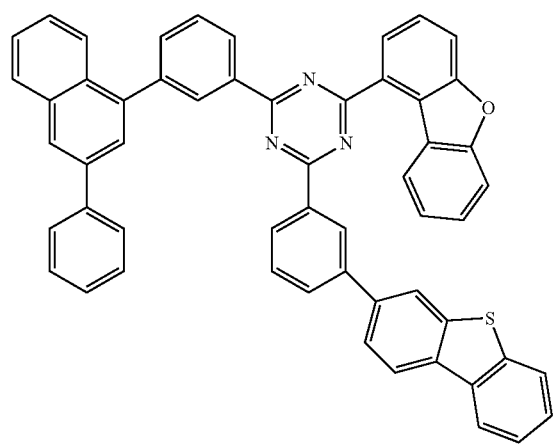
P-3
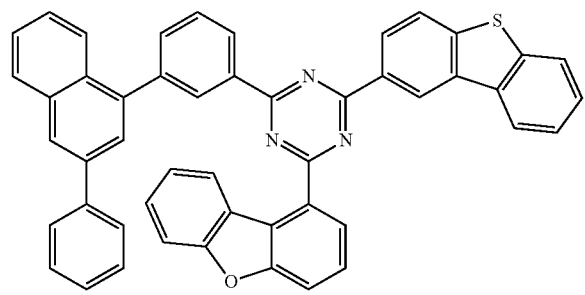
P-4
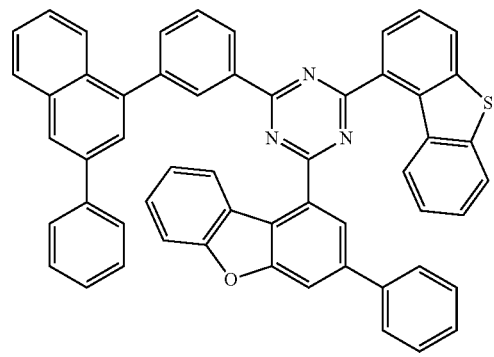
P-5
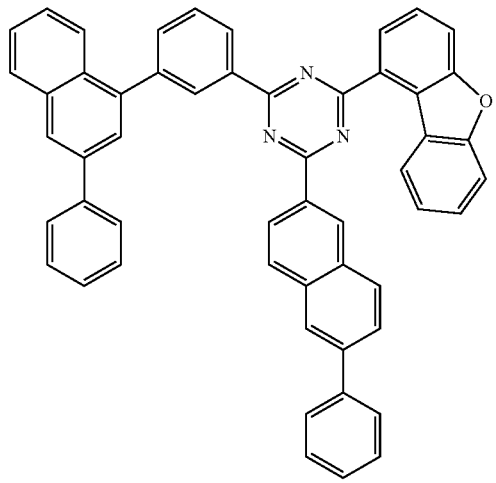
P-6
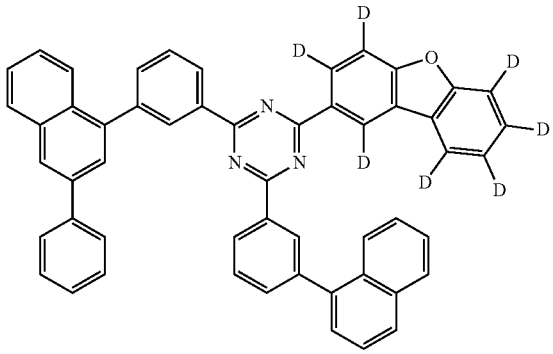
P-7
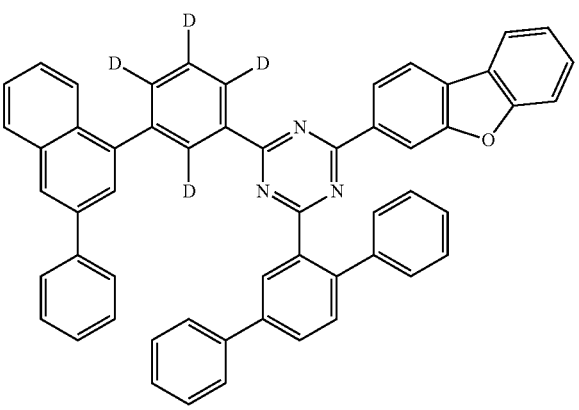
P-8
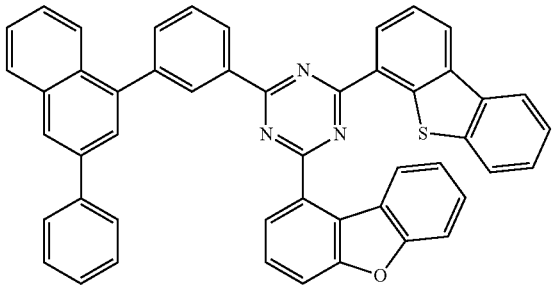

P-9
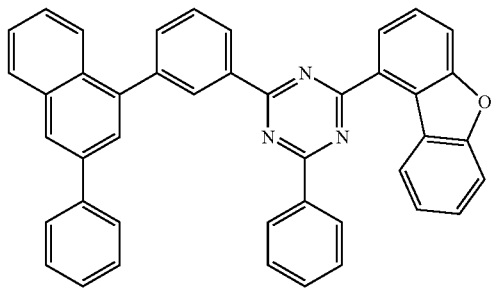
P-10
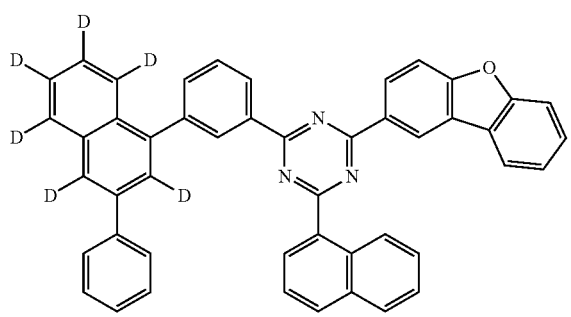
P-11
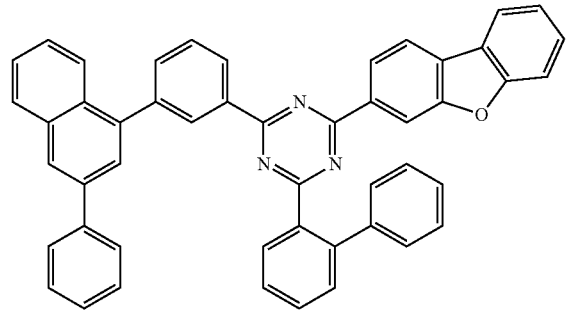
P-12
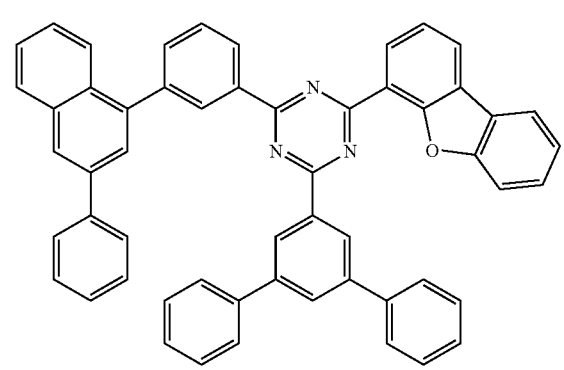
P-13
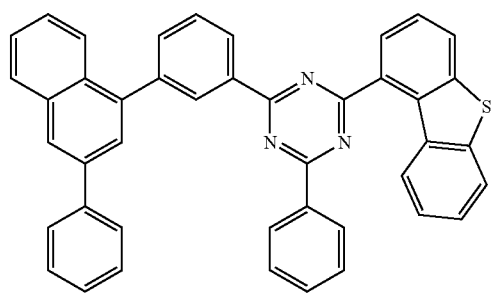
P-14
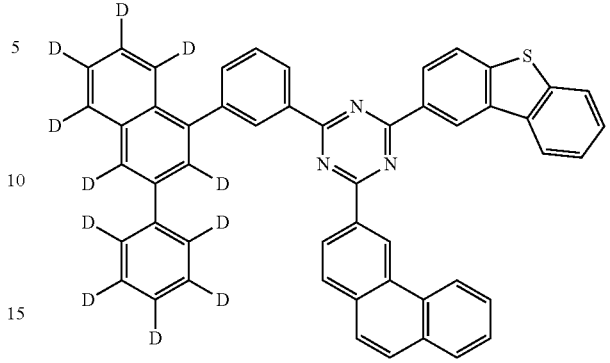
P-15
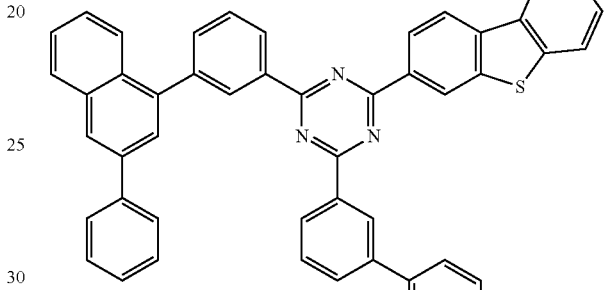
P-16
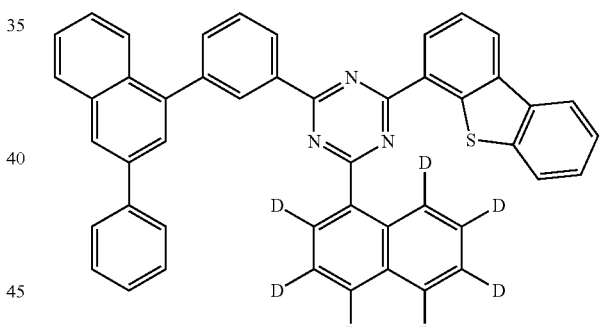
P-17
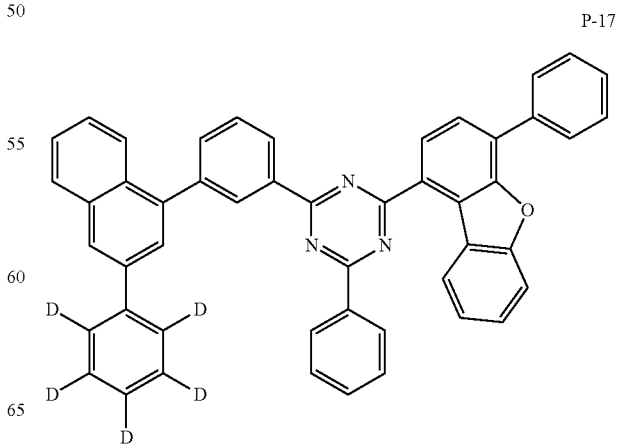

P-18
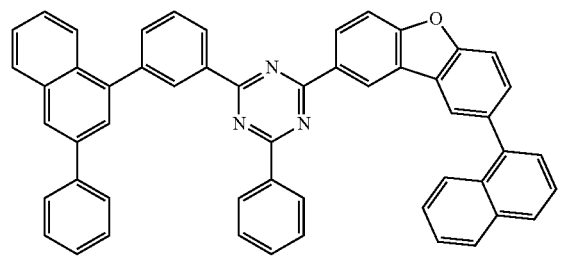
P-19
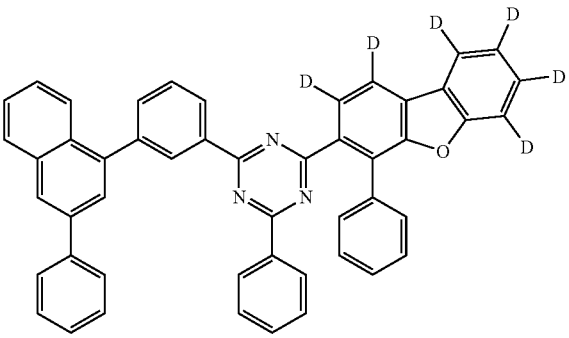
P-20
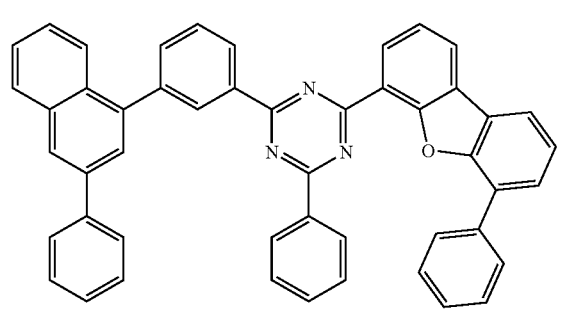
P-21
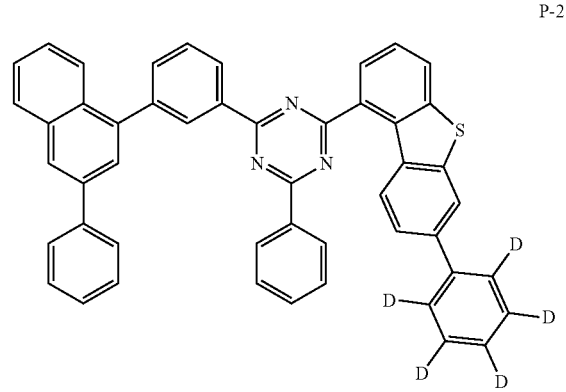
P-22
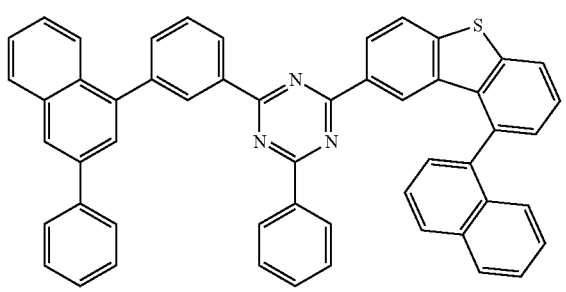
P-23
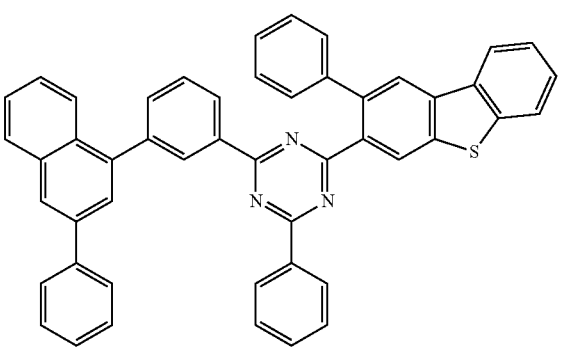
P-24
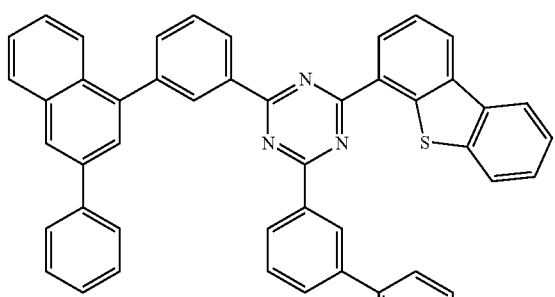
P-25
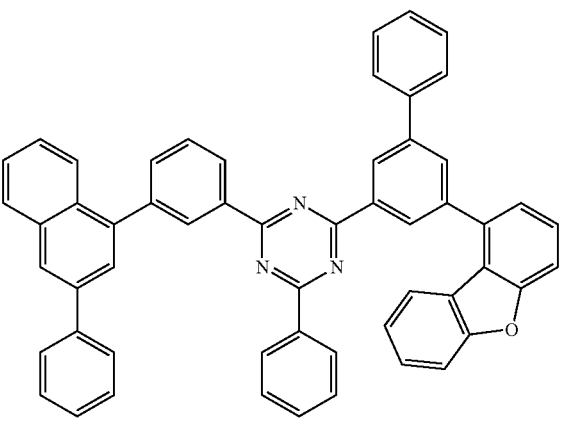
P-26
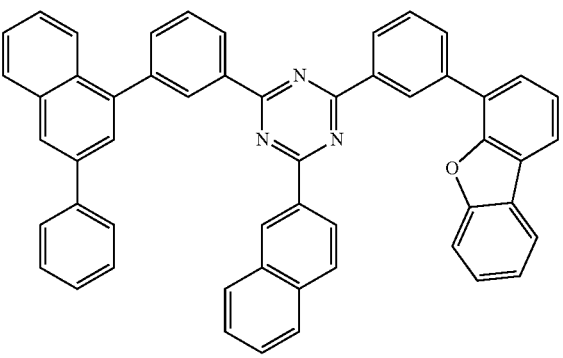

P-27
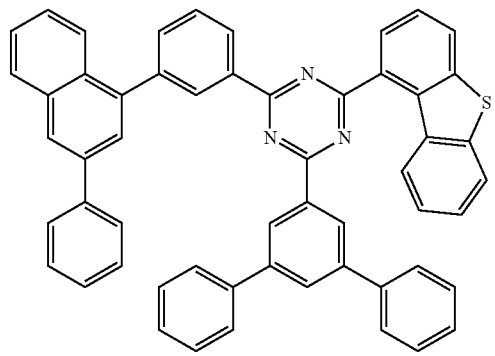
P-31
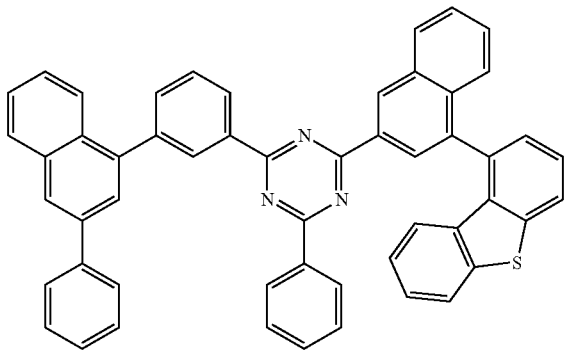
P-28
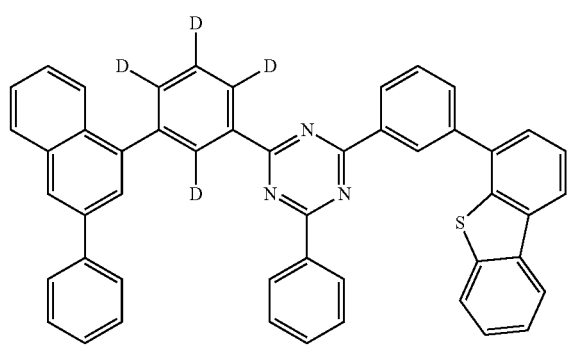
P-32
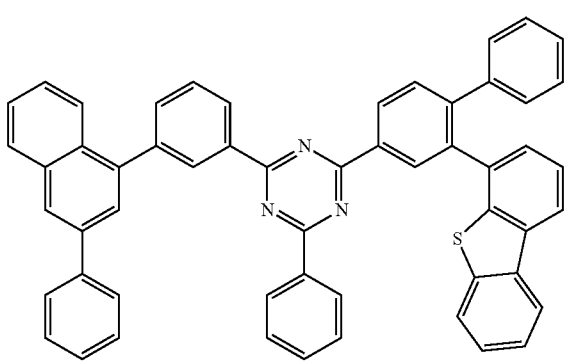
P-29
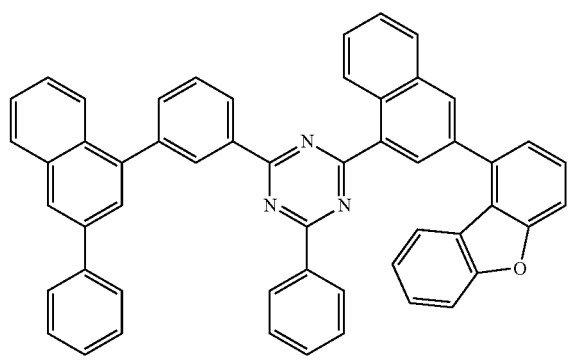
P-33
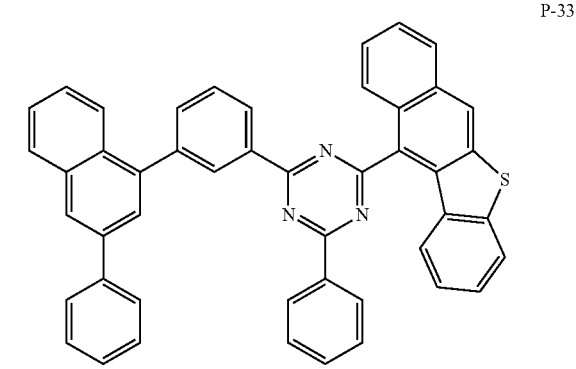
P-30
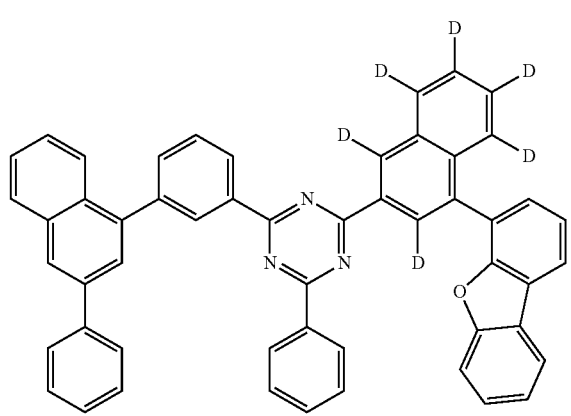
P-34
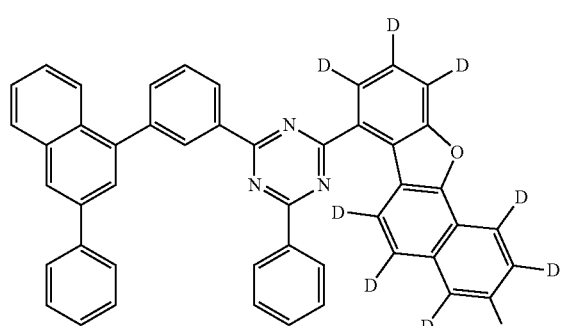

P-35
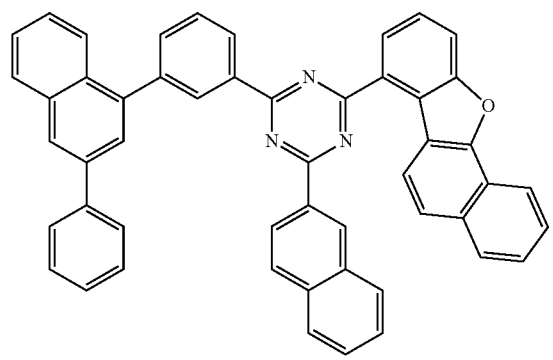
P-36
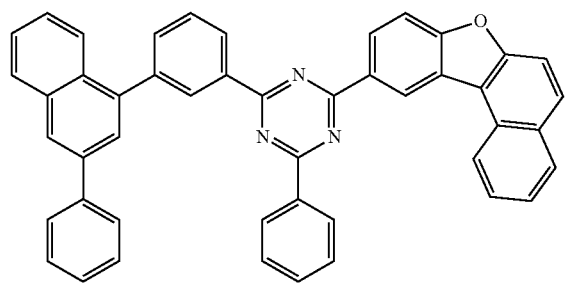
P-37
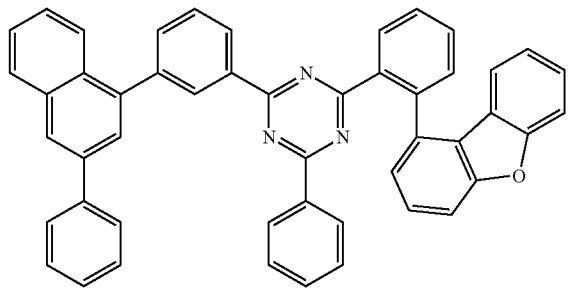
P-38
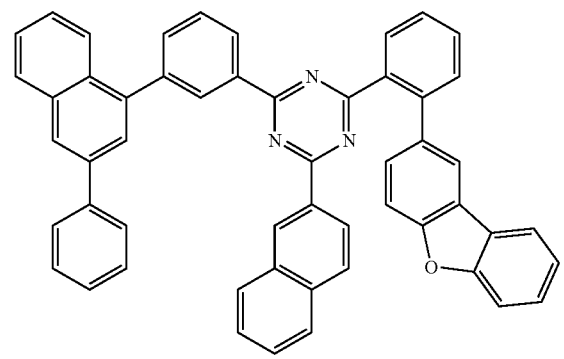
P-39
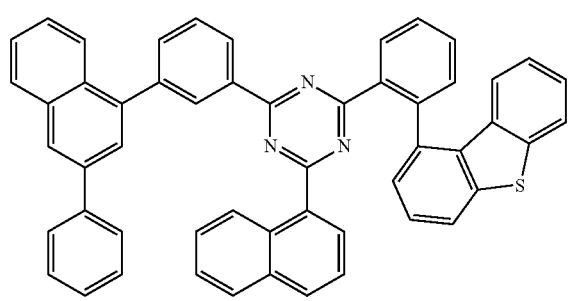
P-40
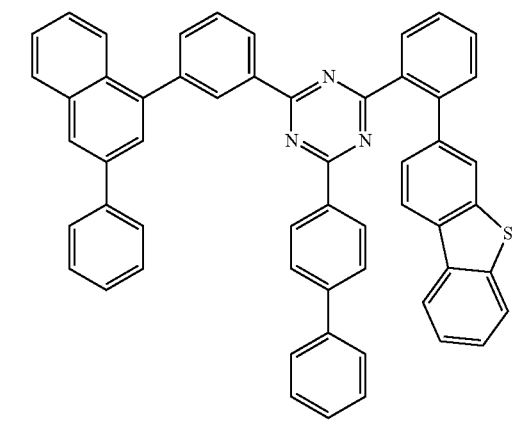
P-41
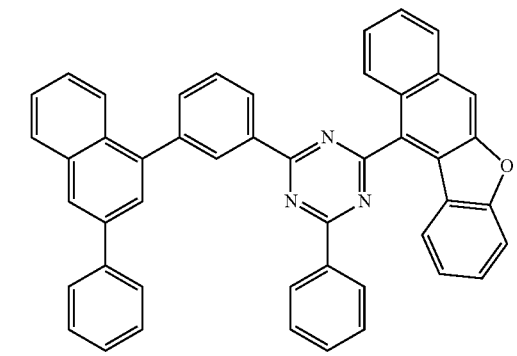
P-42
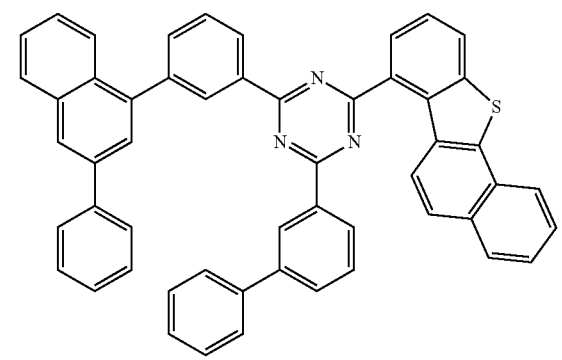

-continued
P-43
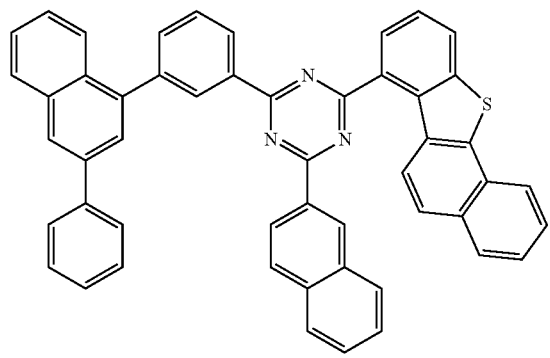
P-44
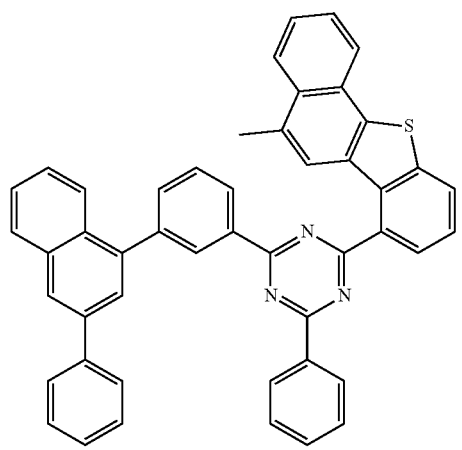
P-45
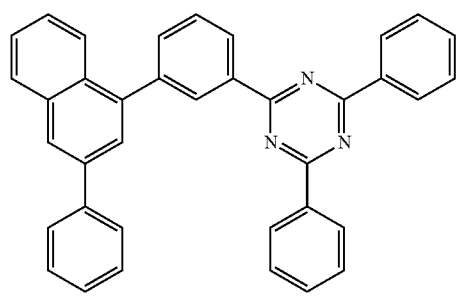
P-46
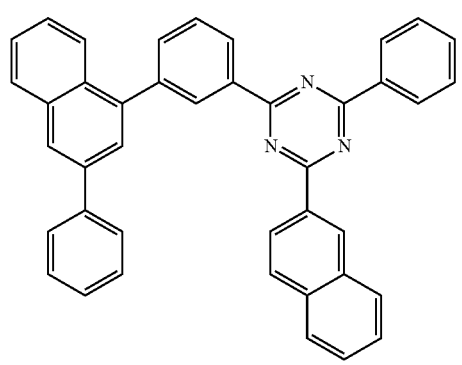
-continued
P-47
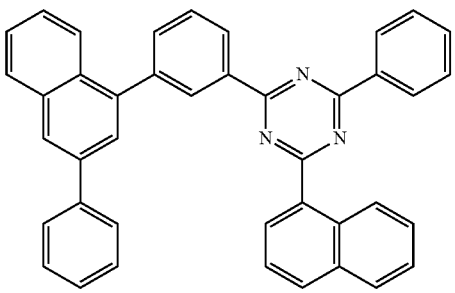
P-48
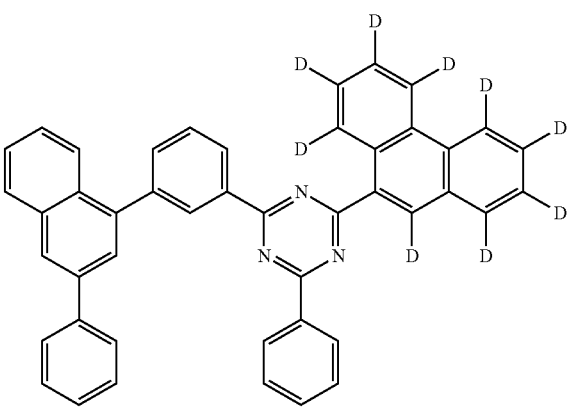
P-49
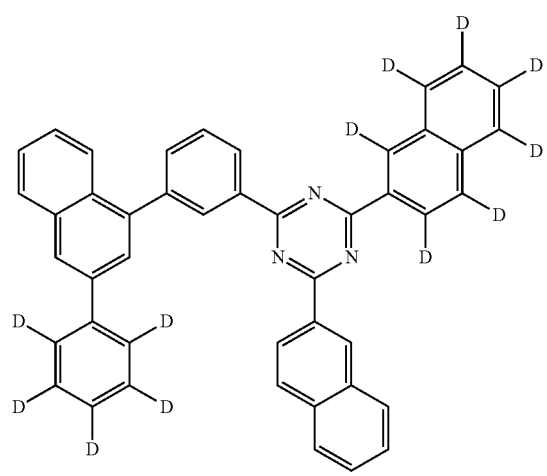
P-50
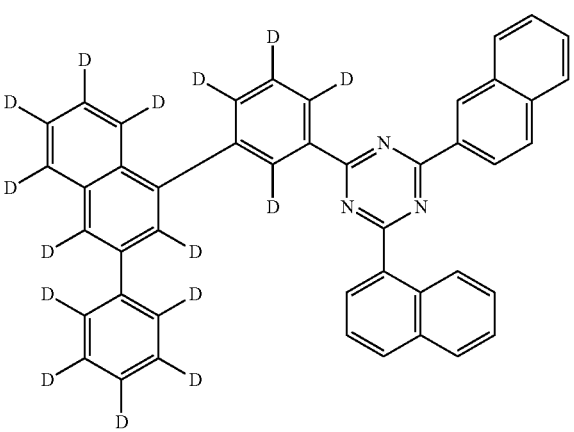

P-51
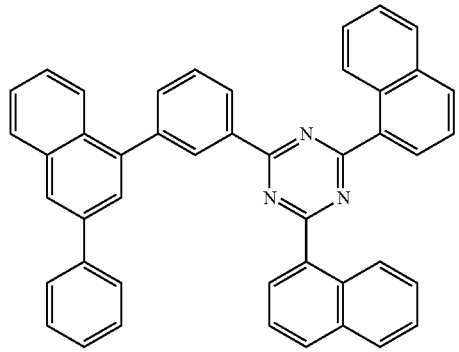
P-52
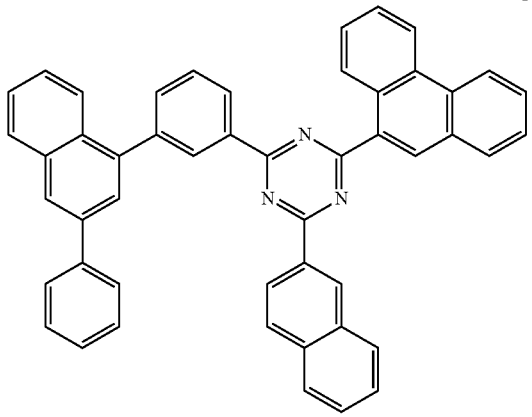
P-53
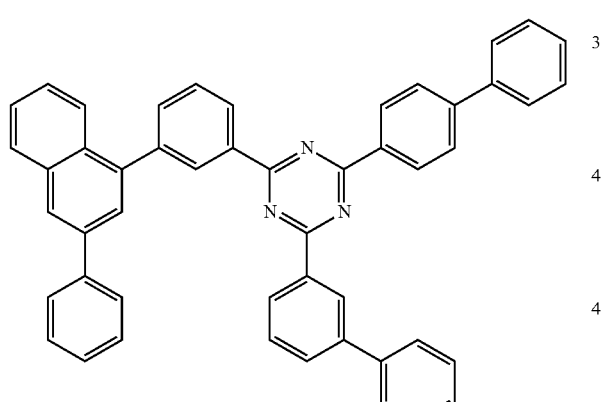
P-54
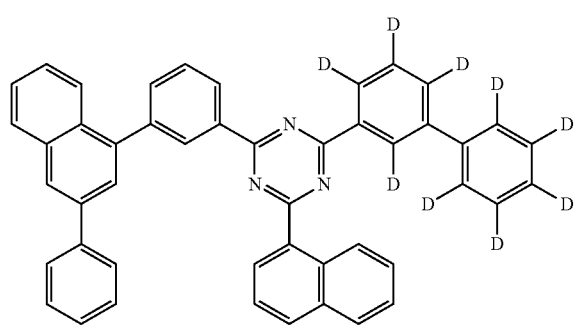
P-55
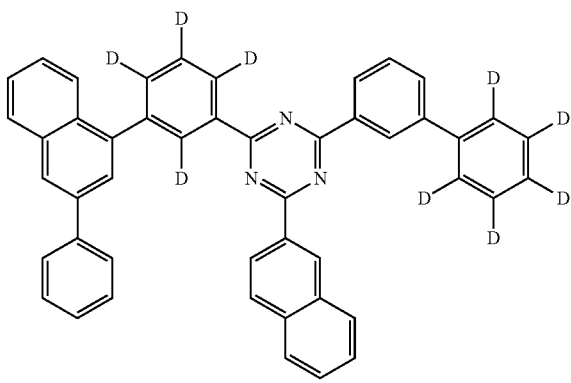
P-56
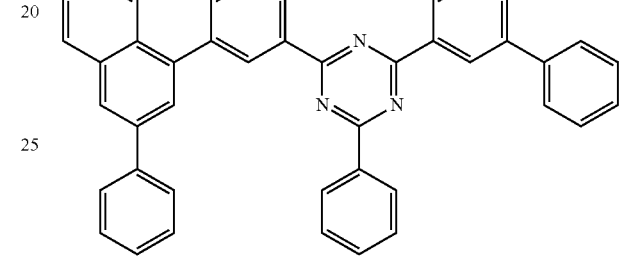
P-57
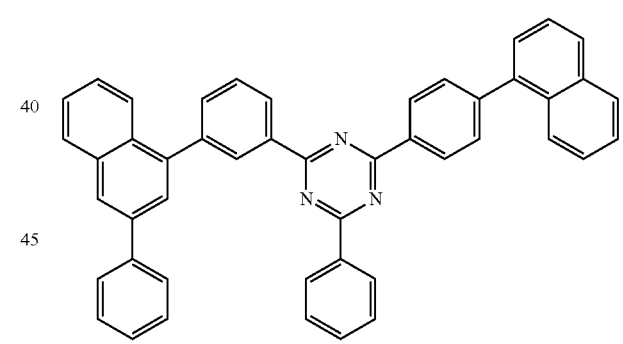
P-58
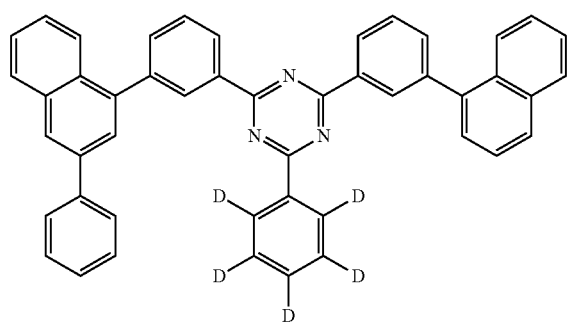

P-59
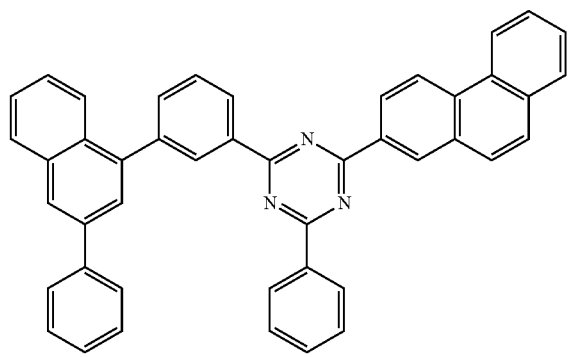
P-60
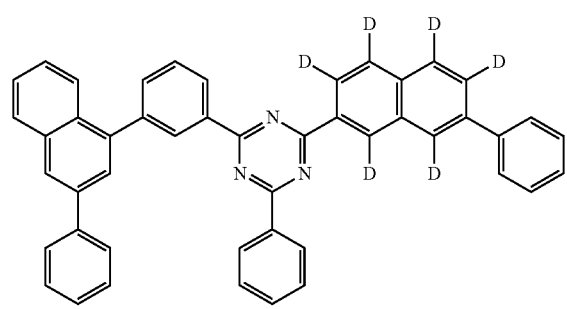
P-61
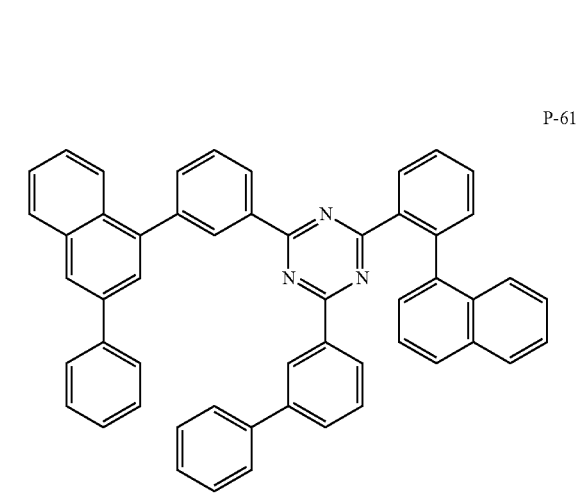
P-62
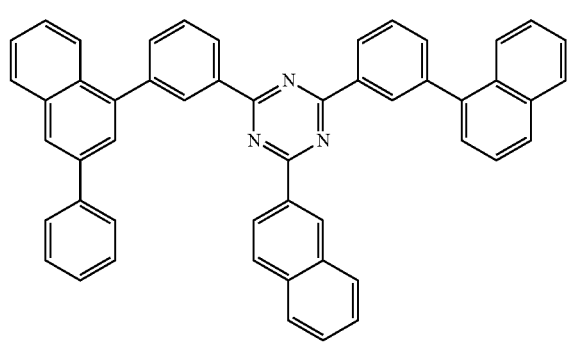
P-63
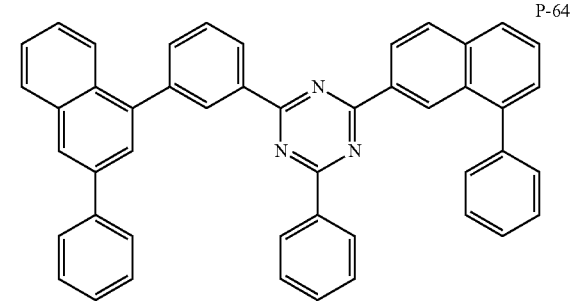
P-64
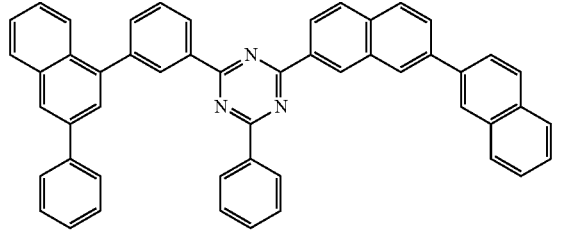
P-65
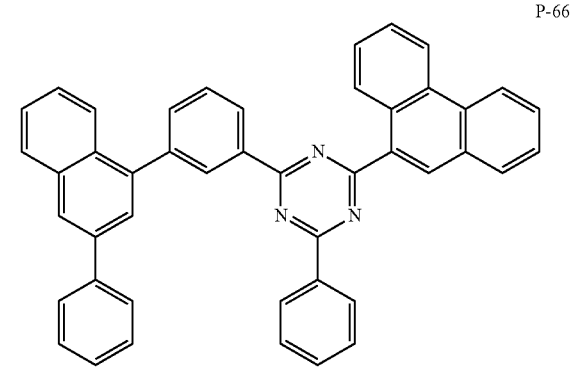
P-66
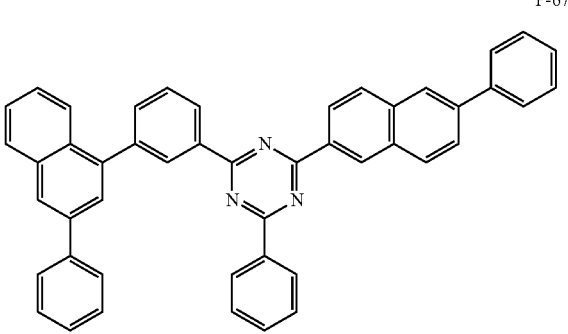
P-67

P-68
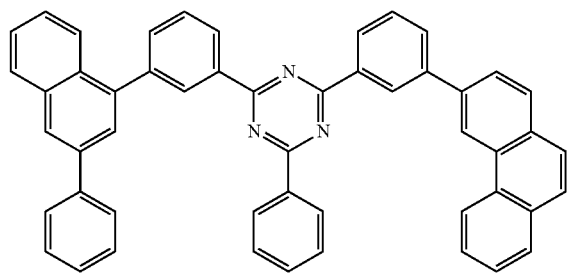
P-69
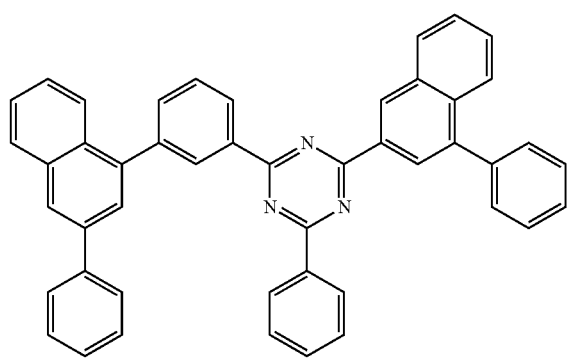
P-70
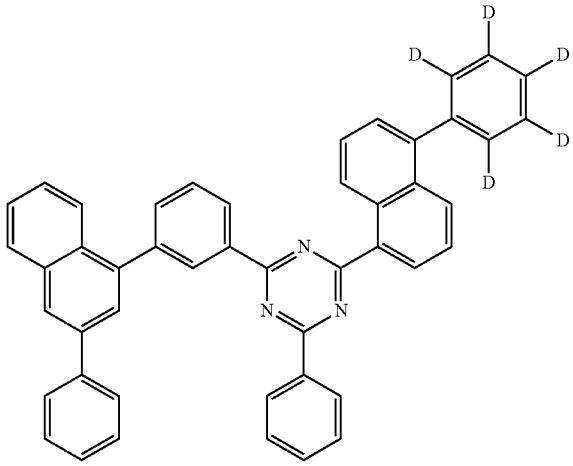
P-71
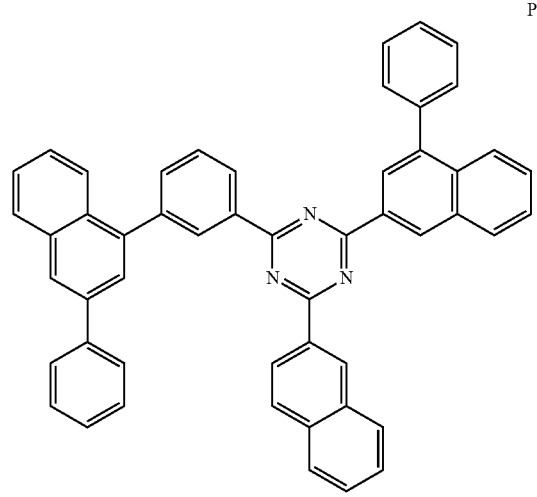
P-72
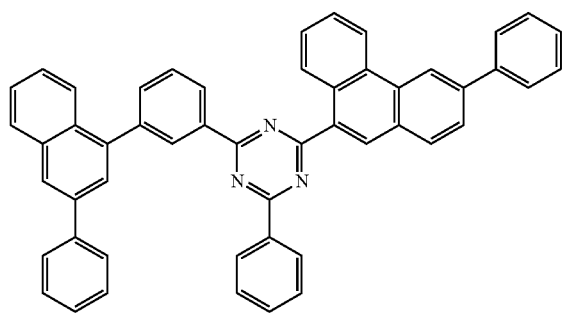
P-73
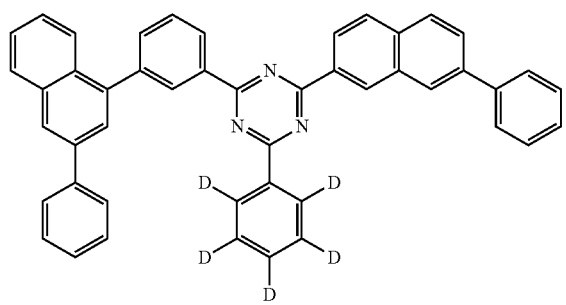
P-74
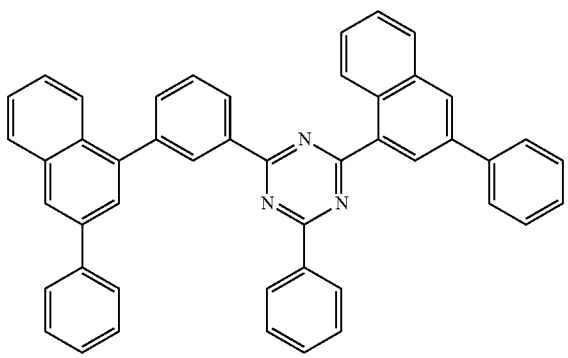
P-75
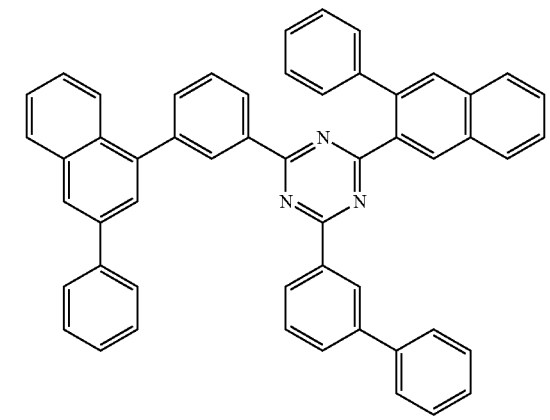

-continued
P-76
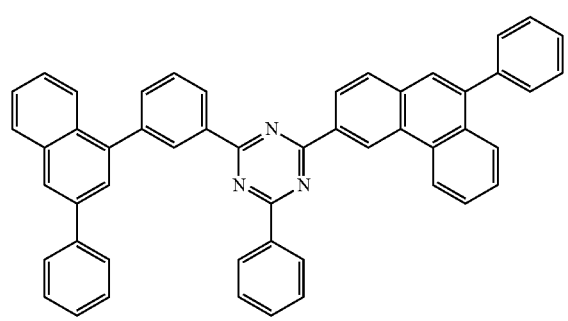
P-77
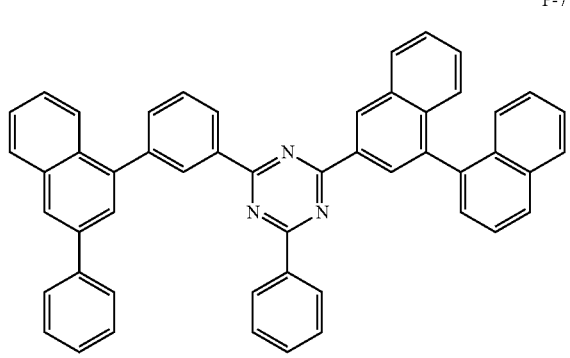
P-78
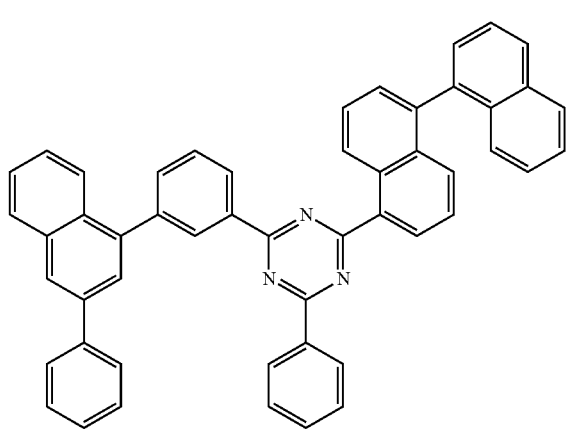
P-79
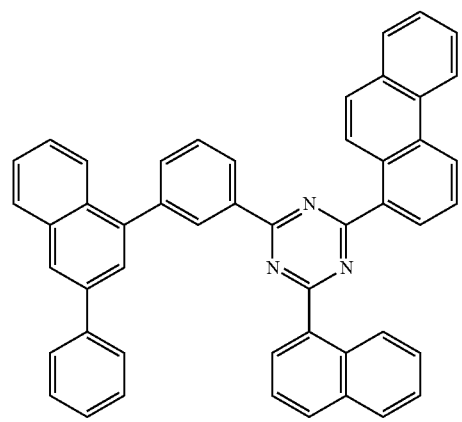
-continued
P-80
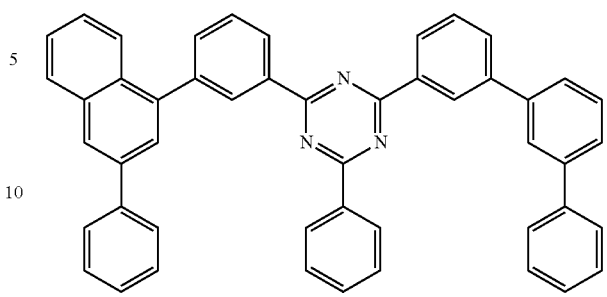
P-81
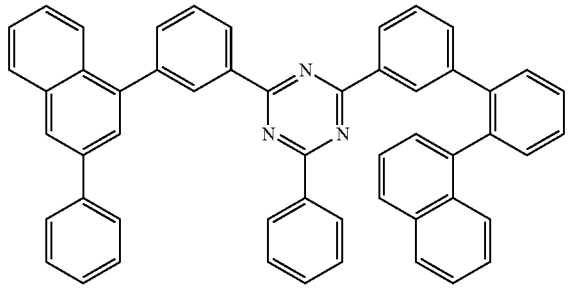
P-82
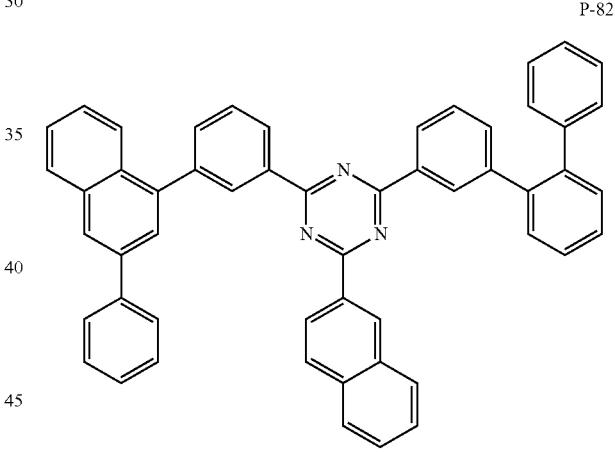
P-83
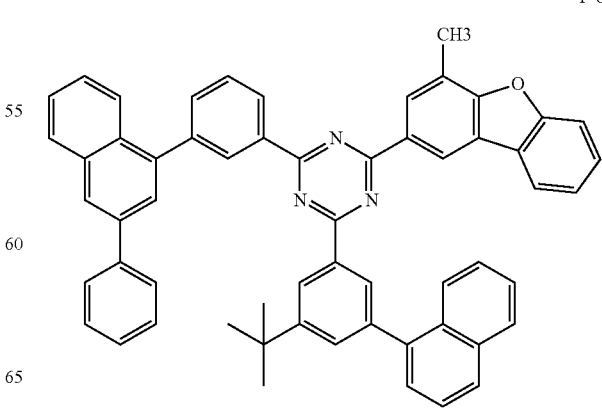

P-84
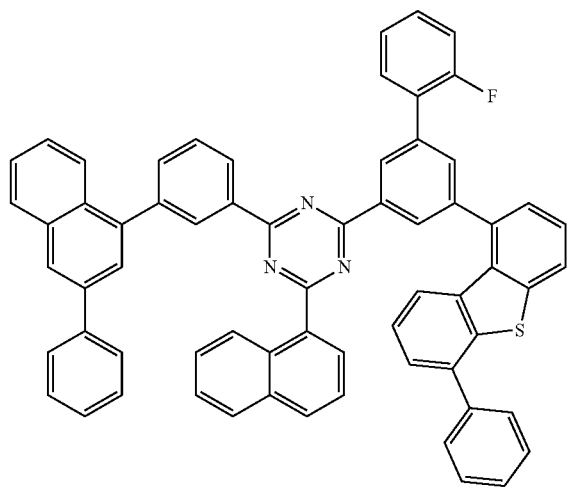
P-85
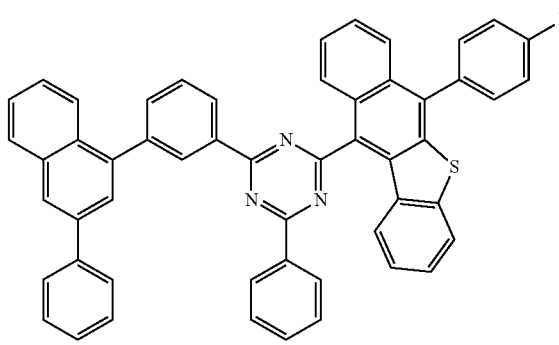
P-86
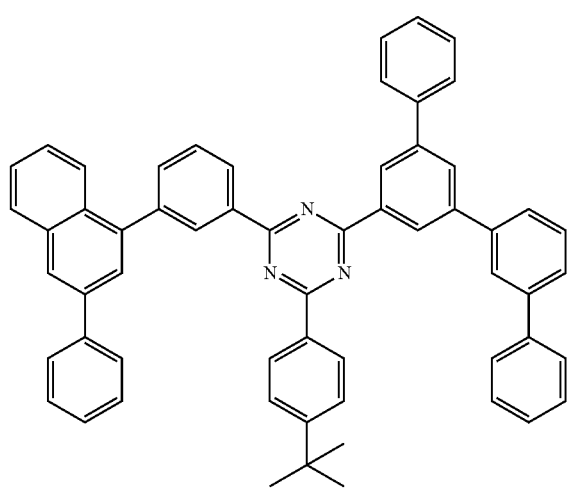
P-87
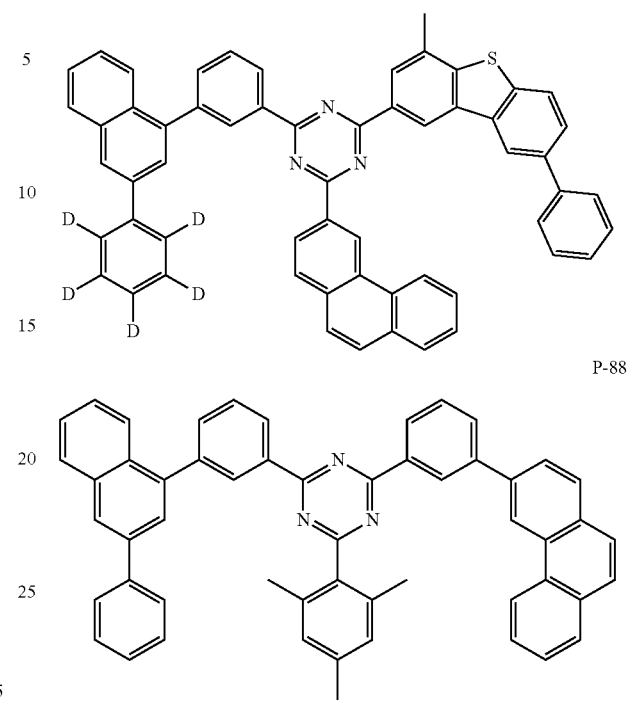
P-88
P-89
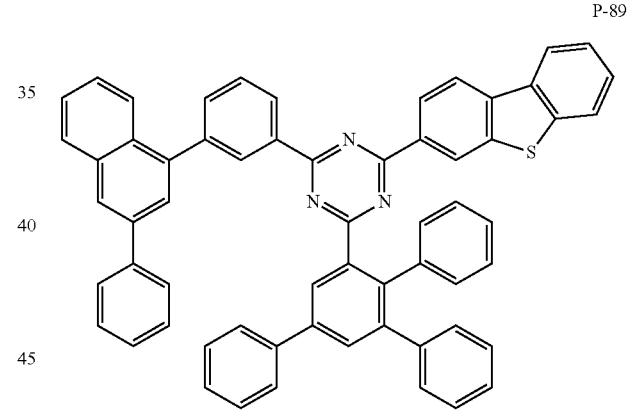
P-90
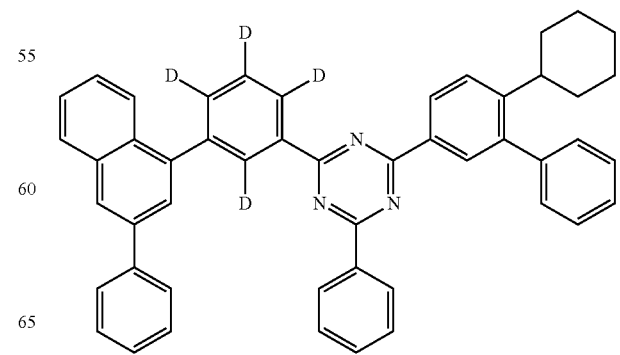

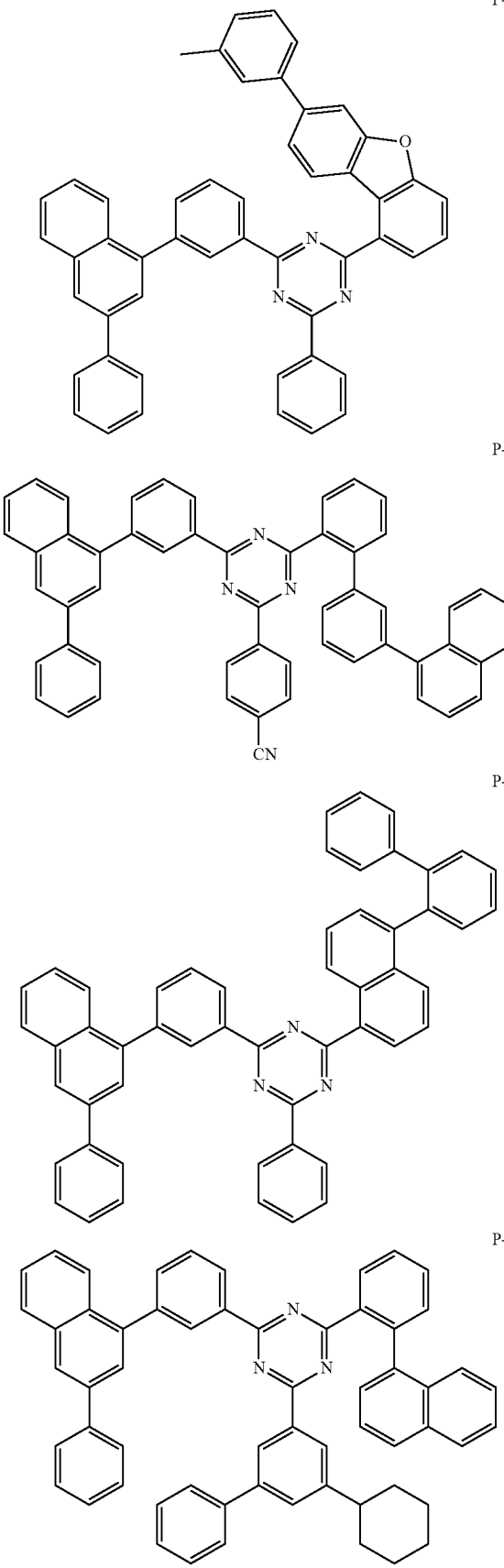

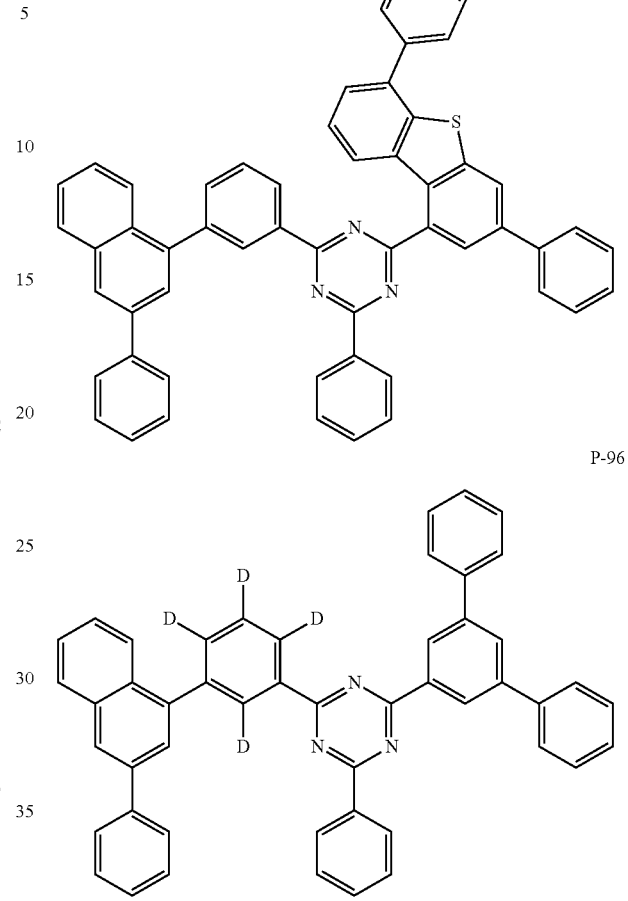

In another aspect, the present invention provides a composition for an organic electronic element comprising a mixture of a compound represented by Formula (1) and a compound represented by Formula 4 or Formula 5.

Formula 4

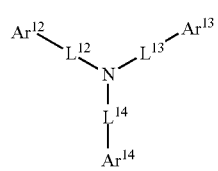

Formula 5

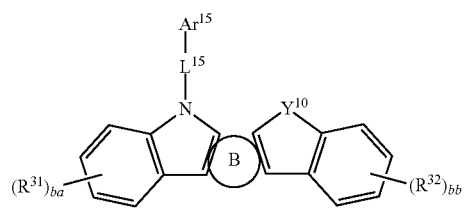

Wherein:

$L^{12}$, $L^{13}$, $L^{14}$ and $L^{15}$ are each independently selected from the group consisting of single bond; a $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

When $L^{12}$, $L^{13}$, $L^{14}$ and $L^{15}$ are an arylene group, it is preferably an $C_6$-$C_{30}$ arylene group, more preferably an $C_6$-$C_{25}$ arylene group, for example, it may be phenylene, biphenylene, naphthylene, terphenylene, anthracenylene, phenanthrenylene, and the like.

When $L^{12}$, $L^{13}$, $L^{14}$ and $L^{15}$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyridazine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc.

When $L^{12}$, $L^{13}$, $L^{14}$ and $L^{15}$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

$Ar^{12}$, $Ar^{13}$ and $Ar^{14}$ are each independently selected from the group consisting of an $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

When $Ar^{12}$, $Ar^{13}$ and $Ar^{14}$ are an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene, triphenylene, and the like.

When $Ar^{12}$, $Ar^{13}$ and $Ar^{14}$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc.

When $Ar^{12}$, $Ar^{13}$ and $Ar^{14}$ are a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

When $Ar^{12}$, $Ar^{13}$ and $Ar^{14}$ are an alkyl group, it is preferably a $C_1$-$C_{30}$ alkyl group, and more preferably a $C_1$-$C_{24}$ alkyl group.

When $Ar^{12}$, $Ar^{13}$ and $Ar^{14}$ are an alkoxyl group, it is preferably a $C_1$-$C_{24}$ alkoxyl group.

When $Ar^{12}$, $Ar^{13}$ and $Ar^{14}$ are an aryloxy group, it is preferably a $C_6$-$C_{24}$ aryloxy group.

$Ar^{15}$ is each independently selected from the group consisting of an $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring; and —L'—NR'R";

When $Ar^{15}$ is an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene and the like.

When $Ar^{15}$ is a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc.

When $Ar^{15}$ is a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

$Y^{10}$ is O, S, $CR^{51}R^{52}$ or $NR^{53}$,

Ring B is an $C_6$-$C_{20}$ aryl group,

L' is selected from the group consisting of single bond; a $C_6$-$C_{60}$ arylene group; a fluorenylene group; a $C_2$-$C_{60}$ heterocyclic group including at least one heteroatom of O, N, S, Si or P; and a $C_3$-$C_{60}$ aliphatic ring;

When L' is an arylene group, it is preferably an $C_6$-$C_{30}$ arylene group, more preferably an $C_6$-$C_{26}$ arylene group, for example, it may be phenylene, biphenylene, naphthylene, terphenylene, anthracenylene, phenanthrenylene, and the like.

When L' is a heterocyclic group, it is preferably a $C_2$-$C_{30}$ heterocyclic group, and more preferably a $C_2$-$C_{24}$ heterocyclic group, for example, it may be pyrazine, thiophene, pyridine, pyridazine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc.

When L' is an aliphatic ring group, preferably a $C_3$-$C_{30}$ aliphatic ring group, more preferably a $C_3$-$C_{24}$ aliphatic ring group.

$R^{51}$, $R^{52}$, $R^{53}$, R' and R" are the same as the definition of $Ar^{12}$, or $R^{51}$ and $R^{52}$ are bonded to each other to form a spiro, $R^{31}$ and $R^{32}$ are each the same or different, and each independently selected from the group consisting of hydrogen; deuterium; halogen; cyano group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^{31}$ or plurality of $R^{32}$ may be bonded to each other to form a ring, When $R^{31}$ and $R^{32}$ are an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene, and the like.

When $R^{31}$ and $R^{32}$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc.

When $R^{31}$ and $R^{32}$ are a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

When $R^{31}$ and $R^{32}$ are an alkyl group, it is preferably a $C_1$-$C_{30}$ alkyl group, and more preferably a $C_1$-$C_{24}$ alkyl group.

When $R^{31}$ and $R^{32}$ are an alkoxyl group, it is preferably a $C_1$-$C_{24}$ alkoxyl group.

When $R^{31}$ and $R^{32}$ are an aryloxy group, it is preferably a $C_6$-$C_{24}$ aryloxy group.

ba and bb are each independently an integer of 0 to 4, wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; and —L'—NR'R"; also the hydrogen of these substituents may be further substituted with one or more deuteriums, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Preferably, the composition for an organic electronic element may be used as a host for an emitting layer.

Formula 4 is represented by any one of the following Formulas 4-1 to 4-3.

Wherein:

$Ar^{13}$, $Ar^{14}$, $L^{12}$, $L^{13}$ and $L^{14}$ are the same as the defined in Formula 4, $X^{11}$, $X^{12}$ and $X^{13}$ are the same as the definition of $Y^{10}$ in Formula 5, $R^{33}$, $R^{34}$, $R^{35}$, $R^{36}$, $R^{37}$ and $R^{38}$ are each independently same or different, and each independently selected from the group consisting of a hydrogen; deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; or an adjacent plurality of $R^{33}$ or plurality of $R^{34}$ or plurality of $R^{35}$ or plurality of $R^{36}$ or plurality of $R^{37}$ or plurality of $R^{38}$ may be bonded to each other to form a ring, bc, be and bg are each independently an integer from 0 to 4, bd, bf and bh are each independently an integer from 0 to 3.

Formula 5 is represented by any one of the following Formulas 5-1 to 5-6:

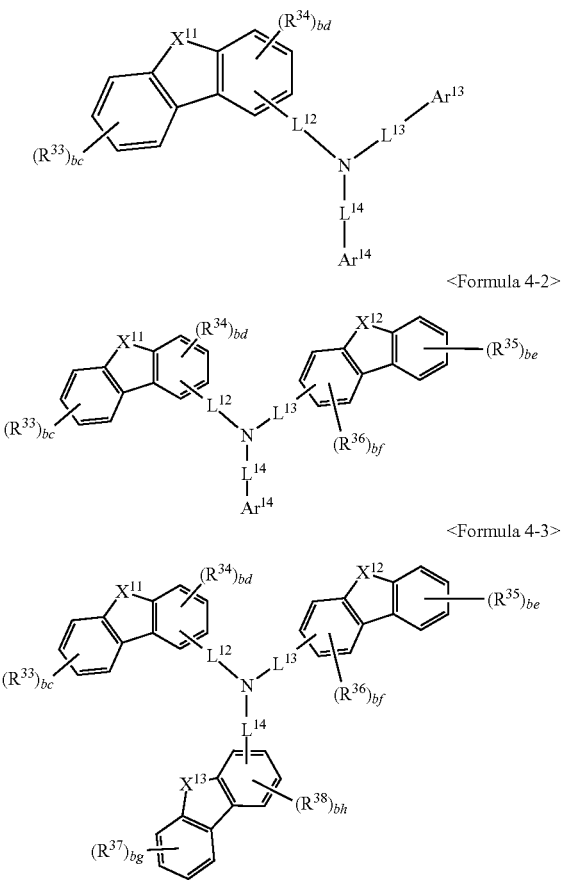

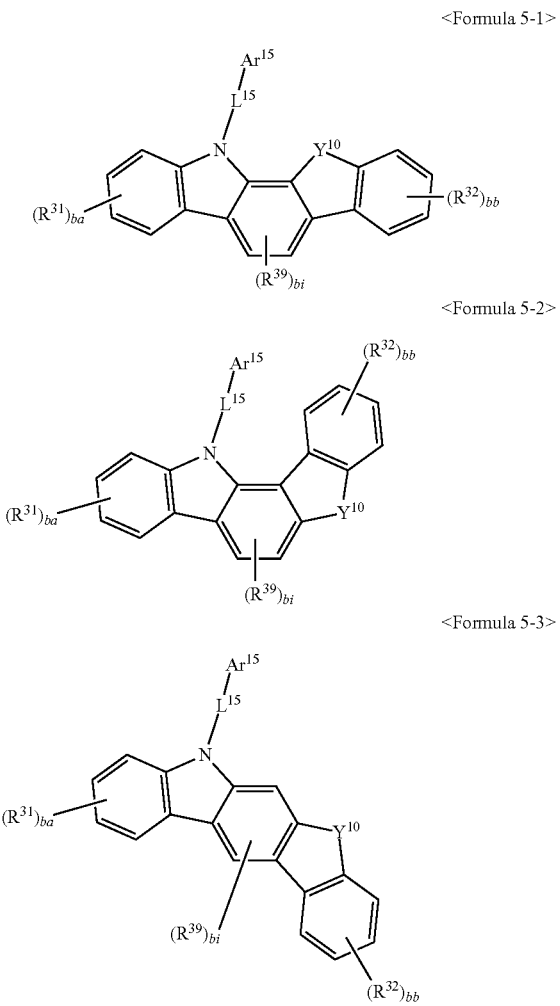

<Formula 5-4>

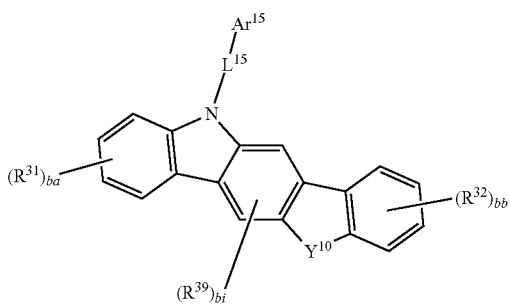

<Formula 5-5>

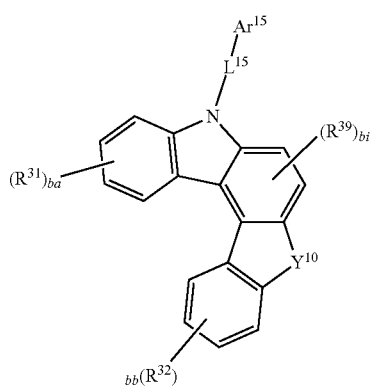

<Formula 5-5>

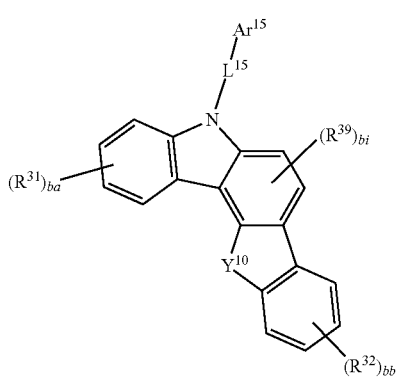

Wherein:
$Y^{10}$, $Ar^{15}$, $L^{15}$, $R^{31}$, $R^{32}$, ba and bb are the same as defined in Formula 5,
$R^{39}$ is the same as the definition of $R^{31}$, or adjacent plurality of $R^{39}$ may be bonded to each other to form a ring,
bi is an integer from 0 to 2.
Formula 5 is represented by any one of Formulas 5-7 to 5-9.

<Formula 5-7>

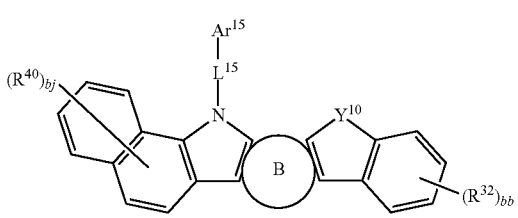

<Formula 5-8>

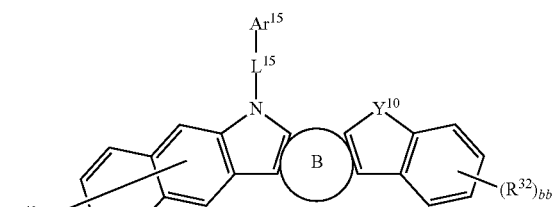

<Formula 5-9>

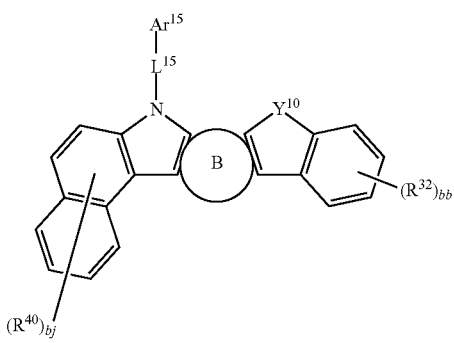

Wherein:
$Y^{10}$, Ring B, $Ar^{15}$, $L^{15}$, $R^{32}$ and bb are the same as defined in Formula 5,
$R^{40}$ is the same as the definition of $R^{31}$, or adjacent plurality of $R^{40}$ may be bonded to each other to form a ring,
bj is an integer from 0 to 6.
Formula 5 is represented by any one of Formulas 5-10 to 5-12.

<Formula 5-10>

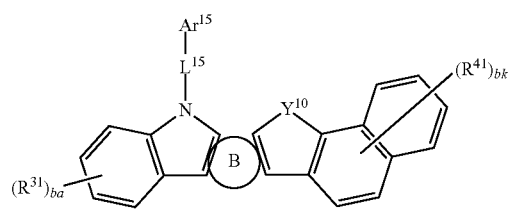

<Formula 5-11>

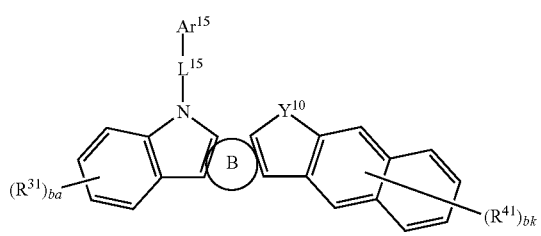

<Formula 5-12>
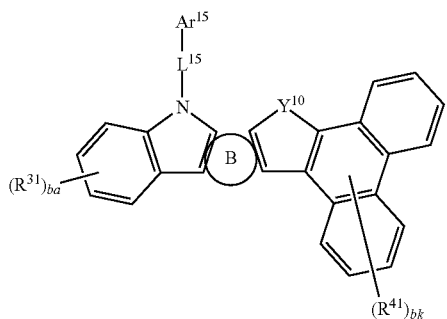
Wherein:
$Y^{10}$, Ring B, $Ar^{15}$, $L^{15}$, $R^{31}$ and ba are the same as defined in Formula 5,
$R^{41}$ is the same as the definition of $R^{31}$, or adjacent plurality of $R^{41}$ may be bonded to each other to form a ring,
bk is an integer from 0 to 6.
Also, Formula 5 is represented by any one of Formulas 5-13 to 5-18.
<Formula 5-13>
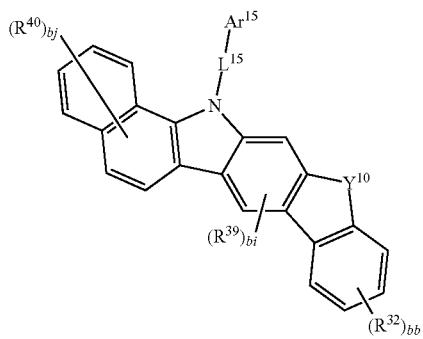
<Formula 5-14>
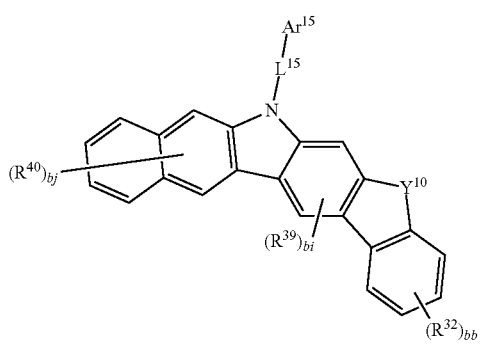
<Formula 5-15>
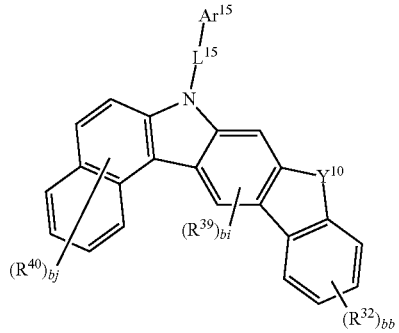
<Formula 5-16>
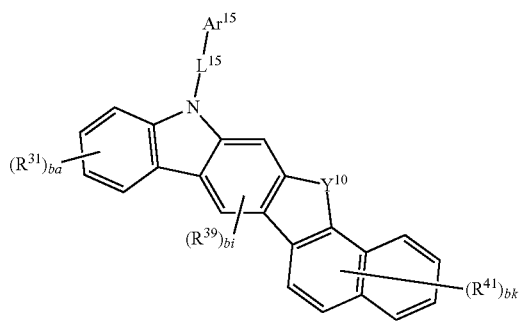
<Formula 5-17>
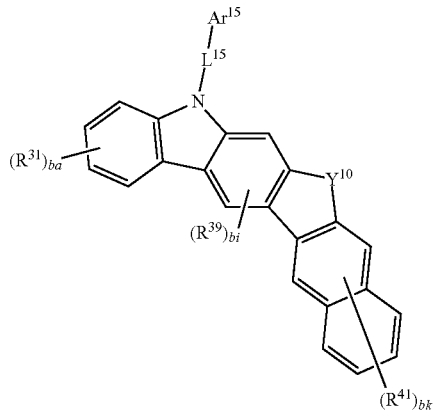
<Formula 5-18>
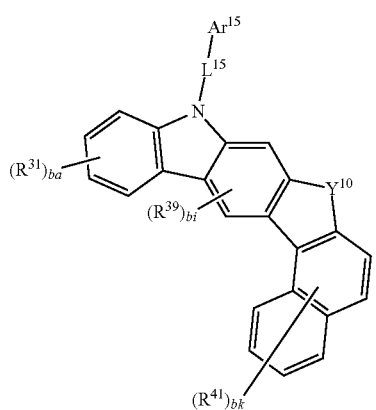

Wherein:

$Y^{10}, Ar^{15}, L^{15}, R^{31}, R^{32}$, ba and bb are the same as defined in Formula 5, $R^{39}, R^{40}$ and $R^{41}$ are the same as the definition of $R^{31}$, or adjacent plurality of $R^{39}$ or plurality of $R^{40}$ or plurality of $R^{41}$ may be bonded to each other to form a ring, bi is an integer from 0 to 2, bj and bk are each independently an integer from 0 to 6.

Formula 5 is represented by Formula 5-19.

<Formula 5-19>

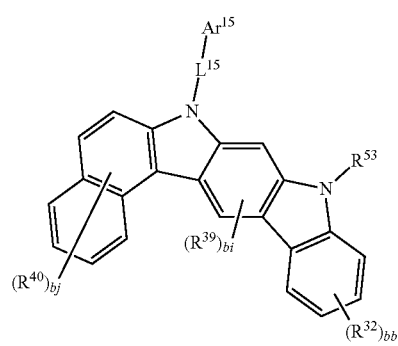

Wherein:

$Ar^{15}, L^{15}, R^{53}, R^{32}$ and bb are the same as defined in Formula 5, $R^{39}$ and $R^{49}$ are the same as the definition of $R^{31}$, adjacent plurality of $R^{39}$ or plurality of $R^{49}$ may be bonded to each other to form a ring, bi is an integer from 0 to 2, bj is an integer from 0 to 6.

Specifically, the compound represented by Formula 4 may be a compound represented by any one of the following compounds H-1 to H-124, but is not limited thereto.

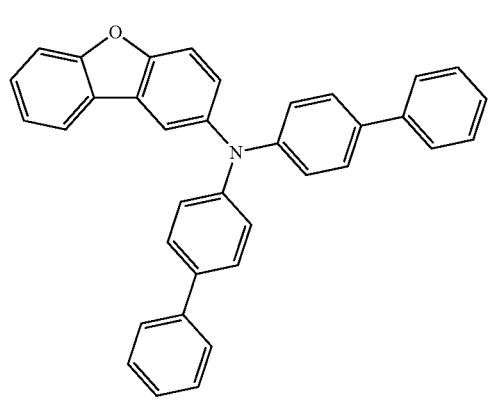

H-1

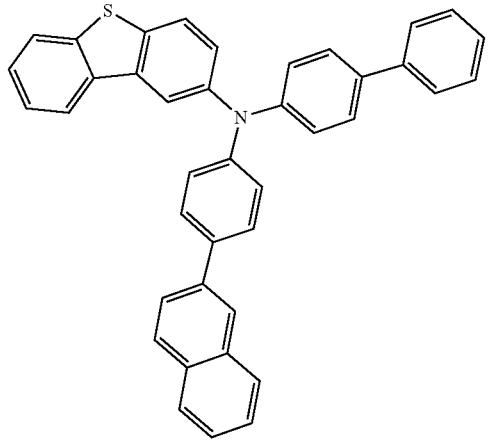

H-2

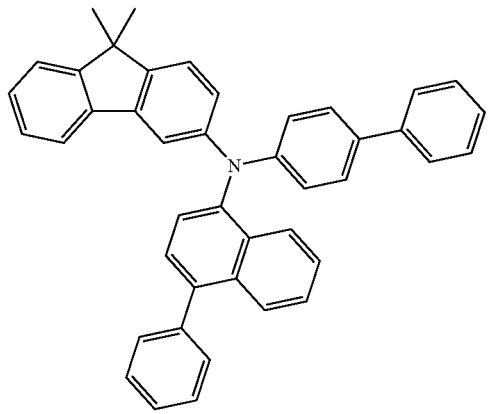

H-3

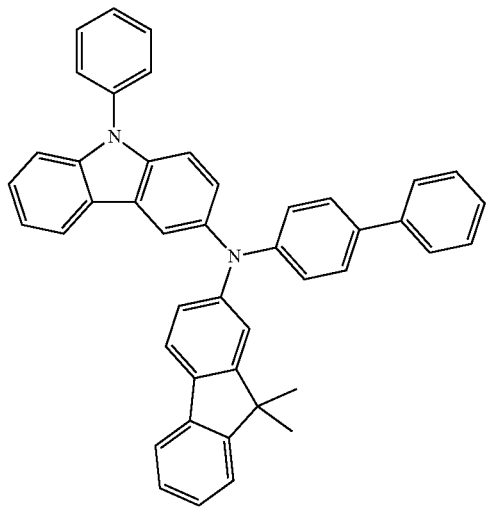

H-4

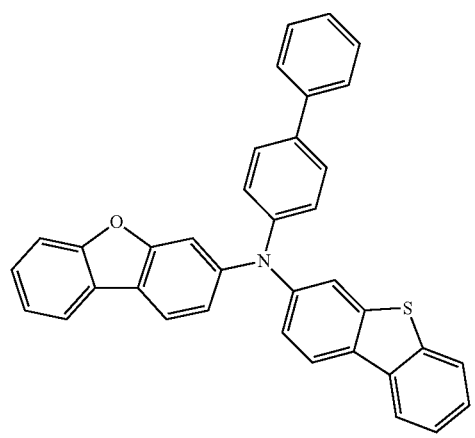
H-5
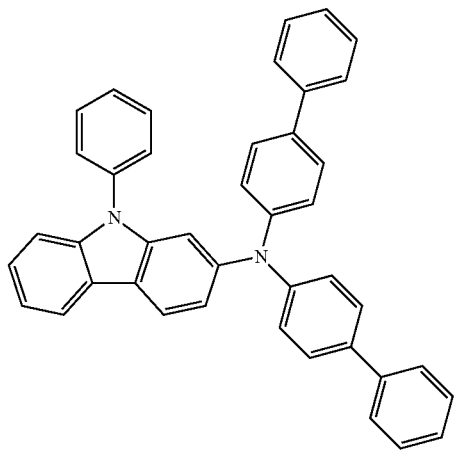
H-8
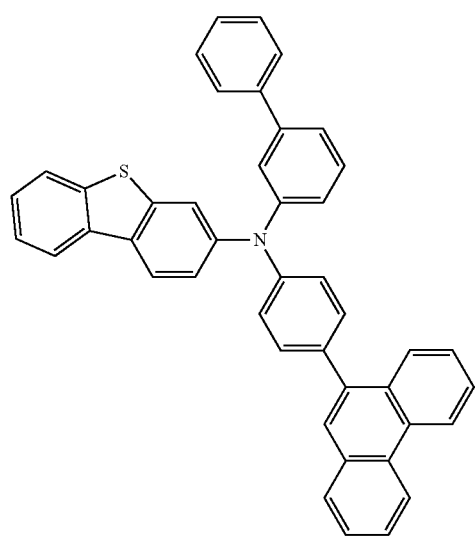
H-6
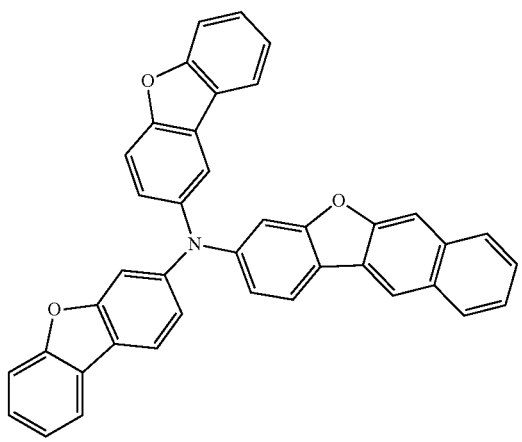
H-9
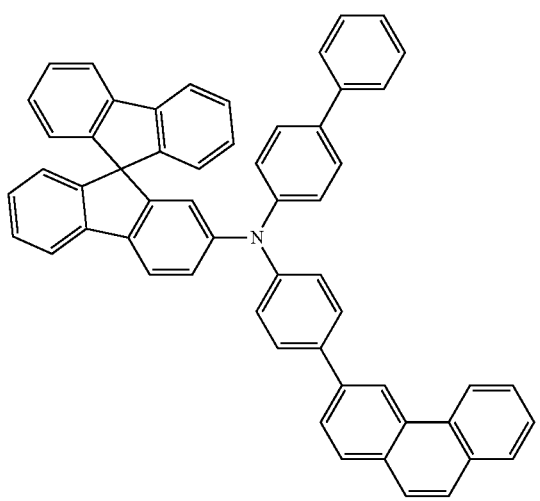
H-7
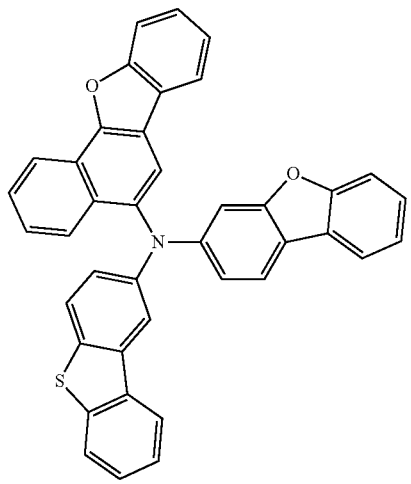
H-10

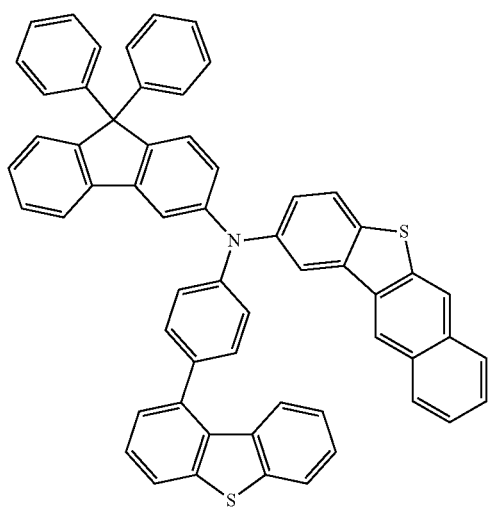
H-11
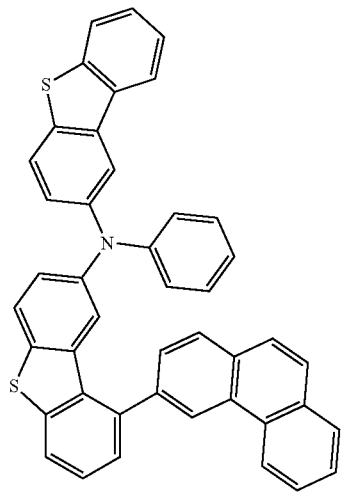
H-14
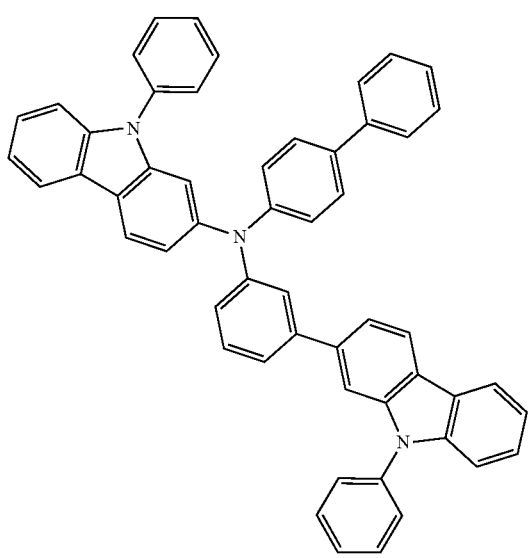
H-12
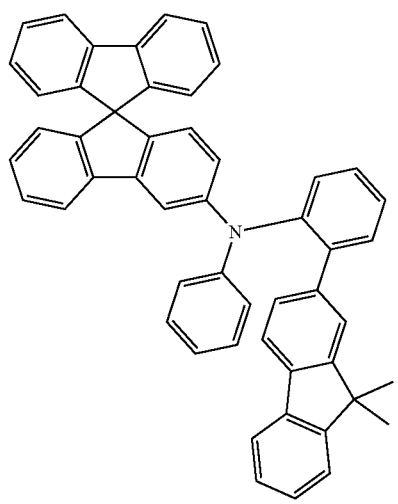
H-15
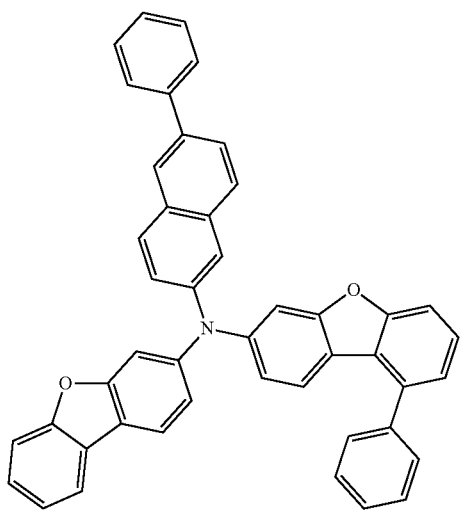
H-13
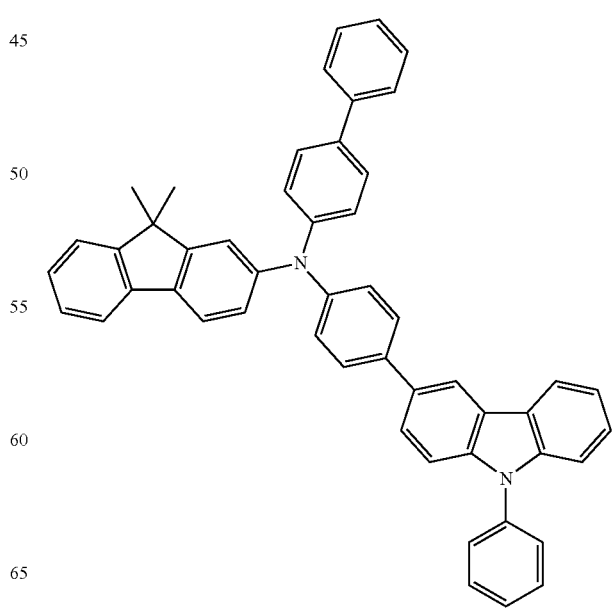
H-16

-continued
H-17
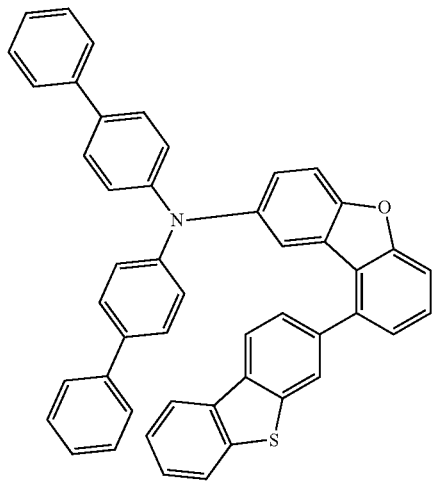
H-18
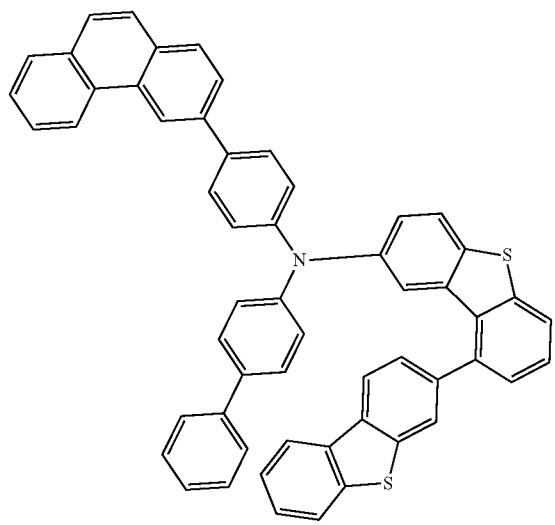
H-19
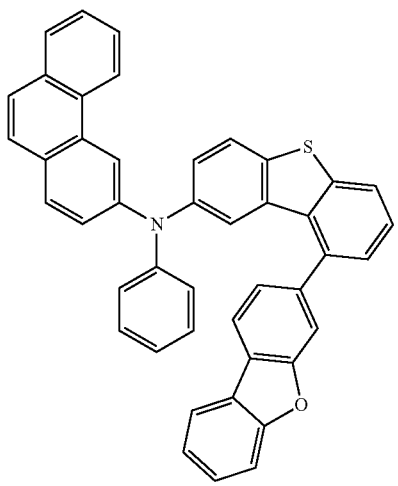
-continued
H-20
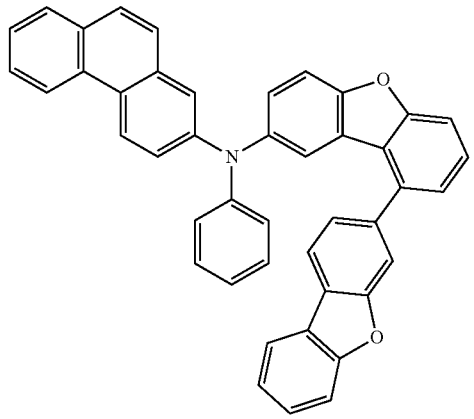
H-21
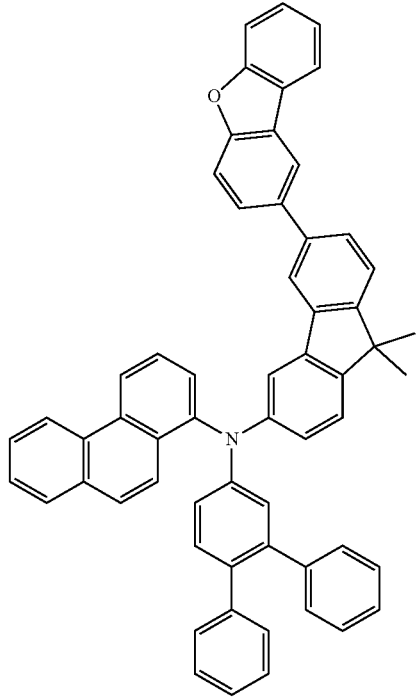
H-22
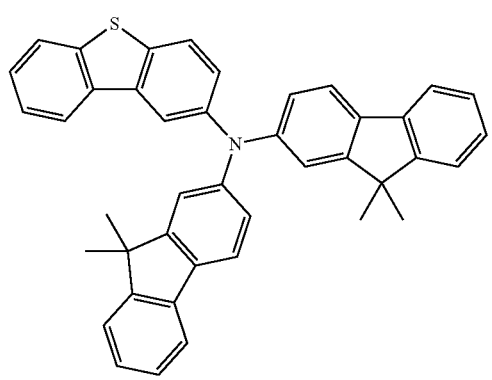

-continued
H-23
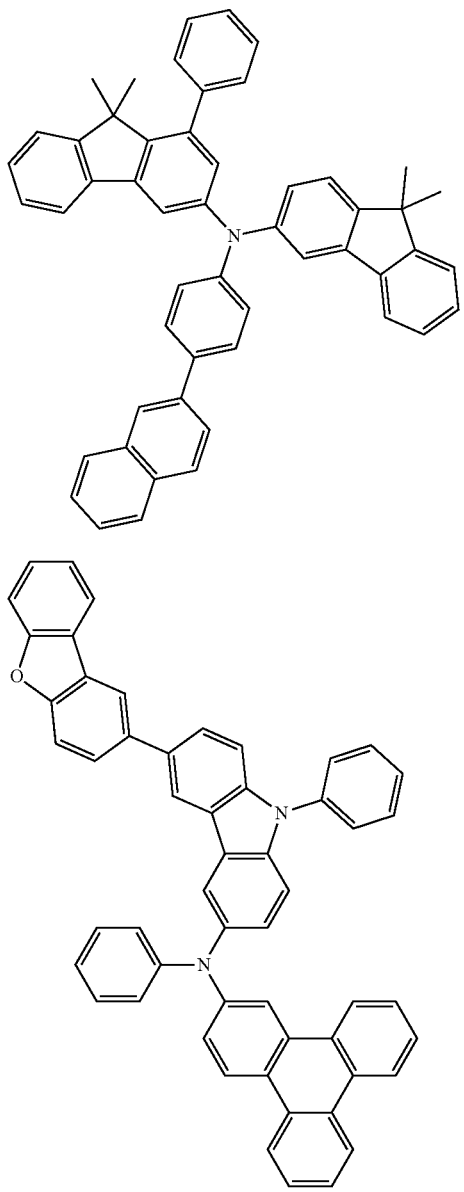
H-24
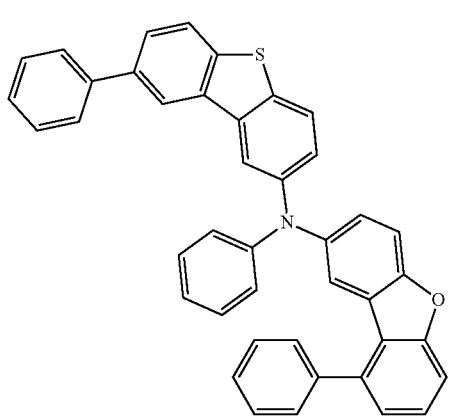
H-25
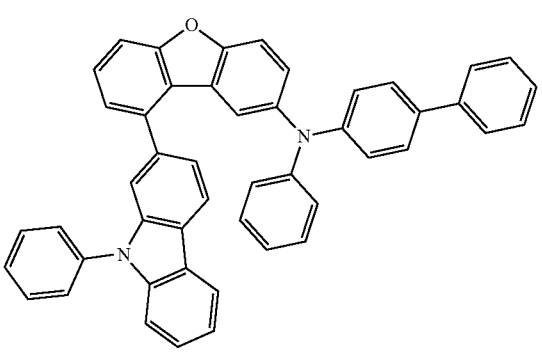
-continued
H-26
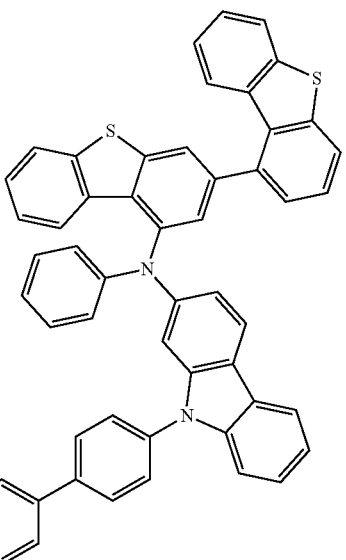
H-27
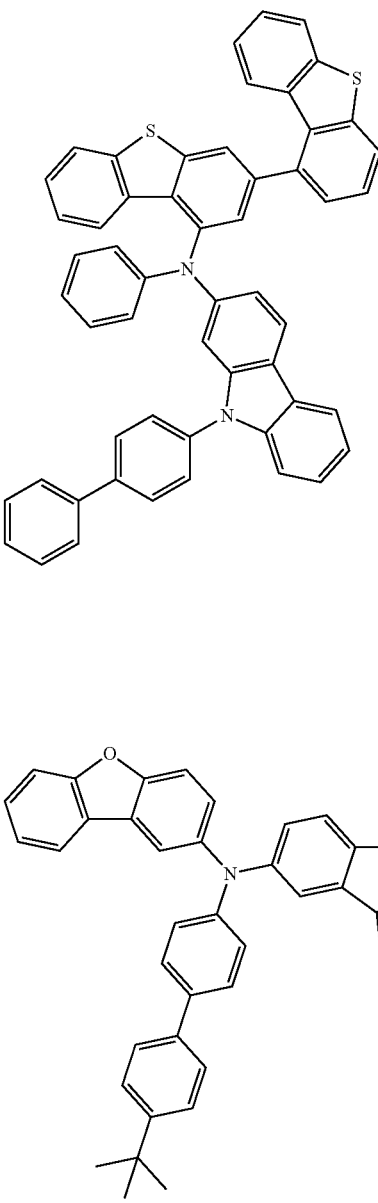
H-28
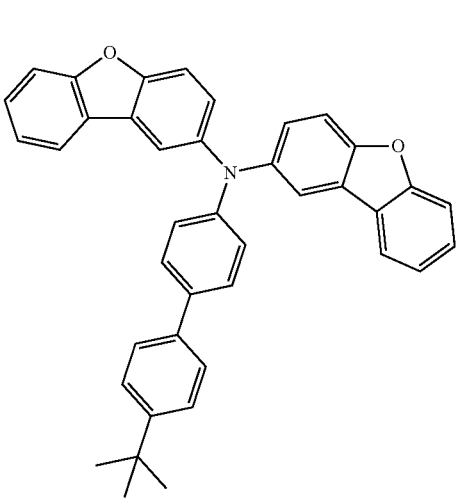

-continued
H-29
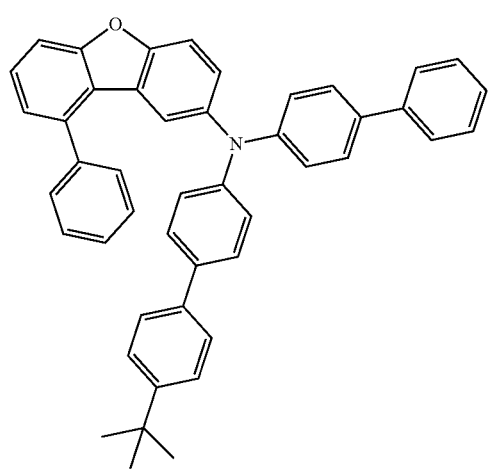
H-30
H-31
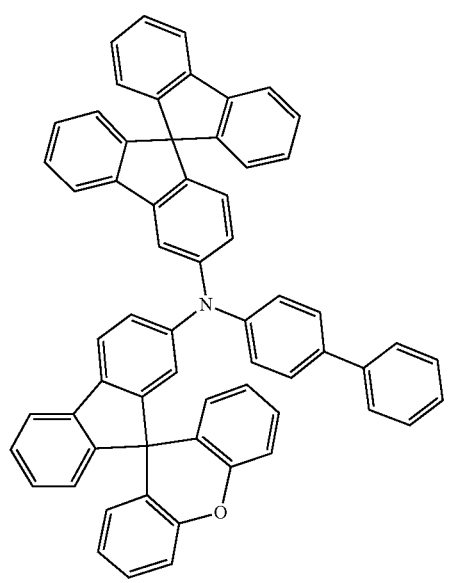
H-32
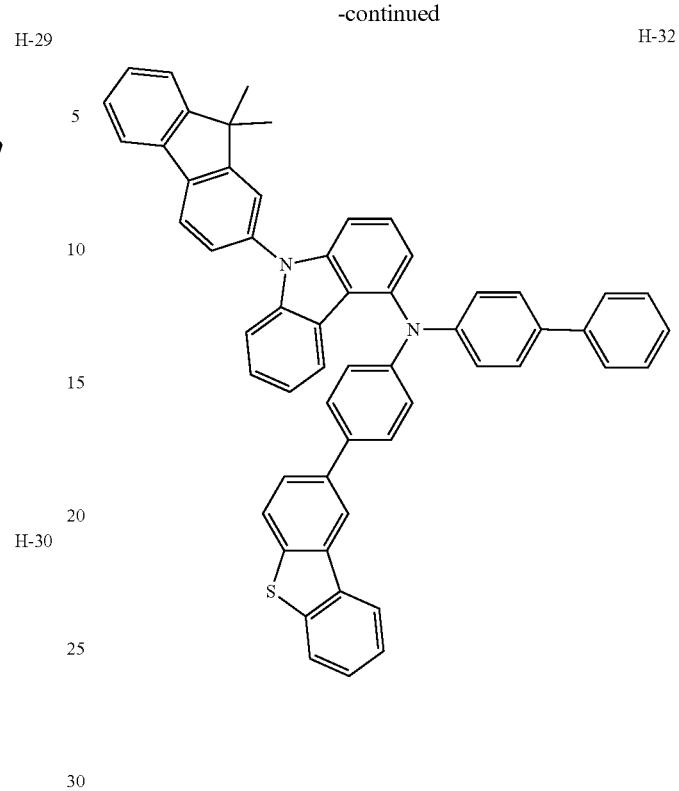
H-33
H-34

H-35
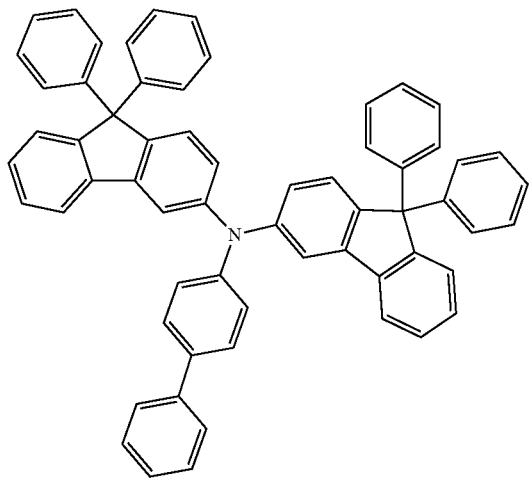
H-39
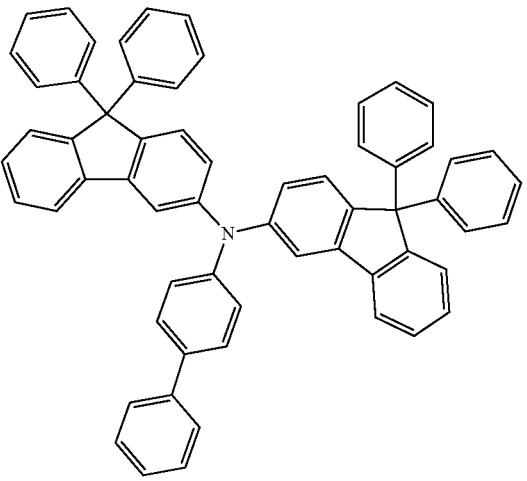
H-36
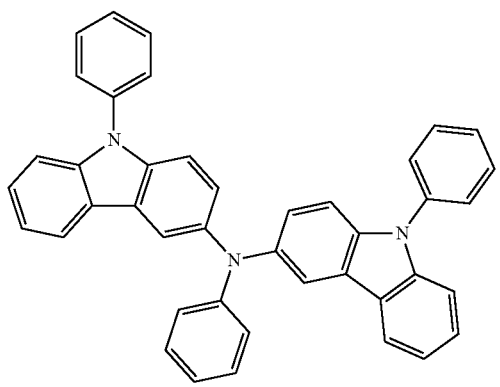
H-40
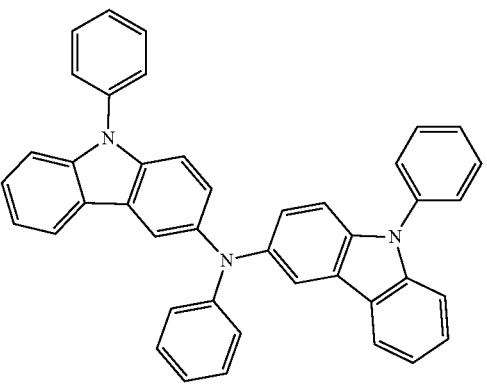
H-37
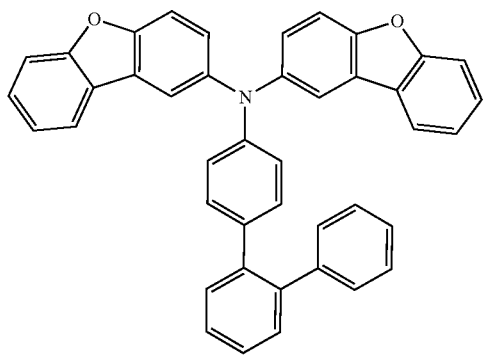
H-41
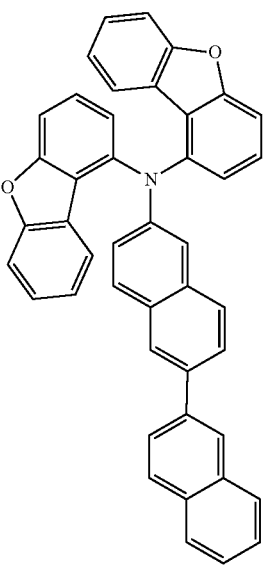
H-38

H-42
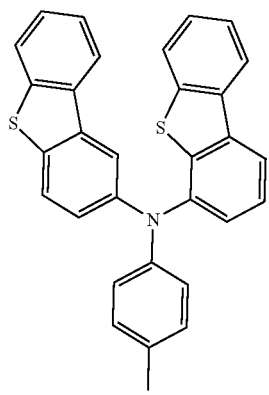
H-45
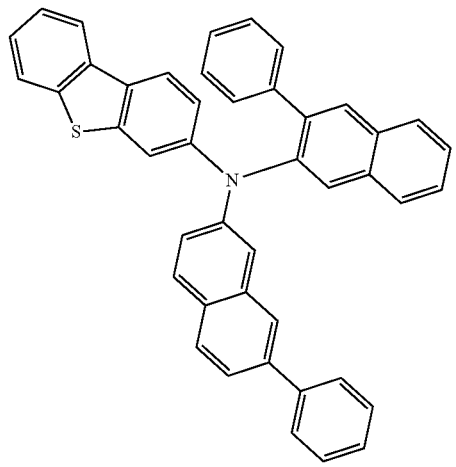
H-43
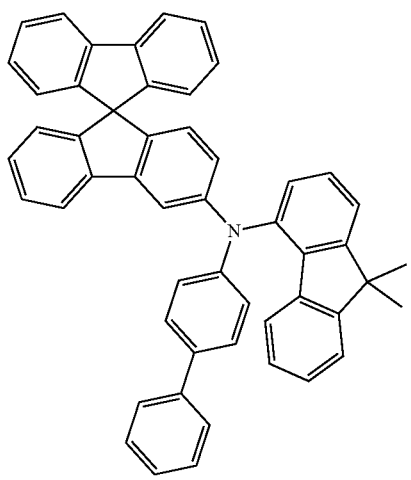
H-46
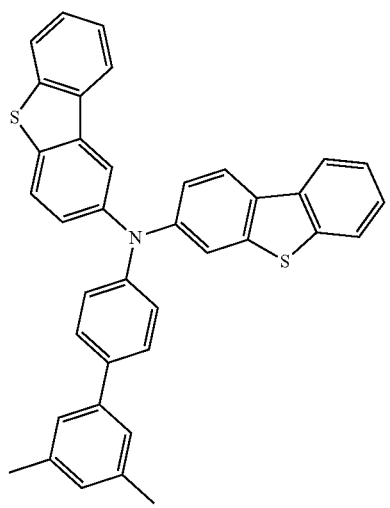
H-44
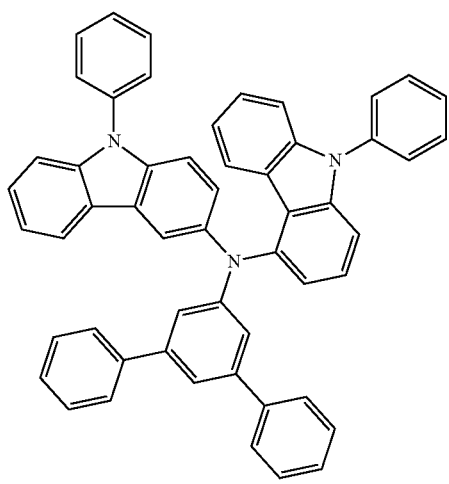
H-47
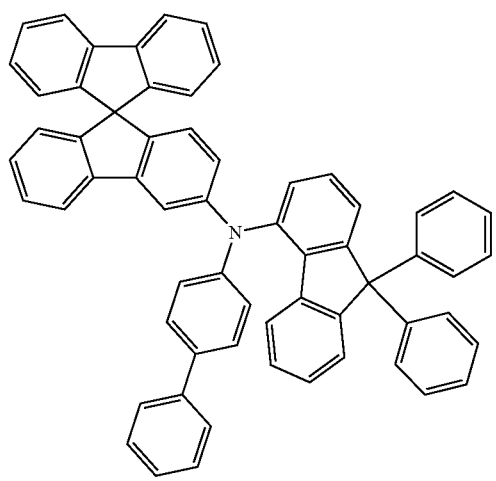

H-48
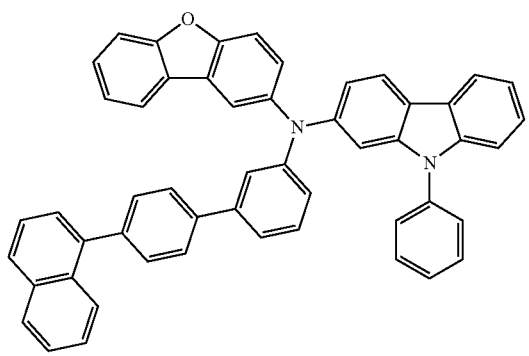
H-49
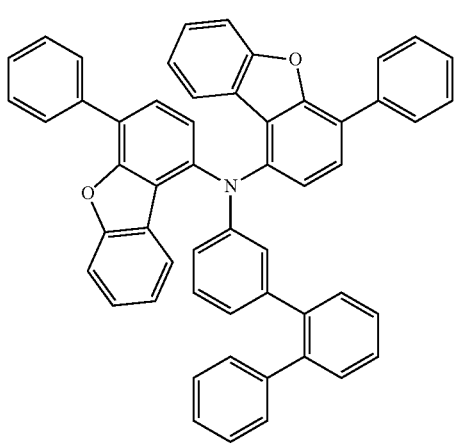
H-50
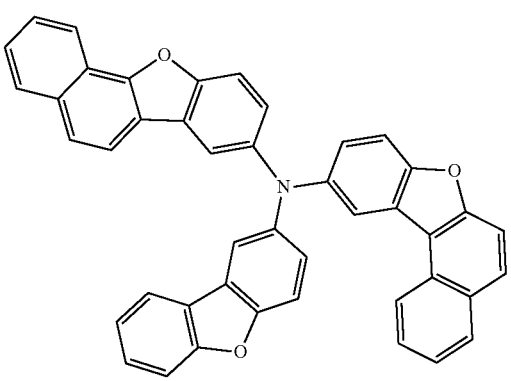
H-51
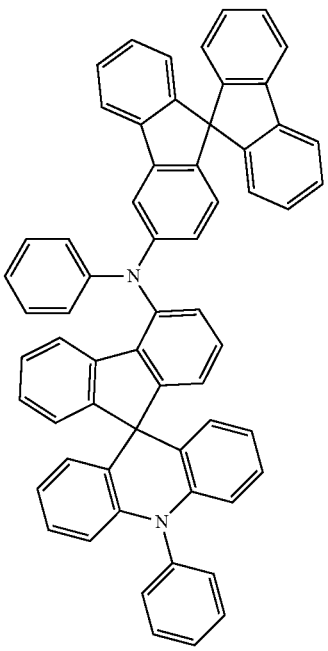
H-52
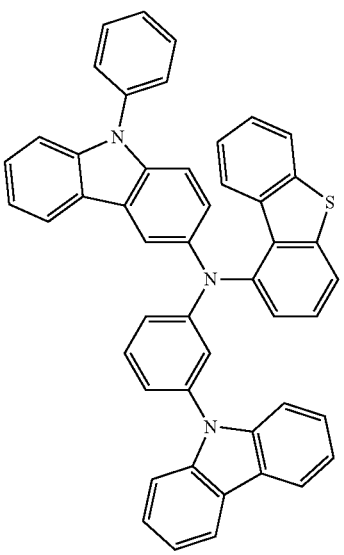
H-53

H-54
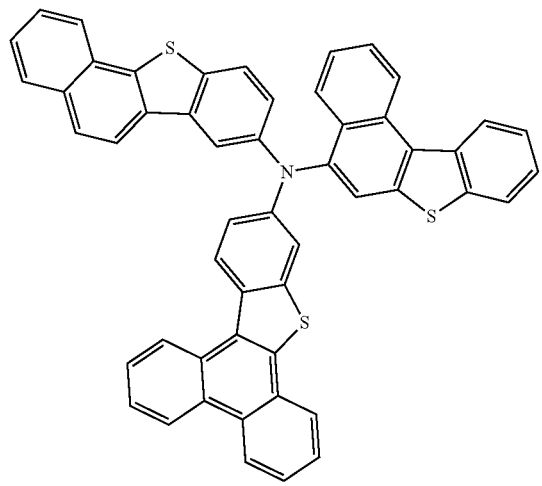
H-57
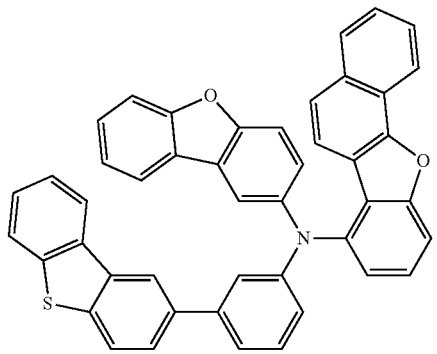
H-55
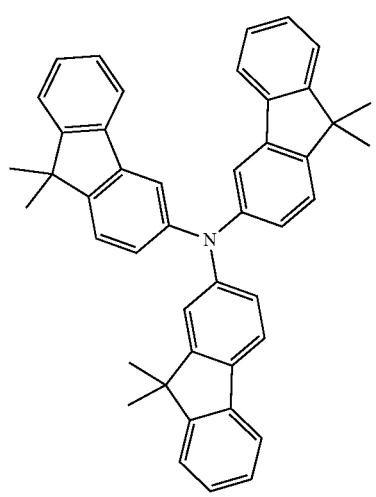
H-58
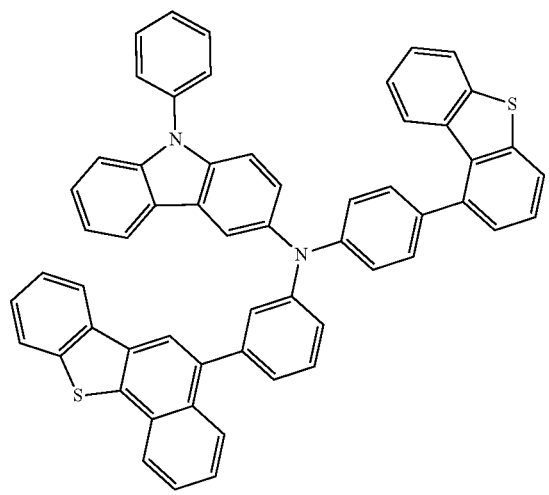
H-56
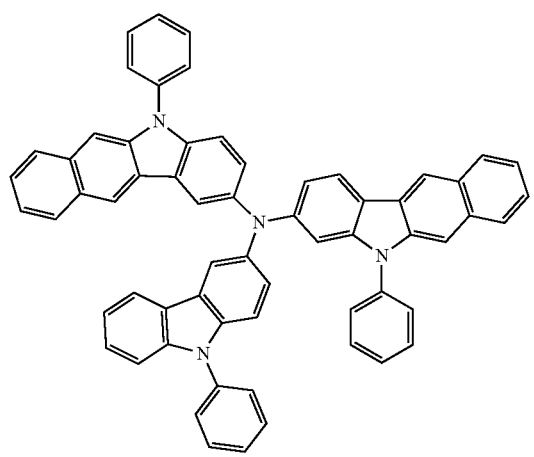
H-59
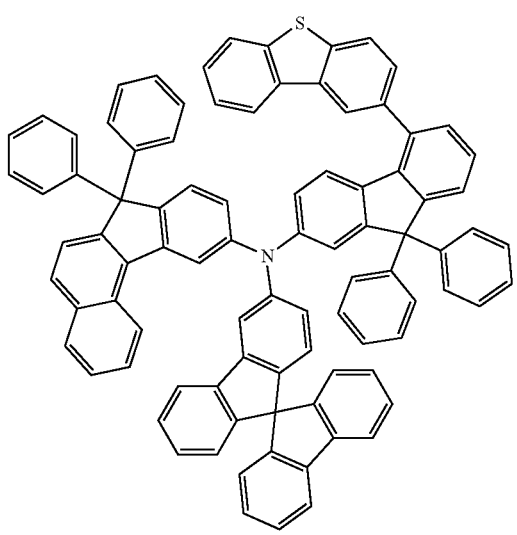

-continued
H-60
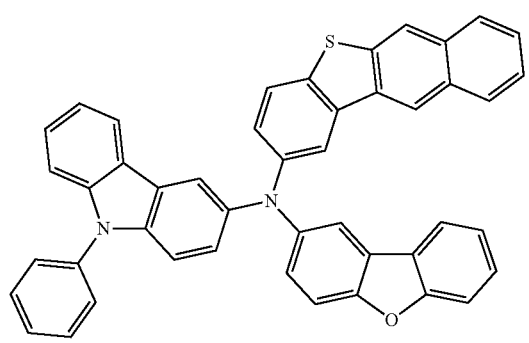
H-61
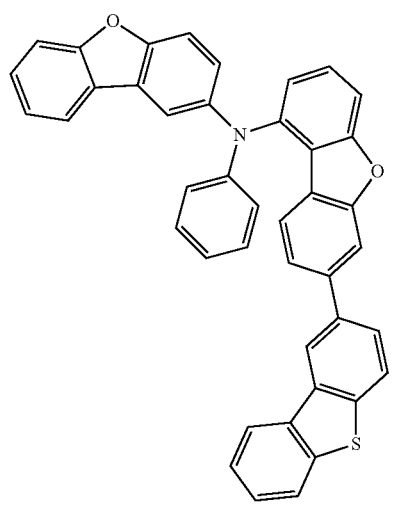
H-62
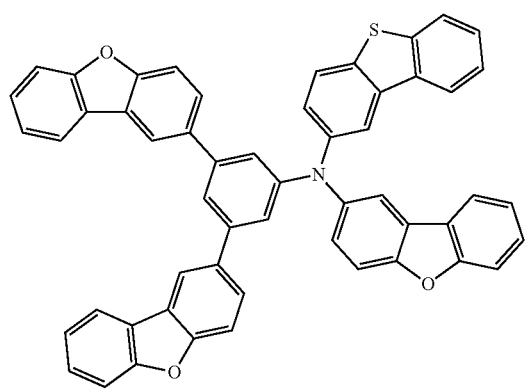
-continued
H-63
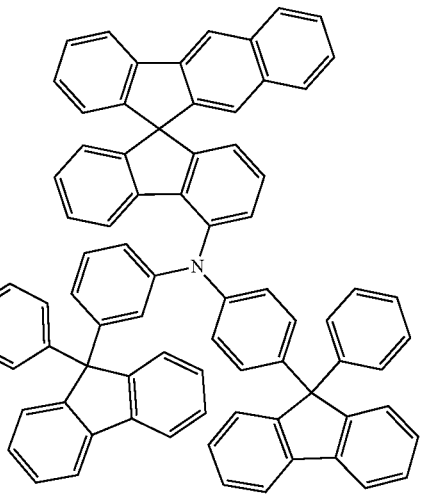
H-64
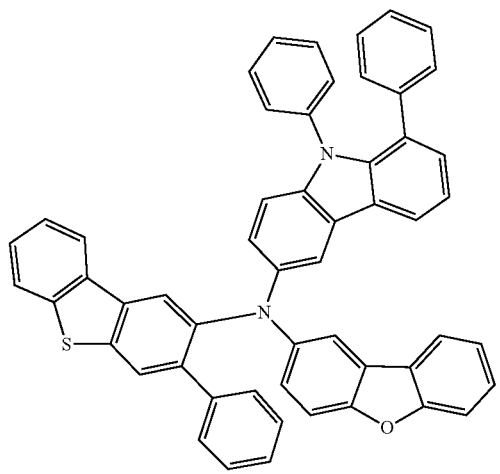
H-65
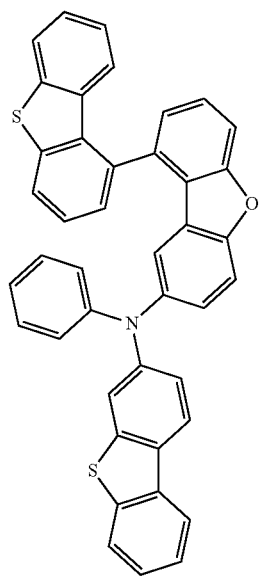

H-66
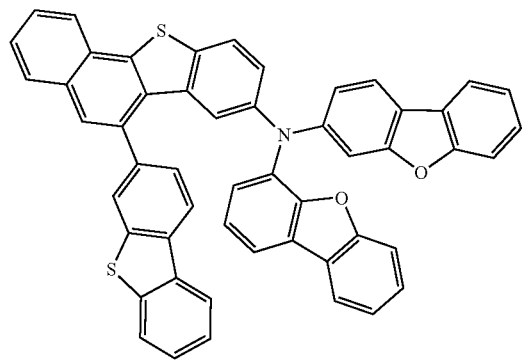
H-67
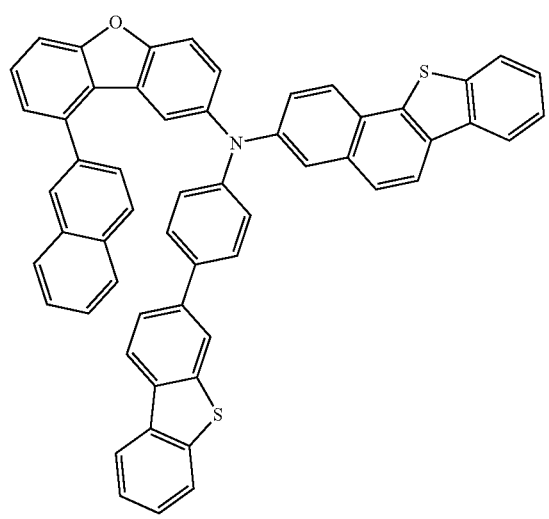
H-68
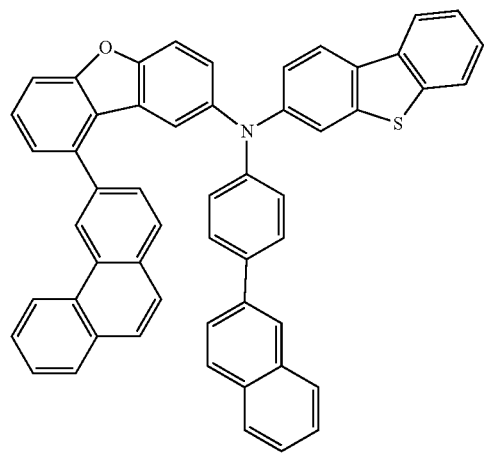
H-69
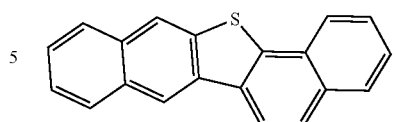
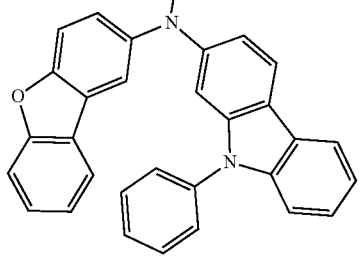
H-70
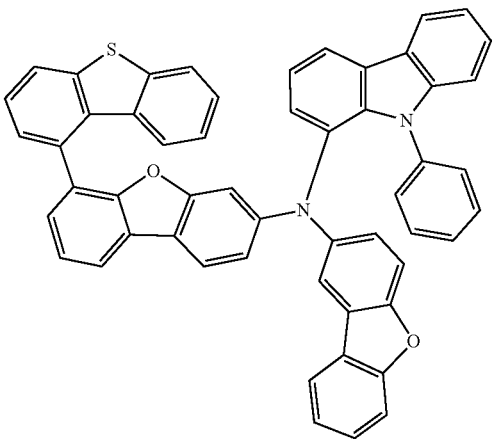
H-71
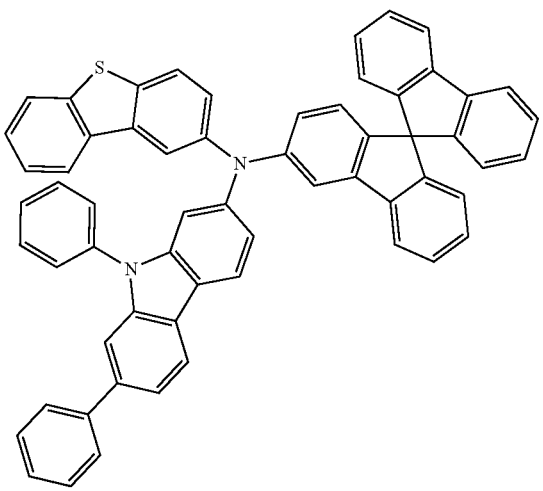

-continued
H-72
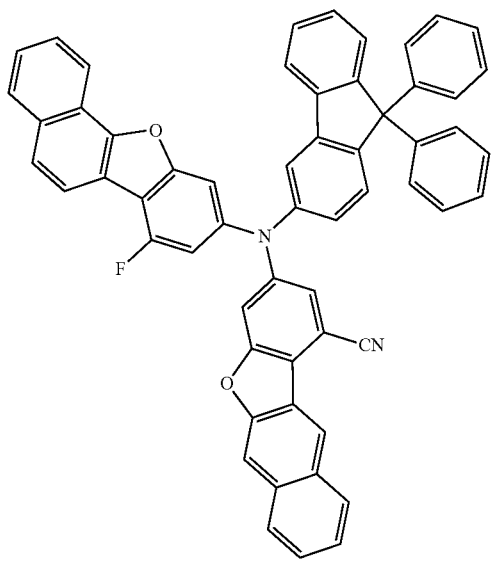
H-73
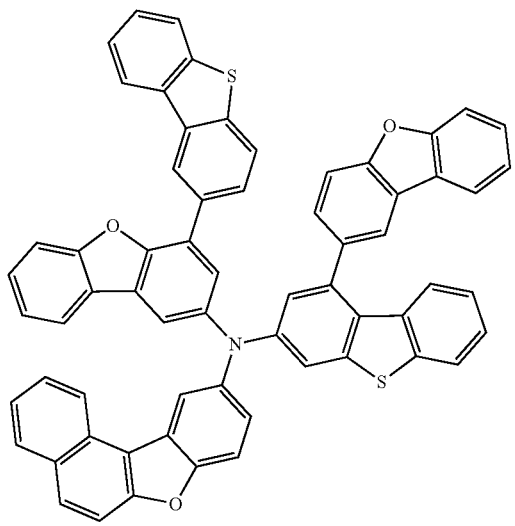
-continued
H-74
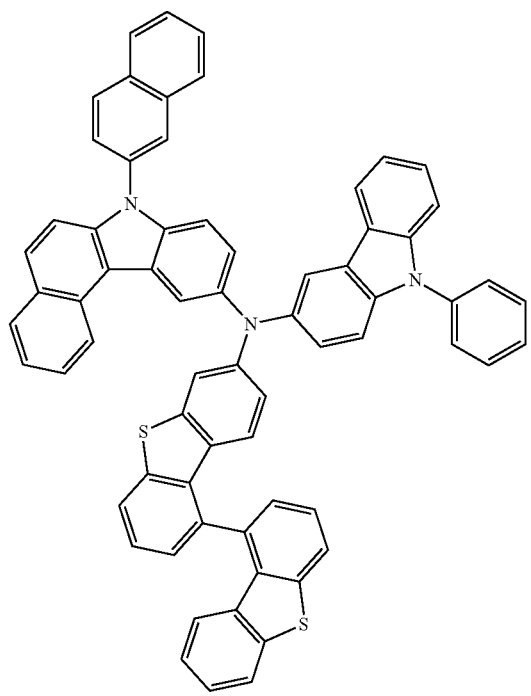
H-75
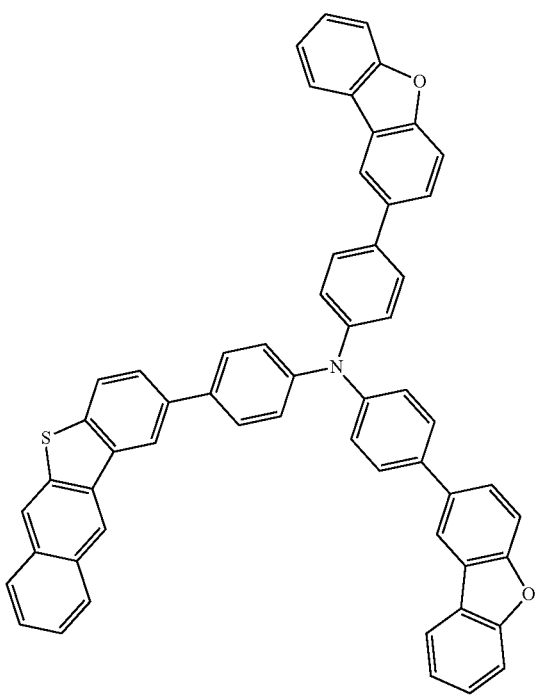

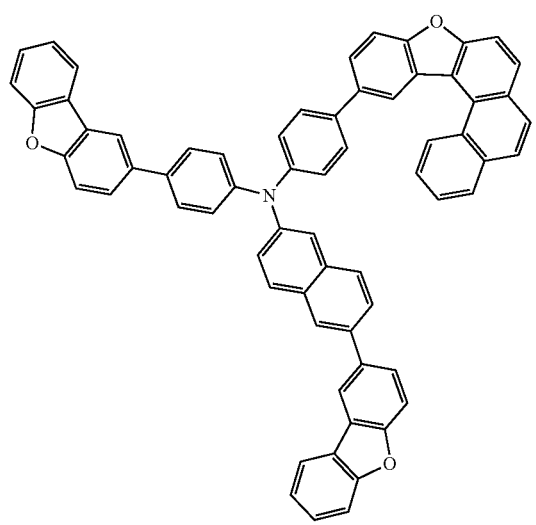
H-76
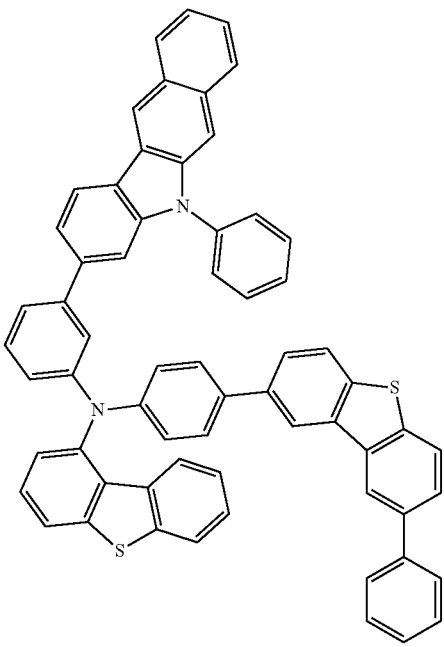
H-78
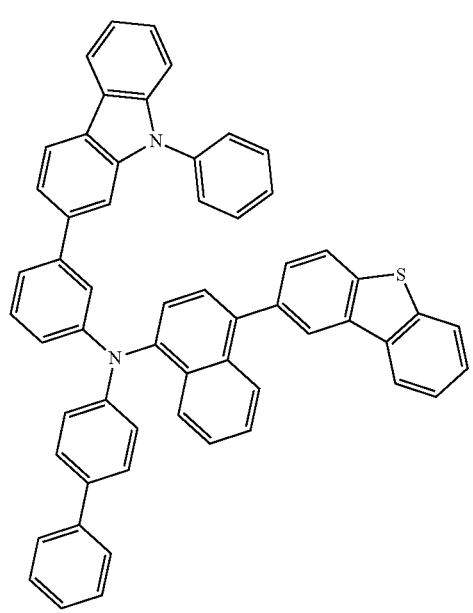
H-77
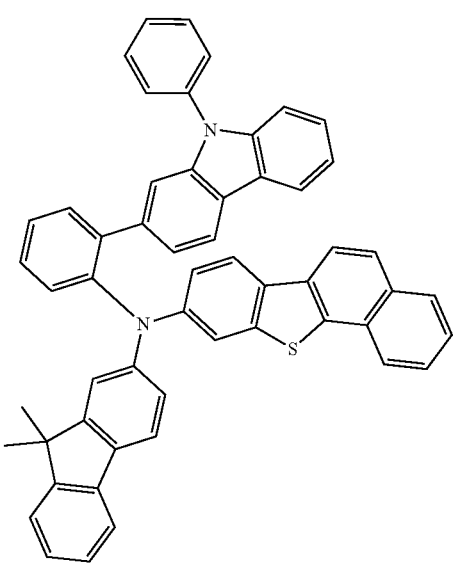
H-79

H-80
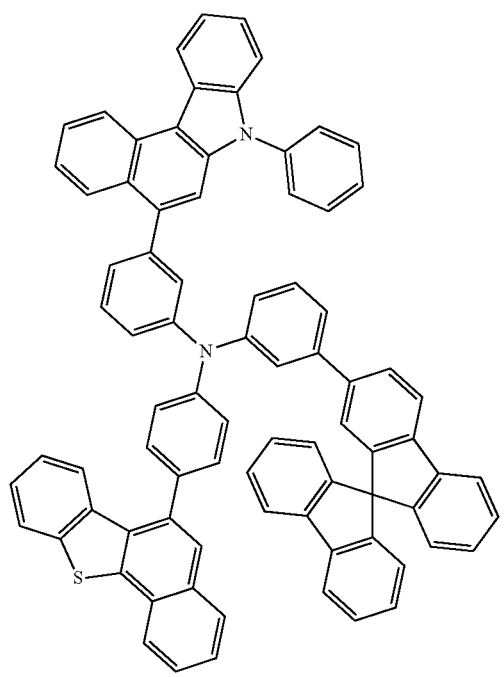
H-82
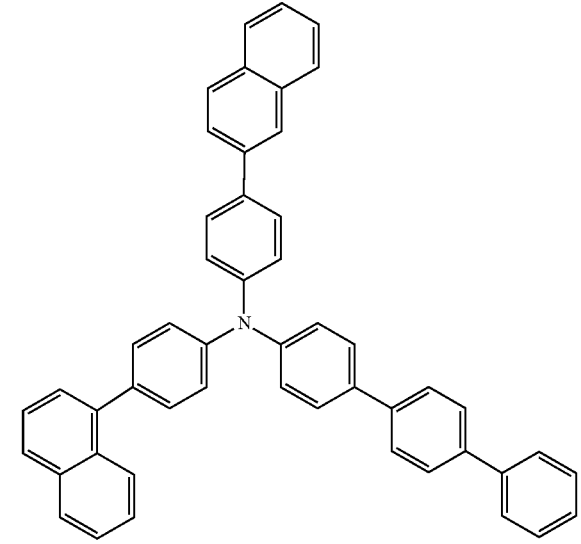
H-81
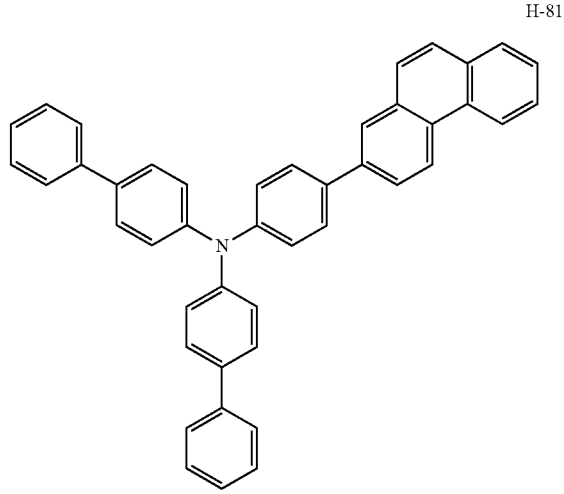
H-83
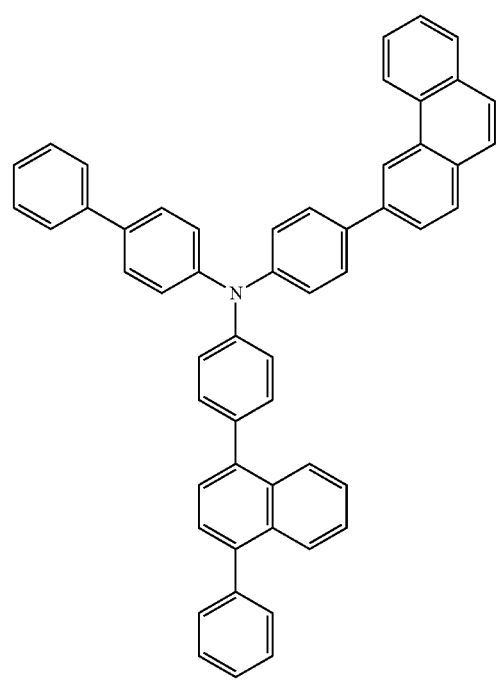

H-84
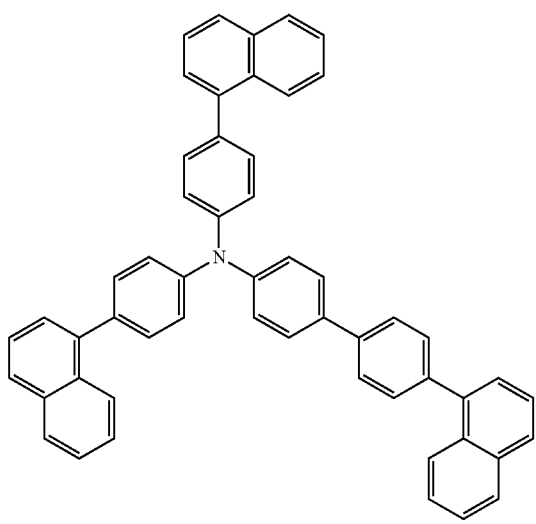
H-85
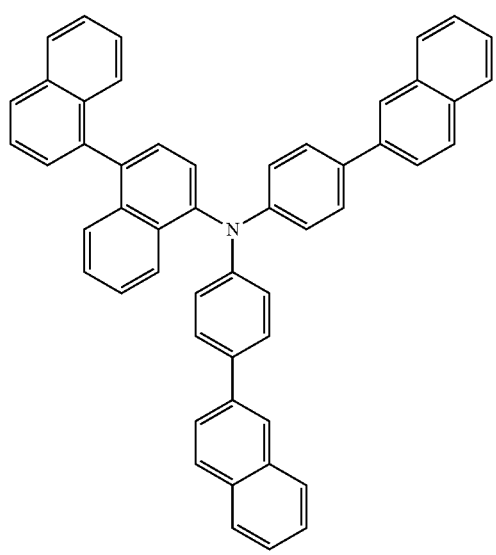
H-86
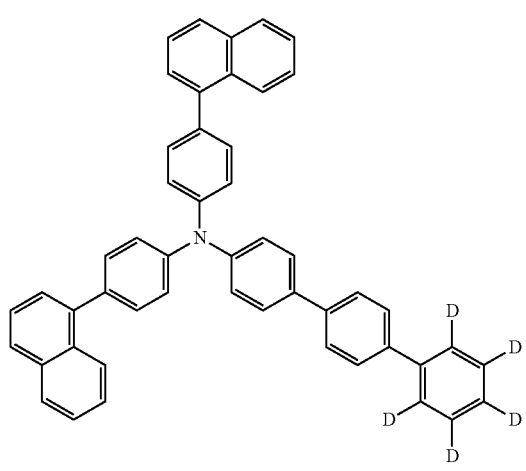
H-87
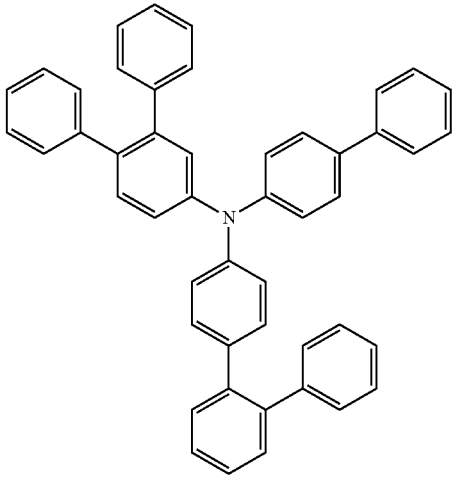
H-88
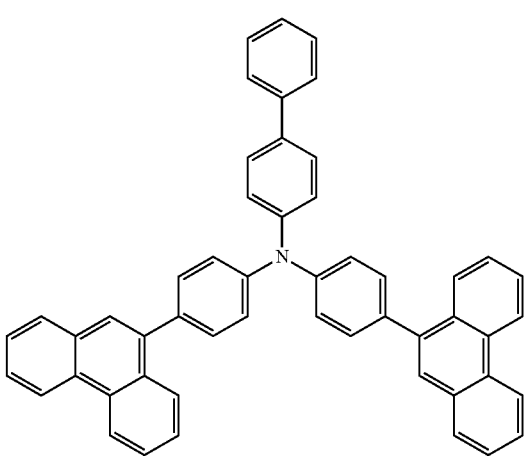
H-89
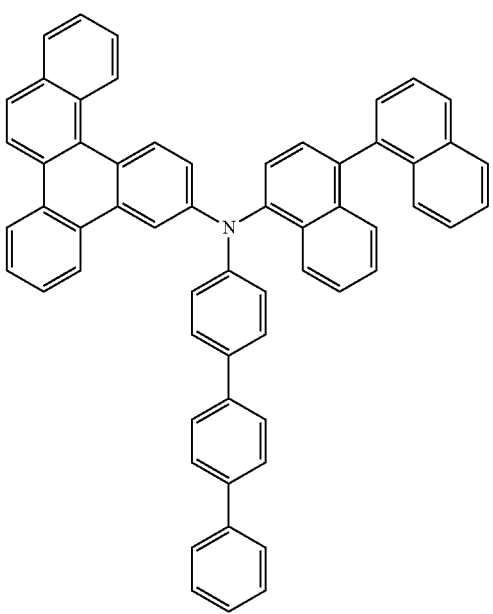

H-90
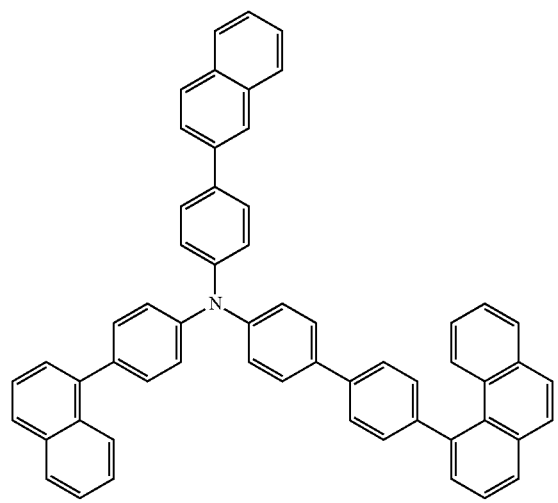
H-93
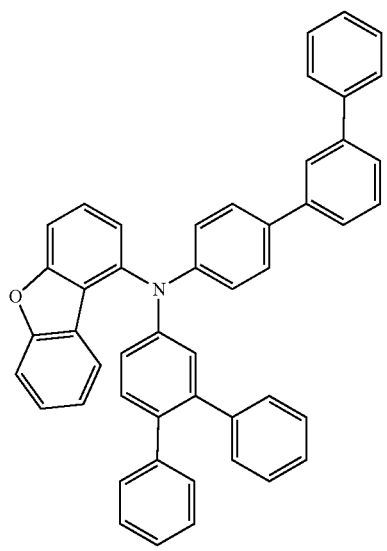
H-91
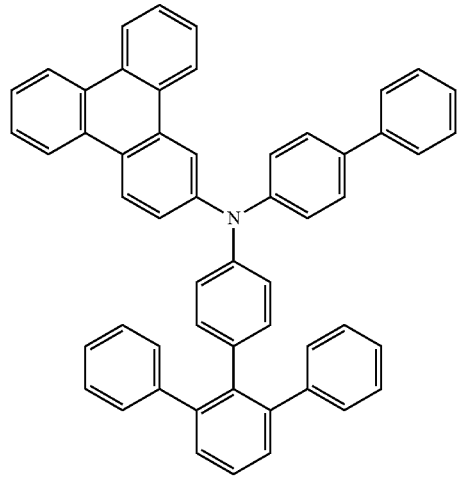
H-94
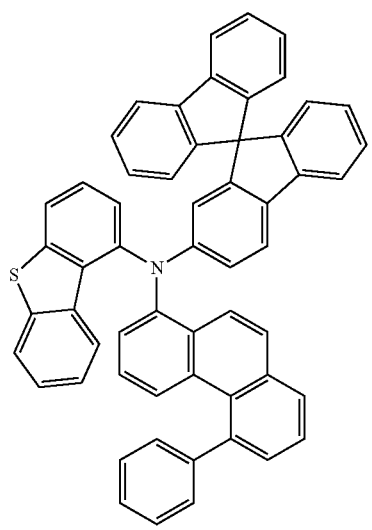
H-92
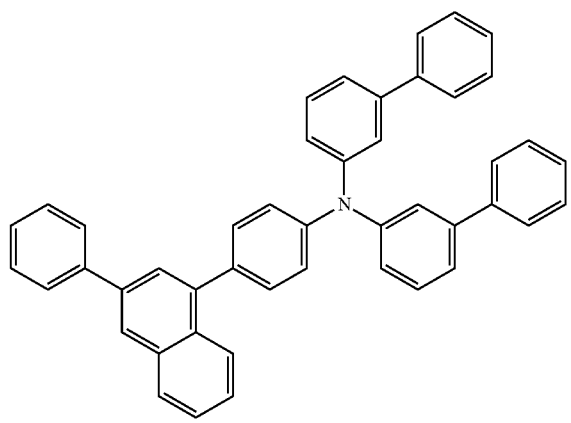
H-95
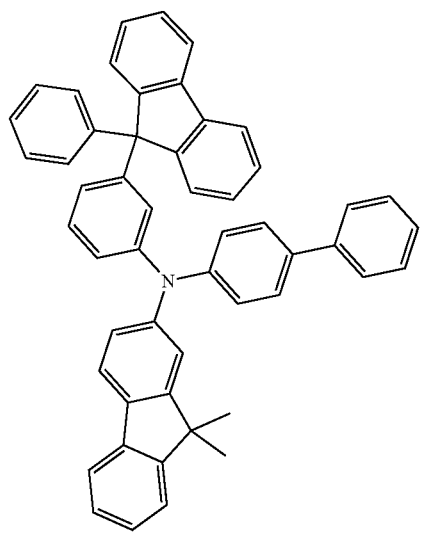

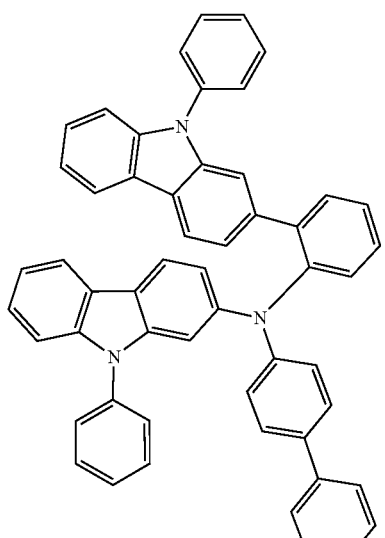
H-96
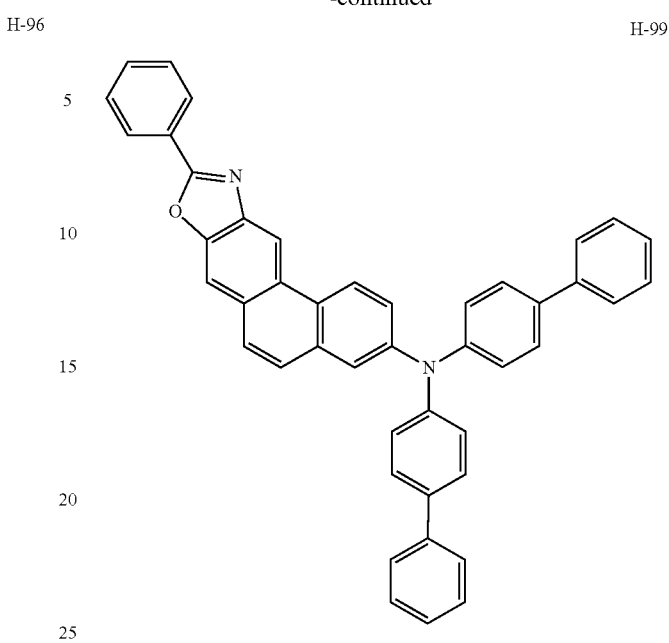
H-99
H-100
H-101
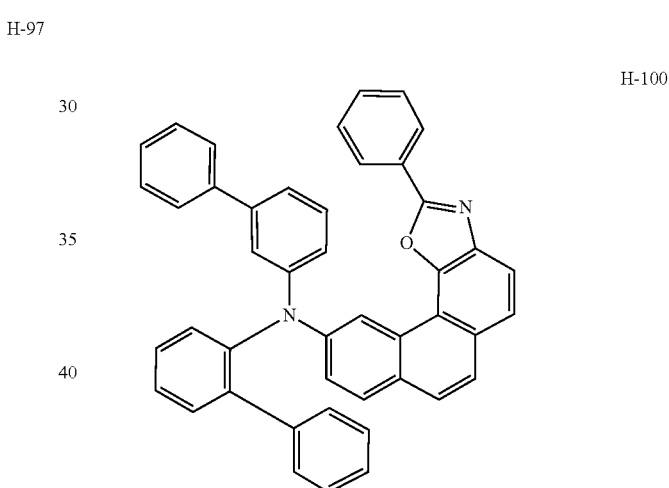
H-97
H-98

-continued
H-102
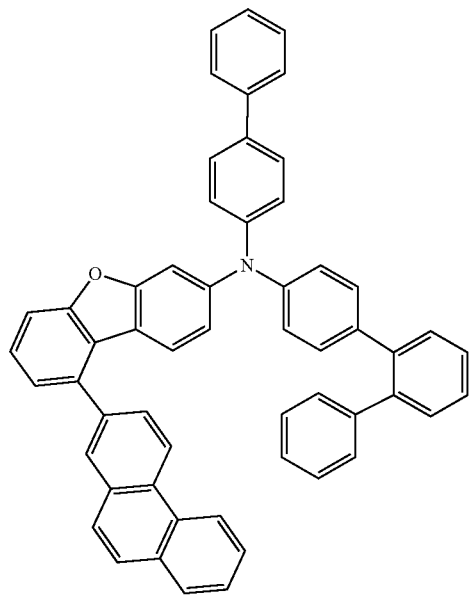
H-103
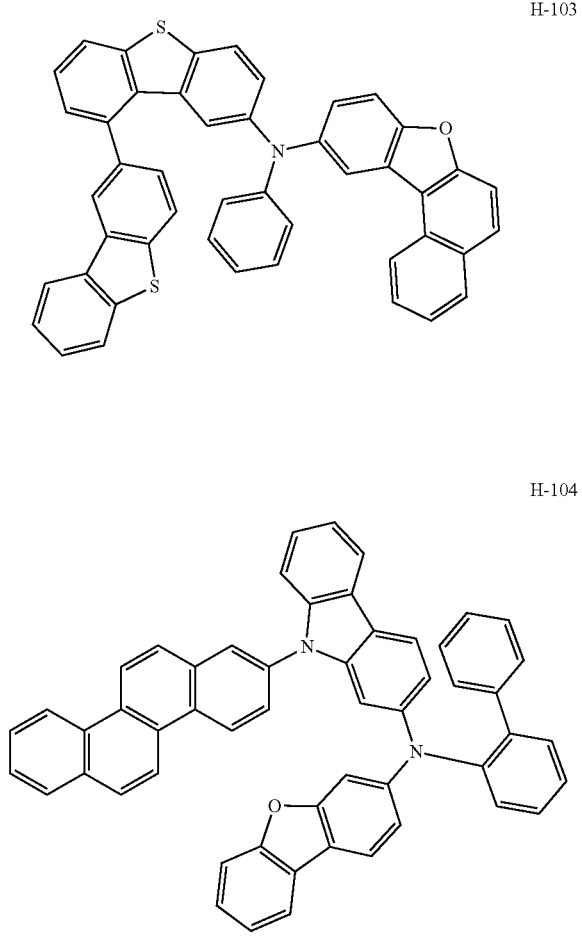
H-104
-continued
H-105
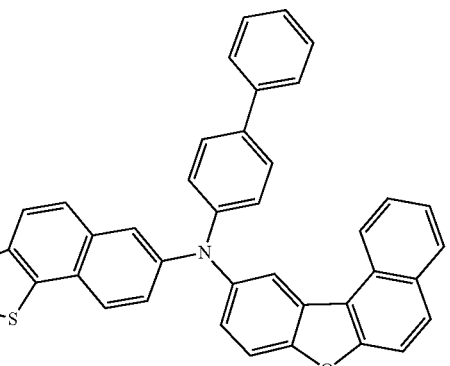
H-106
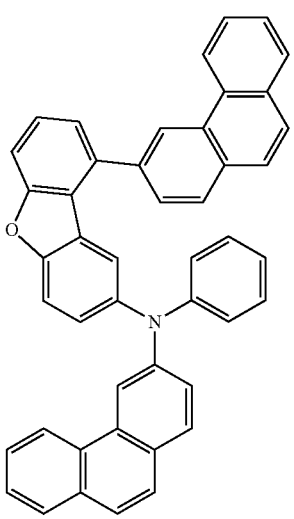
H-107
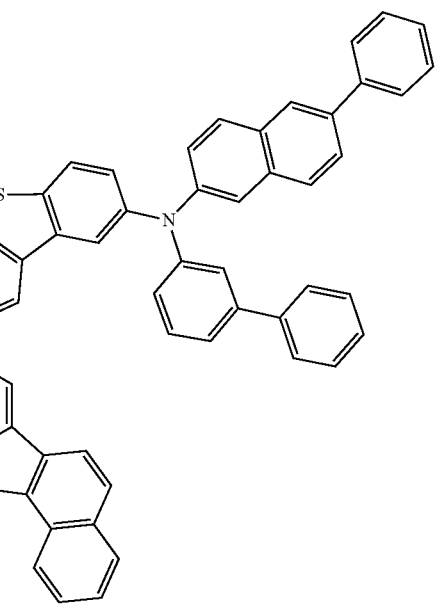

H-108
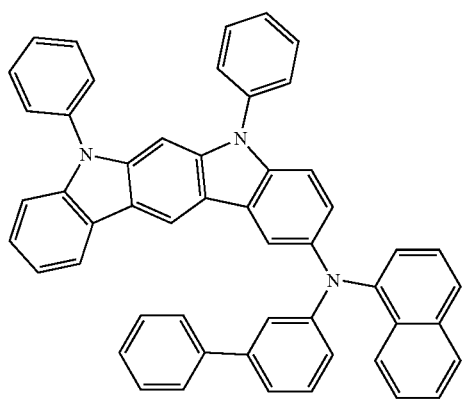
H-111
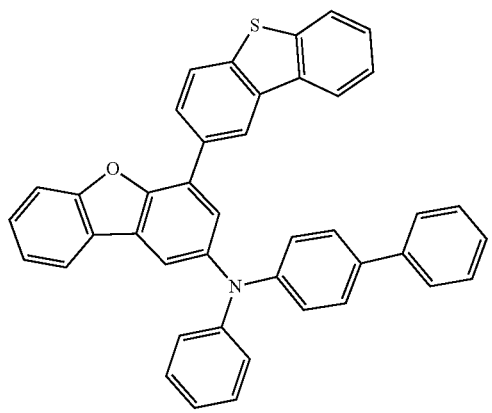
H-109
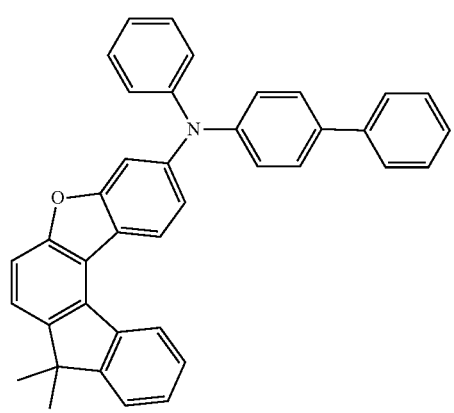
H-112
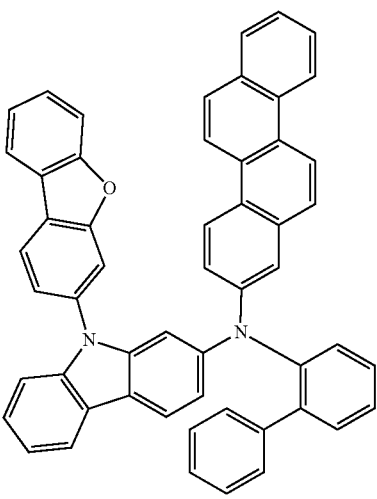
H-110
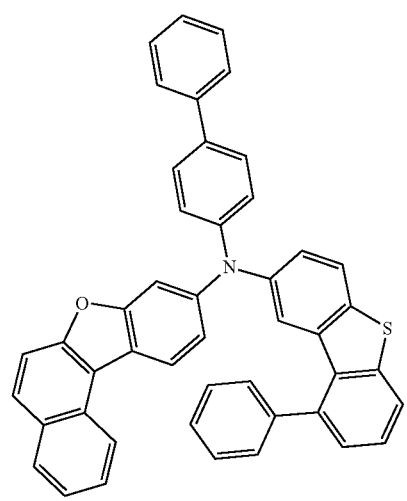
H-113
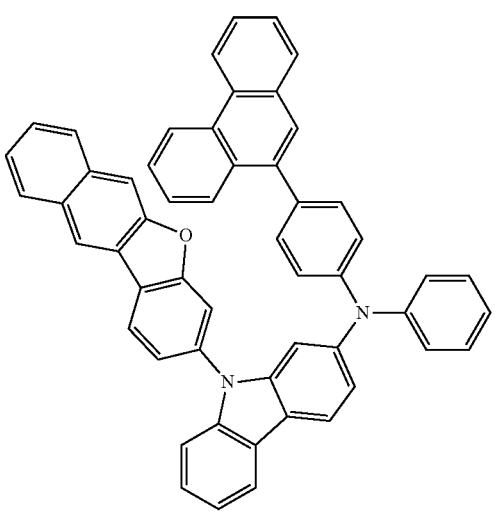

H-114
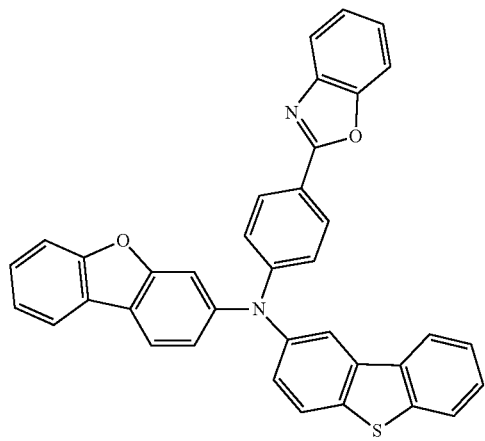
H-115
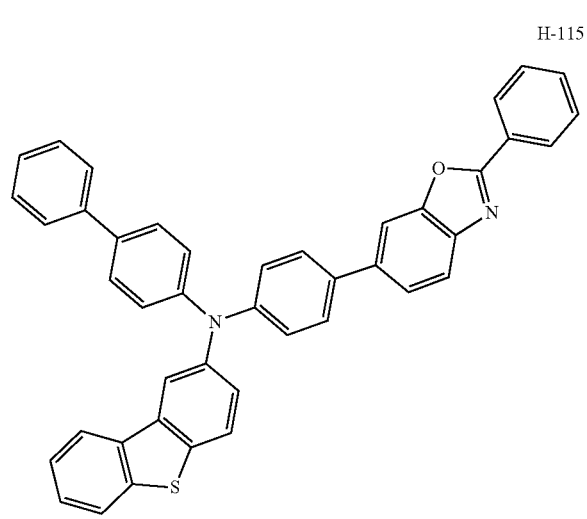
H-116
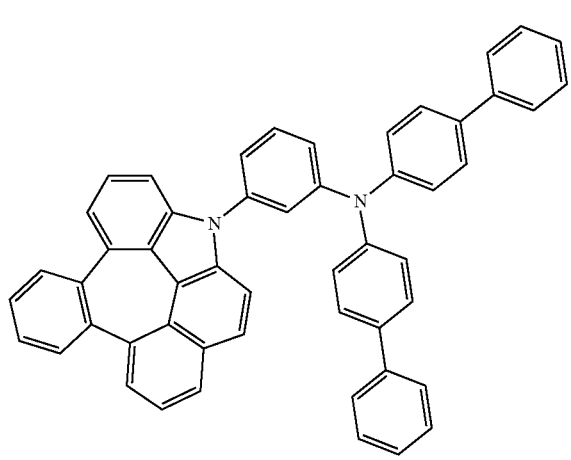
H-117
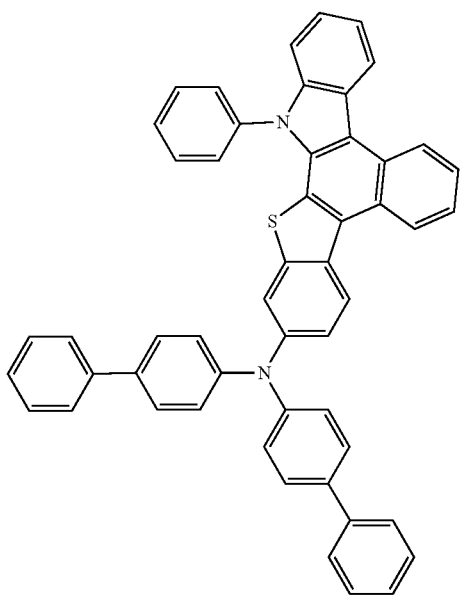
H-118
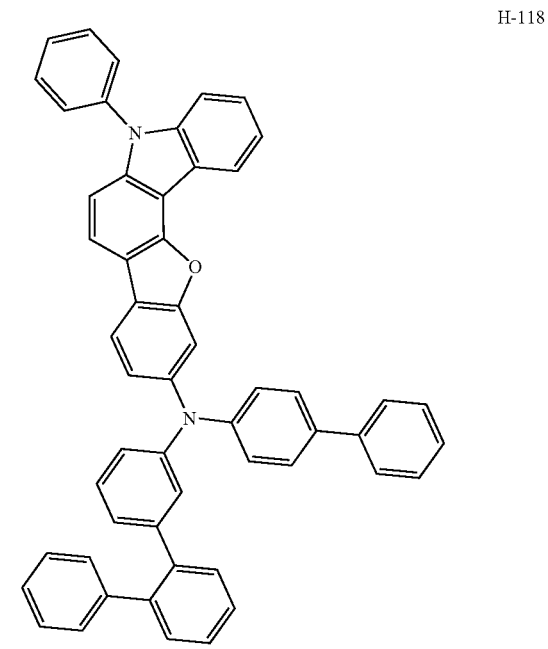
H-119
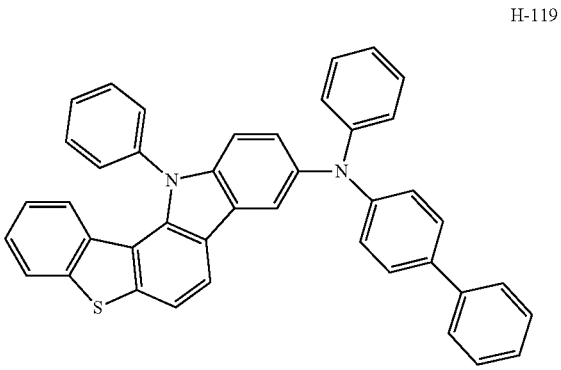

H-120
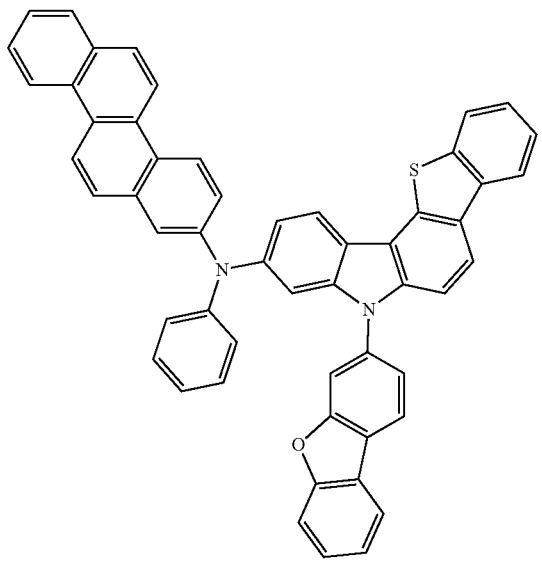
H-121
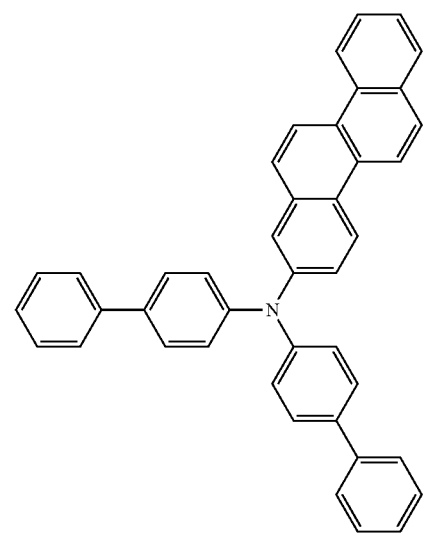
H-122
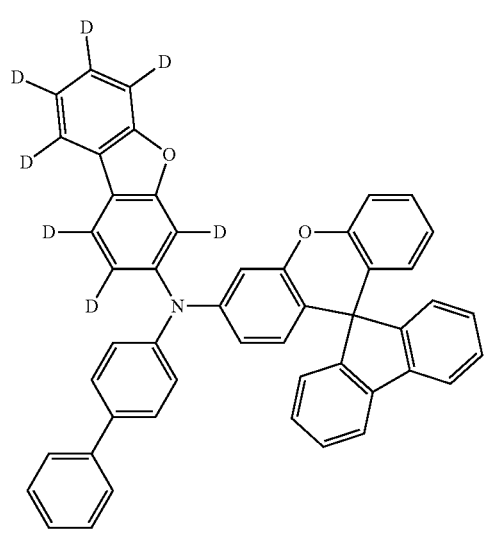
H-123
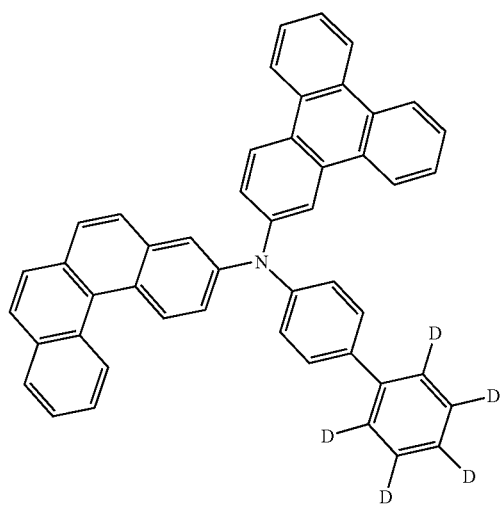
H-124
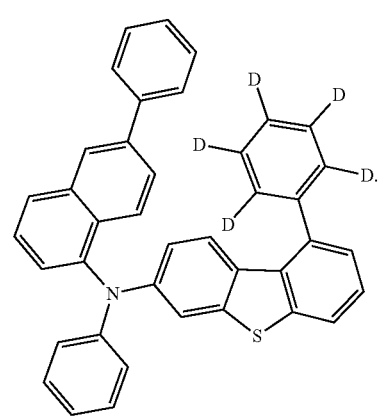
Specifically, the compound represented by Formula 5 may be represented by any one of the following compounds S-1 to S-116, but is not limited thereto.
S-1
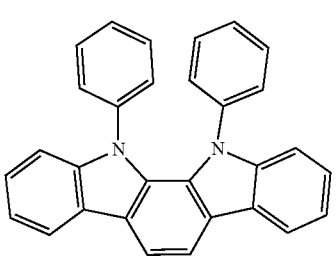

S-2
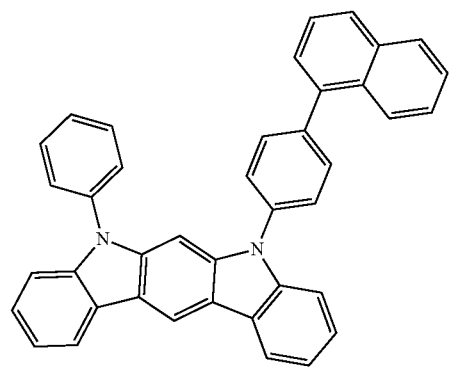
S-3
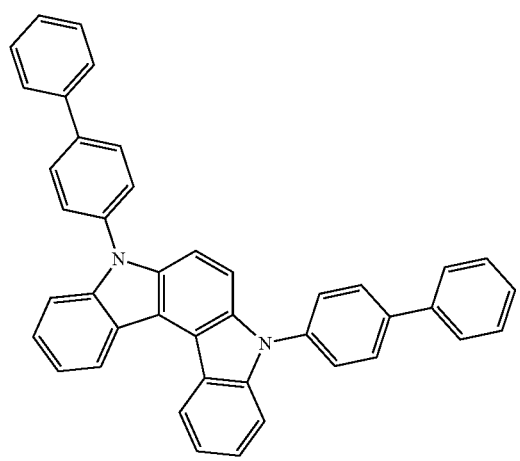
S-4
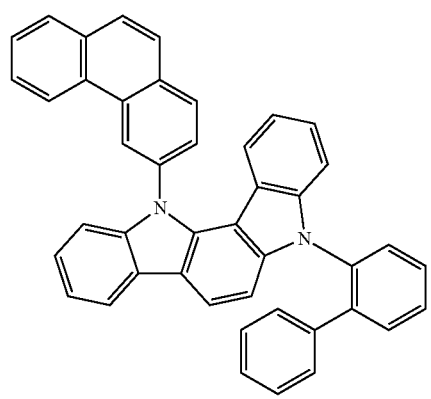
S-5
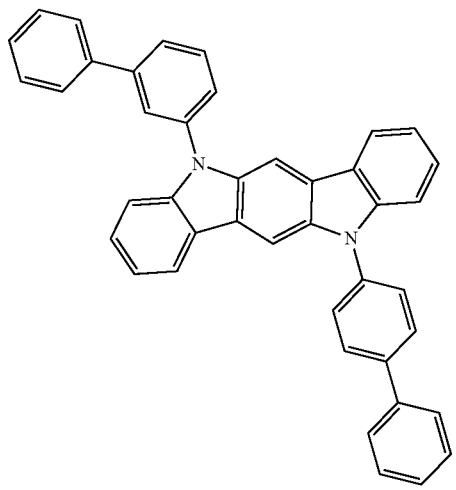
S-6
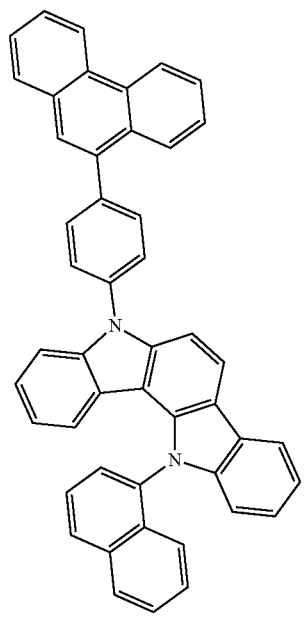
S-7
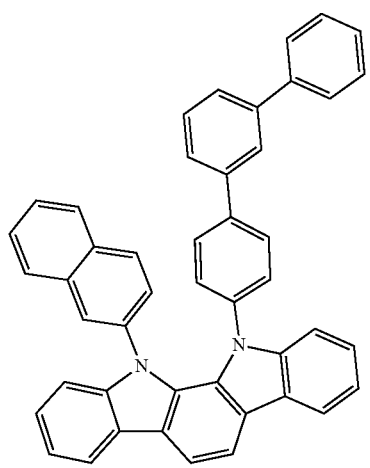

S-8
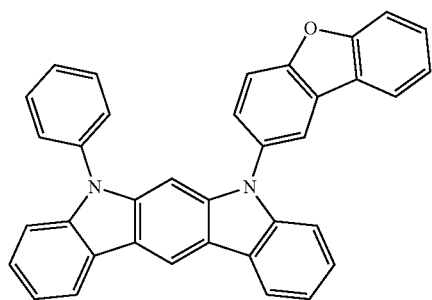
S-9
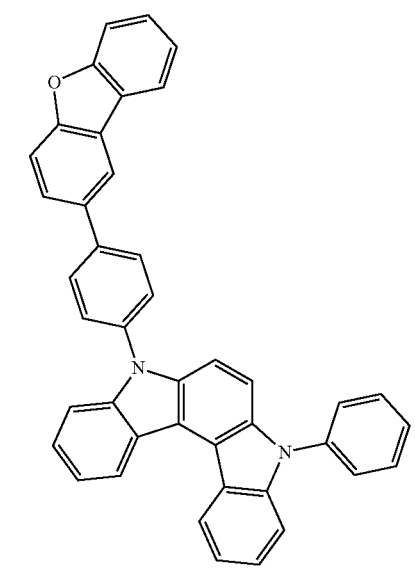
S-10
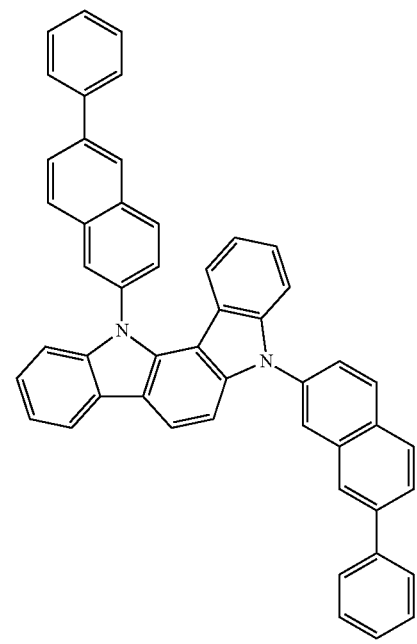
S-11
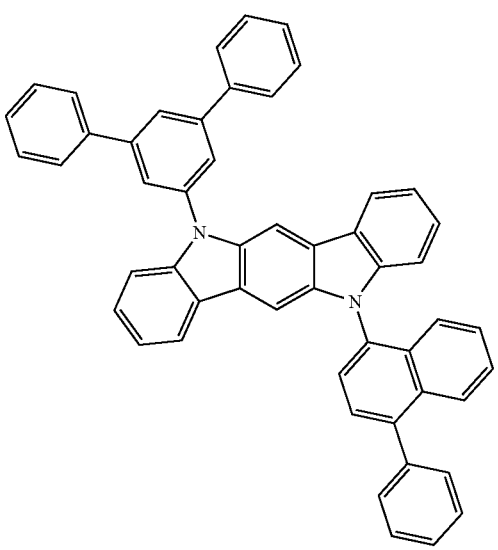
S-12
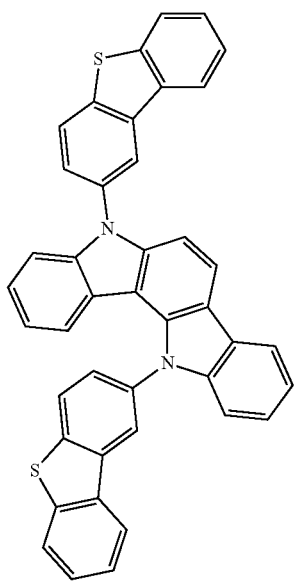
S-13
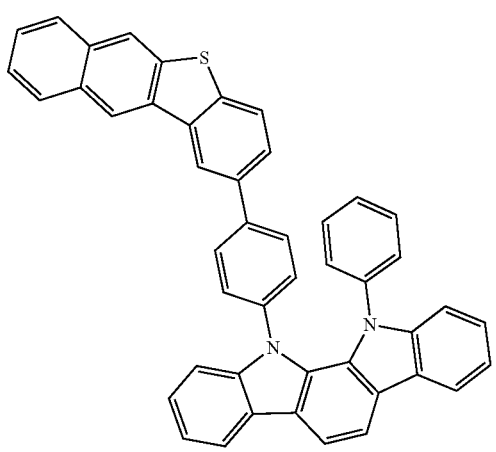

-continued
S-14
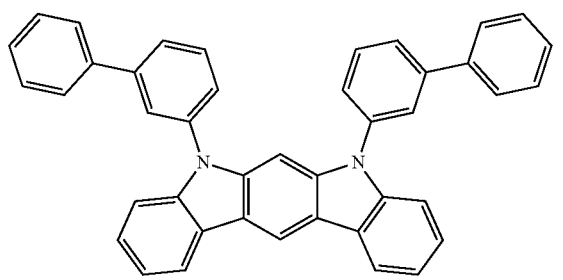
S-15
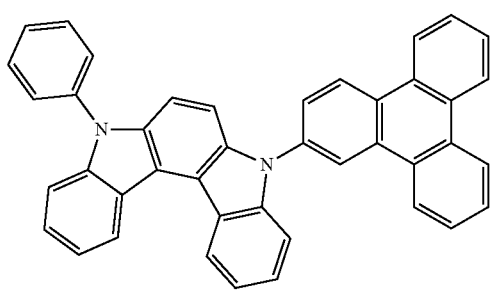
S-16
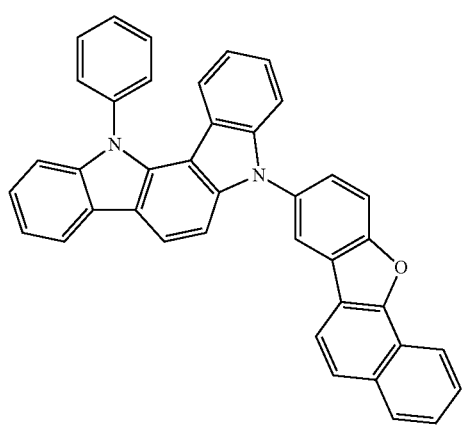
S-17
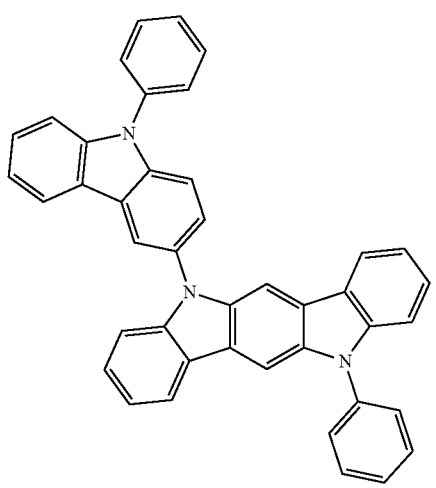
-continued
S-18
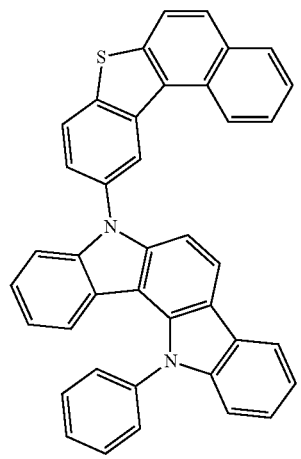
S-19
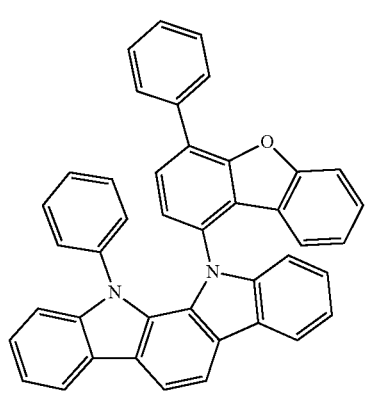
S-20
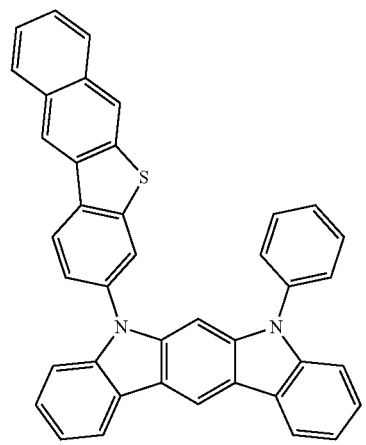

-continued
S-21
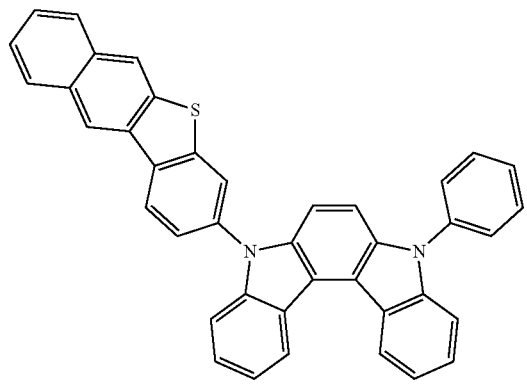
S-22
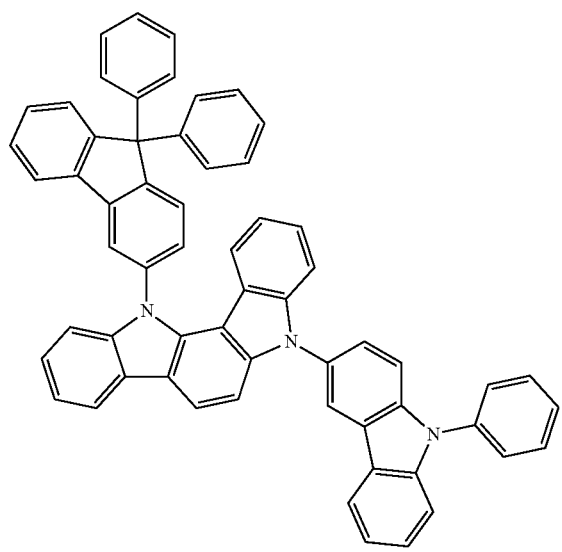
S-23
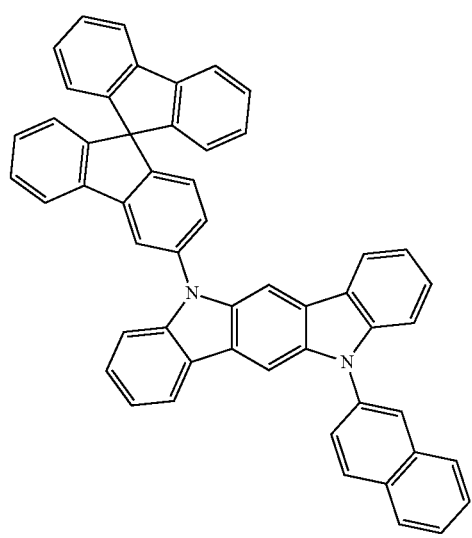
-continued
S-24
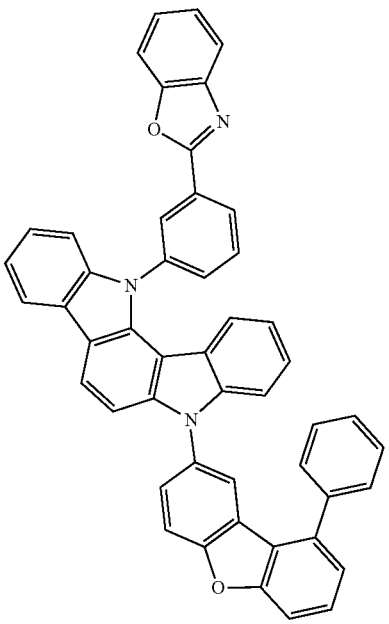
S-25
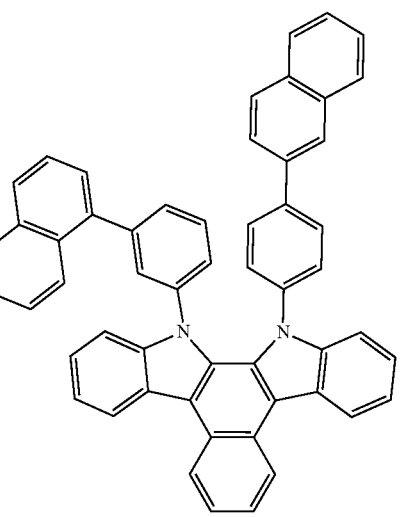
S-26
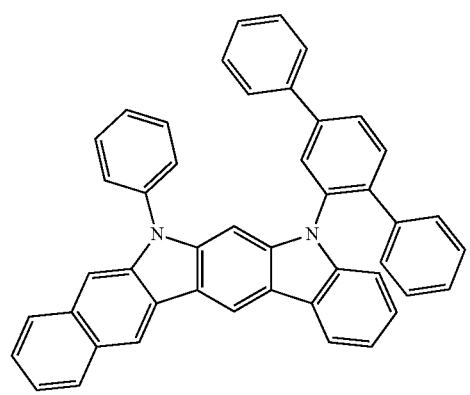

S-27
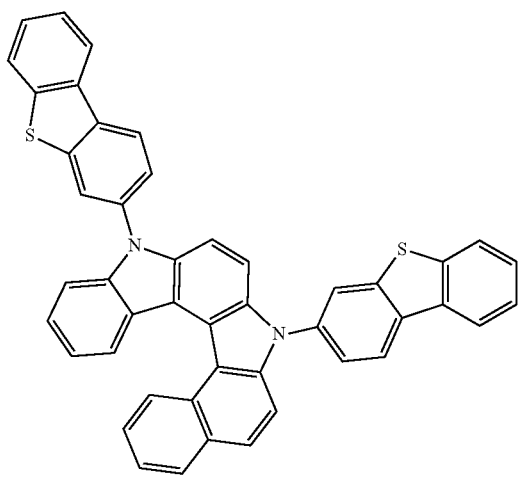
S-28
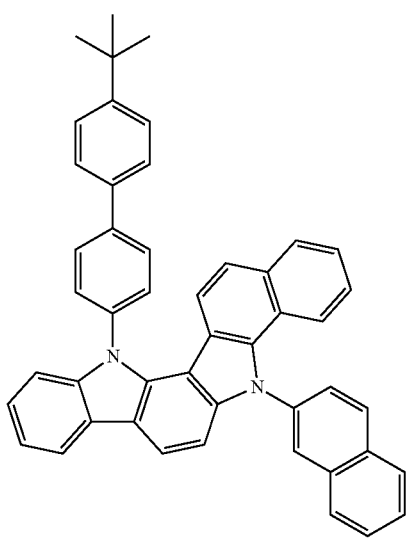
S-29
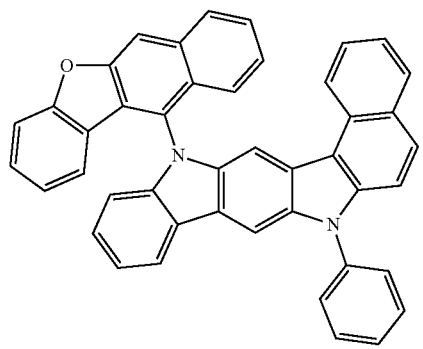
S-30
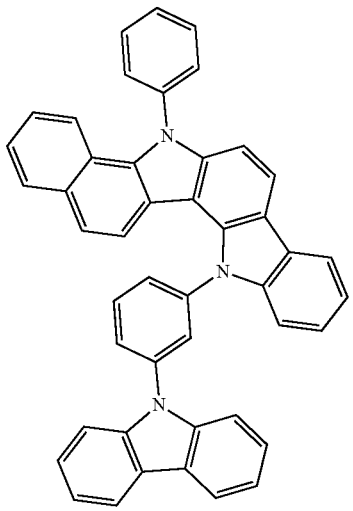
S-31
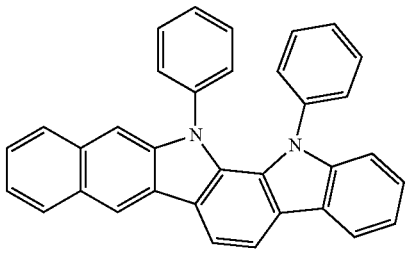
S-32
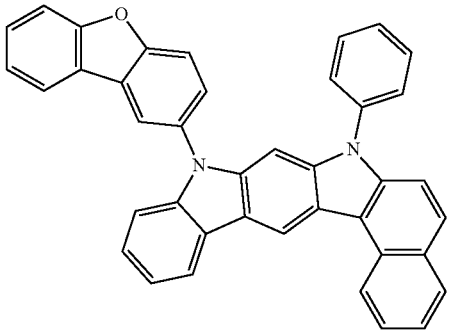
S-33
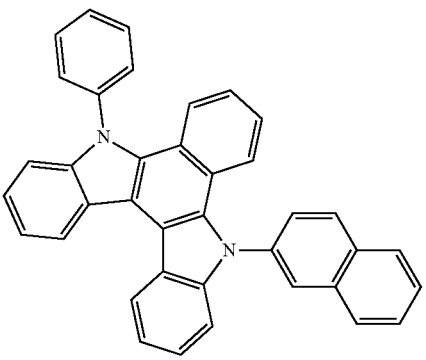

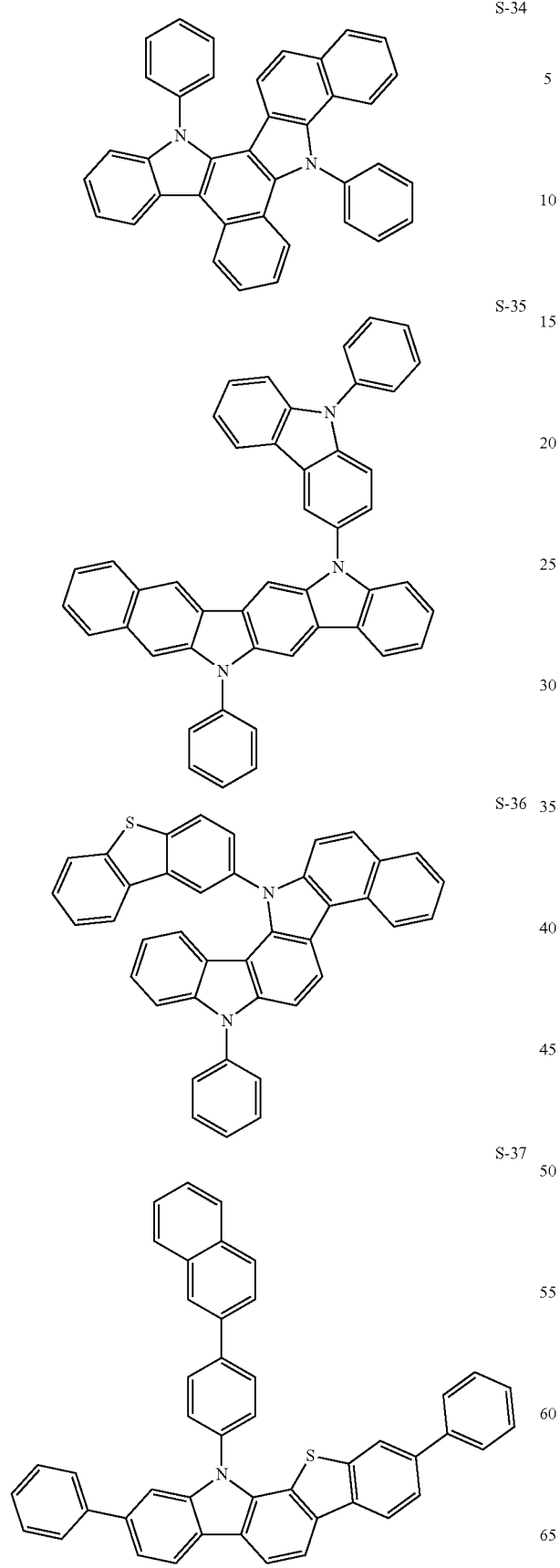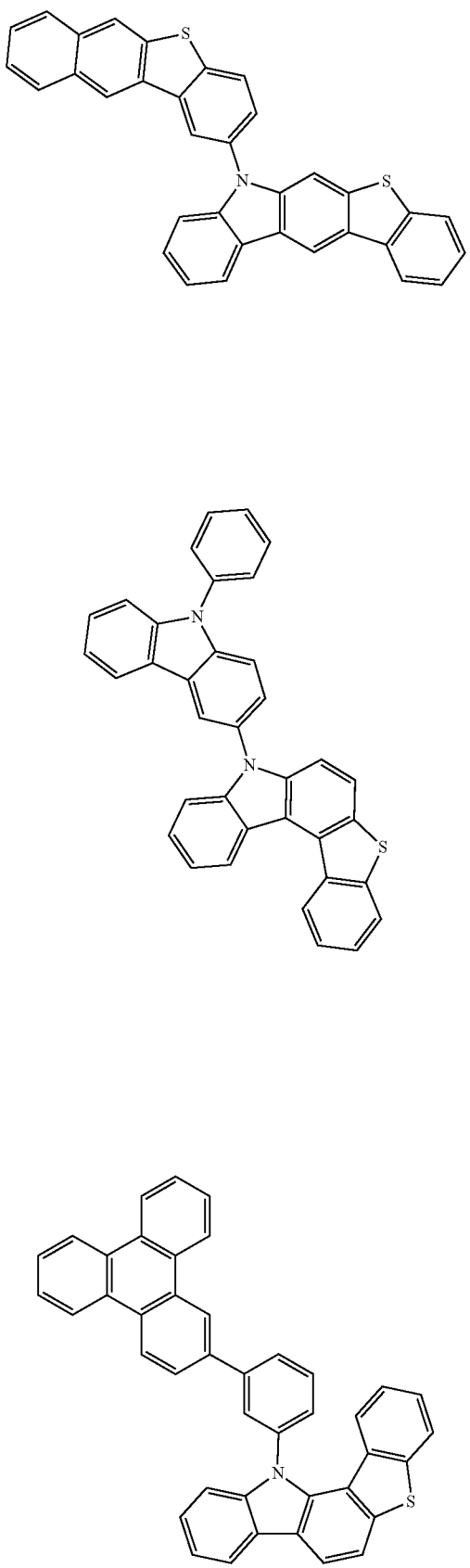

S-41
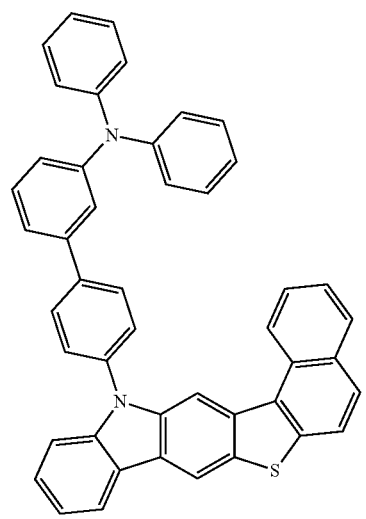
S-42
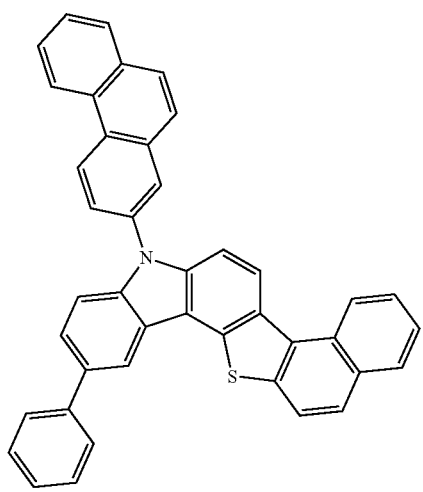
S-43
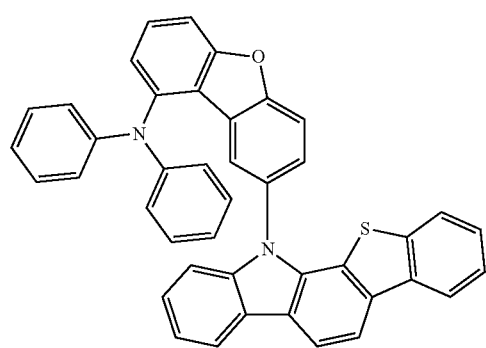
S-44
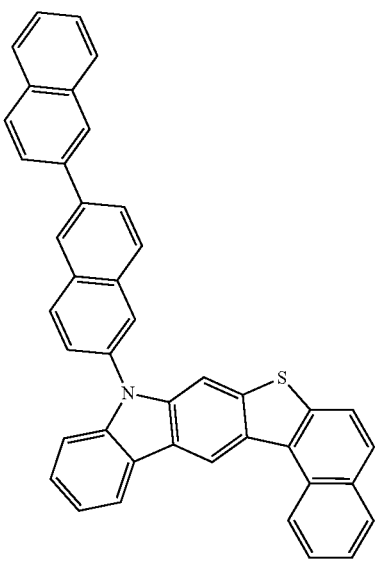
S-45
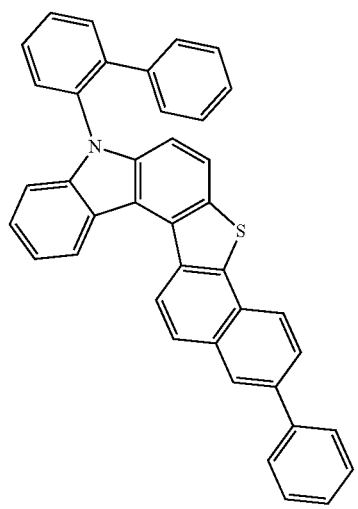
S-46
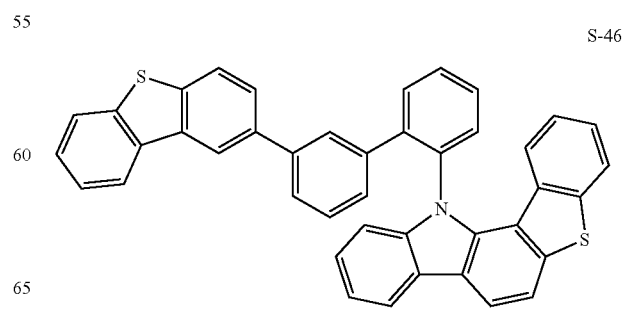

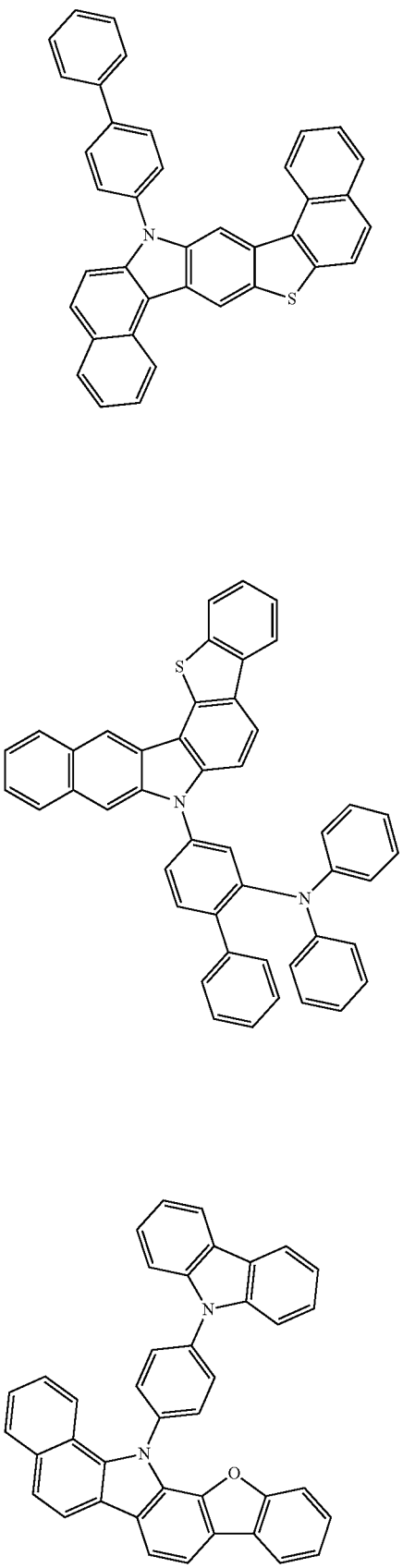
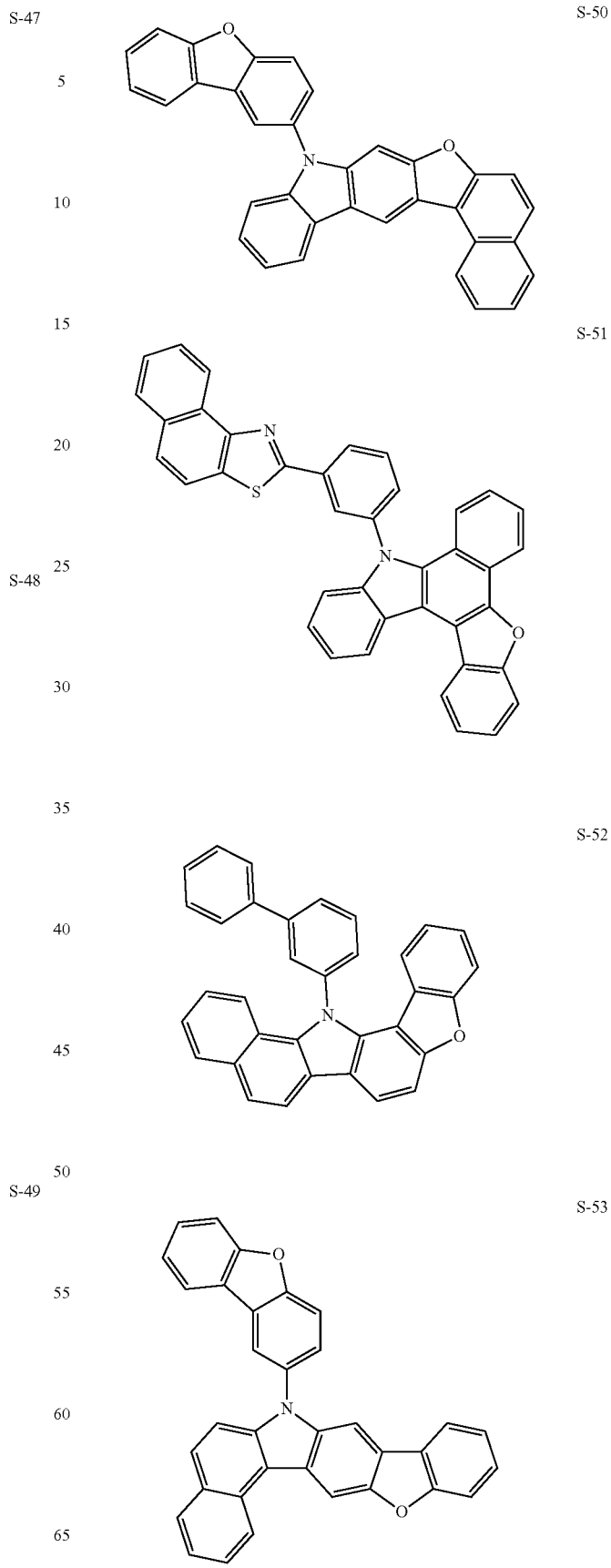

S-54
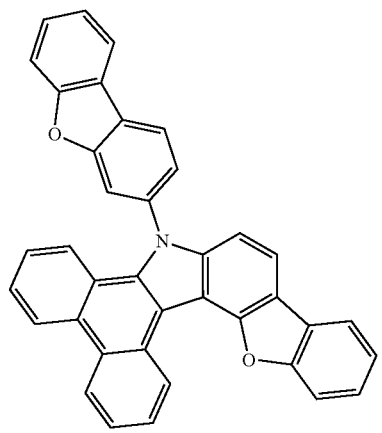
S-55
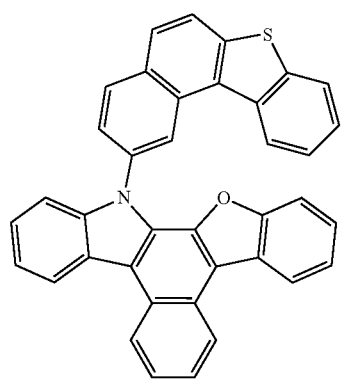
S-56
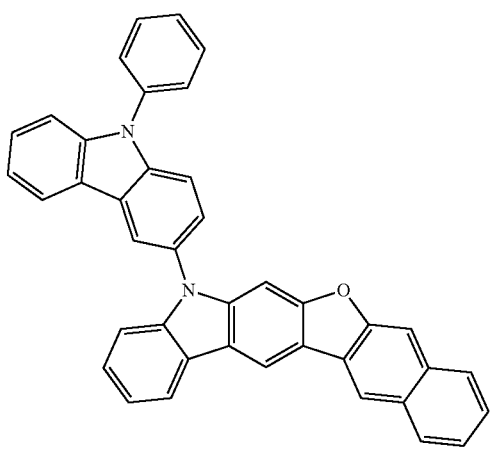
S-57
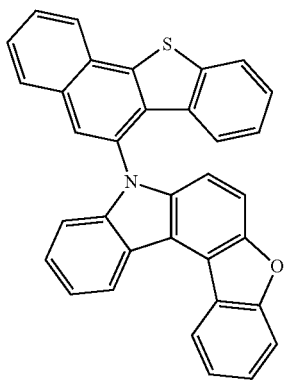
S-58
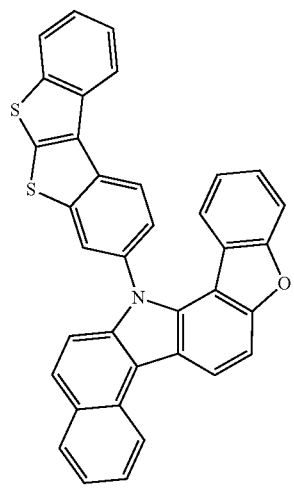
S-59
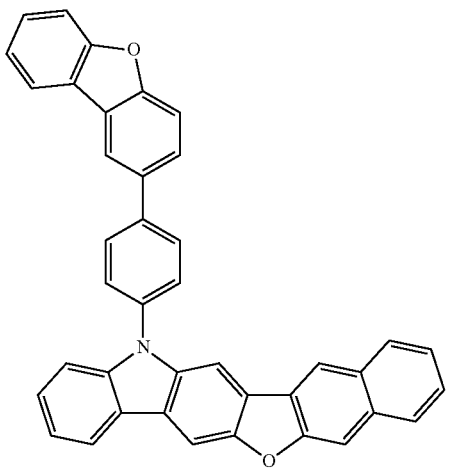
S-60
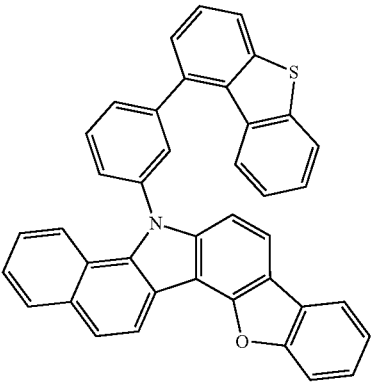

-continued
S-61
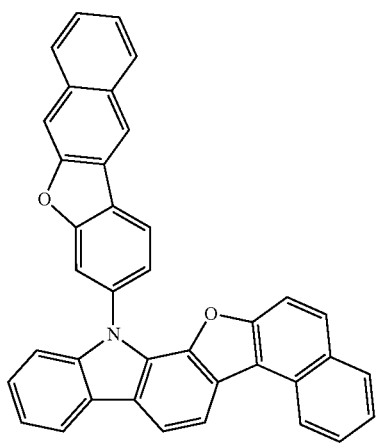
S-62
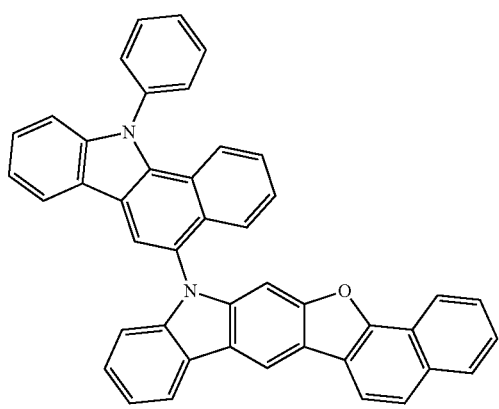
S-63
-continued
S-64
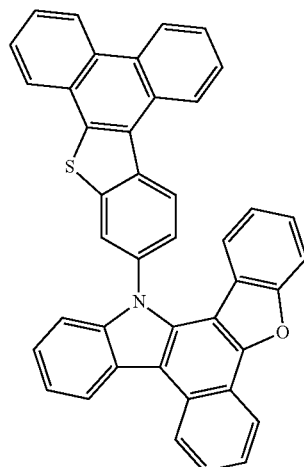
S-65
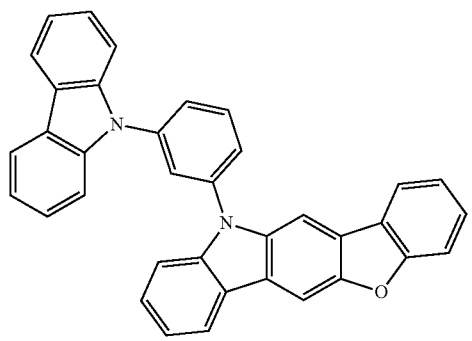
S-66
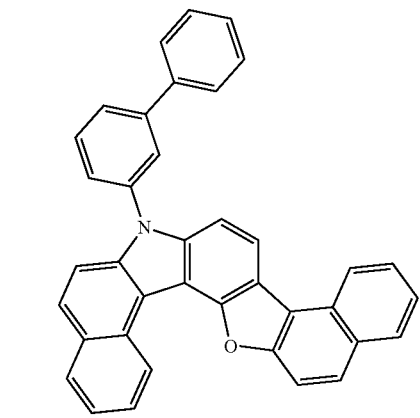
S-67
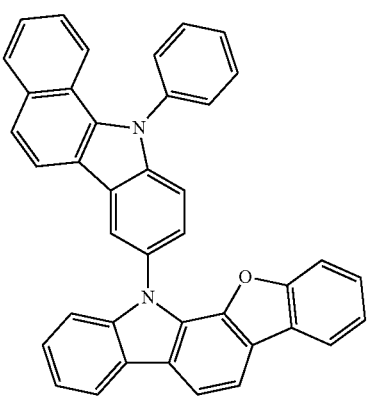

S-68
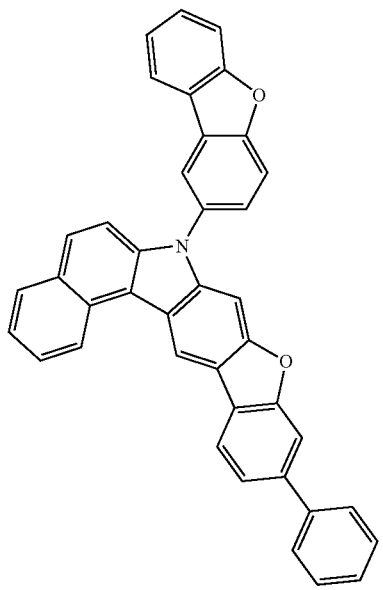
S-69
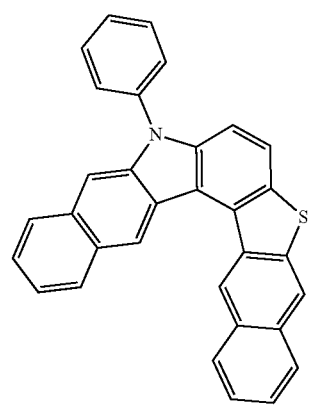
S-70
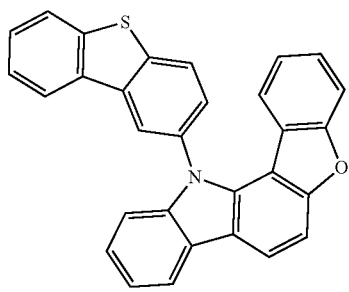
S-71
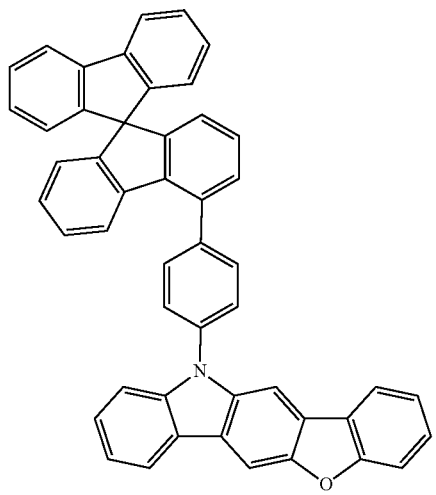
S-72
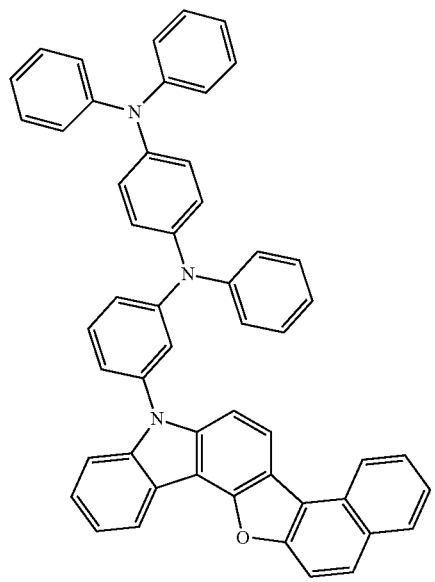
S-73
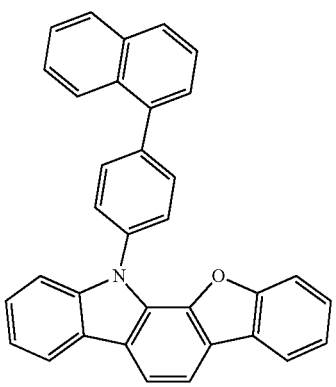

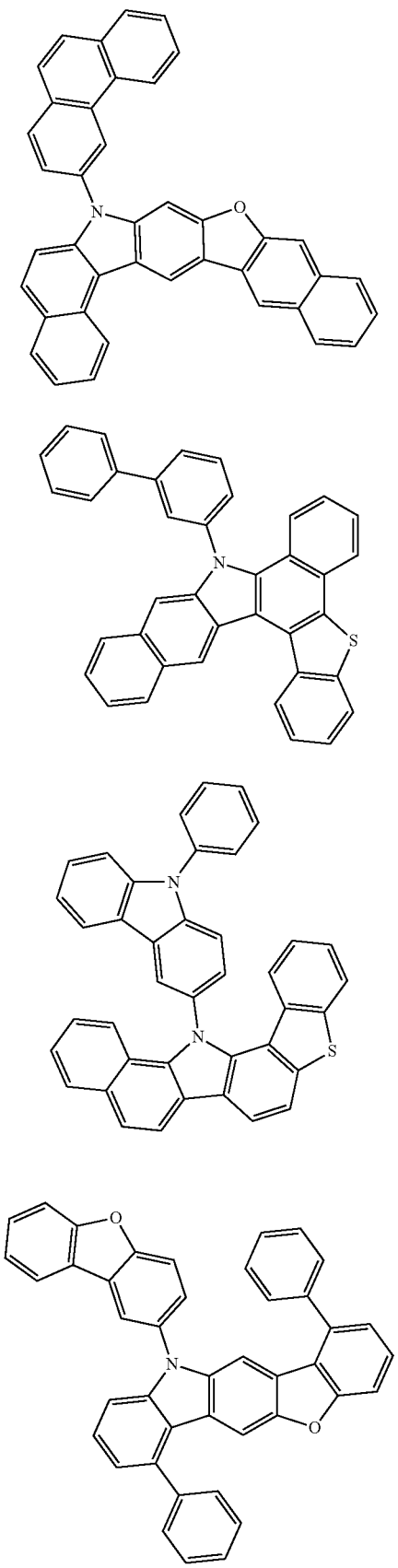
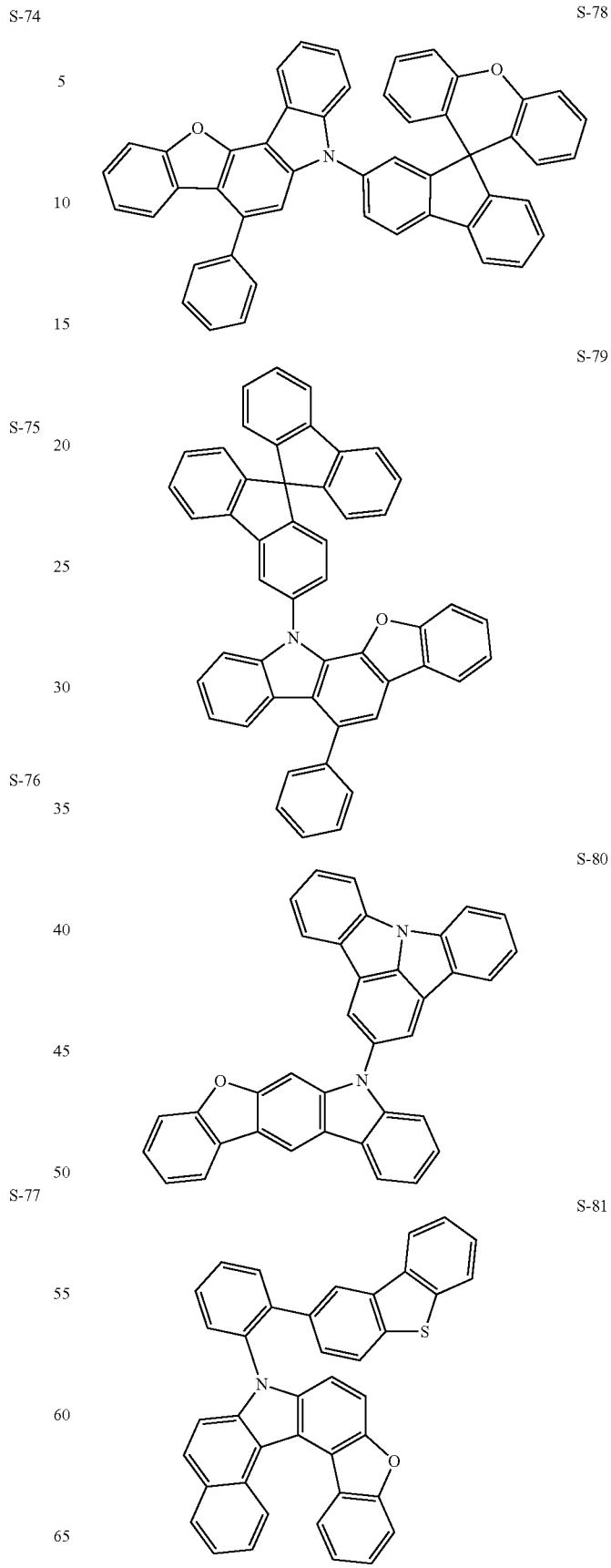

S-82
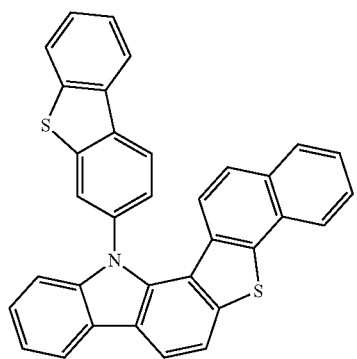
S-83
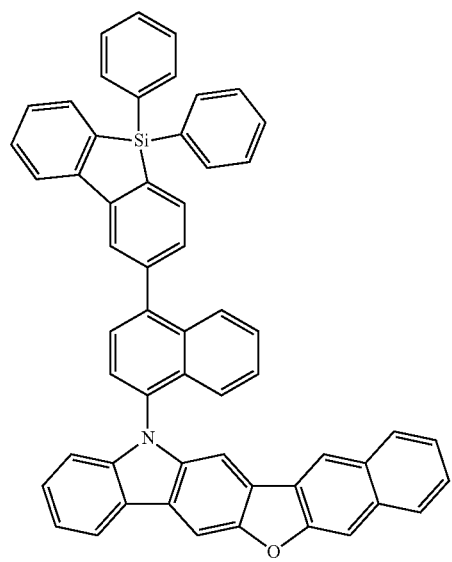
S-84
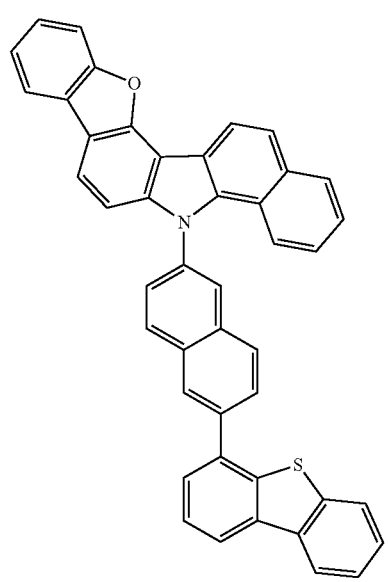
S-85
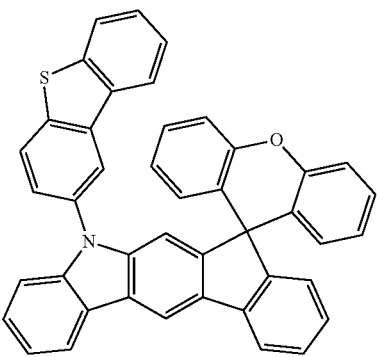
S-86
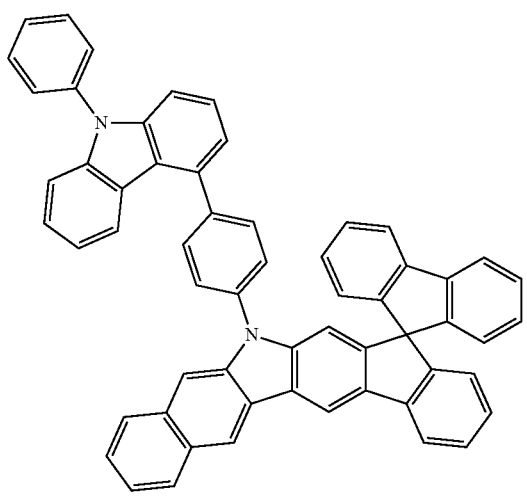
S-87
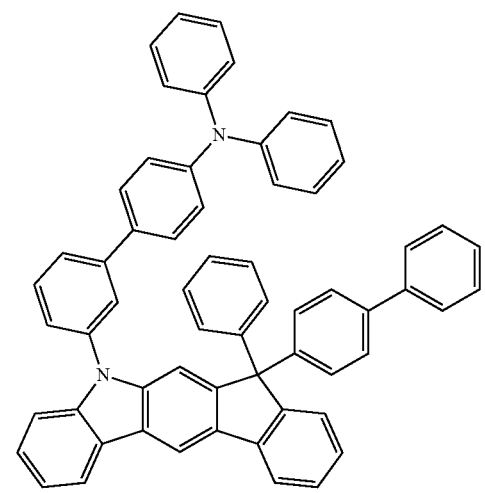

-continued
S-88
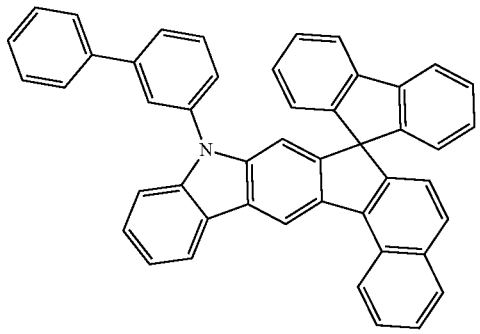
S-89
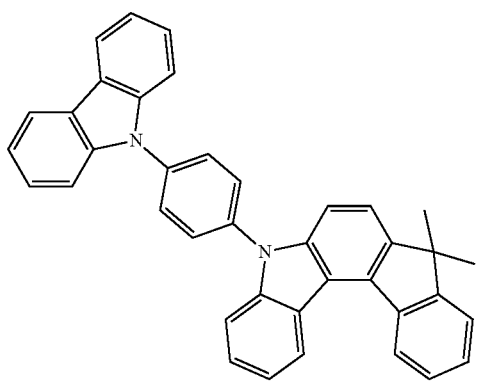
S-90
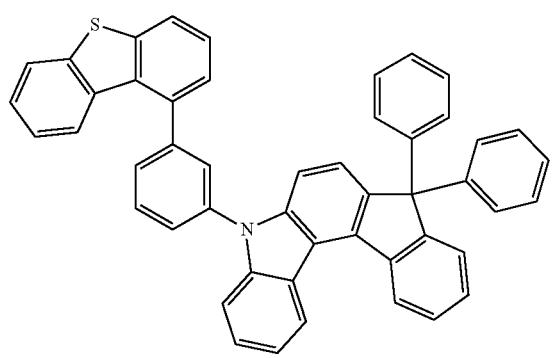
S-91
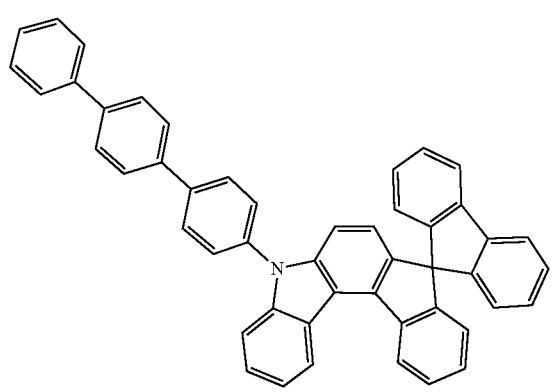
-continued
S-92
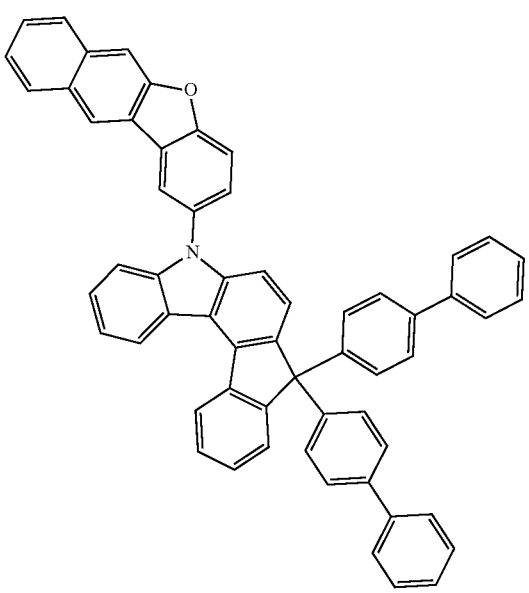
S-93
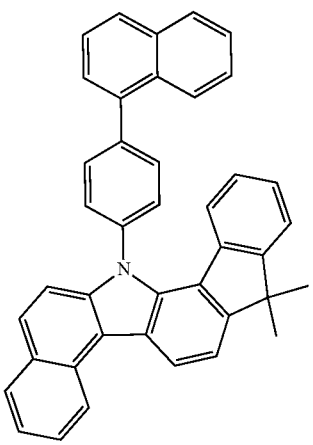
S-94
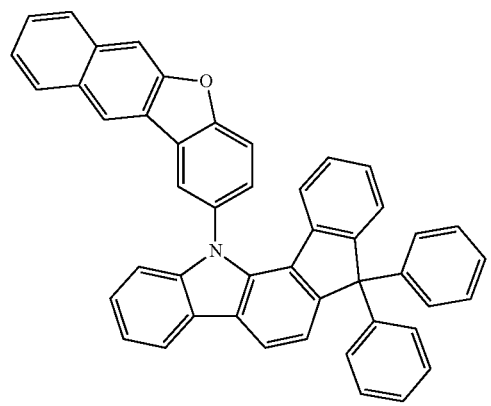

S-95
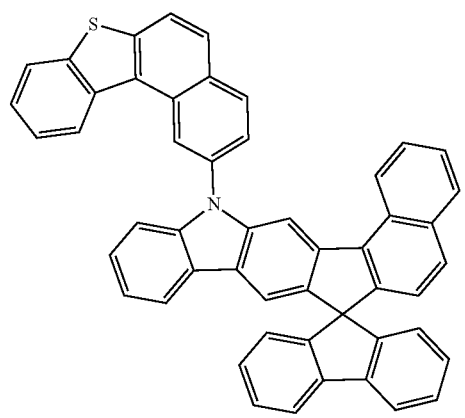
S-96
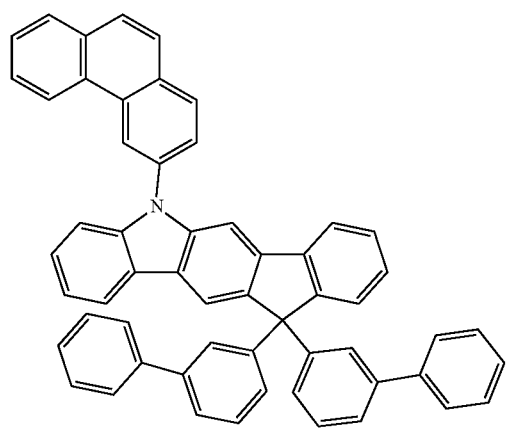
S-97
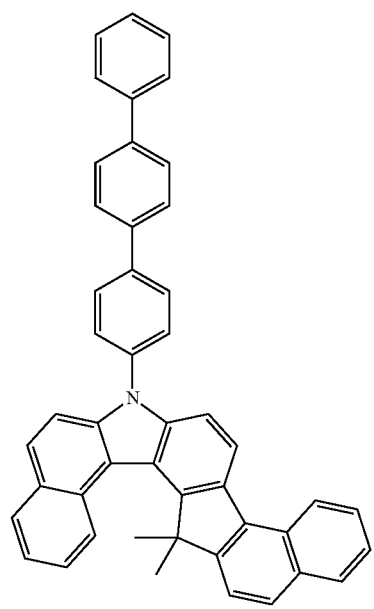
S-98
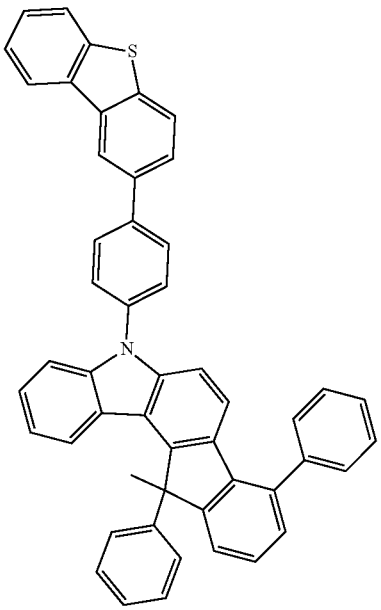
S-99
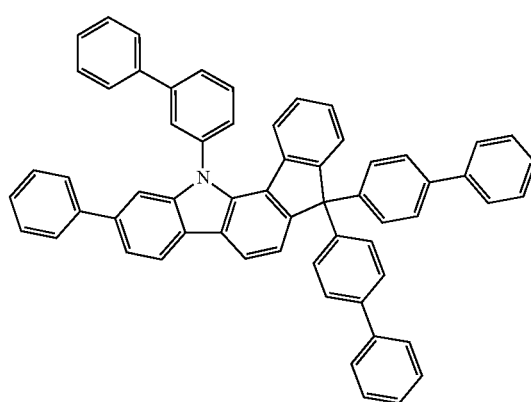
S-100
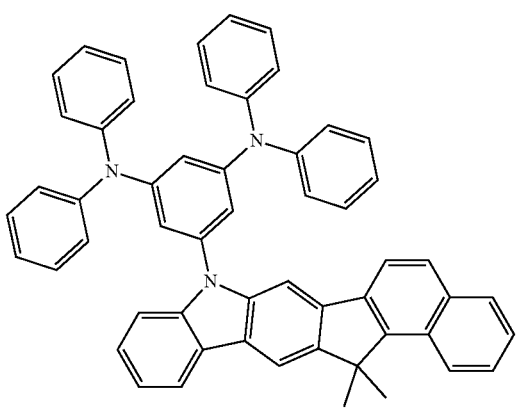

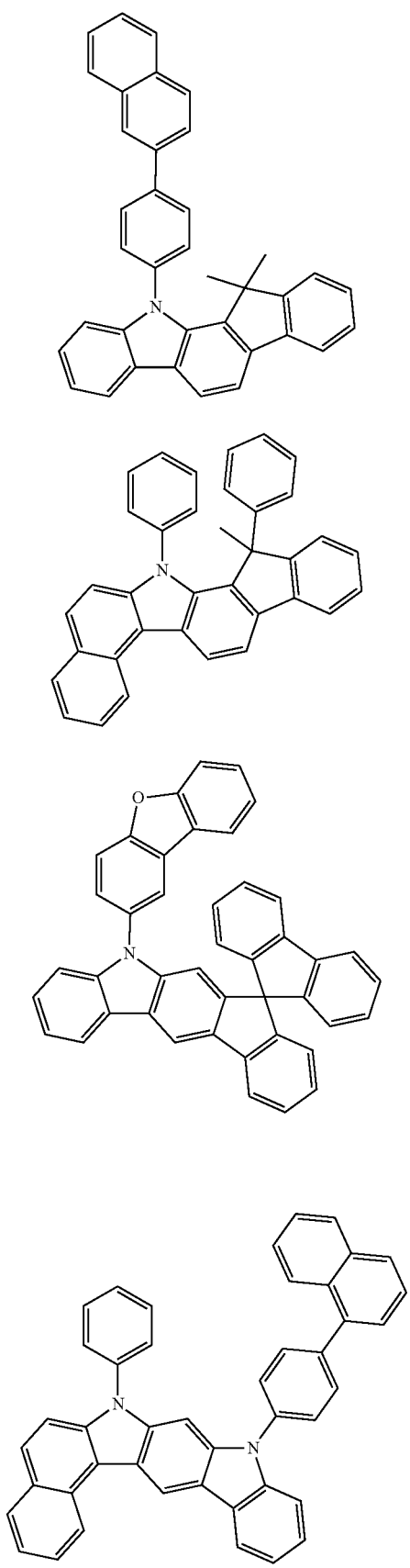
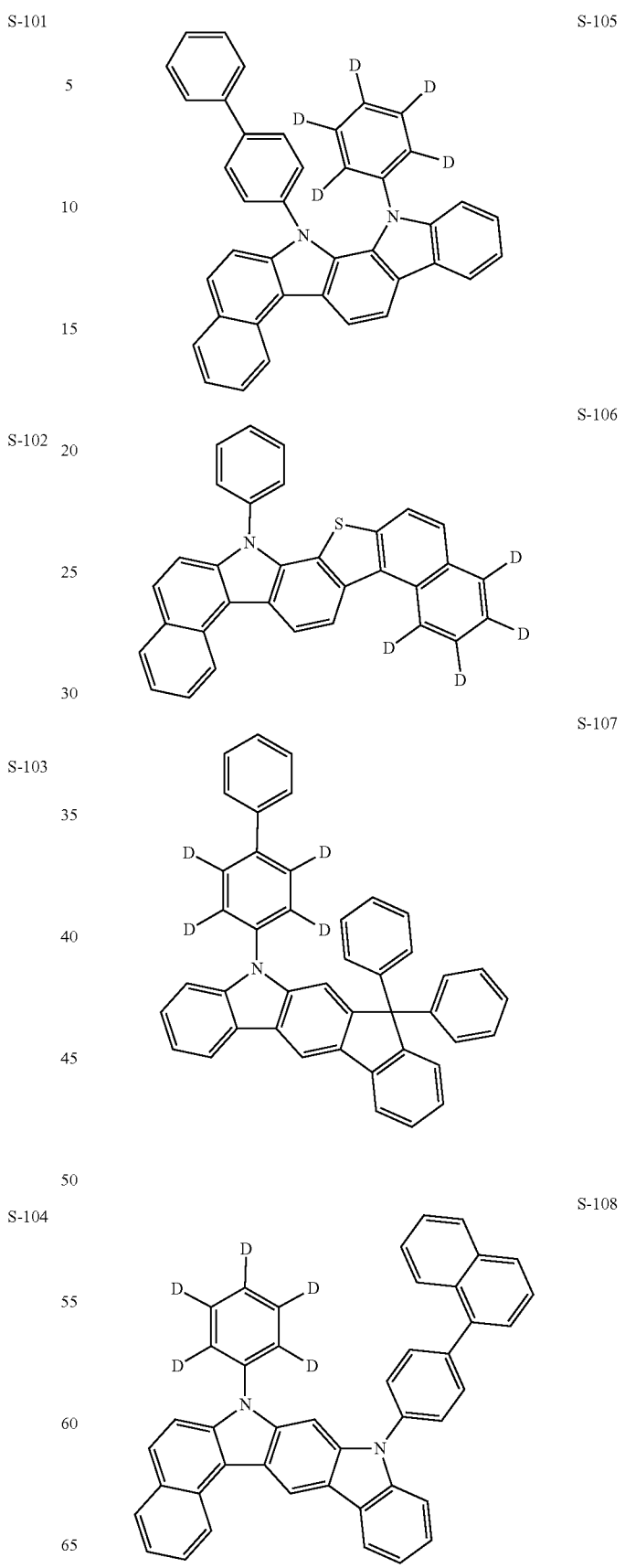

S-109
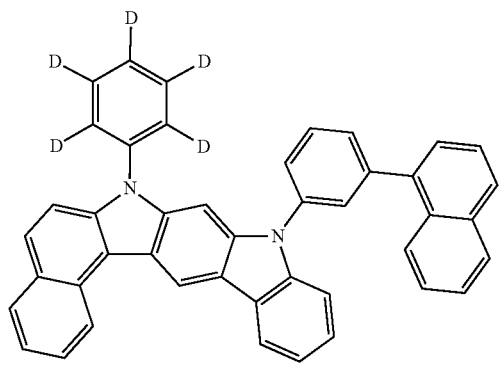
S-110
S-113
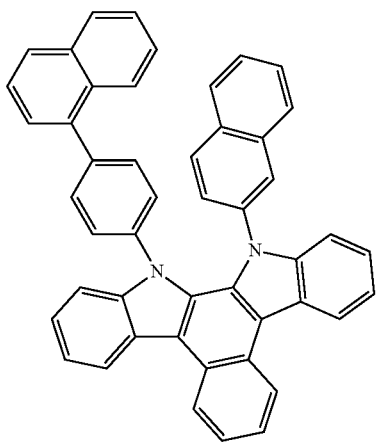
S-111
S-114
S-112
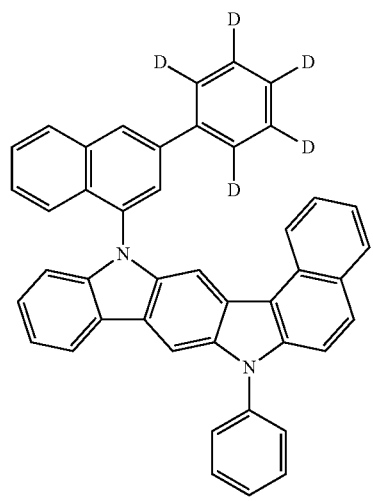
S-115
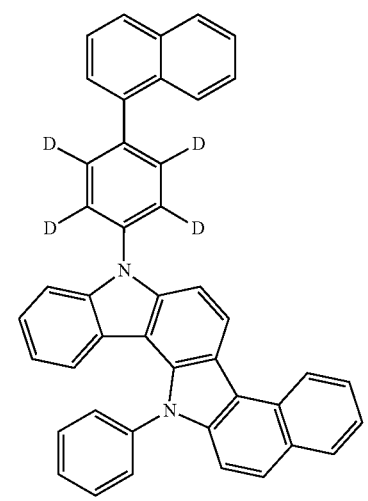

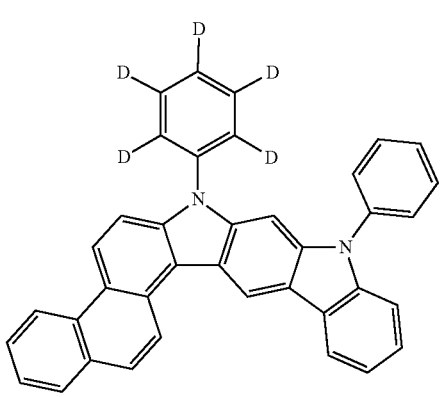

S-116

Also, in another aspect, the present invention provides an organic electronic element comprising a first electrode; a second electrode; and an organic material layer formed between the first electrode and the second electrode; wherein the organic material layer comprises a compound represented by Formula (1) or the composition for the organic electronic element.

In another aspect, the present invention provides a method for reusing a compound of Formula (1) comprising:

recovering a crude organic light emitting material comprising the compound of Formula (1) of claim 1 from a deposition apparatus used in the process for depositing the organic emitting material to prepare an organic light emitting device;

removing impurities from the crude organic light emitting material;

recovering the organic light emitting material after the impurities are removed; and purifying the recovered organic light emitting material to have a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent may preferably be used by mixing N-Methylpyrrolidone (NMP) single solvent; or a polar solvent mixed any one selected from the group consisting of 1,3-Dimethyl-2-imidazolidinone, 2-pyrrolidone, N,N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention comprises a first electrode (110), a second electrode (170), an organic material layer comprising single compound or 2 or more compounds represented by Formula (1) between the first electrode (110) and the second electrode (170). Wherein, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
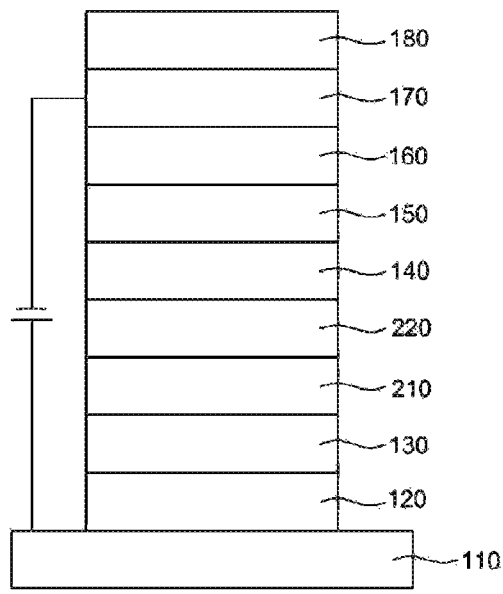

The organic material layer may sequentially comprise a hole injection layer (120), a hole transport layer (130), an emitting layer (140), an electron transport layer (150), and an electron injection layer (160) formed in sequence on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound or materials for organic electronic element according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, the composition for an organic electronic element comprising a compound represented by Formula (1) of the present invention, or a mixture of a compound represented by Formula (1) and a compound represented by Formula 4 or Formula 5 can be used as a host material for the emitting layer.

Figure 3:
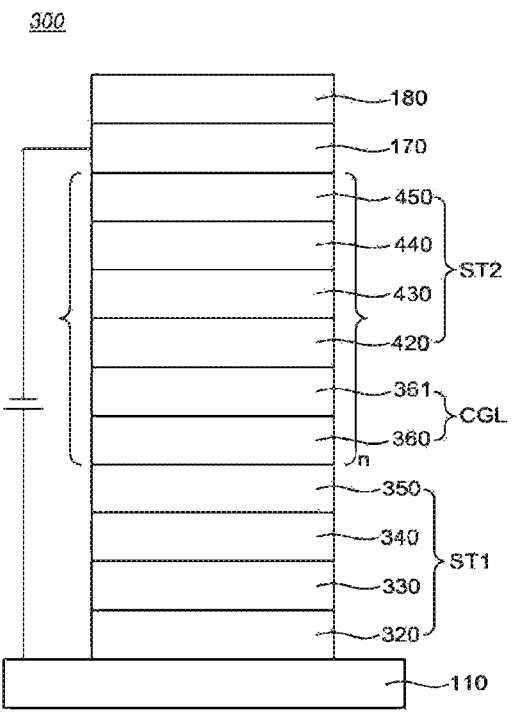
Figure 4:
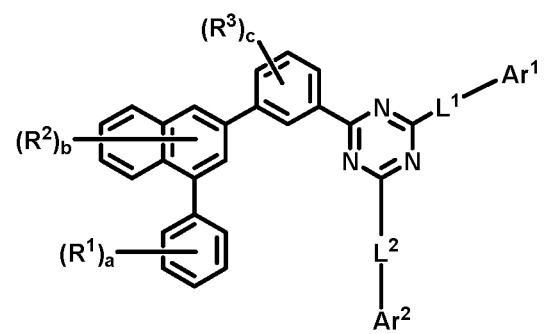
FIG. 4 shows a Formula according to one aspect of the present invention.

The organic material layer may include 2 or more stacks comprising a hole transport layer, an emitting layer, and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials(mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer(120), the hole transport layer(130), the emitting layer (140), the electron transport layer(150), and the electron injection layer(160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element that is used by mixing the same or different compounds of the compound represented by Formula (1) to the organic material layer. Preferably, the organic material layer comprises an emitting layer, wherein the emitting layer comprises a composition for an organic electronic element comprising a compound represented by Formula (1) or a mixture of a compound represented by Formula (1) and a compound represented by Formula 4 or Formula 5.

Also, the present invention provides a composition for an organic electronic element comprising a compound represented by Formula (1), or a mixture of a compound represented by Formula (1) and a compound represented by Formula 4 or Formula 5, and provides an organic electronic element comprising the composition.

Also, the present invention also provides an electronic device comprising a display device comprising the organic electronic element; and a control unit for driving the display device.

According to another aspect, the present invention provides an electronic device wherein the organic electronic element is at least one of an OLED, an organic solar cell, an organic photo conductor, an organic transistor (organic TFT) and an element for monochromic or white illumination. Wherein, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, Synthesis examples of the compound represented by Formula (1), Formula 4 and Formula 5 of the present invention and preparation examples of the organic electronic element of the present invention will be described in detail by way of example, but are not limited to the following examples.

SYNTHESIS EXAMPLE

The compound (final products) represented by Formula (1) according to the present invention is synthesized by reacting Sub1 and Sub 2 as shown in Reaction Scheme 1, but is not limited thereto.

Reaction Scheme 1

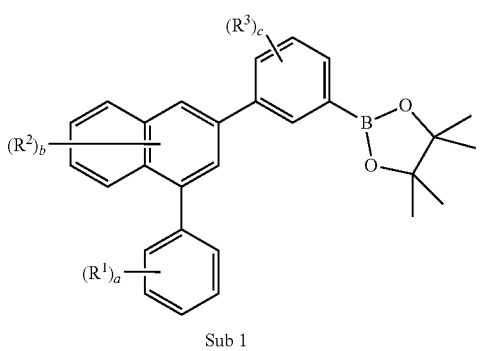

Sub 1

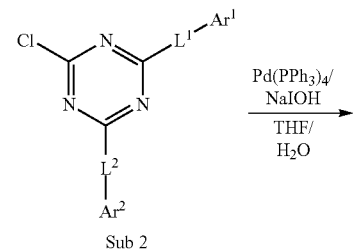

Sub 2

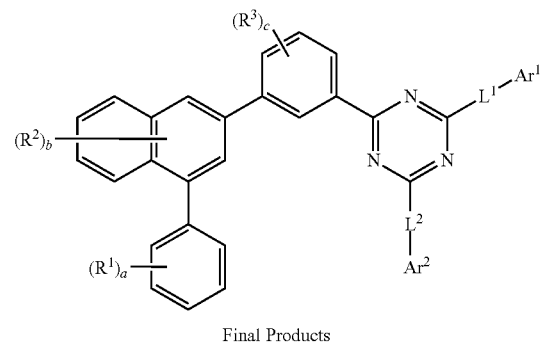

Final Products

Wherein, $R^1$, $R^2$, $R^3$, $L^1$, $L^2$, $Ar^1$, $Ar^2$, a, b and c are the same as defined in Formula 1.

I. Synthesis of Final Product
1. Synthesis Example of P-1

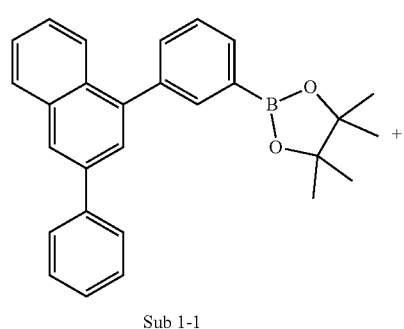

Sub 1-1

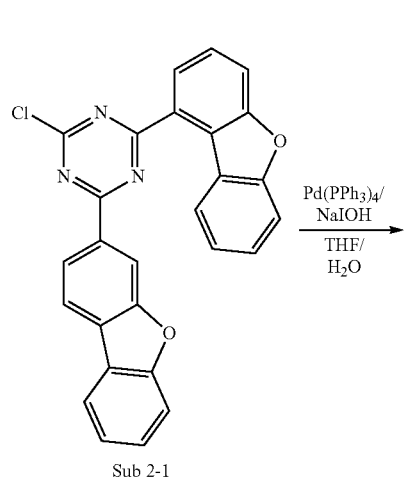

Sub 2-1

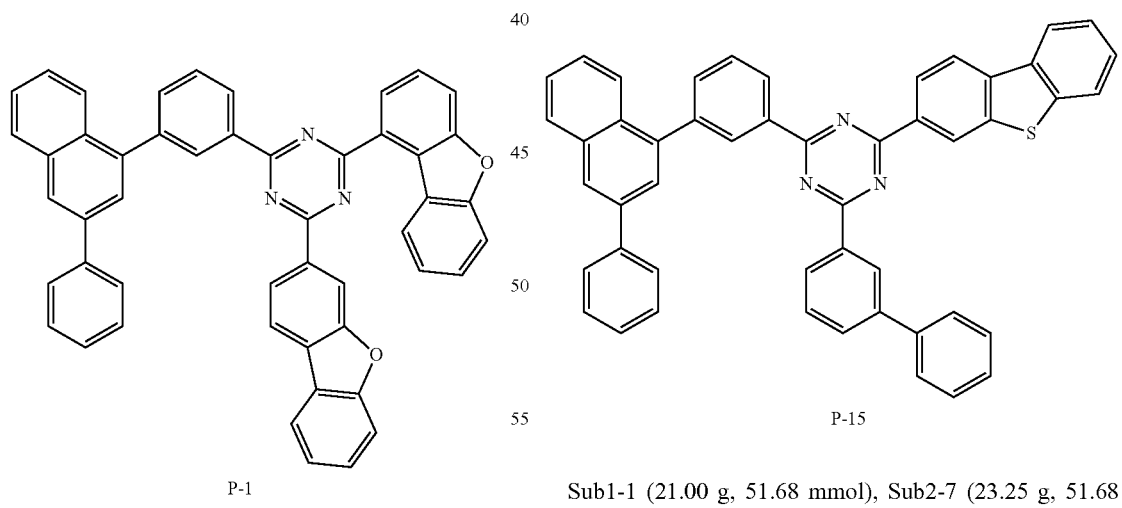

P-1

Sub1-1 (20.00 g, 49.22 mmol), Sub2-1 (22.05 g, 49.22 mmol), Pd(PPh$_3$)$_4$ (1.71 g, 1.48 mmol), NaOH (3.94 g, 98.44 mmol), THF (164 mL) and water (55 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 26.56 g (78%) of product P-1.

2. Synthesis Example of P-15

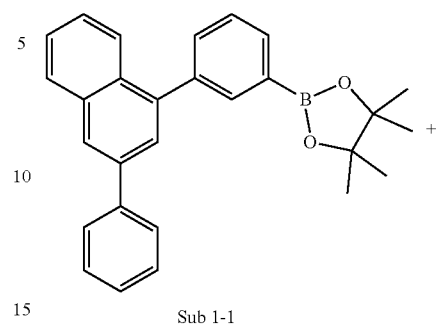

Sub 1-1

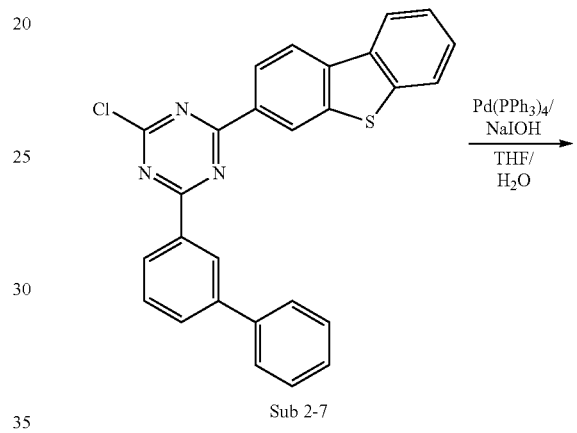

Sub 2-7

P-15

Sub1-1 (21.00 g, 51.68 mmol), Sub2-7 (23.25 g, 51.68 mmol), Pd(PPh$_3$)$_4$ (1.79 g, 1.55 mmol), NaOH (4.13 g, 103.36 mmol), THF (172 mL) and water (57 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 22.95 g (64%) of product P-15.

3. Synthesis Example of P-17

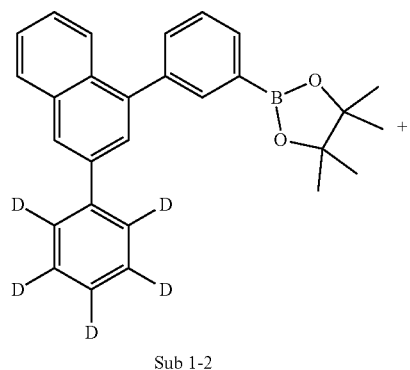

Sub 1-2

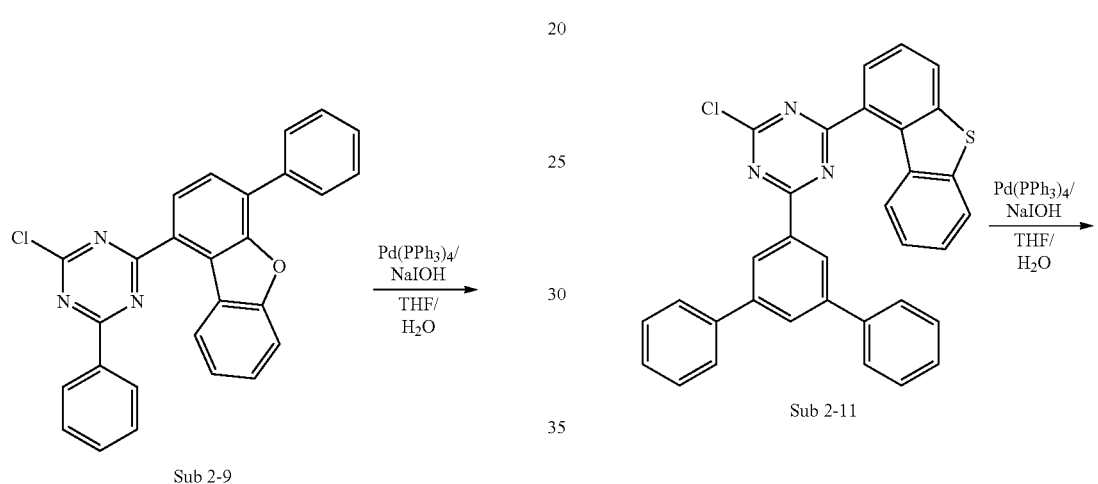

Sub 2-9

P-17

4. Synthesis Example of P-27

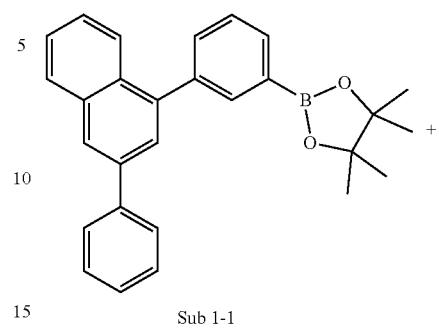

Sub 1-1

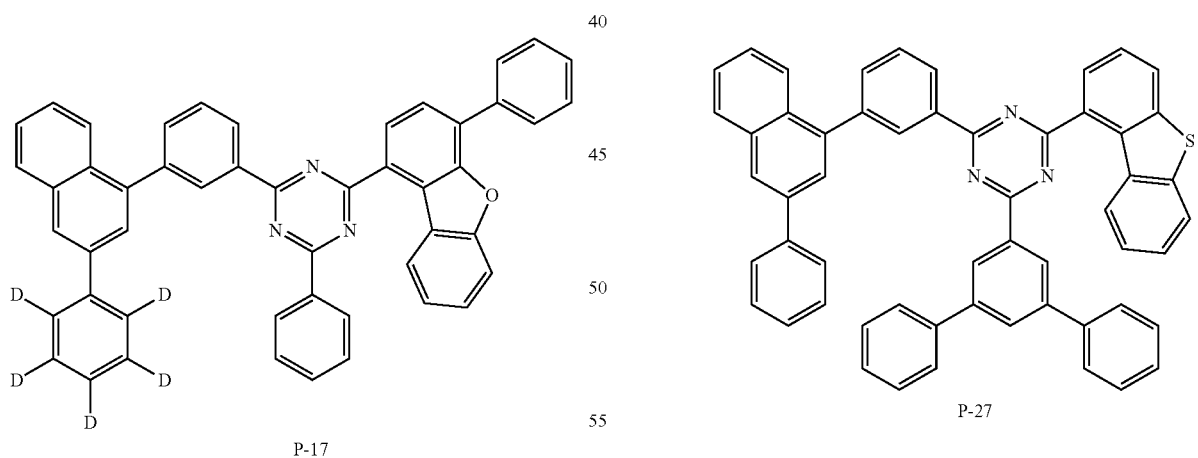

Sub 2-11

P-27

Sub1-2 (17.00 g, 41.33 mmol), Sub2-9 (17.93 g, 41.33 mmol), Pd(PPh₃)₄ (1.43 g, 1.24 mmol), NaOH (3.31 g, 82.65 mmol), and THF (138 mL) and water (46 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 20.60 g (73%) of product P-17.

Sub1-1 (19.00 g, 46.76 mmol), Sub2-11 (24.60 g, 46.76 mmol), Pd(PPh₃)₄ (1.62 g, 1.40 mmol), NaOH (3.74 g, 93.52 mmol), and THF (156 mL) and water (32 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 25.56 g (71%) of product P-27.

5. Synthesis Example of P-44

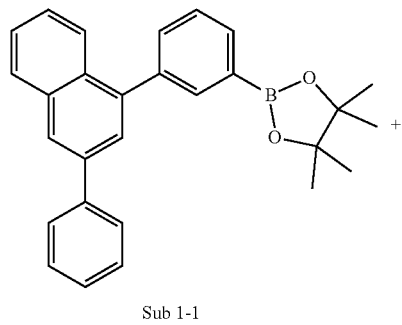

Sub 1-1

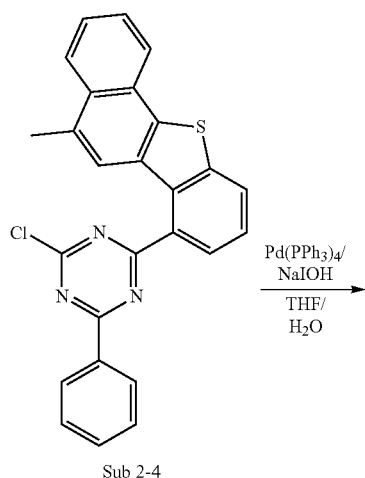

Sub 2-4

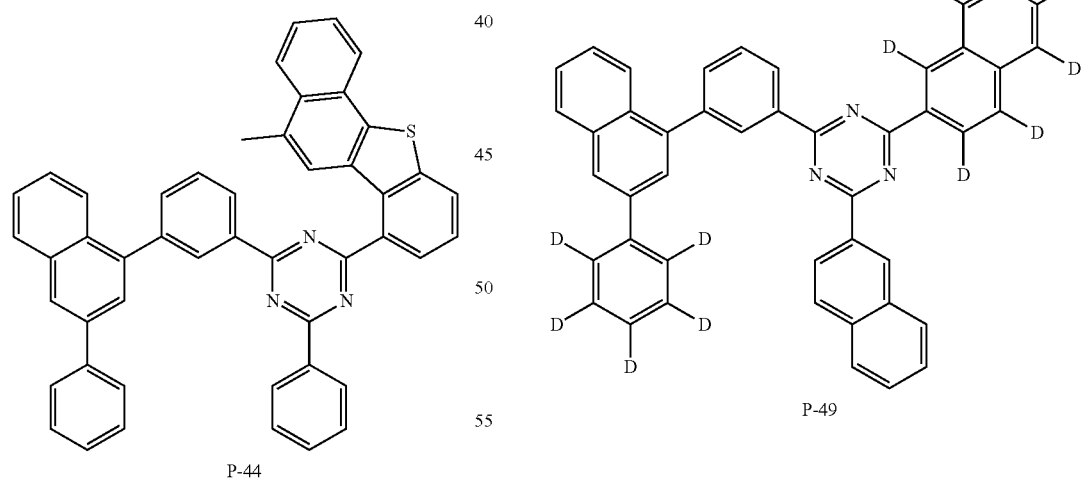

P-44

Sub1-1 (30.00 g, 73.83 mmol), Sub2-4 (32.33 g, 73.83 mmol), Pd(PPh$_3$)$_4$ (2.56 g, 2.21 mmol), NaOH (5.91 g, 147.66 mmol), THF (246 mL) and water (82 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 31.21 g (62%) of product P-44.

6. Synthesis Example of P-49

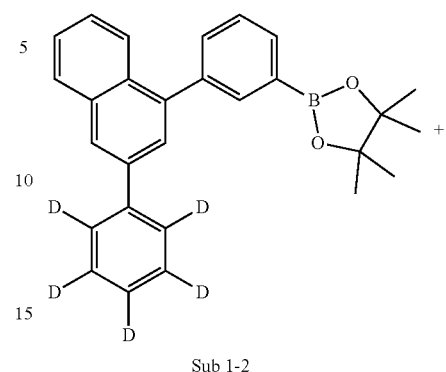

Sub 1-2

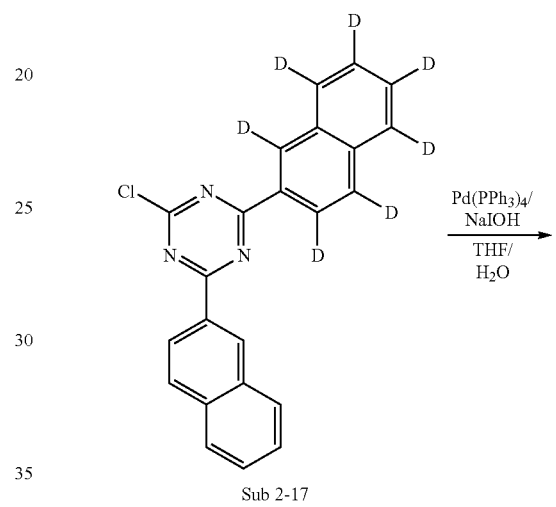

Sub 2-17

P-49

Sub1-2 (25.00 g, 60.77 mmol), Sub2-17 (22.78 g, 60.77 mmol), Pd(PPh$_3$)$_4$ (2.11 g, 1.82 mmol), NaOH (4.86 g, 121.55 mmol), THF (203 mL) and water (68 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 28.43 g (75%) of product P-49.

7. Synthesis Example of P-55

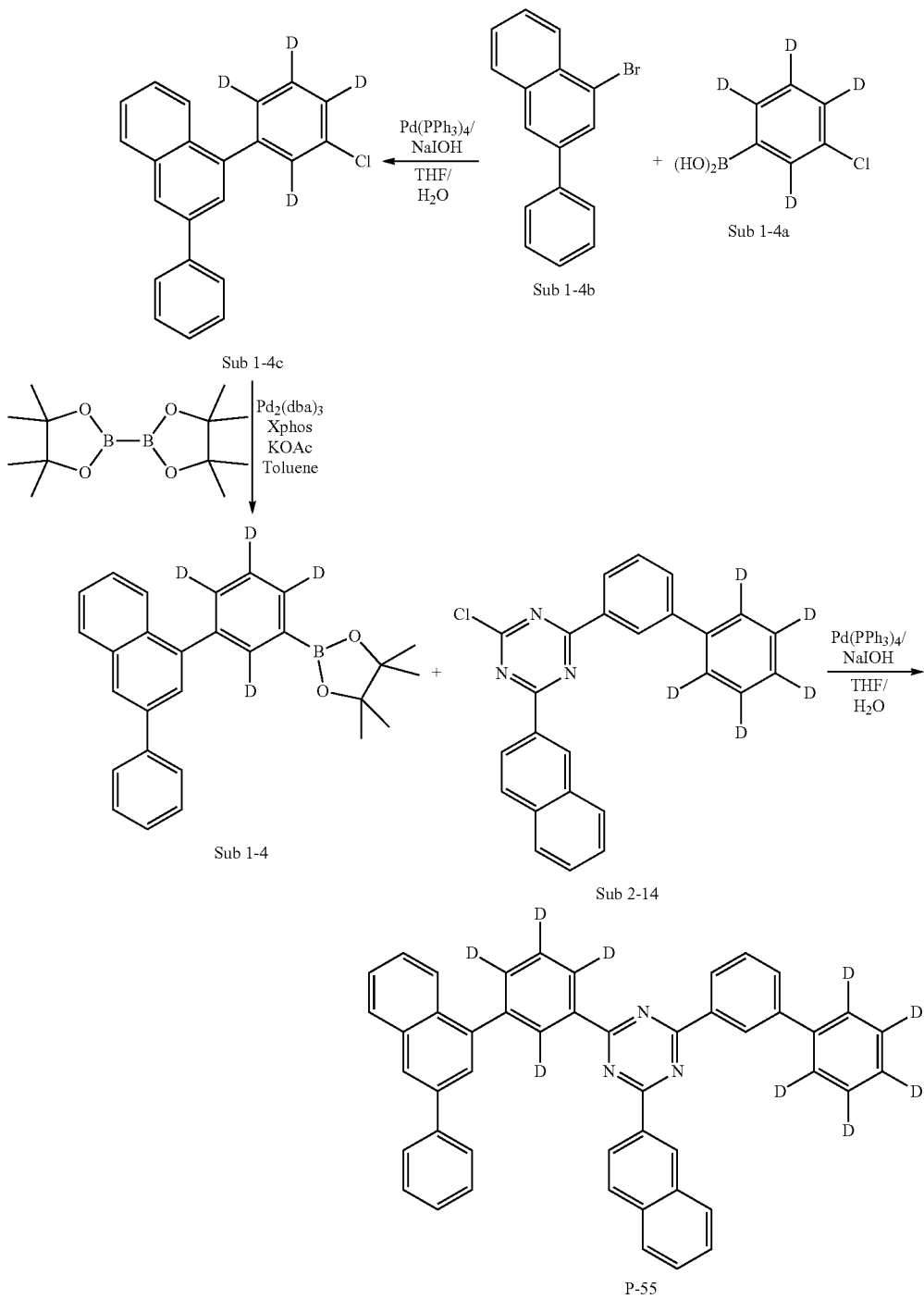

1) Synthesis of Sub 1-4c

Sub1-4a (19.83 g, 123.60 mmol), Sub1-4b (35.00 g, 123.60 mmol), Pd(PPh₃)₄ (4.29 g, 3.71 mmol), K₂CO₃ (34.17 g, 247.20 mmol) were added to a round bottom flask, dissolved in anhydrous THF (412 mL) and water (137 mL), and then refluxed for 12 hours. When the reaction was completed, the temperature of the reactant was cooled to room temperature, extracted with CH₂Cl₂ and water, and then treated with MgSO₄. The product produced by concentrating the organic solvent was recrystallized using a silica-gel column to obtain 34.68 g (88%) of Sub1-4c.

2) Synthesis of Sub 1-4

Sub1-4c (34.00 g, 106.64 mmol), 4,4,4',4',5,5,5',5'-octamethyl-2,2'-bi(1,3,2-dioxaborolane) (35.20 g, 138.63 mmol), Pd₂(dba)₃ (2.93 g, 3.20 mmol), Xphos (3.05 g, 6.40 mmol), KOAc (20.93 g, 213.27 mmol) were added to Toluene (355 mL) and stirred at 120° C. for 2 hours. When the reaction was completed, the reaction solvent was removed and the concentrated organic material was recrystallized using a silicagel column to obtain 25.82 g (59%) of product Sub1-4.

3) Synthesis of P-55

Sub1-4 (15.00 g, 36.55 mmol), Sub2-14 (14.58 g, 36.55 mmol), Pd(PPh$_3$)$_4$ (1.27 g, 1.10 mmol), NaOH (2.92 g, 73.11 mmol) and THF (121 mL) and water (40 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 16.55 g (70%) of product P-55.

8. Synthesis Example of P-73

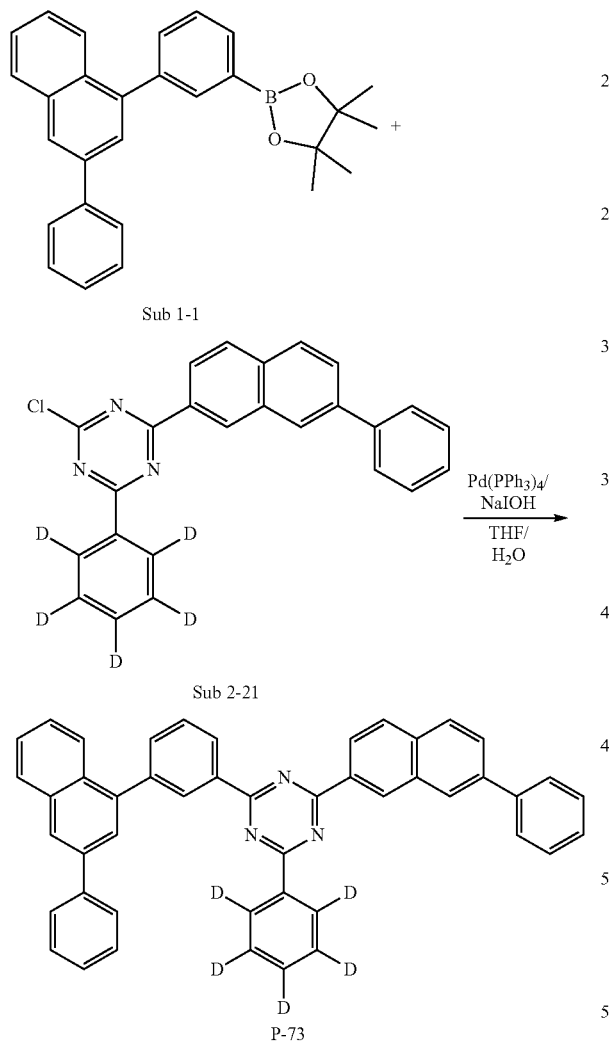

Sub1-1 (16.00 g, 39.38 mmol), Sub2-21 (15.71 g, 39.38 mmol), Pd(PPh$_3$)$_4$ (1.37 g, 1.18 mmol), NaOH (3.15 g, 78.75 mmol) and THF (132 mL) and water (44 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 18.22 g (72%) of product P-73.

9. Synthesis Example of P-91

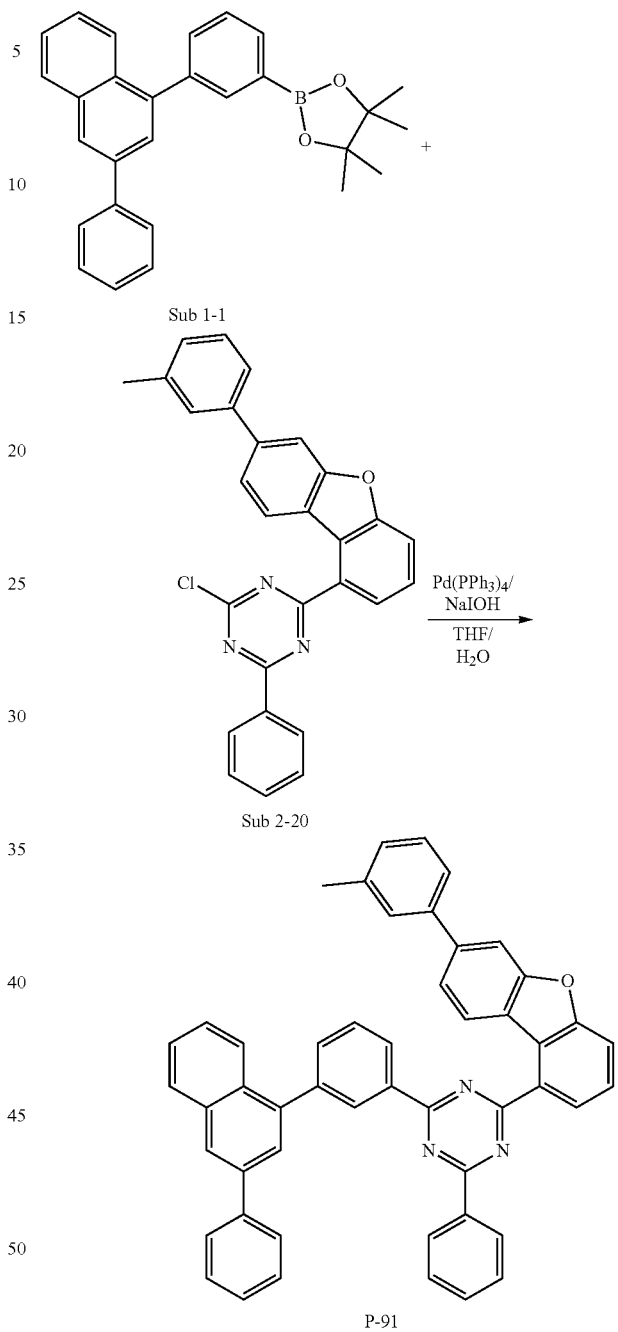

Sub1-1 (21.00 g, 51.68 mmol), Sub2-20 (23.15 g, 51.68 mmol), Pd(PPh$_3$)$_4$ (1.79 g, 1.55 mmol), NaOH (4.13 g, 103.36 mmol) and THF (172 mL) and water (58 mL) were added to the round bottom flask, and reacted at 75° C. for 8 hours. When the reaction is completed, the temperature of the reactant is cooled to room temperature and the reaction solvent is removed. The concentrated reactant was recrystallized using a silicagel column to obtain 23.24 g (65%) of product P-91.

Sub 1 in Reaction Scheme 1 may be the following compound, but is not limited thereto, and the FD-MS (Field Desorption-Mass Spectrometry) values of the compounds belonging to Sub 1 are shown in Table 1.

-continued
| | |
|---|---|
| Sub 1-1 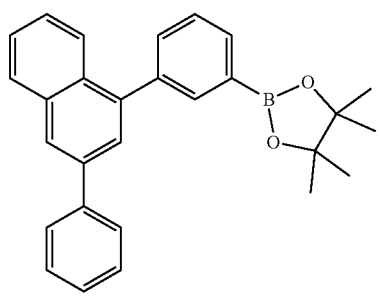 | Sub 1-5 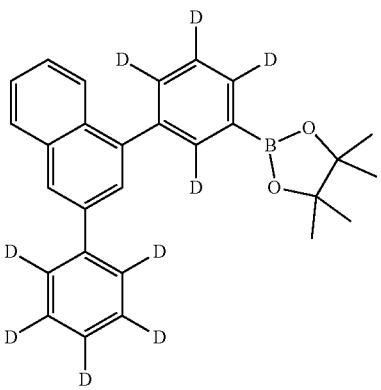 |
| Sub 1-2 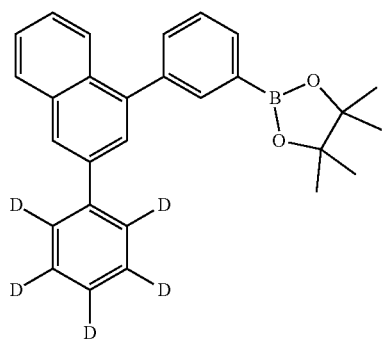 | Sub 1-6 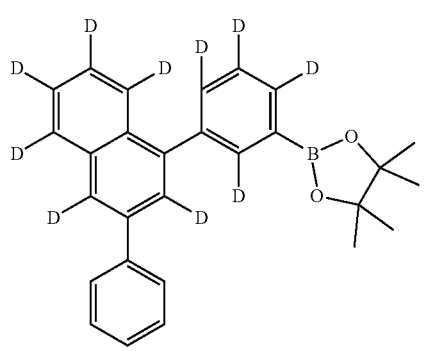 |
| Sub 1-3 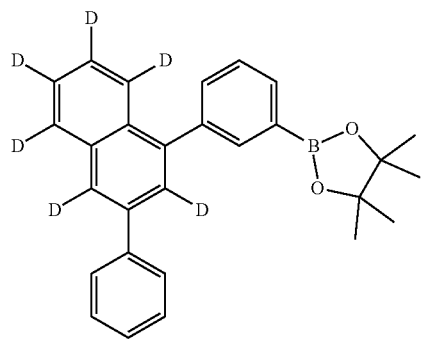 | Sub 1-7 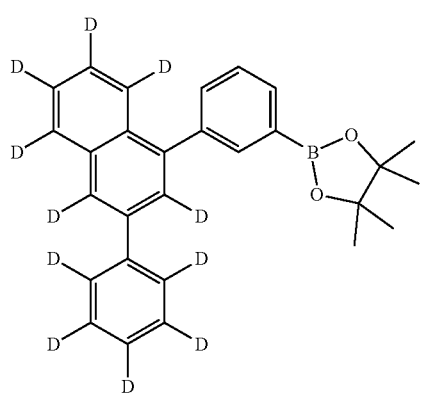 |
| Sub 1-4 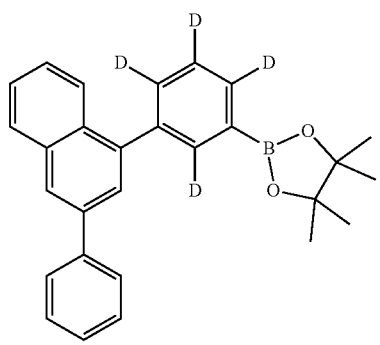 | Sub 1-8 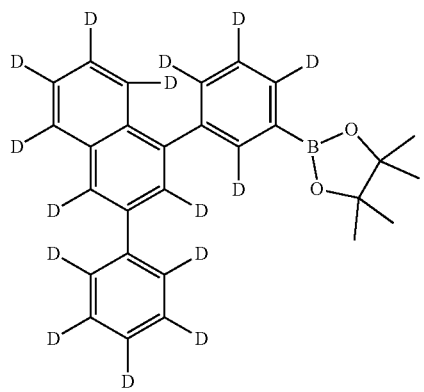 |

TABLE 1

| Compound | FD-MS | compound | FD-MS |
|---|---|---|---|
| Sub1-1 | m/z = 406.21($C_{28}H_{27}BO_2$ = 406.33) | Sub1-2 | m/z = 411.24($C_{28}H_{22}D_5BO_2$ = 411.36) |
| Sub1-3 | m/z = 412.25($C_{28}H_{21}D_6BO_2$ = 412.37) | Sub1-4 | m/z = 410.24($C_{28}H_{23}D_4BO_2$ = 410.36) |
| Sub1-5 | m/z = 415.27($C_{28}H_{18}D_9BO_2$ = 415.39) | Sub1-6 | m/z = 416.27($C_{28}H_{17}D_{10}BO_2$ = 416.39) |
| Sub1-7 | m/z = 417.28($C_{28}H_{16}D_{11}BO_2$ = 417.4) | Sub1-8 | m/z = 421.3($C_{28}H_{12}D_{15}BO_2$ = 421.42) |

Sub 2 in Reaction Scheme 1 may be the following compound, but is not limited thereto, and the FD-MS (Field Desorption-Mass Spectrometry) values of the compounds belonging to Sub 2 are shown in Table 2.

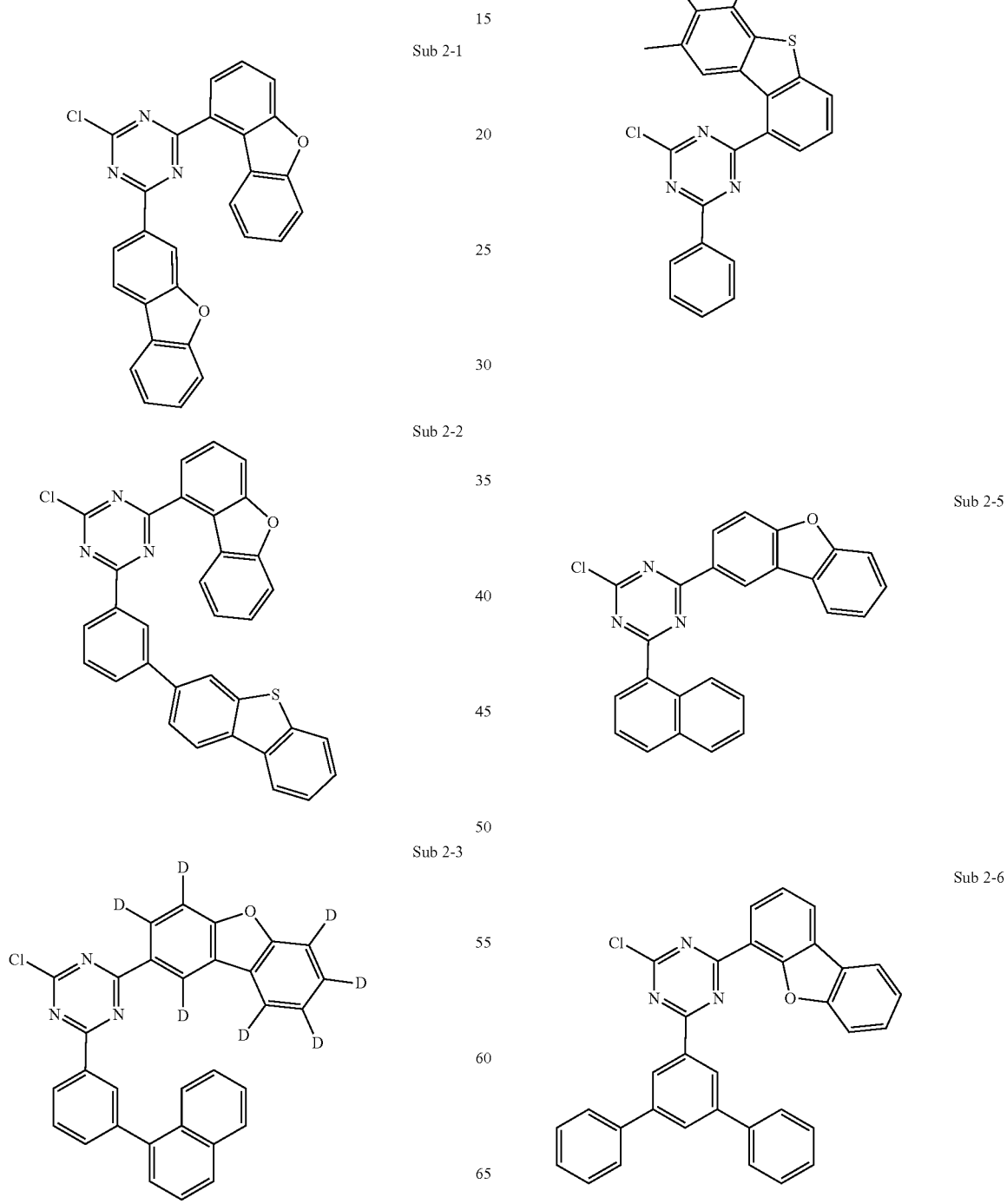

Sub 2-7
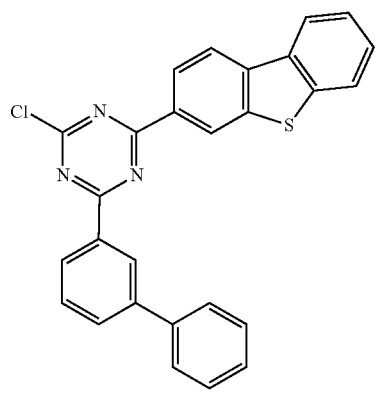
Sub 2-8
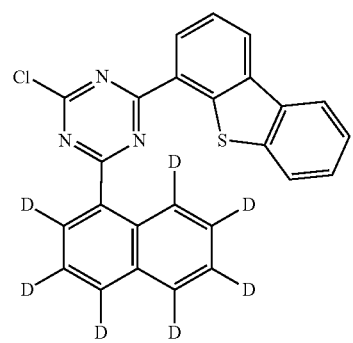
Sub 2-9
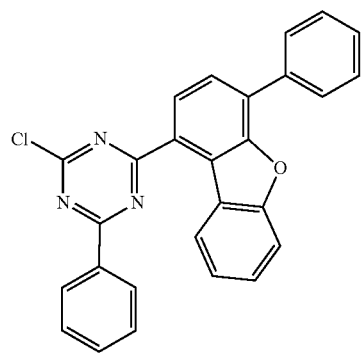
Sub 2-10
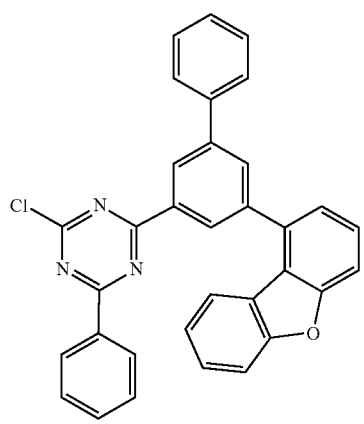
Sub 2-11
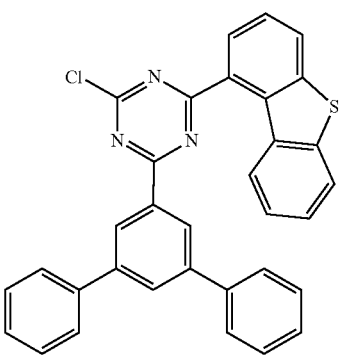
Sub 2-12
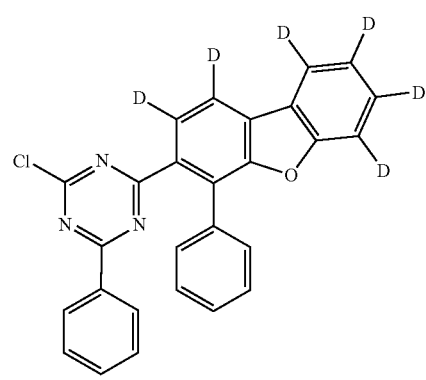
Sub 2-13
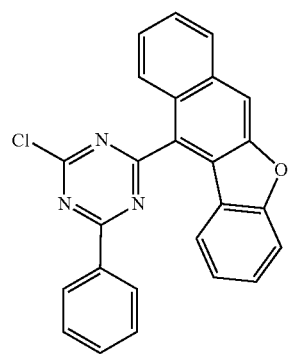
Sub 2-14
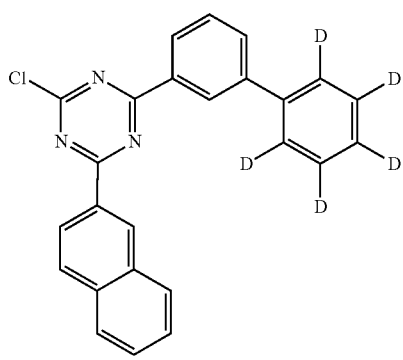

Sub 2-15
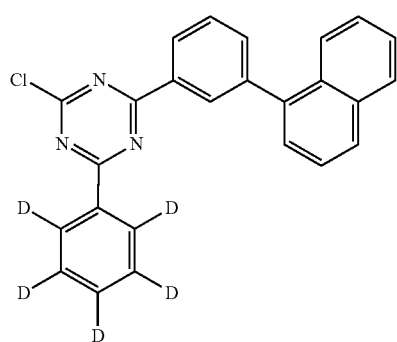
Sub 2-16
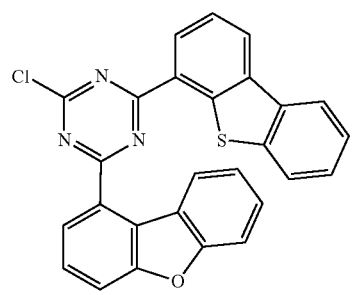
Sub 2-17
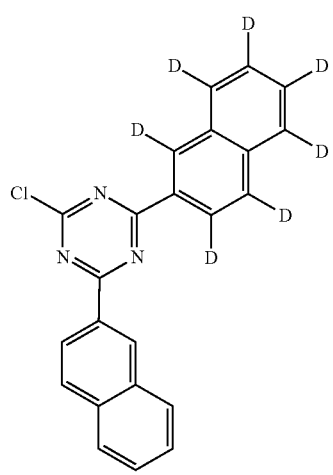
Sub 2-18
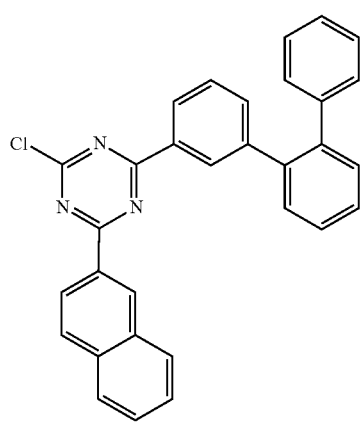
Sub 2-19
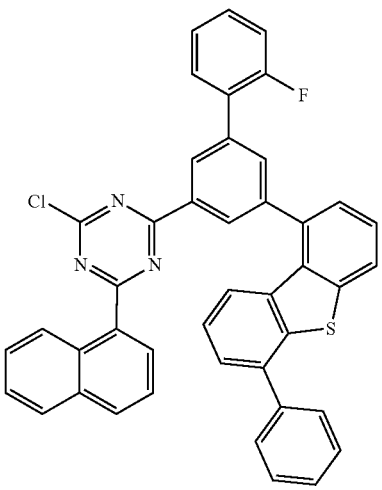
Sub 2-20
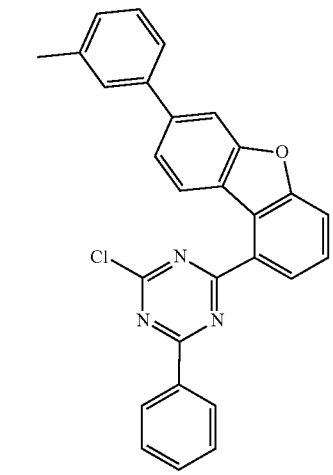
Sub 2-21
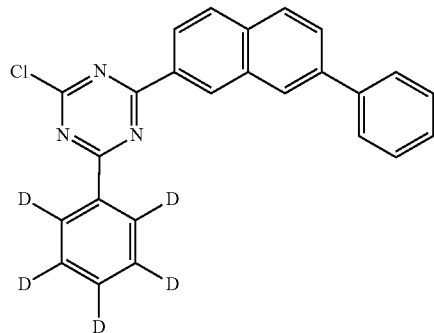
Sub 2-22
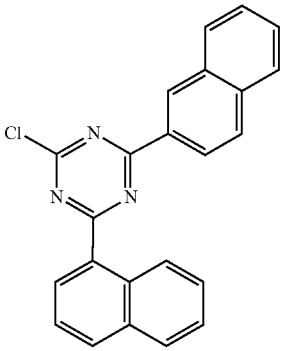

Sub 2-23

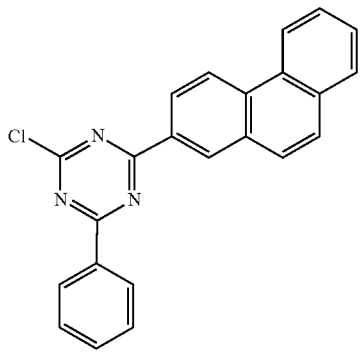

Sub 2-24

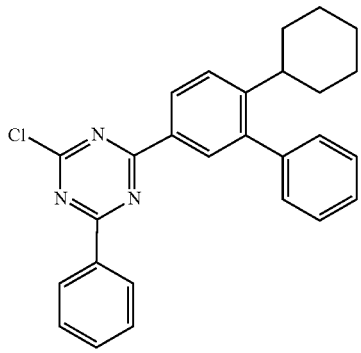

TABLE 2

| Compound | FD-MS | Compound | FD-MS |
| --- | --- | --- | --- |
| Sub2-1 | m/z = 447.08($C_{27}H_{14}ClN_3O_2$ = 447.88) | Sub2-2 | m/z = 539.09($C_{33}H_{18}ClN_3OS$ = 540.04) |
| Sub2-3 | m/z = 490.16($C_{31}H_{11}D_7ClN_3O$ = 491) | Sub2-4 | m/z = 437.08($C_{26}H_{16}ClN_3S$ = 437.95) |
| Sub2-5 | m/z = 407.08($C_{25}H_{14}ClN_3O$ = 407.86) | Sub2-6 | m/z = 509.13($C_{33}H_{20}ClN_3O$ = 509.99) |
| Sub2-7 | m/z = 449.08($C_{27}H_{16}ClN_3S$ = 449.96) | Sub2-8 | m/z = 430.1($C_{25}H_7D_7ClN_3S$ = 430.96) |
| Sub2-9 | m/z = 433.1($C_{27}H_{16}ClN_3O$ = 433.9) | Sub2-10 | m/z = 509.13($C_{33}H_{20}ClN_3O$ = 509.99) |
| Sub2-11 | m/z = 525.11($C_{33}H_{20}ClN_3S$ = 526.05) | Sub2-12 | m/z = 439.14($C_{27}H_{10}D_6ClN_3O$ = 439.93) |
| Sub2-13 | m/z = 407.08($C_{25}H_{14}ClN_3O$ = 407.86) | Sub2-14 | m/z = 398.13($C_{25}H_{11}D_5ClN_3$ = 398.9) |
| Sub2-15 | m/z = 398.13($C_{25}H_{11}D_5ClN_3$ = 398.9) | Sub2-16 | m/z = 463.05($C_{27}H_{14}ClN_3OS$ = 463.94) |
| Sub2-17 | m/z = 374.13($C_{23}H_7D_7ClN_3$ = 374.88) | Sub2-18 | m/z = 469.13($C_{31}H_{20}ClN_3$ = 469.97) |
| Sub2-19 | m/z = 669.14($C_{43}H_{25}ClFN_3S$ = 670.2) | Sub2-20 | m/z = 447.11($C_{28}H_{18}ClN_3O$ = 447.92) |
| Sub2-21 | m/z = 398.13($C_{25}H_{11}D_5ClN_3$ = 398.9) | Sub2-22 | m/z = 367.09($C_{23}H_{14}ClN_3$ = 367.84) |
| Sub2-23 | m/z = 367.09($C_{23}H_{14}ClN_3$ = 367.84) | Sub2-24 | m/z = 425.17($C_{27}H_{24}ClN_3$ = 425.96) |

The FD-MS (Field Desorption-Mass Spectrometry) values of compounds P-1 to P-96 of the present invention prepared according to the above synthesis examples are shown in Table 3.

TABLE 3

| Compound | FD-MS | Compound | FD-MS |
| --- | --- | --- | --- |
| P-1 | m/z = 691.23($C_{49}H_{29}N_3O_2$ = 691.79) | P-2 | m/z = 783.23($C_{55}H_{33}N_3OS$ = 783.95) |
| P-3 | m/z = 707.2($C_{49}H_{29}N_3OS$ = 707.85) | P-4 | m/z = 783.23($C_{55}H_{33}N_3OS$ = 783.95) |
| P-5 | m/z = 727.26($C_{53}H_{33}N_3O$ = 727.87) | P-6 | m/z = 734.31($C_{53}H_{26}D_7N_3O$ = 734.91) |
| P-7 | m/z = 757.3($C_{55}H_{31}D_4N_3O$ = 757.93) | P-8 | m/z = 707.2($C_{49}H_{29}N_3OS$ = 707.85) |
| P-9 | m/z = 601.22($C_{43}H_{27}N_3O$ = 601.71) | P-10 | m/z = 657.27($C_{47}H_{23}D_6N_3O$ = 657.81) |
| P-11 | m/z = 677.25($C_{49}H_{31}N_3O$ = 677.81) | P-12 | m/z = 753.28($C_{55}H_{35}N_3O$ = 753.9) |
| P-13 | m/z = 617.19($C_{43}H_{27}N_3S$ = 617.77) | P-14 | m/z = 728.29($C_{51}H_{20}D_{11}N_3S$ = 728.96) |
| P-15 | m/z = 693.22($C_{49}H_{31}N_3S$ = 693.87) | P-16 | m/z = 674.25($C_{47}H_{22}D_7N_3S$ = 674.87) |
| P-17 | m/z = 682.28($C_{49}H_{26}D_5N_3O$ = 682.84) | P-18 | m/z = 727.26($C_{53}H_{33}N_3O$ = 727.87) |
| P-19 | m/z = 683.28($C_{49}H_{25}D_6N_3O$ = 683.84) | P-20 | m/z = 677.25($C_{49}H_{31}N_3O$ = 677.81) |
| P-21 | m/z = 698.26($C_{49}H_{26}D_5N_3S$ = 698.9) | P-22 | m/z = 743.24($C_{53}H_{33}N_3S$ = 743.93) |
| P-23 | m/z = 693.22($C_{49}H_{31}N_3S$ = 693.87) | P-24 | m/z = 693.22($C_{49}H_{31}N_3S$ = 693.87) |
| P-25 | m/z = 753.28($C_{55}H_{35}N_3O$ = 753.9) | P-26 | m/z = 727.26($C_{53}H_{33}N_3O$ = 727.87) |
| P-27 | m/z = 769.26($C_{55}H_{35}N_3S$ = 769.97) | P-28 | m/z = 697.25($C_{49}H_{27}D_4N_3S$ = 697.89) |

TABLE 3-continued

| Compound | FD-MS | Compound | FD-MS |
|---|---|---|---|
| P-29 | m/z = 727.26($C_{53}H_{33}N_3O$ = 727.87) | P-30 | m/z = 733.3($C_{53}H_{27}D_6N_3O$ = 733.9) |
| P-31 | m/z = 743.24($C_{53}H_{33}N_3S$ = 743.93) | P-32 | m/z = 769.26($C_{55}H_{35}N_3S$ = 769.97) |
| P-33 | m/z = 667.21($C_{47}H_{29}N_3S$ = 667.83) | P-34 | m/z = 660.29($C_{47}H_{20}D_9N_3O$ = 660.82) |
| P-35 | m/z = 701.25($C_{51}H_{31}N_3O$ = 701.83) | P-36 | m/z = 651.23($C_{47}H_{29}N_3O$ = 651.77) |
| P-37 | m/z = 677.25($C_{49}H_{31}N_3O$ = 677.81) | P-38 | m/z = 727.26($C_{53}H_{33}N_3O$ = 727.87) |
| P-39 | m/z = 743.24($C_{53}H_{33}N_3S$ = 743.93) | P-40 | m/z = 769.26($C_{55}H_{35}N_3S$ = 769.97) |
| P-41 | m/z = 651.23($C_{47}H_{29}N_3O$ = 651.77) | P-42 | m/z = 743.24($C_{53}H_{33}N_3S$ = 743.93) |
| P-43 | m/z = 717.22($C_{51}H_{31}N_3S$ = 717.89) | P-44 | m/z = 681.22($C_{48}H_{31}N_3S$ = 681.86) |
| P-45 | m/z = 511.2($C_{37}H_{25}N_3$ = 511.63) | P-46 | m/z = 561.22($C_{41}H_{27}N_3$ = 561.69) |
| P-47 | m/z = 561.22($C_{41}H_{27}N_3$ = 561.69) | P-48 | m/z = 620.29($C_{45}H_{20}D_9N_3$ = 620.8) |
| P-49 | m/z = 623.31($C_{45}H_{17}D_{12}N_3$ = 623.82) | P-50 | m/z = 626.33($C_{45}H_{14}D_{15}N_3$ = 626.84) |
| P-51 | m/z = 611.24($C_{45}H_{29}N_3$ = 611.75) | P-52 | m/z = 661.25($C_{49}H_{31}N_3$ = 661.81) |
| P-53 | m/z = 663.27($C_{49}H_{33}N_3$ = 663.82) | P-54 | m/z = 646.31($C_{47}H_{22}D_9N_3$ = 646.84) |
| P-55 | m/z = 646.31($C_{47}H_{22}D_9N_3$ = 646.84) | P-56 | m/z = 587.24($C_{43}H_{29}N_3$ = 587.73) |
| P-57 | m/z = 637.25($C_{47}H_{31}N_3$ = 637.79) | P-58 | m/z = 642.28($C_{47}H_{26}D_5N_3$ = 642.82) |
| P-59 | m/z = 611.24($C_{45}H_{29}N_3$ = 611.75) | P-60 | m/z = 643.29($C_{47}H_{25}D_6N_3$ = 643.82) |
| P-61 | m/z = 713.28($C_{53}H_{35}N_3$ = 713.88) | P-62 | m/z = 687.27($C_{51}H_{33}N_3$ = 687.85) |
| P-63 | m/z = 694.31($C_{51}H_{26}D_7N_3$ = 694.89) | P-64 | m/z = 637.25($C_{47}H_{31}N_3$ = 637.79) |
| P-65 | m/z = 687.27($C_{51}H_{33}N_3$ = 687.85) | P-66 | m/z = 611.24($C_{45}H_{29}N_3$ = 611.75) |
| P-67 | m/z = 637.25($C_{47}H_{31}N_3$ = 637.79) | P-68 | m/z = 687.27($C_{51}H_{33}N_3$ = 687.85) |
| P-69 | m/z = 637.25($C_{47}H_{31}N_3$ = 637.79) | P-70 | m/z = 642.28($C_{47}H_{26}D_5N_3$ = 642.82) |
| P-71 | m/z = 687.27($C_{51}H_{33}N_3$ = 687.85) | P-72 | m/z = 687.27($C_{51}H_{33}N_3$ = 687.85) |
| P-73 | m/z = 642.28($C_{47}H_{26}D_5N_3$ = 642.82) | P-74 | m/z = 637.25($C_{47}H_{31}N_3$ = 637.79) |
| P-75 | m/z = 713.28($C_{53}H_{35}N_3$ = 713.88) | P-76 | m/z = 687.27($C_{51}H_{33}N_3$ = 687.85) |
| P-77 | m/z = 687.27($C_{51}H_{33}N_3$ = 687.85) | P-78 | m/z = 687.27($C_{51}H_{33}N_3$ = 687.85) |
| P-79 | m/z = 661.25($C_{49}H_{31}N_3$ = 661.81) | P-80 | m/z = 663.27($C_{49}H_{33}N_3$ = 663.82) |
| P-81 | m/z = 713.28($C_{53}H_{35}N_3$ = 713.88) | P-82 | m/z = 713.28($C_{53}H_{35}N_3$ = 713.88) |
| P-83 | m/z = 797.34($C_{58}H_{43}N_3O$ = 798) | P-84 | m/z = 913.29($C_{65}H_{40}FN_3S$ = 914.11) |
| P-85 | m/z = 761.23($C_{53}H_{32}FN_3S$ = 761.92) | P-86 | m/z = 795.36($C_{59}H_{45}N_3$ = 796.03) |
| P-87 | m/z = 812.3($C_{58}H_{32}D_5N_3S$ = 813.05) | P-88 | m/z = 729.31($C_{54}H_{39}N_3$ = 729.93) |
| P-89 | m/z = 845.29($C_{61}H_{39}N_3S$ = 846.06) | P-90 | m/z = 673.34($C_{49}H_{35}N_3D_4$ = 673.9) |
| P-91 | m/z = 691.26($C_{50}H_{33}N_3O$ = 691.83) | P-92 | m/z = 738.28($C_{54}H_{34}N_4$ = 738.89) |
| P-93 | m/z = 713.28($C_{53}H_{35}N_3$ = 713.88) | P-94 | m/z = 795.36($C_{59}H_{45}N_3$ = 796.03) |
| P-95 | m/z = 769.26($C_{55}H_{35}N_3S$ = 769.97) | P-96 | m/z = 667.29($C_{49}H_{29}D_4N_3$ = 667.85) |

Compounds represented by Formula 4 or Formula 5 may be prepared by referring to known synthetic methods (named reactions) or published patent publications, for example, Korean Patent Registration No. 10-2395819, U.S. Patent Publication No. 2023-0129535, etc., but are not limited thereto.

Meanwhile, the FD-MS values of the compounds H-1 to H-124 and S-1 to S-116 of the present invention are shown in Tables 4 and 5.

TABLE 4

| Compound | FD-MS | Compound | FD-MS |
|---|---|---|---|
| H-1 | m/z = 487.19($C_{36}H_{25}NO$ = 487.6) | H-2 | m/z = 553.19($C_{40}H_{27}NS$ = 553.72) |
| H-3 | m/z = 563.26($C_{43}H_{33}N$ = 563.74) | H-4 | m/z = 602.27($C_{45}H_{34}N_2$ = 602.78) |
| H-5 | m/z = 517.15($C_{36}H_{23}NOS$ = 517.65) | H-6 | m/z = 603.2($C_{44}H_{29}NS$ = 603.78) |
| H-7 | m/z = 735.29($C_{57}H_{37}N$ = 735.93) | H-8 | m/z = 562.24($C_{42}H_{30}N_2$ = 562.72) |
| H-9 | m/z = 565.17($C_{40}H_{23}NO_3$ = 565.63) | H-10 | m/z = 581.14($C_{40}H_{23}NO_2S$ = 581.69) |
| H-11 | m/z = 823.24($C_{59}H_{37}NS_2$ = 824.07) | H-12 | m/z = 727.3($C_{54}H_{37}N_3$ = 727.91) |
| H-13 | m/z = 627.22($C_{46}H_{29}NO_2$ = 627.74) | H-14 | m/z = 633.16($C_{44}H_{27}NS_2$ = 633.83) |
| H-15 | m/z = 675.29($C_{52}H_{37}N$ = 675.88) | H-16 | m/z = 678.3($C_{51}H_{38}N_2$ = 678.88) |
| H-17 | m/z = 669.21($C_{48}H_{31}NOS$ = 669.84) | H-18 | m/z = 785.22($C_{56}H_{35}NS_2$ = 786.02) |
| H-19 | m/z = 617.18($C_{44}H_{27}NOS$ = 617.77) | H-20 | m/z = 601.2($C_{44}H_{27}NO_2$ = 601.71) |
| H-21 | m/z = 779.32($C_{59}H_{41}NO$ = 779.98) | H-22 | m/z = 583.23($C_{42}H_{33}NS$ = 583.79) |
| H-23 | m/z = 679.32($C_{52}H_{41}N$ = 679.91) | H-24 | m/z = 726.27($C_{54}H_{34}N_2O$ = 726.88) |
| H-25 | m/z = 593.18($C_{42}H_{27}NOS$ = 593.74) | H-26 | m/z = 774.22($C_{54}H_{34}N_2S_2$ = 775) |
| H-27 | m/z = 557.24($C_{40}H_{31}NO_2$ = 557.69) | H-28 | m/z = 652.25($C_{48}H_{32}N_2O$ = 652.8) |
| H-29 | m/z = 619.29($C_{46}H_{37}NO$ = 619.81) | H-30 | m/z = 603.2($C_{44}H_{29}NS$ = 603.78) |
| H-31 | m/z = 813.3($C_{62}H_{39}NO$ = 814) | H-32 | m/z = 784.29($C_{57}H_{40}N_2S$ = 785.02) |
| H-33 | m/z = 577.2($C_{42}H_{27}NO_2$ = 577.68) | H-34 | m/z = 607.14($C_{42}H_{25}NS_2$ = 607.79) |
| H-35 | m/z = 801.34($C_{62}H_{43}N$ = 802.03) | H-36 | m/z = 575.24($C_{42}H_{29}N_3$ = 575.72) |
| H-37 | m/z = 577.2($C_{42}H_{27}NO_2$ = 577.68) | H-38 | m/z = 607.14($C_{42}H_{25}NS_2$ = 607.79) |
| H-39 | m/z = 801.34($C_{62}H_{43}N$ = 802.03) | H-40 | m/z = 575.24($C_{42}H_{29}N_3$ = 575.72) |
| H-41 | m/z = 601.2($C_{44}H_{27}NO_2$ = 601.71) | H-42 | m/z = 471.11($C_{31}H_{21}NS_2$ = 471.64) |
| H-43 | m/z = 675.29($C_{52}H_{37}N$ = 675.88) | H-44 | m/z = 727.3($C_{54}H_{37}N_3$ = 727.91) |
| H-45 | m/z = 603.2($C_{44}H_{29}NS$ = 603.78) | H-46 | m/z = 561.16($C_{38}H_{27}NS_2$ = 561.76) |
| H-47 | m/z = 799.32($C_{62}H_{41}N$ = 800.02) | H-48 | m/z = 702.27($C_{52}H_{34}N_2O$ = 702.86) |
| H-49 | m/z = 729.27($C_{54}H_{35}NO_2$ = 729.88) | H-50 | m/z = 785.22($C_{56}H_{35}NS_2$ = 786.02) |

TABLE 4-continued

| Compound | FD-MS | Compound | FD-MS |
|---|---|---|---|
| H-51 | m/z = 812.32($C_{62}H_{40}N_2$ = 813.02) | H-52 | m/z = 681.22($C_{48}H_{31}N_3S$ = 681.86) |
| H-53 | m/z = 615.18($C_{44}H_{25}NO_3$ = 615.69) | H-54 | m/z = 763.15($C_{52}H_{29}NS_3$ = 763.99) |
| H-55 | m/z = 593.31($C_{45}H_{39}N$ = 593.81) | H-56 | m/z = 840.33($C_{62}H_{40}N_4$ = 841.03) |
| H-57 | m/z = 657.18($C_{46}H_{27}NO_2S$ = 657.79) | H-58 | m/z = 824.23($C_{58}H_{36}N_2S_2$ = 825.06) |
| H-59 | m/z = 1195.42($C_{91}H_{57}NS$ = 1196.52) | H-60 | m/z = 656.19($C_{46}H_{28}N_2OS$ = 656.8) |
| H-61 | m/z = 607.16($C_{42}H_{25}NO_2S$ = 607.73) | H-62 | m/z = 773.2($C_{54}H_{31}NO_3S$ = 773.91) |
| H-63 | m/z = 1013.4($C_{79}H_{51}N$ = 1014.28) | H-64 | m/z = 758.24($C_{54}H_{34}N_2OS$ = 758.94) |
| H-65 | m/z = 623.14($C_{42}H_{25}NOS_2$ = 623.79) | H-66 | m/z = 763.16($C_{52}H_{29}NO_2S_2$ = 763.93) |
| H-67 | m/z = 799.2($C_{56}H_{33}NOS_2$ = 800.01) | H-68 | m/z = 743.23($C_{54}H_{33}NOS$ = 743.92) |
| H-69 | m/z = 872.25($C_{62}H_{36}N_2O_2S$ = 873.04) | H-70 | m/z = 772.22($C_{54}H_{32}N_2O_2S$ = 772.92) |
| H-71 | m/z = 830.28($C_{61}H_{38}N_2S$ = 831.05) | H-72 | m/z = 808.25($C_{58}H_{33}FN_2O_2$ = 808.91) |
| H-73 | m/z = 929.21($C_{64}H_{35}NO_3S_2$ = 930.11) | H-74 | m/z = 963.27($C_{68}H_{41}N_3S_2$ = 964.22) |
| H-75 | m/z = 809.24($C_{58}H_{35}NO_2S$ = 809.98) | H-76 | m/z = 893.29($C_{66}H_{39}NO_3$ = 894.04) |
| H-77 | m/z = 794.28($C_{58}H_{38}N_2S$ = 795.02) | H-78 | m/z = 900.26($C_{64}H_{40}N_2S_2$ = 901.16) |
| H-79 | m/z = 758.28($C_{55}H_{38}N_2S$ = 758.98) | H-80 | m/z = 1082.37($C_{81}H_{50}N_2S$ = 1083.37) |
| H-81 | m/z = 573.25($C_{44}H_{31}N$ = 573.74) | H-82 | m/z = 649.28($C_{50}H_{35}N$ = 649.84) |
| H-83 | m/z = 699.29($C_{54}H_{37}N$ = 699.9) | H-84 | m/z = 699.29($C_{54}H_{37}N$ = 699.9) |
| H-85 | m/z = 673.28($C_{52}H_{35}N$ = 673.86) | H-86 | m/z = 649.28($C_{50}H_{35}N$ = 649.84) |
| H-87 | m/z = 625.28($C_{48}H_{35}N$ = 625.82) | H-88 | m/z = 673.28($C_{52}H_{35}N$ = 673.86) |
| H-89 | m/z = 773.31($C_{60}H_{39}N$ = 773.98) | H-90 | m/z = 749.31($C_{58}H_{39}N$ = 749.96) |
| H-91 | m/z = 699.29($C_{54}H_{37}N$ = 699.9) | H-92 | m/z = 599.26($C_{46}H_{33}N$ = 599.78) |
| H-93 | m/z = 639.26($C_{48}H_{33}NO$ = 639.8) | H-94 | m/z = 765.25($C_{57}H_{35}NS$ = 765.97) |
| H-95 | m/z = 677.31($C_{52}H_{39}N$ = 677.89) | H-96 | m/z = 727.3($C_{54}H_{37}N_3$ = 727.91) |
| H-97 | m/z = 552.18($C_{39}H_{24}N_2O_2$ = 552.63) | H-98 | m/z = 628.22($C_{45}H_{28}N_2O_2$ = 628.73) |
| H-99 | m/z = 614.24($C_{45}H_{30}N_2O$ = 614.75) | H-100 | m/z = 614.24($C_{45}H_{30}N_2O$ = 614.75) |
| H-101 | m/z = 691.21($C_{50}H_{29}NO_3$ = 691.79) | H-102 | m/z = 739.29($C_{56}H_{37}NO$ = 739.92) |
| H-103 | m/z = 673.15($C_{46}H_{27}NOS_2$ = 673.85) | H-104 | m/z = 726.27($C_{54}H_{34}N_2O$ = 726.88) |
| H-105 | m/z = 617.18($C_{44}H_{27}NOS$ = 617.77) | H-106 | m/z = 611.22($C_{46}H_{29}NOS$ = 611.74) |
| H-107 | m/z = 769.24($C_{56}H_{35}NOS$ = 769.96) | H-108 | m/z = 701.28($C_{52}H_{35}N_3$ = 701.87) |
| H-109 | m/z = 527.22($C_{39}H_{29}NO$ = 527.67) | H-110 | m/z = 643.2($C_{46}H_{29}NOS$ = 643.8) |
| H-111 | m/z = 593.18($C_{42}H_{27}NOS$ = 593.74) | H-112 | m/z = 726.27($C_{54}H_{34}N_2O$ = 726.88) |
| H-113 | m/z = 726.27($C_{54}H_{34}N_2O$ = 726.88) | H-114 | m/z = 558.14($C_{37}H_{22}N_2O_2S$ = 558.65) |
| H-115 | m/z = 620.19($C_{43}H_{28}N_2OS$ = 620.77) | H-116 | m/z = 686.27($C_{52}H_{34}N_2$ = 686.86) |
| H-117 | m/z = 718.24($C_{52}H_{34}N_2S$ = 718.92) | H-118 | m/z = 728.28($C_{54}H_{36}N_2O$ = 728.89) |
| H-119 | m/z = 592.2($C_{42}H_{28}N_2S$ = 592.76) | H-120 | m/z = 756.22($C_{54}H_{32}N_2OS$ = 756.92) |
| H-121 | m/z = 547.70($C_{42}H_{29}N$ = 547.70) | H-122 | m/z = 672.28($C_{49}H_{24}D_7NO_2$ = 672.83) |
| H-123 | m/z = 626.28($C_{48}H_{26}D_5N$ = 558.75) | H-124 | m/z = 558.22($C_{40}H_{22}D_5NS$ = 558.75) |

TABLE 5

| Compound | FD-MS | Compound | FD-MS |
|---|---|---|---|
| S-1 | m/z = 408.16($C_{30}H_{29}N_2$ = 408.5) | S-2 | m/z = 534.21($C_{40}H_{26}N_2$ = 534.66) |
| S-3 | m/z = 560.23($C_{42}H_{28}N_2$ = 560.7) | S-4 | m/z = 584.23($C_{44}H_{28}N_2$ = 584.72) |
| S-5 | m/z = 560.23($C_{42}H_{28}N_2$ = 560.7) | S-6 | m/z = 634.24($C_{48}H_{30}N_2$ = 634.78) |
| S-7 | m/z = 610.24($C_{46}H_{30}N_2$ = 610.76) | S-8 | m/z = 498.17($C_{36}H_{22}N_2O$ = 498.59) |
| S-9 | m/z = 574.2($C_{42}H_{26}N_2O$ = 574.68) | S-10 | m/z = 660.26($C_{50}H_{32}N_2$ = 660.82) |
| S-11 | m/z = 686.27($C_{52}H_{34}N_2$ = 686.86) | S-12 | m/z = 620.14($C_{42}H_{24}N_2S_2$ = 620.79) |
| S-13 | m/z = 640.2($C_{46}H_{28}N_2S$ = 640.8) | S-14 | m/z = 560.23($C_{42}H_{28}N_2$ = 560.7) |
| S-15 | m/z = 558.21($C_{42}H_{26}N_2$ = 558.68) | S-16 | m/z = 548.19($C_{40}H_{24}N_2O$ = 548.65) |
| S-17 | m/z = 573.22($C_{42}H_{27}N_3$ = 573.7) | S-18 | m/z = 564.17($C_{40}H_{24}N_2S$ = 564.71) |
| S-19 | m/z = 574.2($C_{42}H_{26}N_2O$ = 574.68) | S-20 | m/z = 564.17($C_{40}H_{24}N_2S$ = 564.71) |
| S-21 | m/z = 564.17($C_{40}H_{24}N_2S$ = 564.71) | S-22 | m/z = 813.31($C_{61}H_{39}N_3$ = 814) |
| S-23 | m/z = 696.26($C_{53}H_{32}N_2$ = 696.85) | S-24 | m/z = 691.23($C_{49}H_{29}N_3O_2$ = 691.79) |
| S-25 | m/z = 710.27($C_{54}H_{34}N_2$ = 710.88) | S-26 | m/z = 610.24($C_{46}H_{30}N_2$ = 610.76) |
| S-27 | m/z = 670.15($C_{46}H_{26}N_2S_2$ = 670.85) | S-28 | m/z = 640.29($C_{48}H_{36}N_2$ = 640.83) |
| S-29 | m/z = 598.2($C_{44}H_{26}N_2O$ = 598.71) | S-30 | m/z = 623.24($C_{46}H_{29}N_3$ = 623.76) |
| S-31 | m/z = 458.18($C_{34}H_{22}N_2$ = 458.56) | S-32 | m/z = 548.19($C_{40}H_{24}N_2O$ = 548.65) |
| S-33 | m/z = 508.19($C_{38}H_{24}N_2$ = 508.62) | S-34 | m/z = 508.19($C_{38}H_{24}N_2$ = 508.62) |
| S-35 | m/z = 623.24($C_{46}H_{29}N_3$ = 623.76) | S-36 | m/z = 564.17($C_{40}H_{24}N_2S$ = 564.71) |
| S-37 | m/z = 627.2($C_{46}H_{29}NS$ = 627.81) | S-38 | m/z = 505.1($C_{34}H_{19}NS_2$ = 505.65) |
| S-39 | m/z = 514.15($C_{36}H_{22}N_2S$ = 514.65) | S-40 | m/z = 575.17($C_{42}H_{25}NS$ = 575.73) |
| S-41 | m/z = 642.21($C_{46}H_{30}N_2S$ = 642.82) | S-42 | m/z = 575.17($C_{42}H_{25}NS$ = 575.73) |
| S-43 | m/z = 606.18($C_{42}H_{26}N_2OS$ = 606.74) | S-44 | m/z = 575.17($C_{42}H_{25}NS$ = 575.73) |
| S-45 | m/z = 551.17($C_{40}H_{25}NS$ = 551.71) | S-46 | m/z = 607.14($C_{42}H_{25}NS_2$ = 607.79) |
| S-47 | m/z = 525.16($C_{38}H_{23}NS$ = 525.67) | S-48 | m/z = 642.21($C_{46}H_{30}N_2S$ = 642.82) |
| S-49 | m/z = 548.19($C_{40}H_{24}N_2O$ = 548.65) | S-50 | m/z = 473.14($C_{34}H_{19}NO_2$ = 473.53) |
| S-51 | m/z = 566.15($C_{39}H_{22}N_2OS$ = 566.68) | S-52 | m/z = 459.16($C_{34}H_{21}NO$ = 459.55) |
| S-53 | m/z = 473.14($C_{34}H_{19}NO_2$ = 473.53) | S-54 | m/z = 523.16($C_{38}H_{21}NO_2$ = 523.59) |
| S-55 | m/z = 539.13($C_{38}H_{21}NOS$ = 539.65) | S-56 | m/z = 548.19($C_{40}H_{24}N_2O$ = 548.65) |
| S-57 | m/z = 489.12($C_{34}H_{19}NOS$ = 489.59) | S-58 | m/z = 545.09($C_{36}H_{19}NOS_2$ = 545.67) |
| S-59 | m/z = 549.17($C_{40}H_{23}NO_2$ = 549.63) | S-60 | m/z = 565.15($C_{40}H_{23}NOS$ = 565.69) |
| S-61 | m/z = 523.16($C_{38}H_{21}NO_2$ = 523.59) | S-62 | m/z = 598.2($C_{44}H_{26}N_2O$ = 598.71) |
| S-63 | m/z = 539.13($C_{38}H_{21}NOS$ = 539.65) | S-64 | m/z = 589.15($C_{42}H_{23}NOS$ = 589.71) |
| S-65 | m/z = 498.17($C_{36}H_{22}N_2O$ = 498.59) | S-66 | m/z = 509.18($C_{38}H_{23}NO$ = 509.61) |

TABLE 5-continued

| Compound | FD-MS | Compound | FD-MS |
|---|---|---|---|
| S-67 | m/z = 548.19($C_{40}H_{24}N_2O$ = 548.65) | S-68 | m/z = 549.17($C_{40}H_{23}NO_2$ = 549.63) |
| S-69 | m/z = 449.12($C_{32}H_{19}NS$ = 449.57) | S-70 | m/z = 439.1($C_{30}H_{17}NOS$ = 439.53) |
| S-71 | m/z = 647.22($C_{49}H_{29}NO$ = 647.78) | S-72 | m/z = 717.28($C_{52}H_{35}N_3O$ = 717.87) |
| S-73 | m/z = 459.16($C_{34}H_{21}NO$ = 459.55) | S-74 | m/z = 533.18($C_{40}H_{23}NO$ = 533.63) |
| S-75 | m/z = 525.16($C_{38}H_{23}NS$ = 525.67) | S-76 | m/z = 564.17($C_{40}H_{24}N_2S$ = 564.71) |
| S-77 | m/z = 575.19($C_{42}H_{25}NO_2$ = 575.67) | S-78 | m/z = 663.22($C_{49}H_{29}NO$ = 663.78) |
| S-79 | m/z = 647.22($C_{49}H_{29}NO$ = 647.78) | S-80 | m/z = 496.16($C_{36}H_{20}N_2O$ = 496.57) |
| S-81 | m/z = 565.15($C_{40}H_{23}NOS$ = 565.69) | S-82 | m/z = 505.1($C_{34}H_{19}NS_2$ = 505.65) |
| S-83 | m/z = 765.25($C_{56}H_{35}NOSi$ = 765.99) | S-84 | m/z = 615.17($C_{44}H_{25}NOS$ = 615.75) |
| S-85 | m/z = 603.17($C_{43}H_{25}NOS$ = 603.74) | S-86 | m/z = 772.29($C_{59}H_{36}N_2$ = 772.95) |
| S-87 | m/z = 802.33($C_{61}H_{42}N_2$ = 803.02) | S-88 | m/z = 607.23($C_{47}H_{29}N$ = 607.76) |
| S-89 | m/z = 524.23($C_{39}H_{28}N_2$ = 524.67) | S-90 | m/z = 665.22($C_{49}H_{31}NS$ = 665.85) |
| S-91 | m/z = 633.25($C_{49}H_{31}N$ = 633.79) | S-92 | m/z = 775.29($C_{59}H_{37}NO$ = 775.95) |
| S-93 | m/z = 535.23($C_{41}H_{29}N$ = 535.69) | S-94 | m/z = 623.22($C_{47}H_{29}NO$ = 623.76) |
| S-95 | m/z = 687.2($C_{51}H_{29}NS$ = 687.86) | S-96 | m/z = 735.29($C_{57}H_{37}N$ = 735.93) |
| S-97 | m/z = 611.26($C_{47}H_{33}N$ = 611.79) | S-98 | m/z = 679.23($C_{50}H_{33}NS$ = 679.88) |
| S-99 | m/z = 787.32($C_{61}H_{41}N$ = 788.01) | S-100 | m/z = 743.33($C_{55}H_{41}N_3$ = 743.95) |
| S-101 | m/z = 485.21($C_{37}H_{27}N$ = 485.63) | S-102 | m/z = 471.2($C_{36}H_{25}N$ = 471.6) |
| S-103 | m/z = 571.19($C_{43}H_{25}NO$ = 571.68) | S-104 | m/z = 584.23($C_{44}H_{28}N_2$ = 584.72) |
| S-105 | m/z = 539.24($C_{40}H_{21}D_5N_2$ = 539.69) | S-106 | m/z = 453.15($C_{32}H_{15}NS$ = 471.6) |
| S-107 | m/z = 563.26($C_{43}H_{26}D_4NO$ = 563.74) | S-108 | m/z = 589.26($C_{44}H_{23}D_5N_2$ = 584.72) |
| S-109 | m/z = 589.26($C_{44}H_{23}D_5N_2$ = 589.75) | S-110 | m/z = 562.23($C_{42}H_{22}D_4N_2$ = 562.71) |
| S-111 | m/z = 660.26($C_{50}H_{32}N_2$ = 660.82) | S-112 | m/z = 553.22($C_{40}H_{19}D_5N_2O$ = 553.68) |
| S-113 | m/z = 634.24($C_{48}H_{30}N_2$ = 634.78) | S-114 | m/z = 589.26($C_{44}H_{23}D_5N_2$ = 589.75) |
| S-115 | m/z = 588.25($C_{44}H_{24}D_4N_2$ = 588.75) | S-116 | m/z = 513.23($C_{38}H_{19}D_5N_2$ = 513.65) |

Meanwhile, exemplary synthesis examples of the present invention represented by Formula (1), Formula 4, and Formula 5 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), and PPh₃-mediated reductive cyclization reaction (*J. Org. Chem.* 2005, 70, 5014.), and it will be easily understood by those skilled in the art that the reaction proceeds even when other substituents defined in Formula (1), Formula 4, or Formula 5 are bonded in addition to the substituents specified in the specific synthesis examples.

Manufacturing Evaluation of Organic Electronic Elements

Example 1

Red Organic Light Emitting Device
(Phosphorescent Host)

Compound A and Compound B were used on the ITO layer (anode) formed on a glass substrate, and a hole injection layer with a thickness of 10 nm was formed by doping Compound B at a weight ratio of 98:2, and then Compound A was vacuum deposited on the hole injection layer to a thickness of 110 nm to form a hole transport layer. Next, Compound C-R was vacuum deposited to a thickness of 10 nm on the hole transport layer to form an emitting-auxiliary layer. Thereafter, the host material of the emitting layer uses Compound P-1, a compound of the present invention, as the first host, and Compound H-20, a compound of the present invention, as the second host, and a mixture of the first host and the second host in a weight ratio of 5:5 is used, and bis-(1-phenylisoquinolyl)iridium(III) acetylacetonate (hereinafter abbreviated as '(piq)₂Ir(acac)') was used as a dopant material, and an emitting layer with a thickness of 30 nm was formed by doping the dopant so that the weight ratio of the host and the dopant was 95:5.

Next, Compound E is vacuum deposited on the emitting layer to form a hole blocking layer with a thickness of 10 nm, and an electron transport layer with a thickness of 30 nm was formed on the hole blocking layer using a mixture of Compound F and Compound G at a weight ratio of 5:5. Afterwards, Compound G was deposited on the electron transport layer to form an electron injection layer with a thickness of 0.2 nm, and then Al was deposited to form a cathode with a thickness of 150 nm.

Compound A: N-([1,1'-biphenyl]-4-yl)-9,9-dimethyl-N-(4-(9-phenyl-9H-carbazol-3-yl)phenyl)-9H-fluoren-2-amine Compound B: 4,4',4''-((1E,1'E,1''E)-cyclopropane-1,2,3-triylidenetris(cyanomethaneylylidene))tris(2,3,5,6-tetrafluorobenzonitrile)

Compound C-R: $N^7$-(dibenzo[b,d]thiophen-2-yl)-$N^2$,$N^2$, $N^7$-triphenyldibenzo[b,d]thiophene-2,7-diamine Compound E: 2-(4'-(9,9-dimethyl-9H-fluoren-2-yl)-[1,1'-biphenyl]-3-yl)-4,6-diphenyl-1,3,5-triazine Compound F: 2,7-bis(4-(4,6-diphenyl-1,3,5-triazin-2-yl)phenyl)naphthalene Compound G: (8-quinolinolato)lithium Example 2 to Example 36

An organic light emitting device was manufactured in the same manner as in Example 1, except that the compound of the present invention described in Table 6 was used as the host material of the emitting layer.

Comparative Example 1 and Comparative Example 2

An organic light emitting device was manufactured in the same manner as in Example 1, except that Comparative Compound A and Comparative Compound B were used as the first host as the host material of the emitting layer.

[Comparative Compound A]

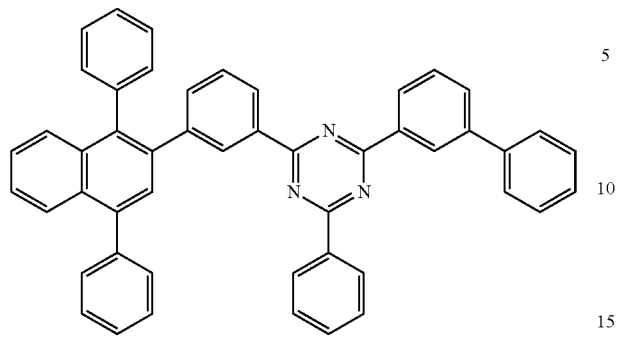

[Comparative Compound B]

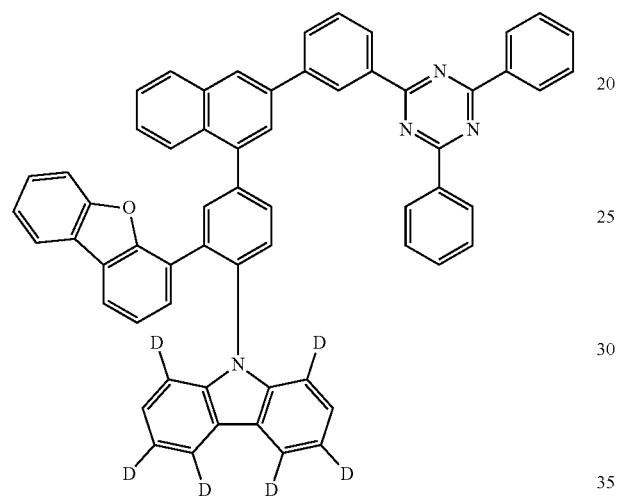

To the organic electroluminescent device manufactured by Examples 1 to 36, Comparative Example 1 and Comparative Example 2 of the present invention, Electroluminescence (EL) characteristics were measured with a PR-650 of Photoresearch Co., by applying a forward bias DC voltage. As a result of the measurement, T95 life was measured at a standard luminance of 2,500 cd/m² through life measuring apparatus manufactured by McScience. Table 6 shows the results of element fabrication and evaluation.

The measuring apparatus can evaluate the performance of new materials compared to comparative compounds under identical conditions, without being affected by possible daily fluctuations in deposition rate, vacuum quality or other parameters.

During the evaluation, one batch contains 4 identically prepared OLEDs including a comparative compound, and the performance of a total of 12 OLEDs is evaluated in 3 batches, so the value of the experimental results obtained in this way indicates statistical significance.

TABLE 6

|  | Frist host | Second host | Voltage | Current Density (mA/cm²) | Brightness (cd/m²) | Efficiency (cd/A) | T(95) |
|---|---|---|---|---|---|---|---|
| comparative example 1 | comparative compound A | H-20 | 5.4 | 11.2 | 2500.0 | 22.3 | 95.8 |
| comparative example 2 | comparative compound B | H-20 | 5.3 | 11.5 | 2500.0 | 21.7 | 90.4 |
| example1 | P-1 | H-20 | 4.2 | 6.9 | 2500.0 | 36.4 | 132.7 |
| example2 | P-5 | H-20 | 4.2 | 6.4 | 2500.0 | 38.9 | 128.8 |
| example3 | P-14 | H-20 | 4.3 | 6.3 | 2500.0 | 39.8 | 129.1 |
| example4 | P-17 | H-20 | 4.2 | 6.4 | 2500.0 | 39.1 | 127.2 |
| example5 | P-25 | H-20 | 4.3 | 6.1 | 2500.0 | 40.8 | 125.6 |
| example6 | P-34 | H-20 | 4.2 | 6.9 | 2500.0 | 36.3 | 132.2 |
| example7 | P-45 | H-20 | 4.1 | 6.1 | 2500.0 | 40.7 | 131.1 |
| example8 | P-52 | H-20 | 4.1 | 6.4 | 2500.0 | 39.1 | 126.6 |
| example9 | P-56 | H-20 | 4.2 | 5.8 | 2500.0 | 42.8 | 127.0 |
| example10 | P-60 | H-20 | 4.1 | 7.0 | 2500.0 | 35.6 | 133.4 |
| example11 | P-72 | H-20 | 4.1 | 6.4 | 2500.0 | 39.2 | 129.9 |
| example12 | P-81 | H-20 | 4.3 | 6.1 | 2500.0 | 41.1 | 129.5 |
| example13 | P-1 | H-104 | 4.2 | 5.6 | 2500.0 | 45.0 | 131.7 |
| example14 | P-17 | H-104 | 4.1 | 6.9 | 2500.0 | 36.3 | 127.0 |
| example15 | P-34 | H-104 | 4.3 | 5.7 | 2500.0 | 43.8 | 125.2 |
| example16 | P-45 | H-104 | 4.3 | 6.0 | 2500.0 | 41.7 | 127.6 |
| example17 | P-56 | H-104 | 4.2 | 7.0 | 2500.0 | 35.8 | 133.6 |
| example18 | P-60 | H-104 | 4.1 | 6.6 | 2500.0 | 38.0 | 134.4 |
| example19 | P-72 | H-104 | 4.1 | 6.0 | 2500.0 | 42.0 | 130.0 |
| example20 | P-81 | H-104 | 4.3 | 6.4 | 2500.0 | 39.2 | 131.7 |
| example21 | P-5 | S-55 | 4.5 | 6.4 | 2500.0 | 39.2 | 143.8 |
| example22 | P-14 | S-55 | 4.4 | 6.8 | 2500.0 | 36.6 | 144.3 |
| example23 | P-34 | S-55 | 4.4 | 5.7 | 2500.0 | 43.7 | 140.3 |
| example24 | P-45 | S-55 | 4.5 | 6.3 | 2500.0 | 40.0 | 138.2 |
| example25 | P-52 | S-55 | 4.5 | 6.8 | 2500.0 | 37.0 | 137.7 |

TABLE 6-continued

| | Frist host | Second host | Voltage | Current Density (mA/cm$^2$) | Brightness (cd/m$^2$) | Efficiency (cd/A) | T(95) |
|---|---|---|---|---|---|---|---|
| example26 | P-56 | S-55 | 4.5 | 6.6 | 2500.0 | 37.8 | 136.5 |
| example27 | P-60 | S-55 | 4.5 | 6.2 | 2500.0 | 40.1 | 142.1 |
| example28 | P-72 | S-55 | 4.4 | 6.3 | 2500.0 | 39.4 | 140.7 |
| example29 | P-1 | S-109 | 4.5 | 6.8 | 2500.0 | 36.9 | 144.6 |
| example30 | P-14 | S-109 | 4.4 | 6.5 | 2500.0 | 38.4 | 139.1 |
| example31 | P-34 | S-109 | 4.5 | 5.7 | 2500.0 | 43.8 | 138.8 |
| example32 | P-45 | S-109 | 4.5 | 5.6 | 2500.0 | 44.5 | 143.6 |
| example33 | P-52 | S-109 | 4.4 | 6.5 | 2500.0 | 38.2 | 143.0 |
| example34 | P-56 | S-109 | 4.4 | 6.3 | 2500.0 | 40.0 | 136.5 |
| example35 | P-60 | S-109 | 4.5 | 6.2 | 2500.0 | 40.4 | 142.9 |
| example36 | P-72 | S-109 | 4.5 | 5.8 | 2500.0 | 42.8 | 141.3 |

As can be seen from the results in Table 6, when a red organic electroluminescent device is manufactured using the material for an organic electroluminescent device of the present invention as a host material for the emitting layer, the driving voltage, luminous efficiency, and lifespan of the organic electroluminescent device can be improved compared to the comparative example using Comparative Compound A or Comparative Compound B, which has a similar basic structure to the compound of the present invention.

Although Comparative Compound A and Comparative Compound B comprise a skeleton similar to that of the compound of the present invention, there is a difference in that the skeleton of the compound of the present invention is further substituted with an additional substituent.

To check the energy level of the compound that changes due to these structural differences, the data measured using the DFT method (B3LYP/6-31g(D)) of the Gaussian program is shown in Table 7.

TABLE 7

| | Comparative compound A | Comparative compound B | P-56 | P-45 |
|---|---|---|---|---|
| HOMO(eV) | −5.5489 | −5.3008 | −5.5772 | −5.6096 |

As can be seen from the results in Table 7, it can be seen that the HOMO energy levels of the compounds of the present invention and the comparative compounds are different. When the compound of the present invention is applied as the first host of the emitting layer in an organic electronic element, it serves as an electron transport host that transfers electrons from the electron transport region.

However, in the case of Comparative Compound A and Comparative Compound B, despite containing a triazine structure with strong electron transport characteristics in the structure, as additional substituents other than hydrogen or deuterium are further substituted at the positions corresponding to R$^1$ to R$^3$ of Compound 1 of the present invention, the HOMO energy level becomes shallower than that of the compound of the present invention. As a result, when Comparative Compound A and Comparative Compound B are applied as the first host of the emitting layer, holes are more easily injected from the hole transport region, and the electron transport characteristics of the compounds themselves are weakened, so that the electron transport role, which is the purpose of the first host, is not performed properly, the charge balance of the element is broken. On the contrary, the compound of the present invention has a deeper HOMO energy level than the comparative compounds, so it has excellent energy transfer characteristics by receiving electrons from the electron transport region to the dopant, and is believed to significantly increase the driving voltage, efficiency, and lifespan of the device because the charge balance of the device is maximized by balancing the hole transport characteristics of the second host.

In addition, compared to the compound of the present invention, Comparative Compound A or Comparative Compound B, which has additional substituents, has a more distorted structure than the compound of the present invention, so the packing density is significantly lower when deposited on the element. Whereas, when the compound of the present invention, which has relatively high planarity, is deposited on the element, the packing density is higher than that of the comparative compound, so charge injection is significantly improved, and charge balance is maximized because rapid electron transfer is also achieved through the hopping mechanism, accordingly, the driving voltage, efficiency, and lifespan are judged to increase significantly.

That is, as can be seen from the results in Table 6 and 7, even if the compound has a similar structure, it can be confirmed that the compound of the present invention, which satisfies all complex factors such as presence of a substituent, type of substituent, and substitution position of the substituent, shows a remarkable effect compared to other comparative compounds in organic electronic element, and through this, it can be seen that the compound of the present invention exhibits a more significant effect in organic electronic elements than simple structural isomers or compounds with similar compositions not described in this specification.

These results show that even in compounds with similar molecular components, depending on the type and substitution position of the substituent, the properties of compounds such as the hole characteristics, light efficiency characteristics, energy level, hole injection and mobility characteristics, charge balance of holes and electrons, volume density, and intermolecular distance of the molecule may vary significantly enough to be difficult to predict, additionally, it suggests that rather than one configuration affecting the overall results of the element, the performance of the element may vary due to complex factors.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis

What is claimed is:

1. A compound represented by Formula (1):

[Formula (1) structure showing a naphthalene-phenyl-triazine compound with substituents $(R^2)_a$, $(R^2)_b$, $(R^2)_c$, $L^1$-$Ar^1$, $L^2$-$Ar^2$]

wherein:
$R^1$, $R^2$ and $R^3$ are each the same or different, and each independently hydrogen or deuterium,
a is an integer of 0 to 5, b is an integer of 0 to 6, c is an integer of 0 to 4,
$L^1$ and $L^2$ are each independently selected from the group consisting of single bond; a $C_6$-$C_{60}$ arylene group; and a $C_2$-$C_{60}$ heterocyclic group including at least one heteroatom of O, N, S, Si or P;
$Ar^1$ and $Ar^2$ are each independently selected from the group consisting of a $C_6$-$C_{60}$ aryl group; a fluorenyl group; a $C_2$-$C_{60}$ heterocyclic group including at least one heteroatom of O, N, S, Si, or P; a $C_3$-$C_{60}$ aliphatic ring; and a fused ring group of a $C_3$-$C_{60}$ aliphatic ring and a $C_6$-$C_{60}$ aromatic ring; wherein the aryl group, arylene group, heterocyclic group, fluorenyl group, fluorenylene group, aliphatic ring group and fused ring group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group, and the hydrogen of these substituents may be further substituted with one or more deuterium, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The compound of claim 1, wherein $L^1$ and $L^2$ are a single bond or represented by any of Formulas L-1 to L-20:

[Formula L-1] through [Formula L-11]: various phenylene and naphthylene linker structures with $(R^4)_d$ and $(R^5)_e$ substituents.

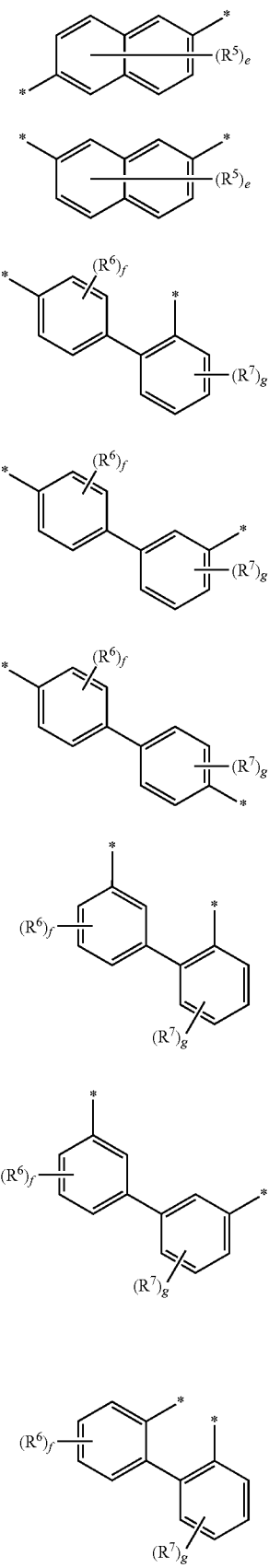

[Formula L-12]

[Formula L-13]

[Formula L-14]

[Formula L-15]

[Formula L-16]

[Formula L-17]

[Formula L-18]

[Formula L-19]

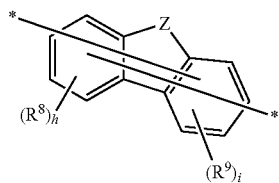

[Formula L-20]

wherein:

Z is O, S, $C(R^{23})(R^{24})$ or $N-Ar^3$, $R^4$, $R^5$, $R^6$, $R^7$, $R^8$, $R^9$, $R^{23}$, $R^{24}$ and $Ar^3$ are each the same or different, and each independently selected from the group consisting of hydrogen; deuterium; halogen; a cyano group; a nitro group; a $C_6$-$C_{20}$ aryl group; a $C_6$-$C_{20}$ aryl group substituted with deuterium; a fluorenyl group; a $C_2$-$C_{20}$ heterocyclic group including at least one hetero atom of O, N, S, Si or P; a $C_3$-$C_{20}$ cycloalkyl group; a $C_1$-$C_{20}$ alkyl group; a $C_2$-$C_{20}$ alkenyl group; a $C_2$-$C_{20}$ alkynyl group; a $C_1$-$C_{20}$ alkoxyl group; or an adjacent plurality of $R^4$ or plurality of $R^5$ or plurality of $R^6$ or plurality of $R^7$ or plurality of $R^8$ or plurality of $R^9$ may be bonded to each other to form a ring, d, f, g, h and i are each independently an integer of 0 to 4, e is an integer of 0 to 6, and \* means the position to be bonded.

3. The compound of claim 1, wherein $Ar^1$ and $Ar^2$ are represented by any one of Formulas Ar-1 to Ar-12:

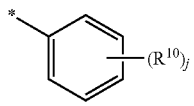

Formula Ar-1

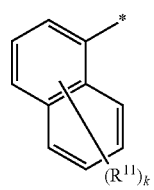

Formula Ar-2

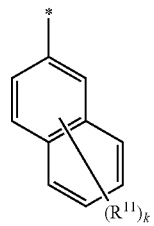

Formula Ar-3

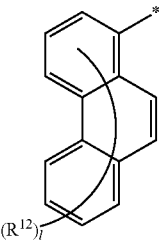

Formula Ar-4

-continued

Formula Ar-5

Formula Ar-6

Formula Ar-7

Formula Ar-8

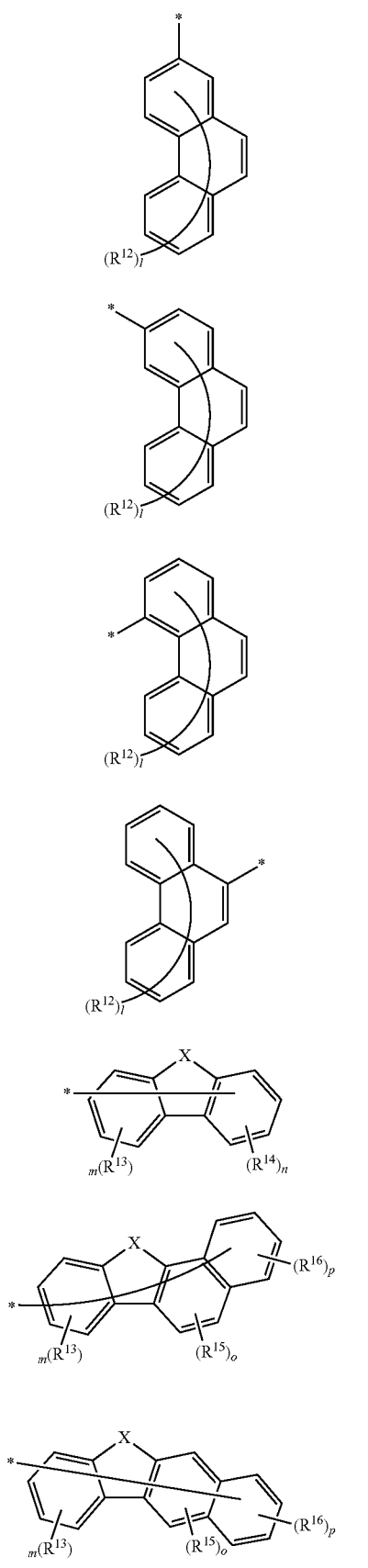

Formula Ar-9

Formula Ar-10

Formula Ar-11

-continued

Formula Ar-12

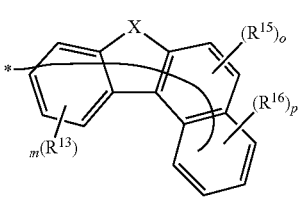

wherein:

X is O, S, $CR^aR^b$ or $NR^c$, $R^a$, $R^b$, $R^c$, $R^{10}$, $R^{11}$, $R^{12}$, $R^{13}$, $R^{14}$, $R^{15}$ and $R^{16}$ are each selected from the group consisting of hydrogen; deuterium; halogen; a cyano group; a nitro group; a $C_6$-$C_{20}$ aryl group; a $C_6$-$C_{20}$ aryl group substituted with deuterium; a fluorenyl group; a $C_2$-$C_{20}$ heterocyclic group including at least one hetero atom of O, N, S, Si or P; a $C_3$-$C_{20}$ cycloalkyl group; a $C_1$-$C_{20}$ alkyl group; a $C_2$-$C_{20}$ alkenyl group; a $C_2$-$C_{20}$ alkynyl group; and a $C_1$-$C_{20}$ alkoxyl group, and adjacent groups thereof may be bonded to each other to form a ring, j is an integer of o to 5, k is an integer of 0 to 7, l is an integer of 0 to 9, m, n and p are each independently an integer of 0 to 4, o is an integer of 0 to 2, and

* means the position to be bonded.

4. A composition for an organic electronic element comprising a mixture of a compound represented by Formula (1) of claim 1, and a compound represented by Formula 4 or Formula 5:

Formula 4

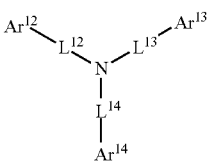

Formula 5

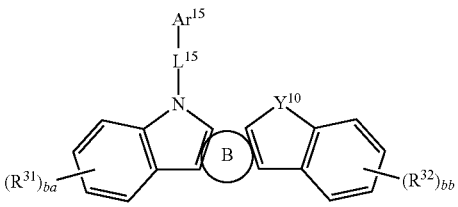

wherein:

$L^{12}$, $L^{13}$, $L^{14}$ and $L^{15}$ are each independently selected from the group consisting of single bond; a $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

$Ar^{12}$, $Ar^{13}$ and $Ar^{14}$ are each independently selected from the group consisting of a $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

$Ar^{15}$ is each independently selected from the group consisting of a $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring; and —L'—NR'R";

$Y^{10}$ is O, S, $CR^{51}R^{52}$ or $NR^{53}$,

Ring B is an $C_6$~$C_{20}$ aryl group,

L' is selected from the group consisting of a single bond; a $C_6$-$C_{60}$ arylene group; a fluorenylene group; a $C_2$-$C_{60}$ heterocyclic group including at least one heteroatom of O, N, S, Si or P; and a $C_3$-$C_{60}$ aliphatic ring, $R^{51}$, $R^{52}$, $R^{53}$, R' and R" are the same as the definition of $Ar^{12}$, or $R^{51}$ and $R^{52}$ are bonded to each other to form a spiro, $R^{31}$ and $R^{32}$ are each the same or different, and each independently selected from the group consisting of hydrogen; deuterium; a halogen; a cyano group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, and an adjacent plurality of $R^{31}$ or plurality of $R^{32}$ may be bonded to each other to form a ring, ba and bb are each independently an integer of 0 to 4, wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; and —L'—NR'R", and the hydrogen of these substituents may be further substituted with one or more deuterium, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

5. The composition for an organic electronic element according to claim 4, wherein the composition for an organic electronic element is for a host for an emitting layer.

6. The composition for an organic electronic element according to claim 4, wherein the compound of Formula 4 is any one of Compounds H-1 to H-124:

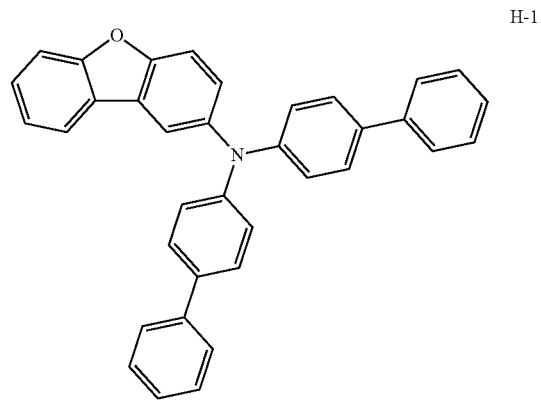

H-1

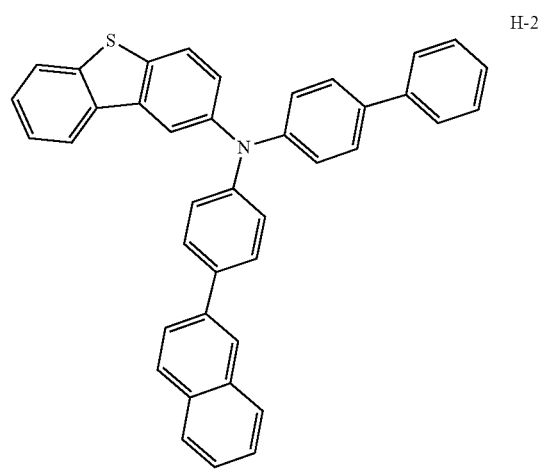

H-2

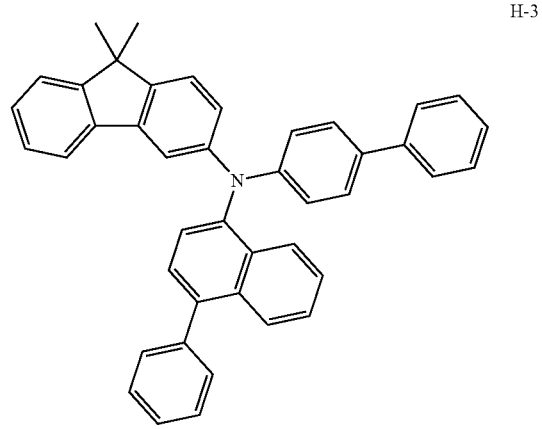

H-3

H-4
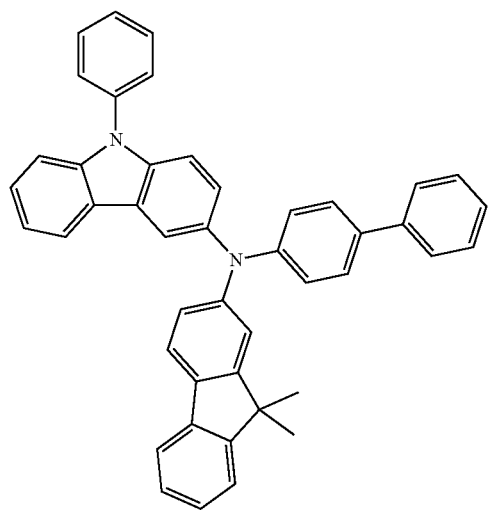
H-7
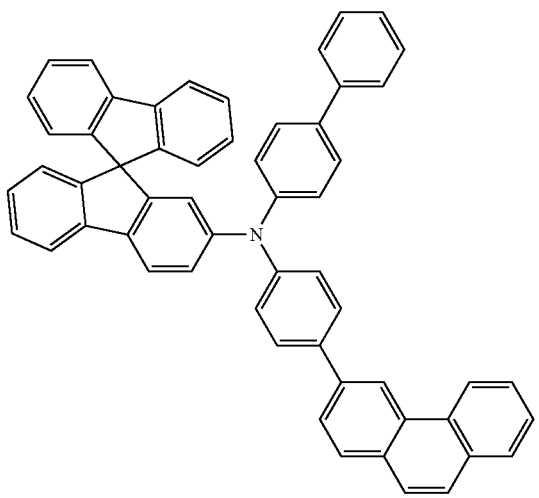
H-5
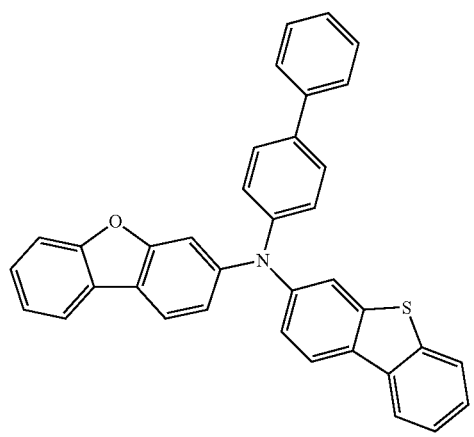
H-8
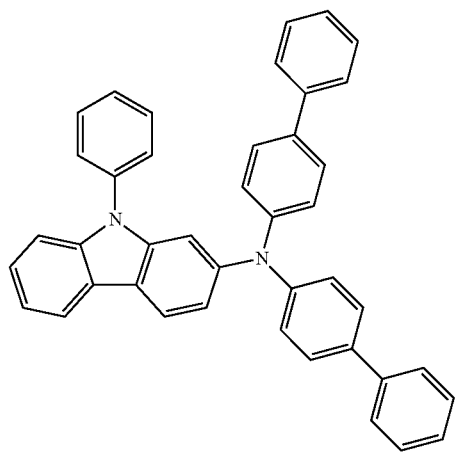
H-6
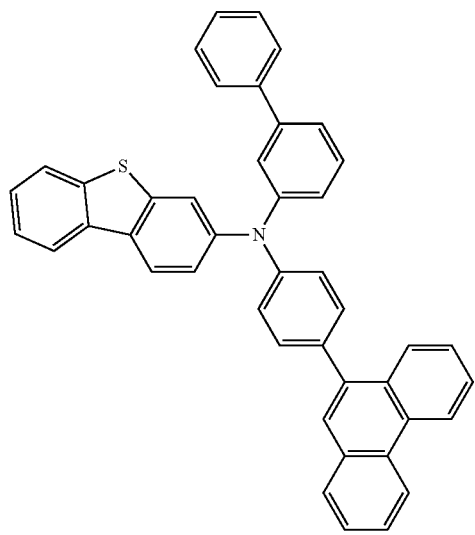
H-9
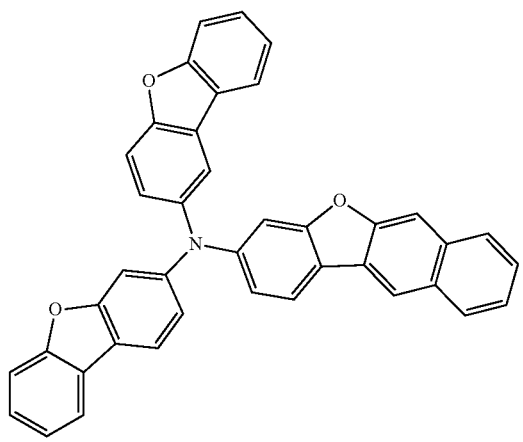

H-10
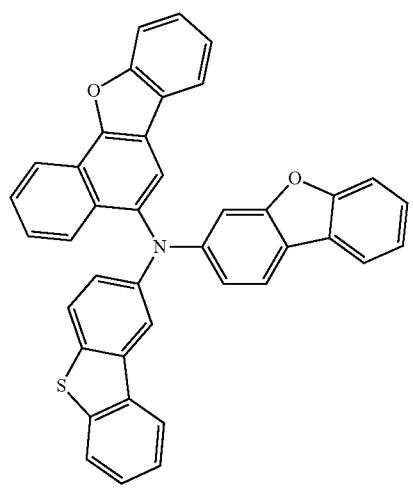
H-11
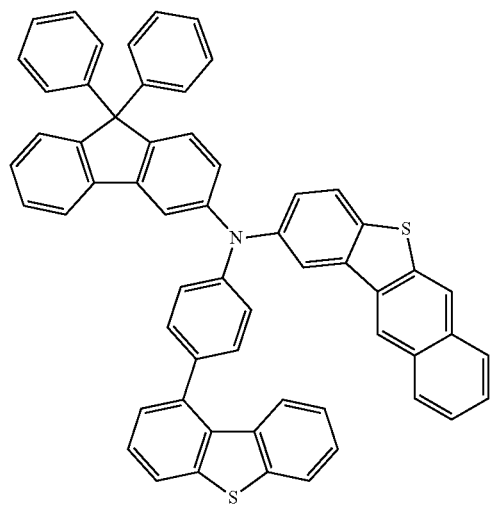
H-12
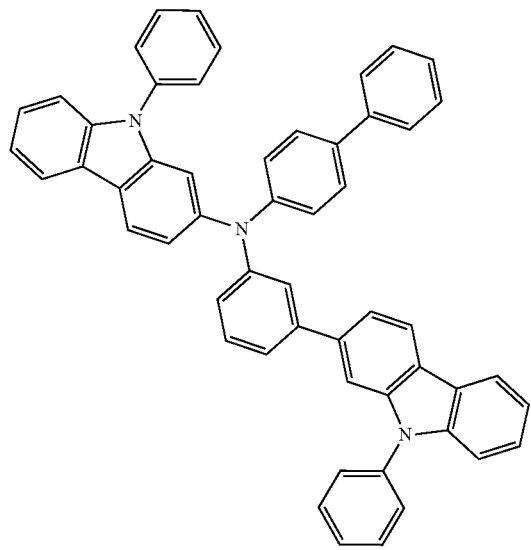
H-13
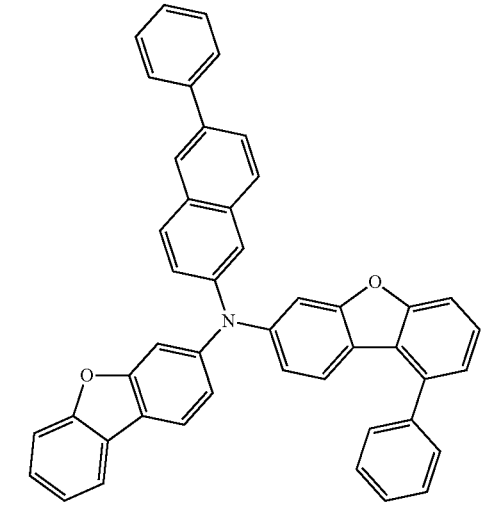
H-14
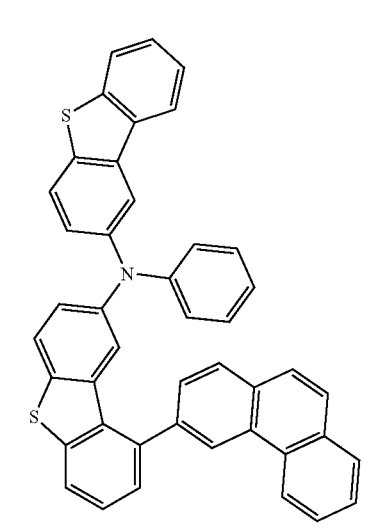
H-15
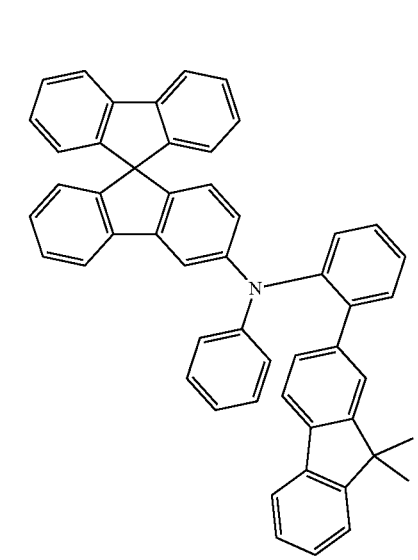

-continued
H-16
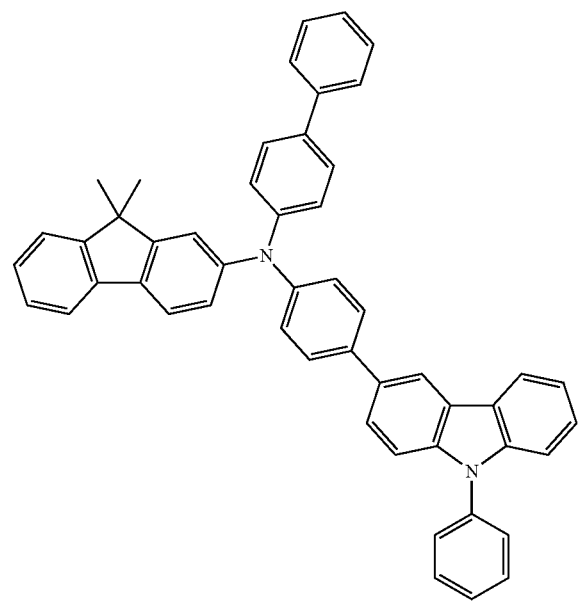
H-17
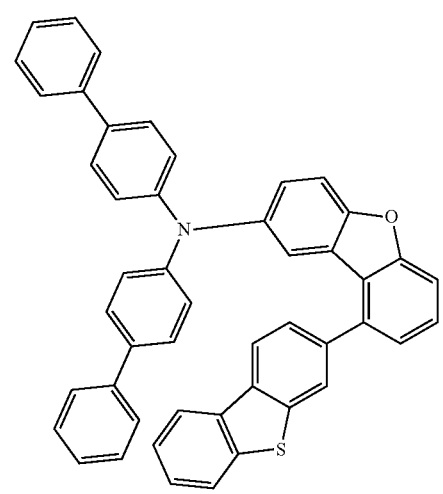
H-18
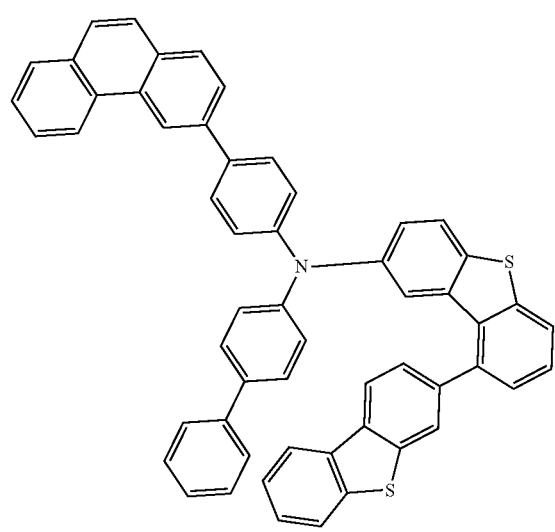
-continued
H-19
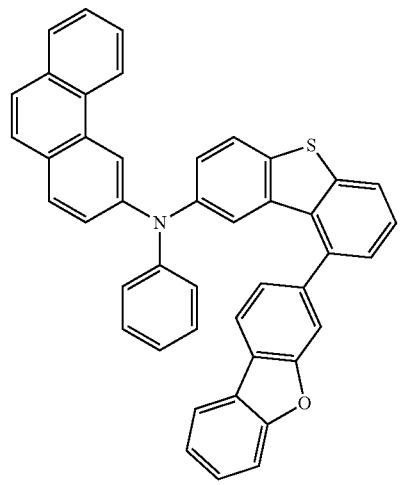
H-20
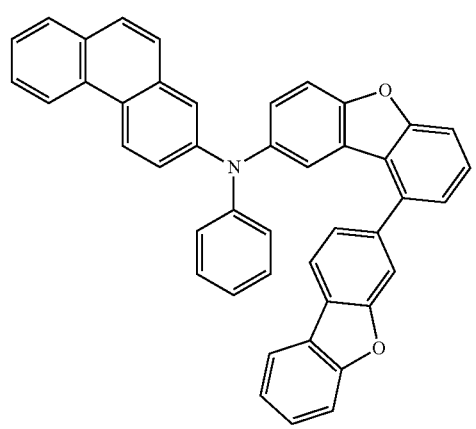
H-21
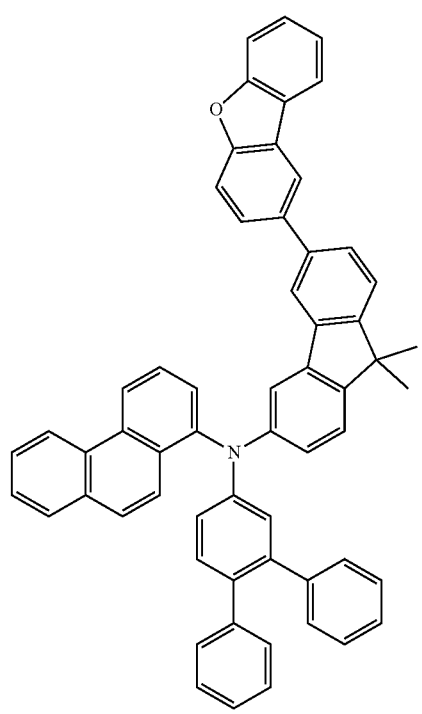

H-22
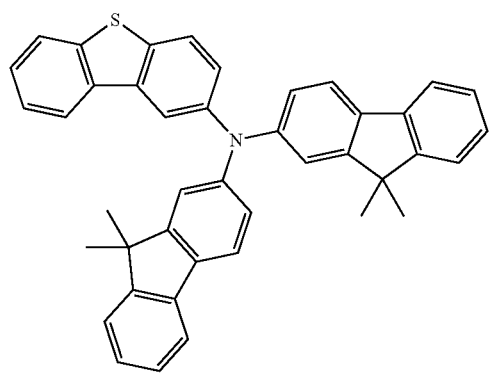
H-23
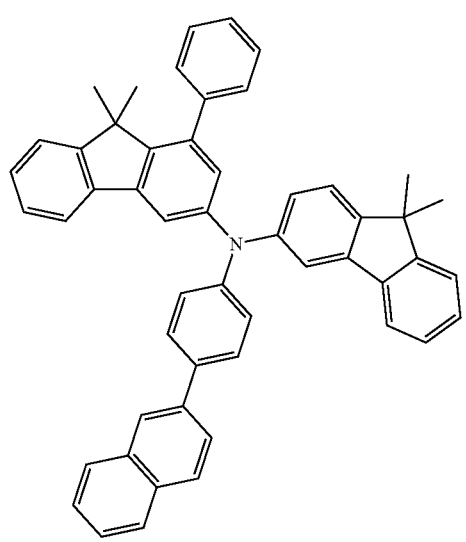
H-24
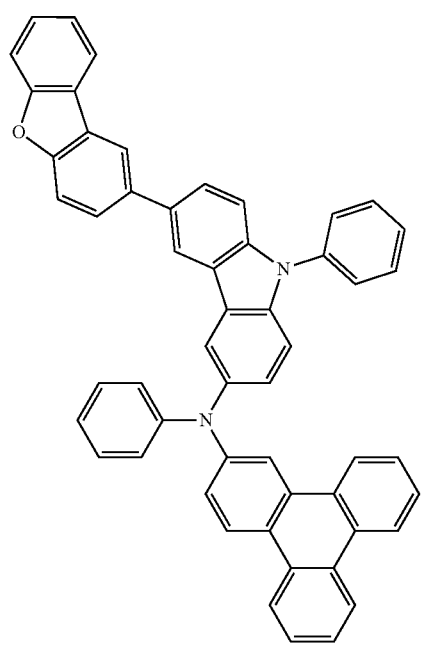
H-25
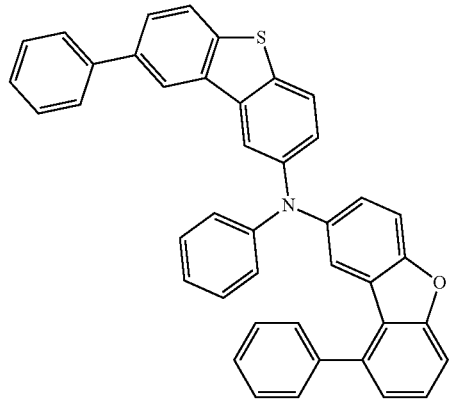
H-26
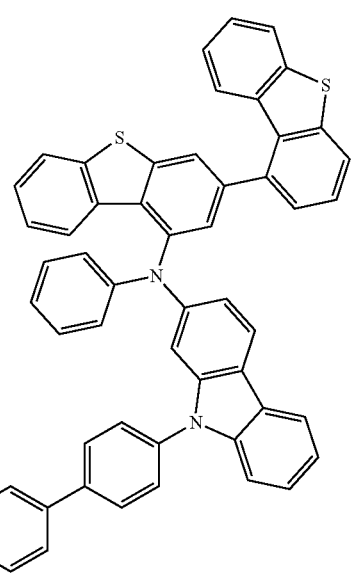
H-27
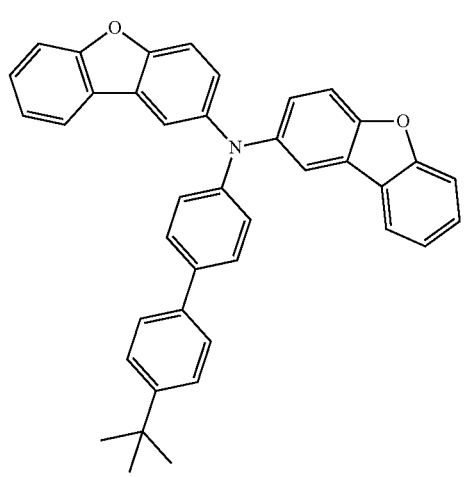

H-28
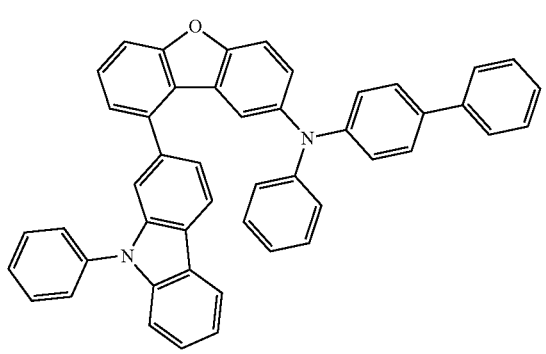
H-29
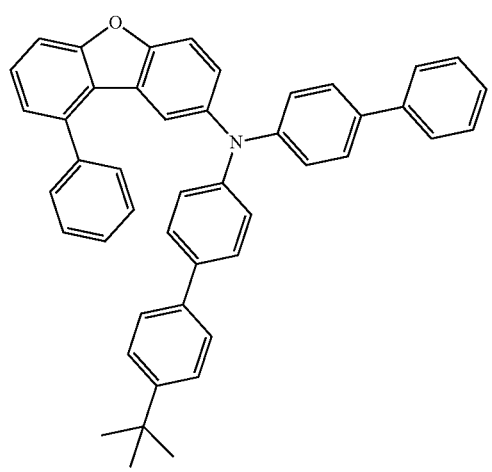
H-30
H-31
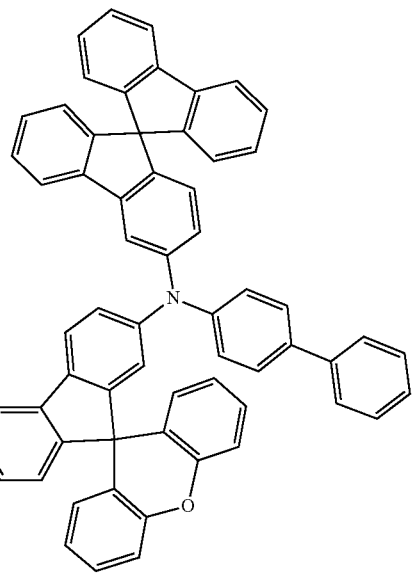
H-32
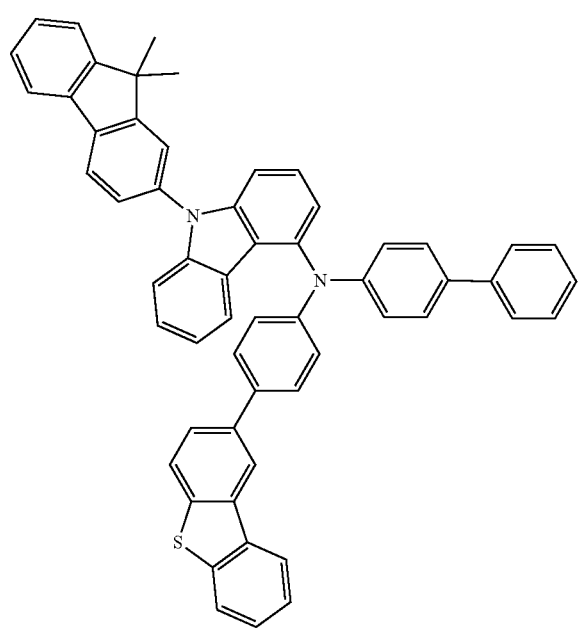
H-33
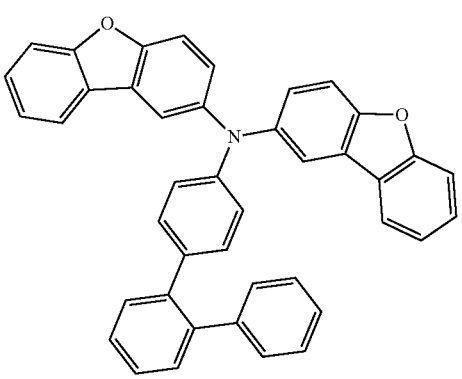

-continued
H-34
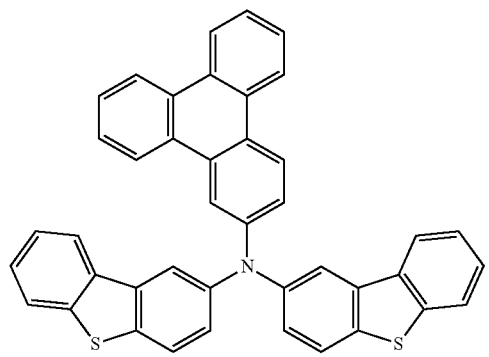
H-35
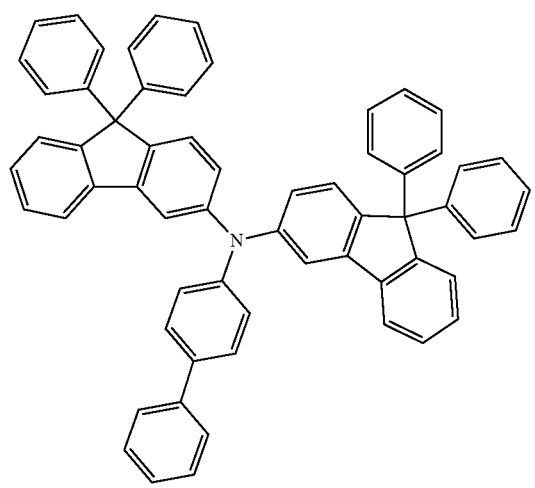
H-36
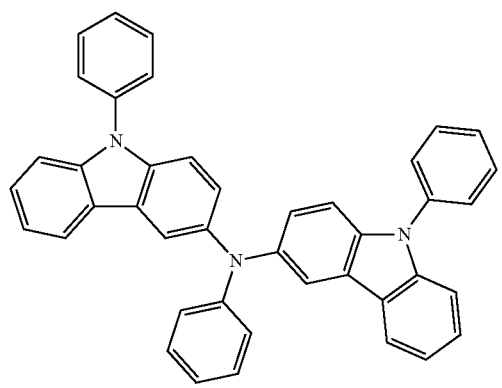
H-37
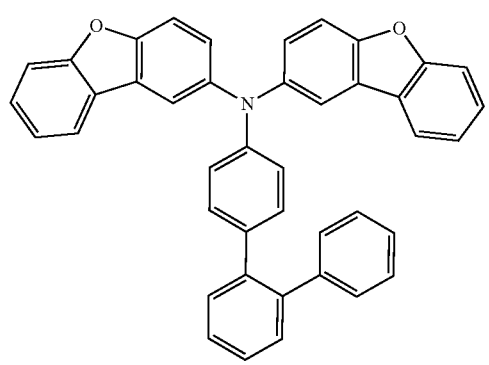
-continued
H-38
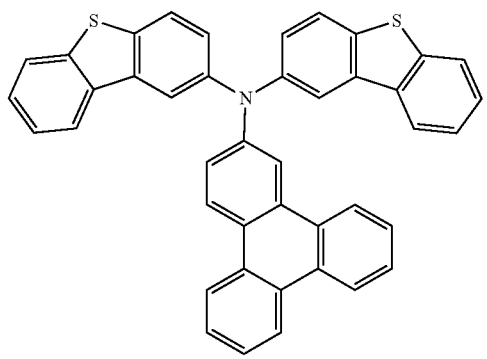
H-39
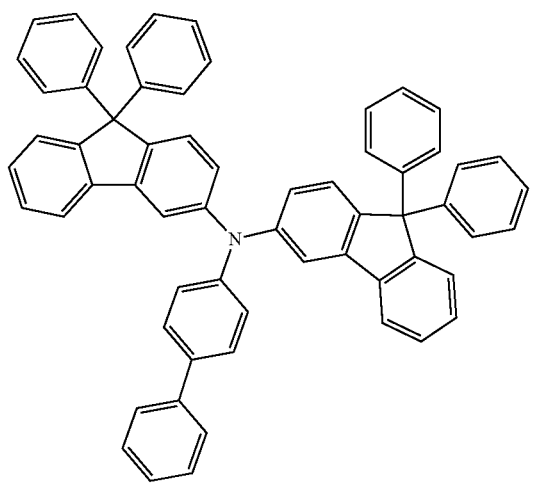
H-40
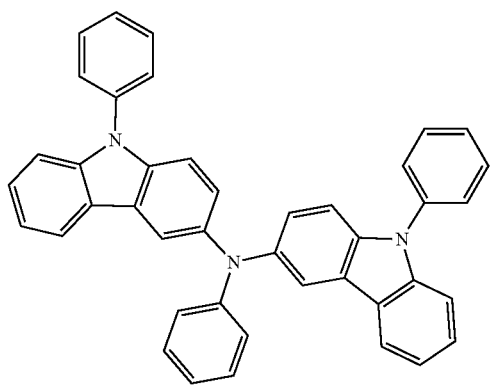

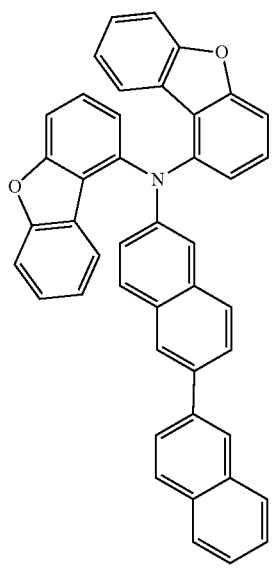
H-41
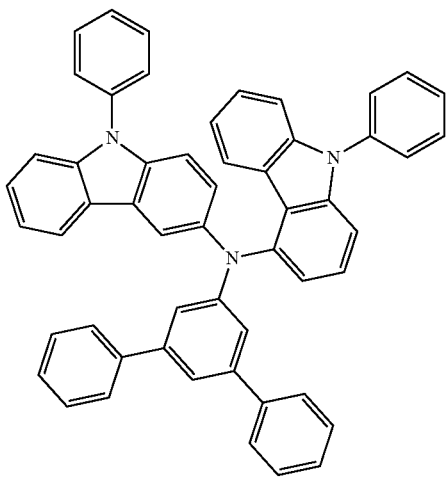
H-44
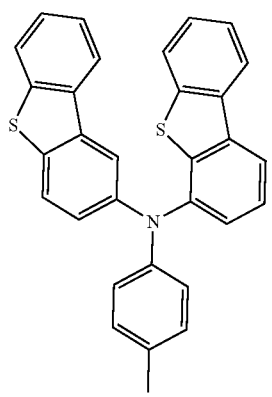
H-42
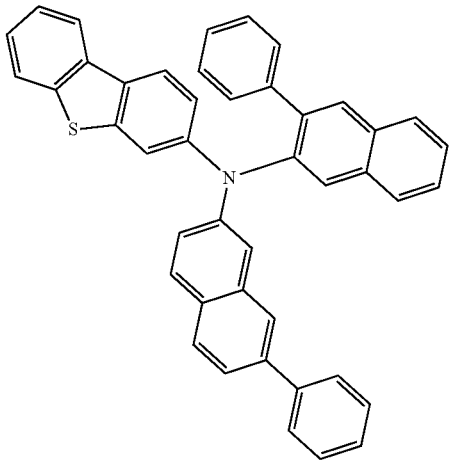
H-45
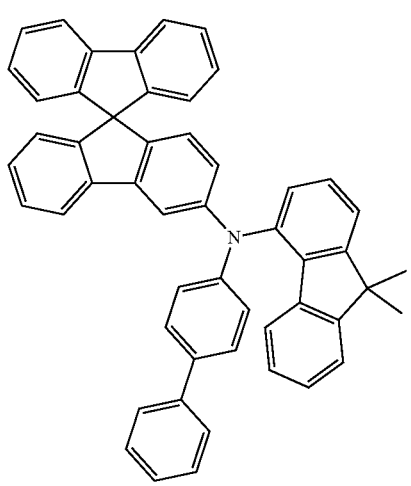
H-43
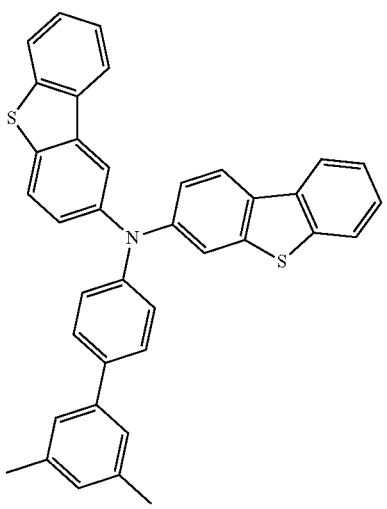
H-46

H-47
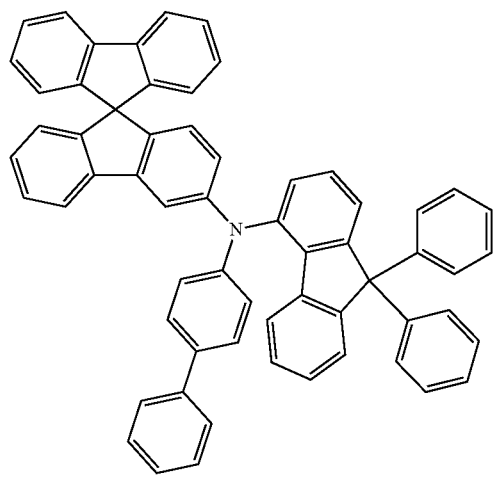
H-50
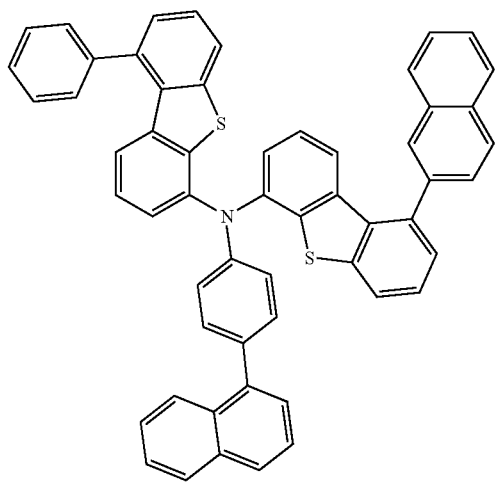
H-48
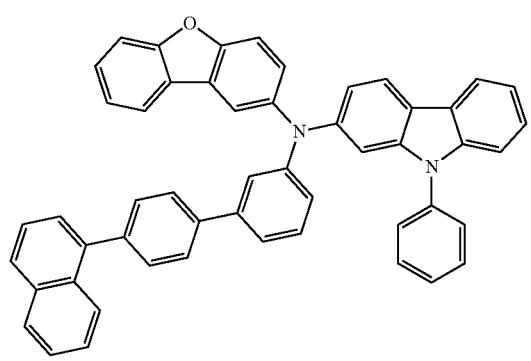
H-51
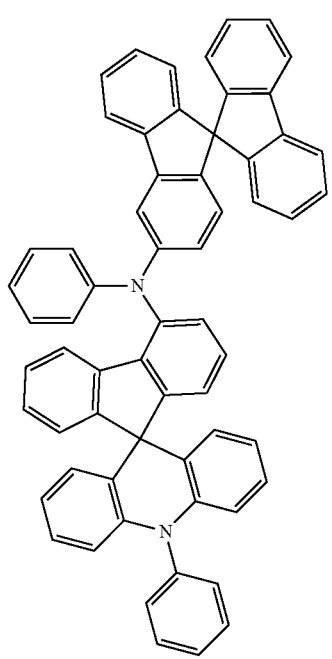
H-49

-continued
H-52
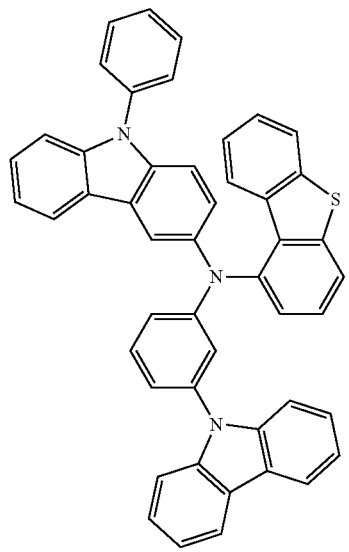
H-53
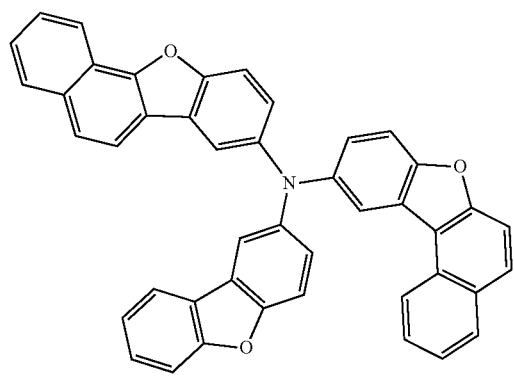
H-54
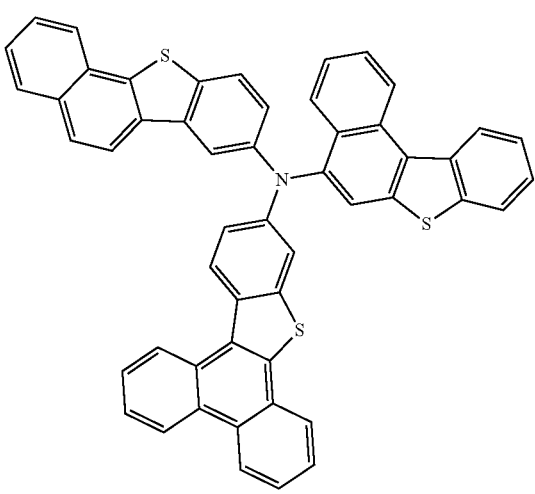
-continued
H-55
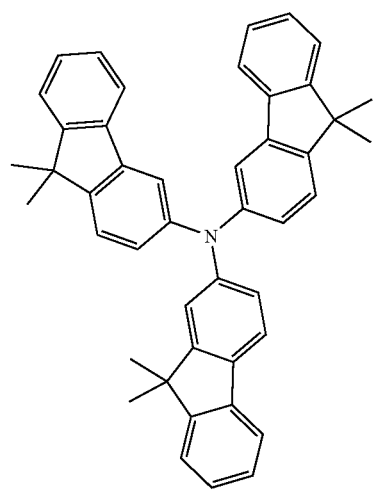
H-56
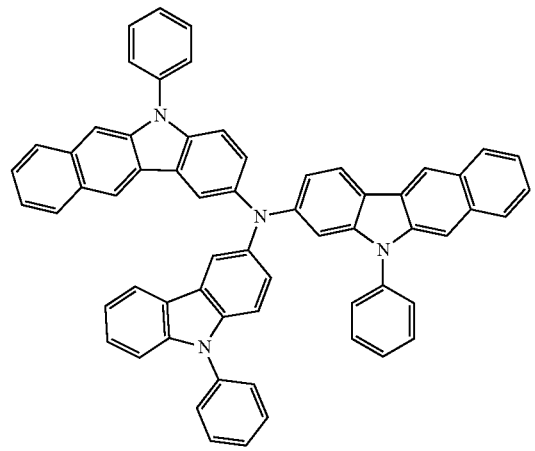
H-57
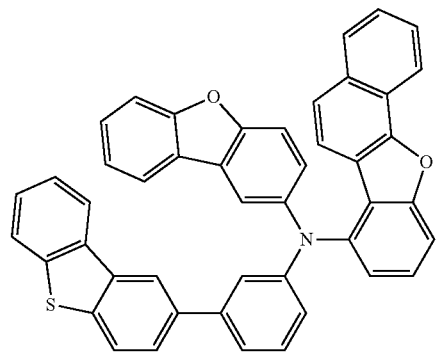

H-58
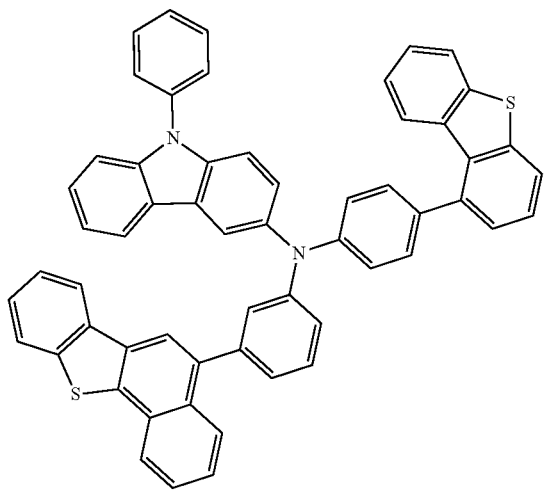
H-59
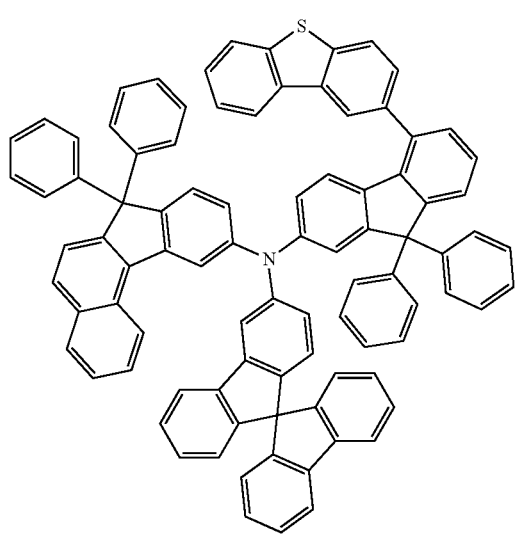
H-60
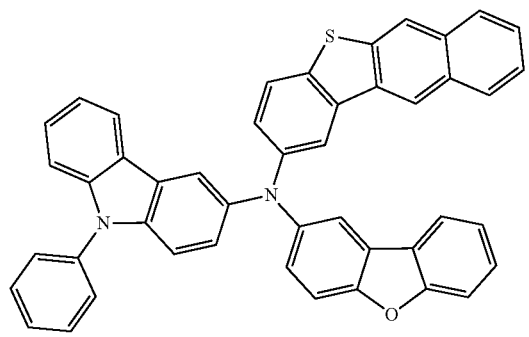
H-61
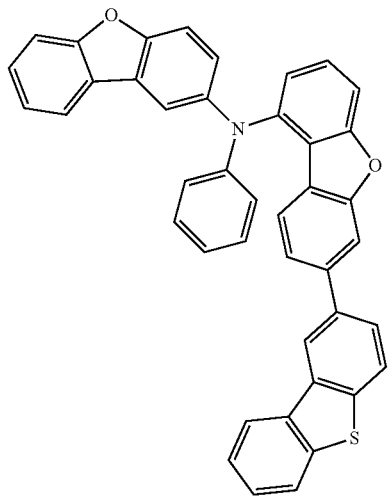
H-62
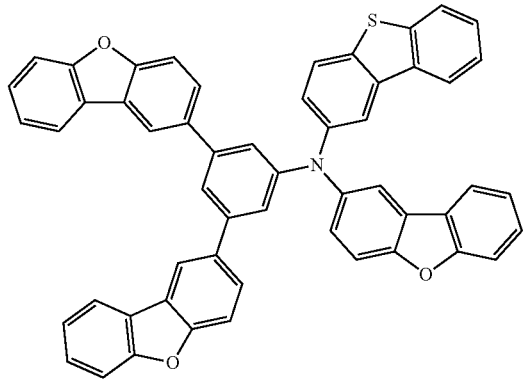
H-63
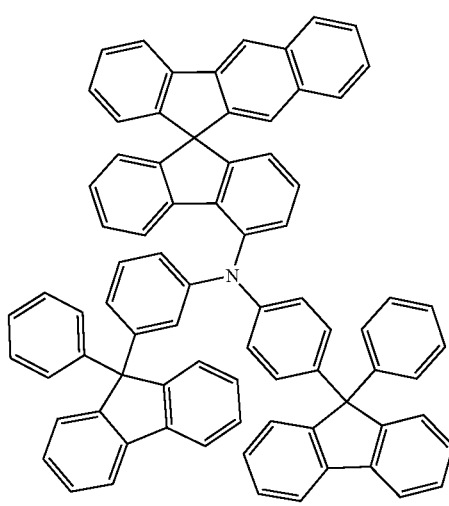

H-64
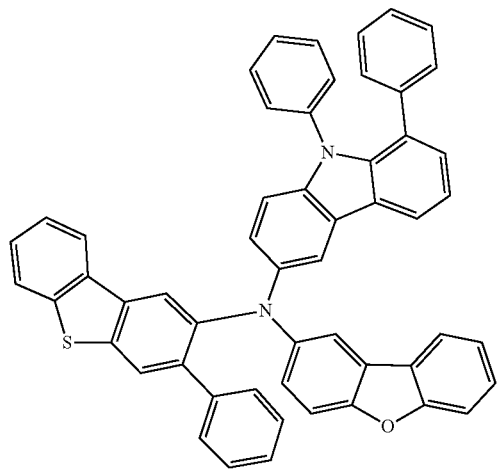
H-67
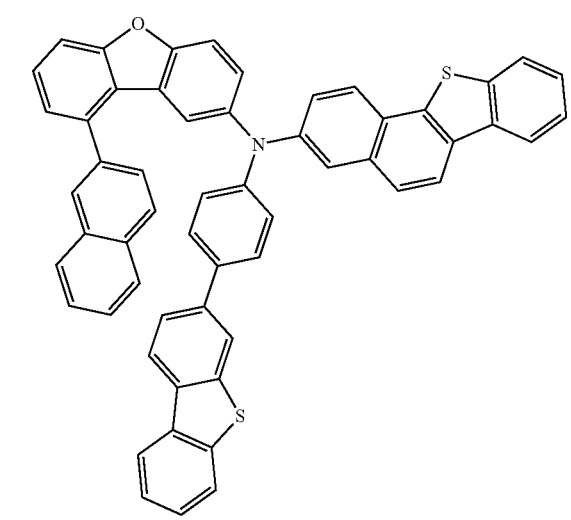
H-65
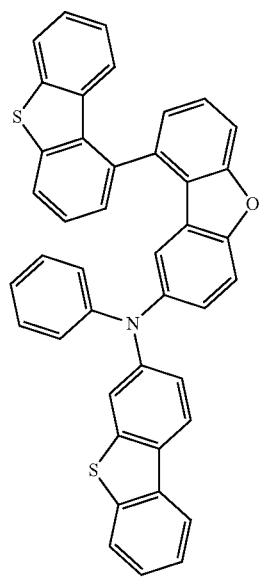
H-68
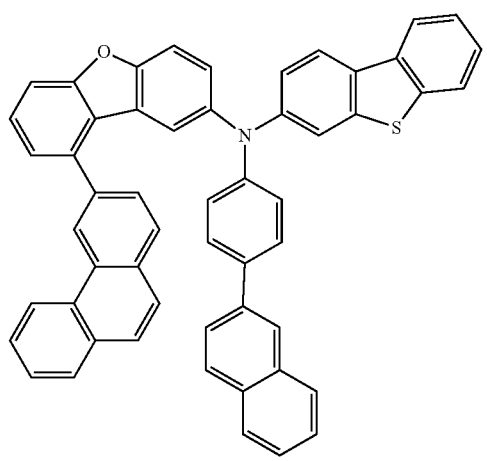
H-69
H-66
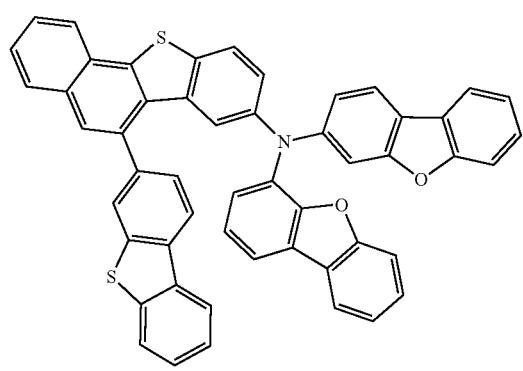
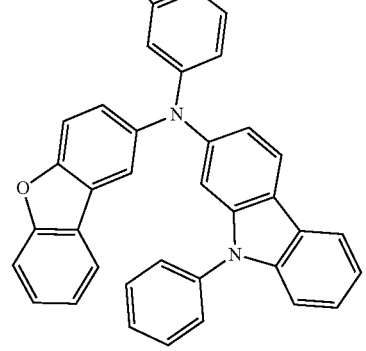

H-70
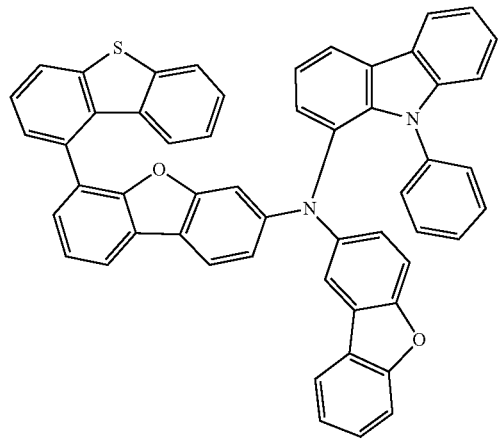
H-71
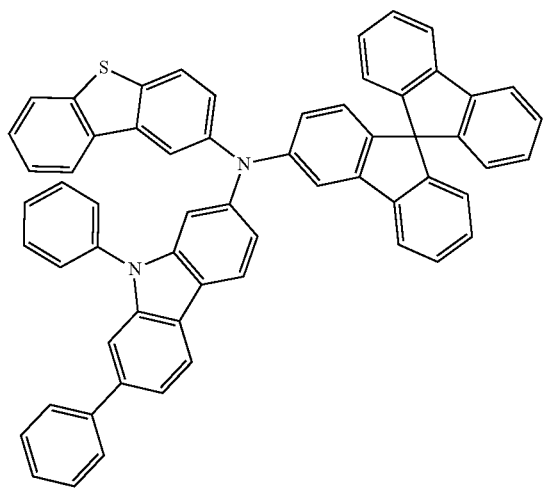
H-72
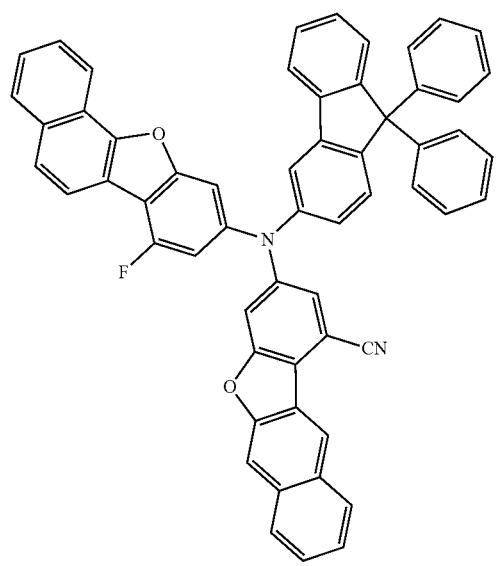
H-73
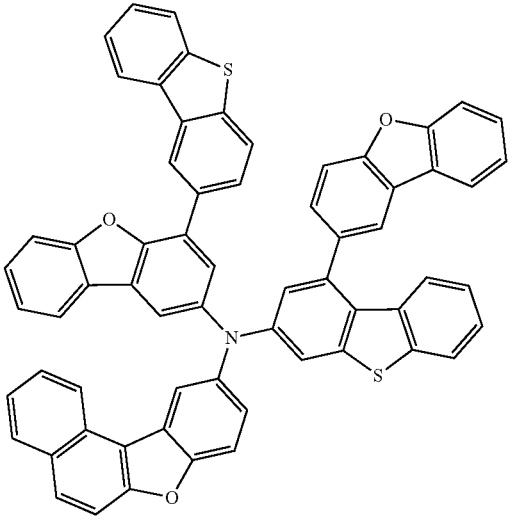
H-74
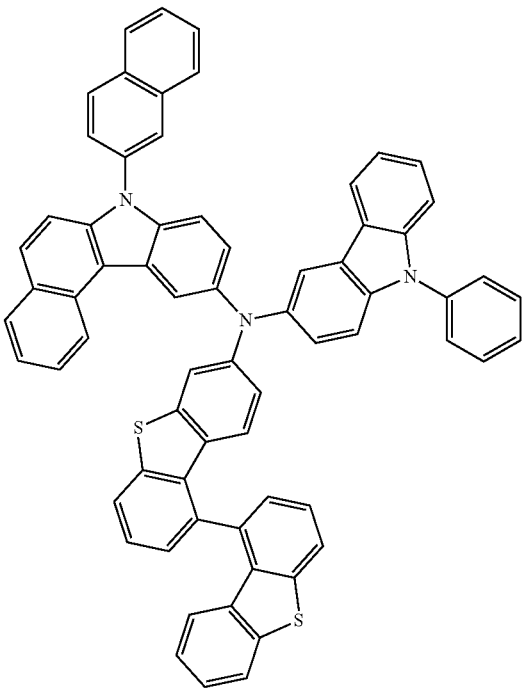

H-75
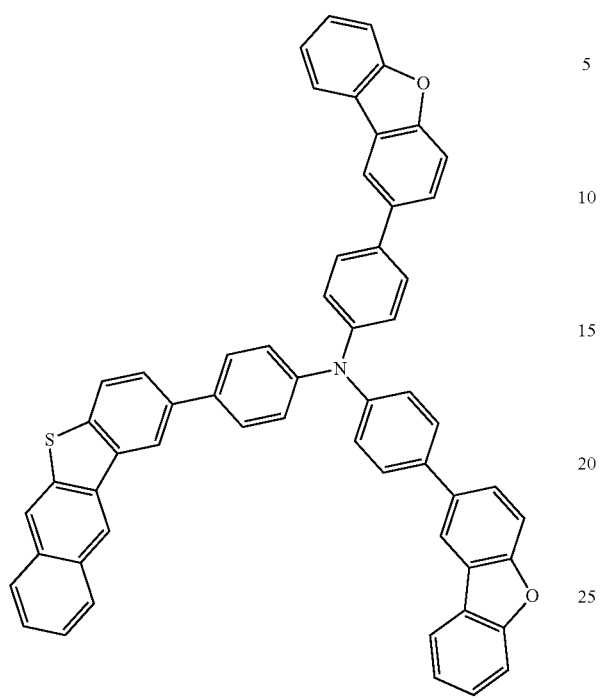
H-77
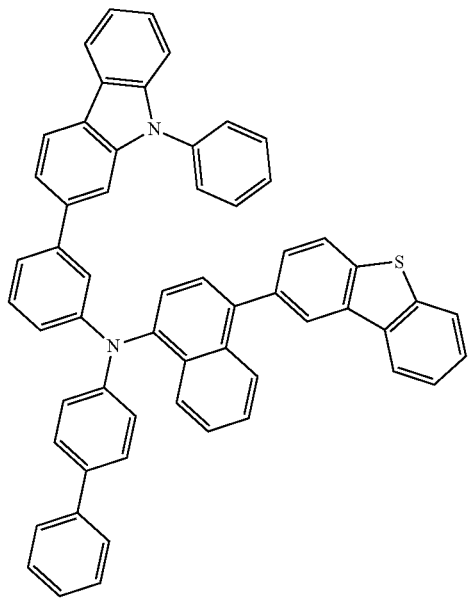
H-76
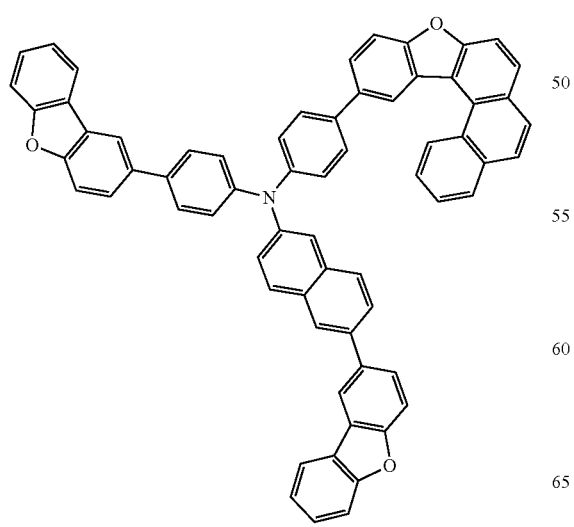
H-78
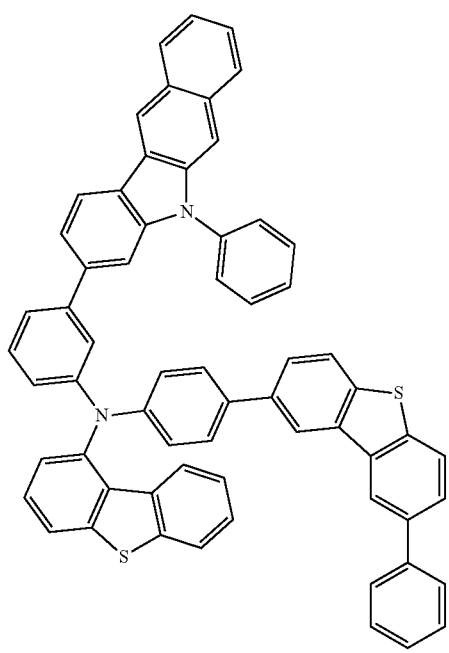

H-79
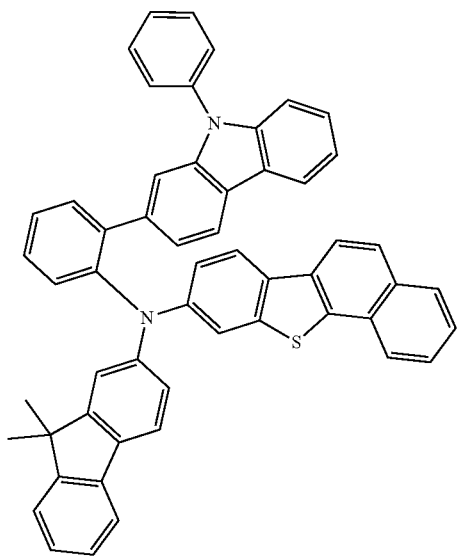
H-81
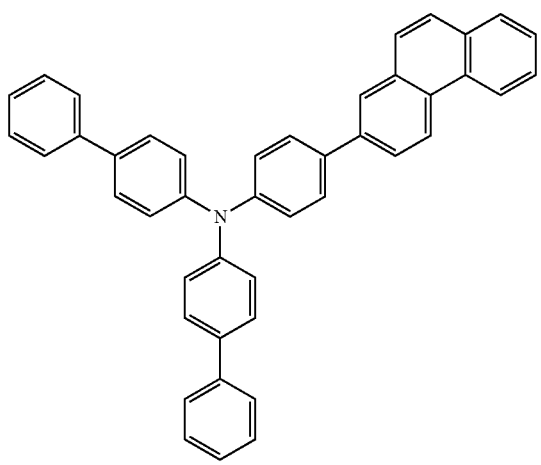
H-80
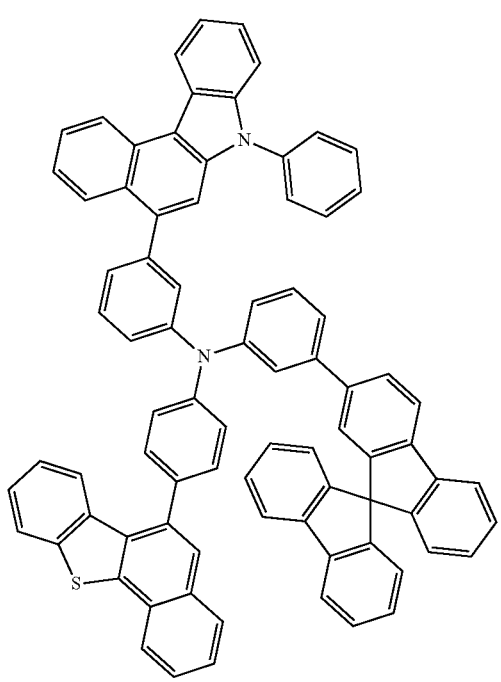
H-82
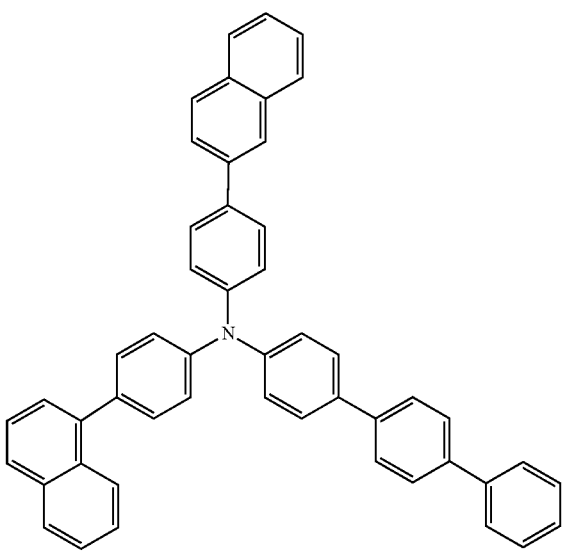

H-83
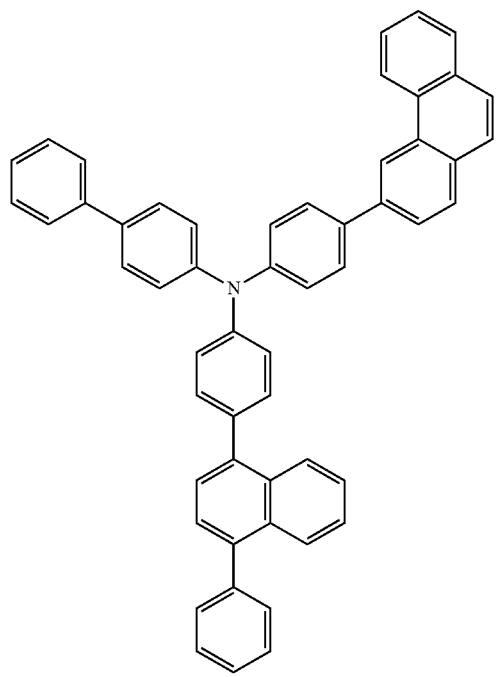
H-84
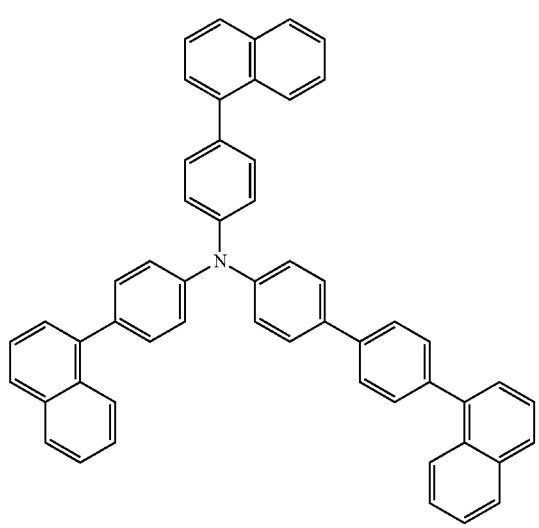
H-85
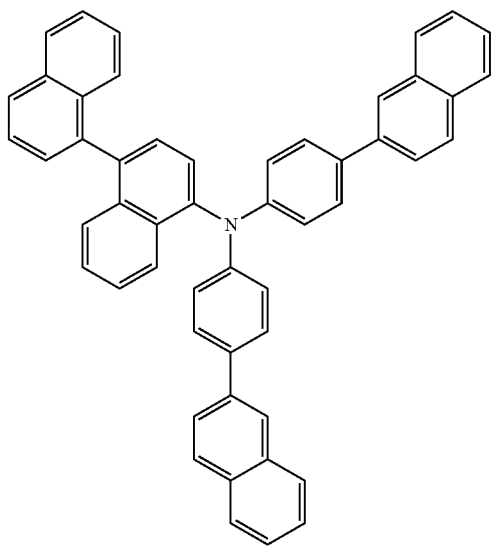
H-86
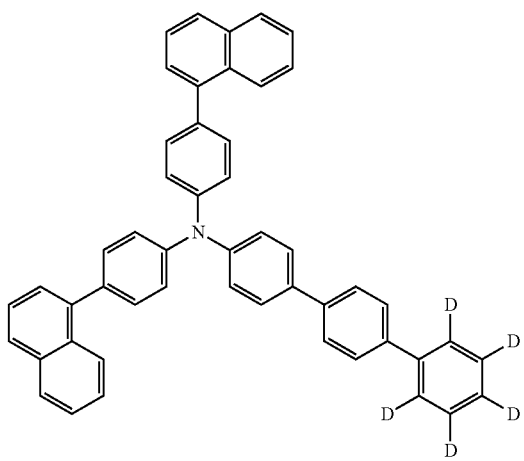
H-87
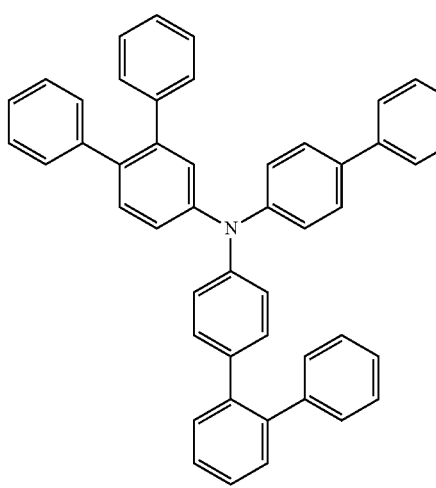

H-88
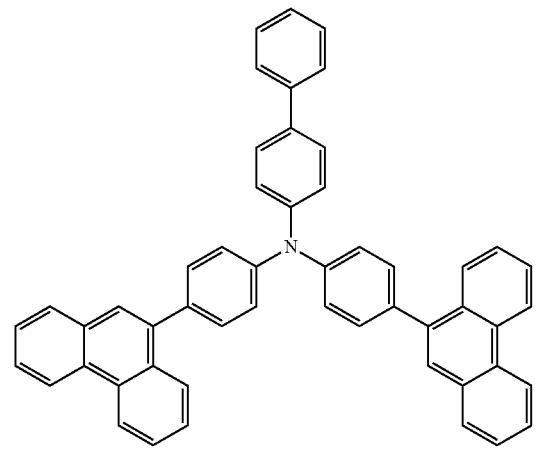
H-89
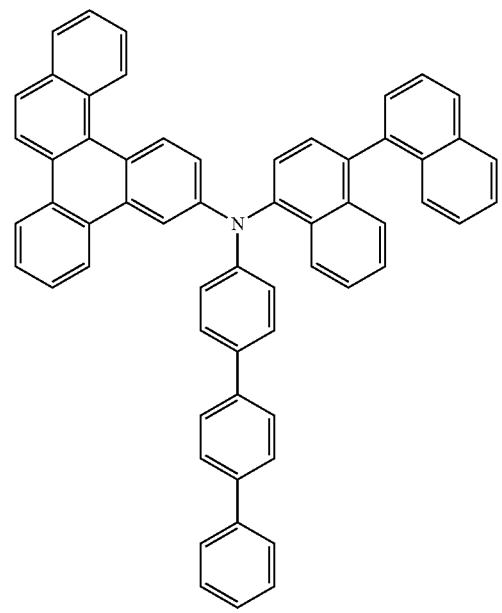
H-90
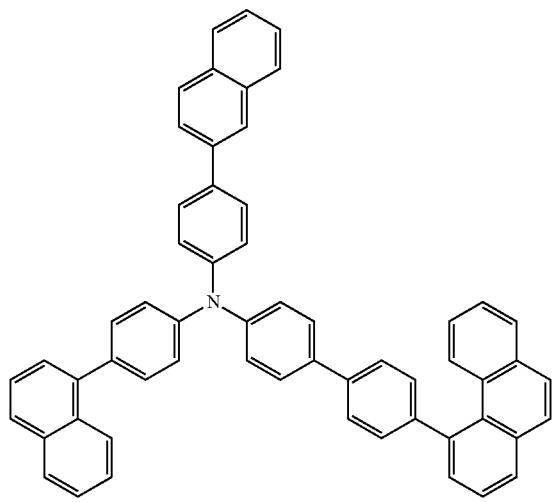
H-91
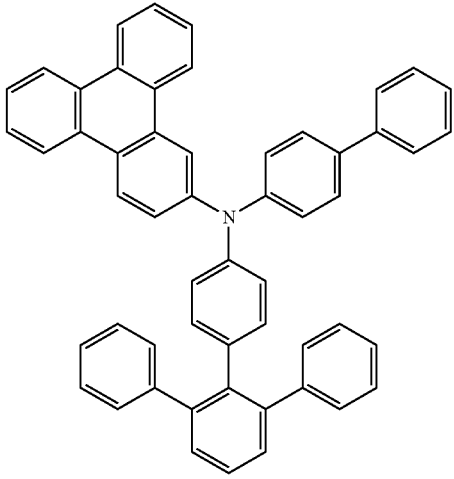
H-92
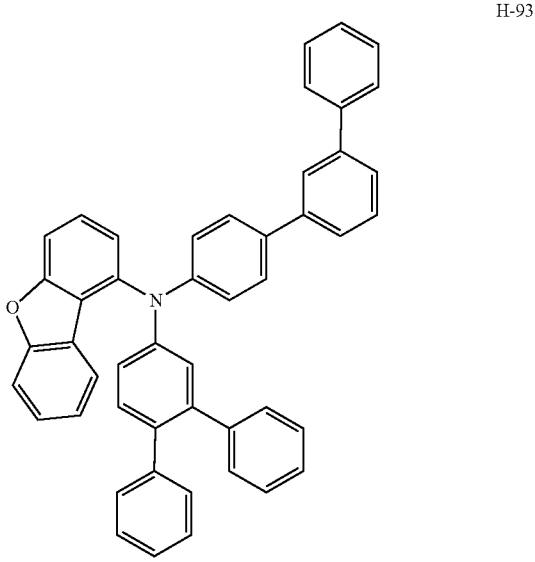
H-93

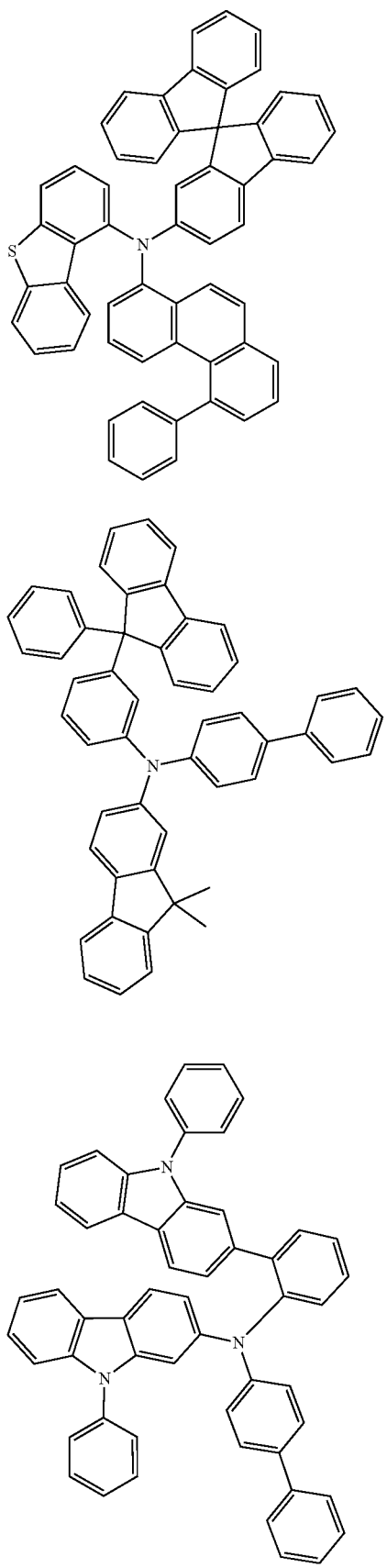
H-94
H-95
H-96
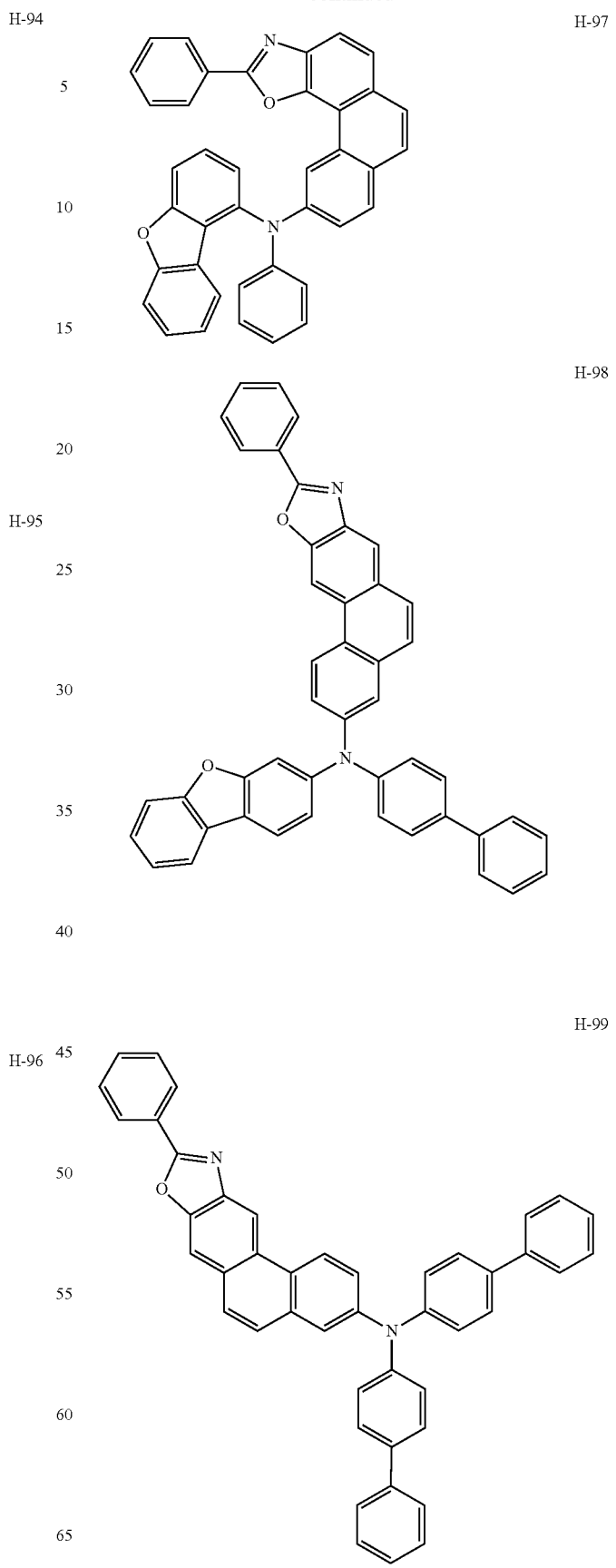
H-97
H-98
H-99

H-100
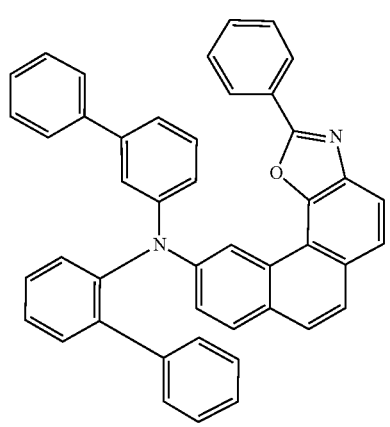
H-103
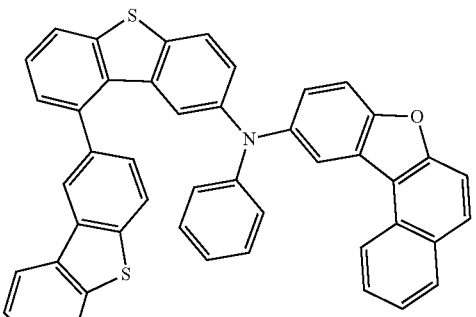
H-101
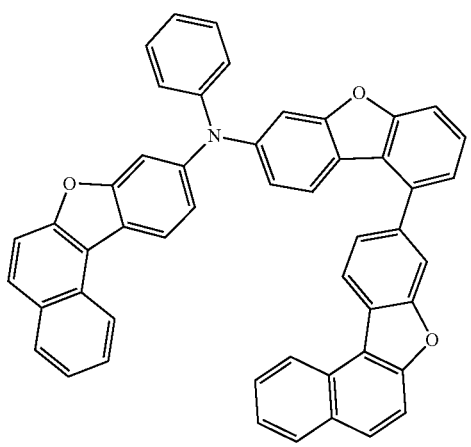
H-104
H-102
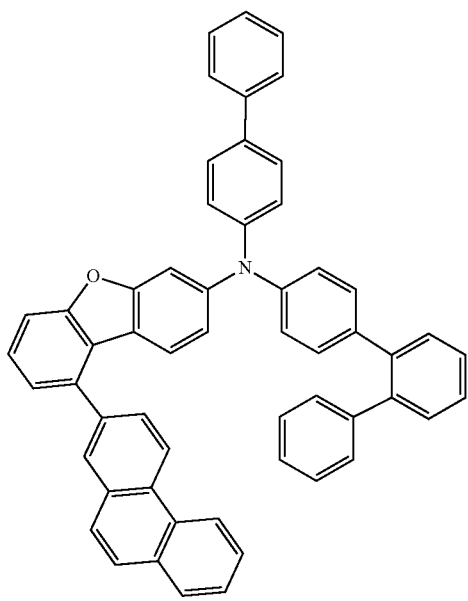
H-105
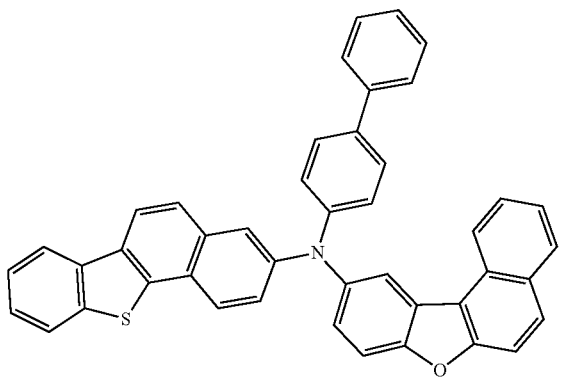

-continued
H-106
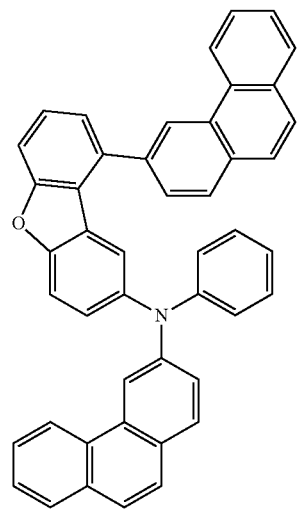
H-107
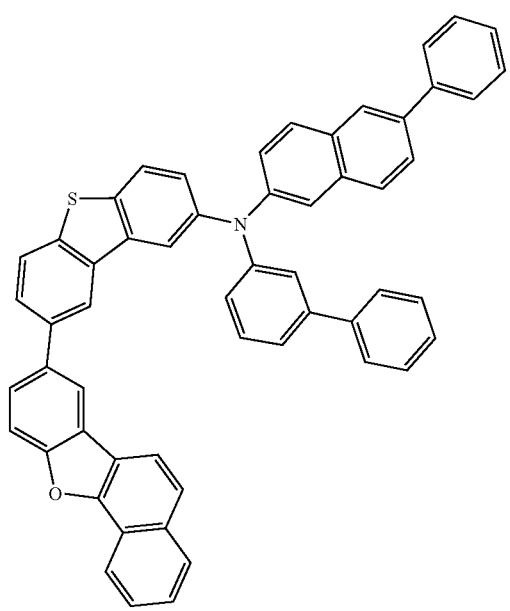
H-108
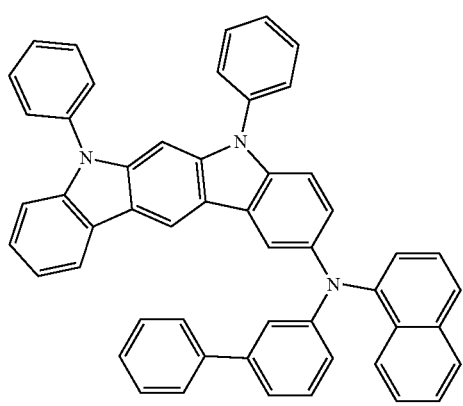
-continued
H-109
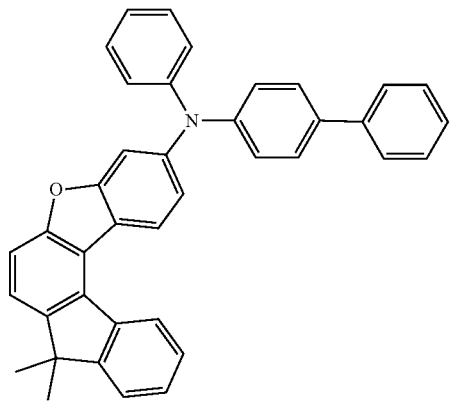
H-110
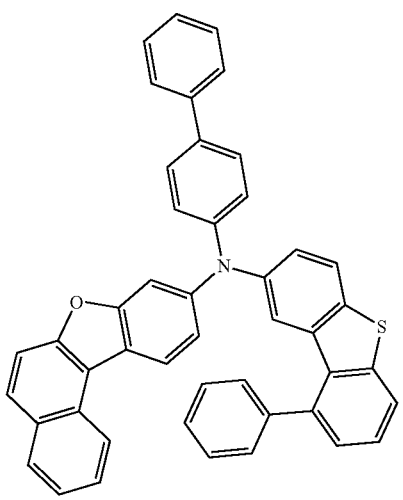
H-111
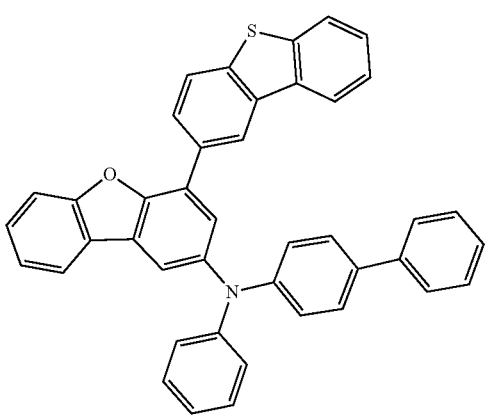

H-112
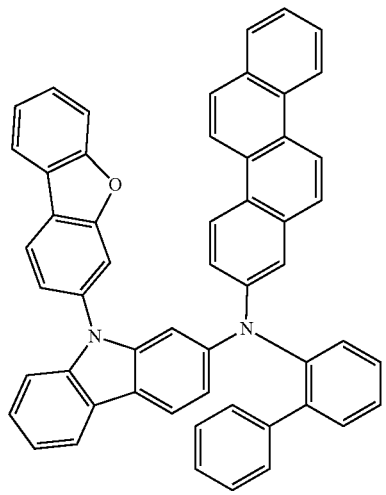
H-115
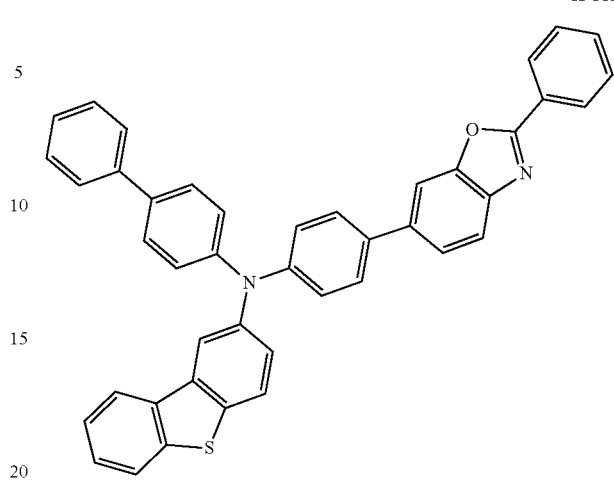
H-113
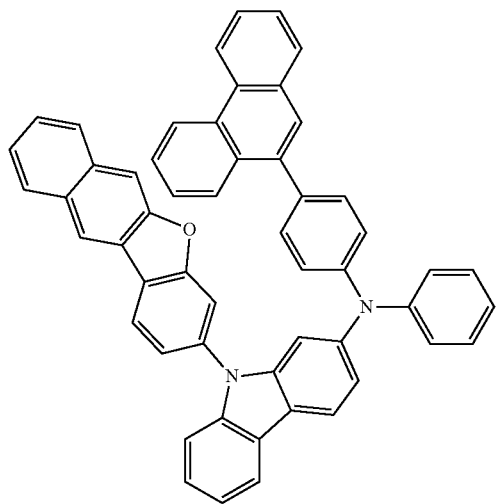
H-116
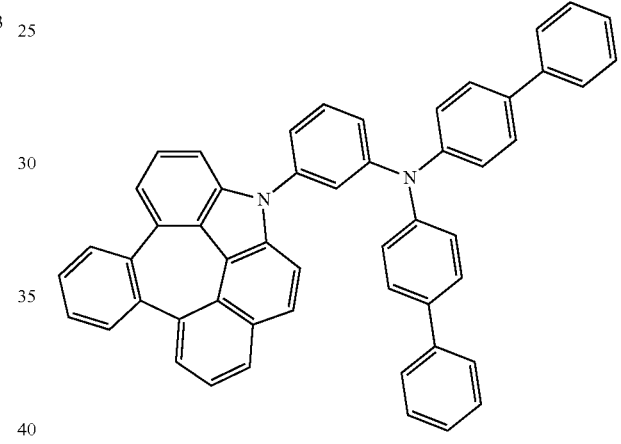
H-114
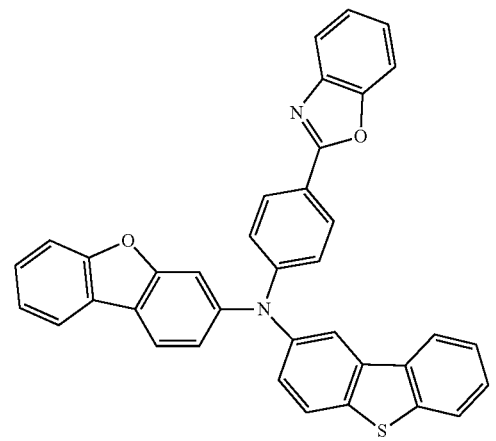
H-117
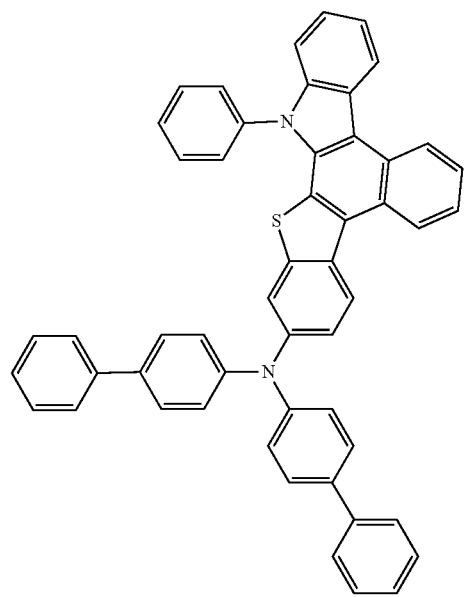

H-118
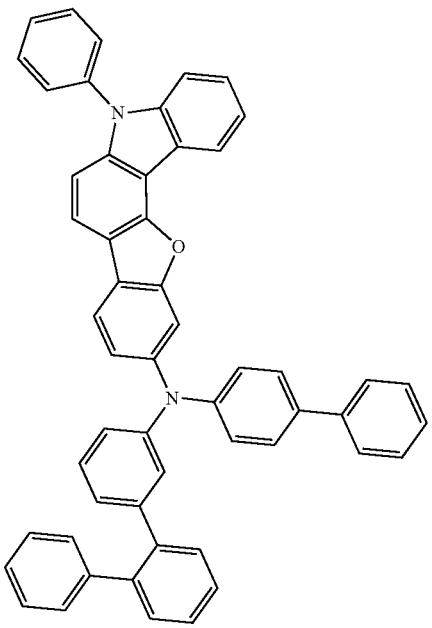
H-119
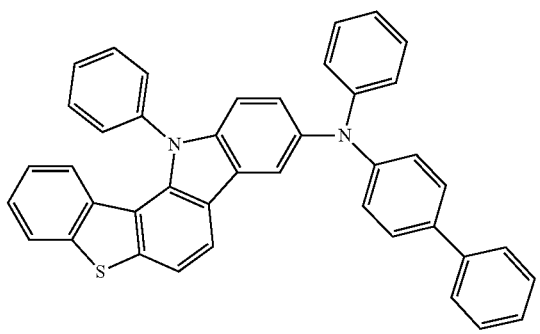
H-120
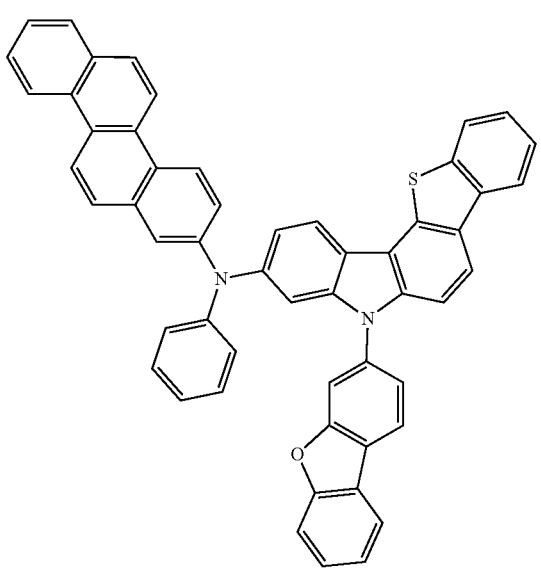
H-121
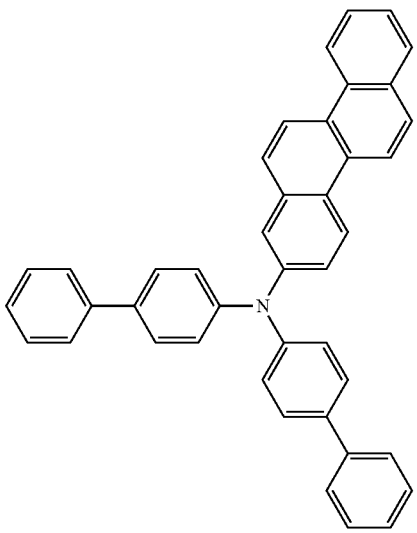
H-122
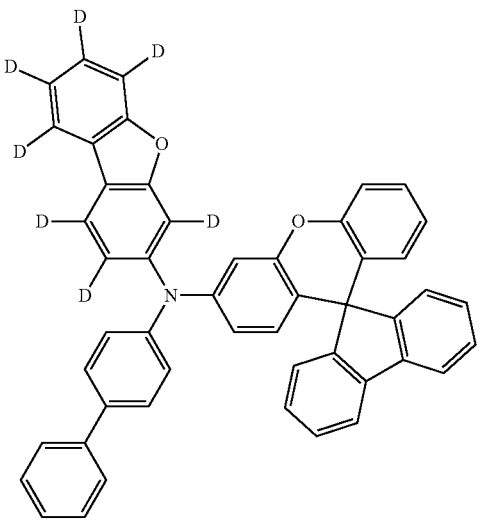
H-123
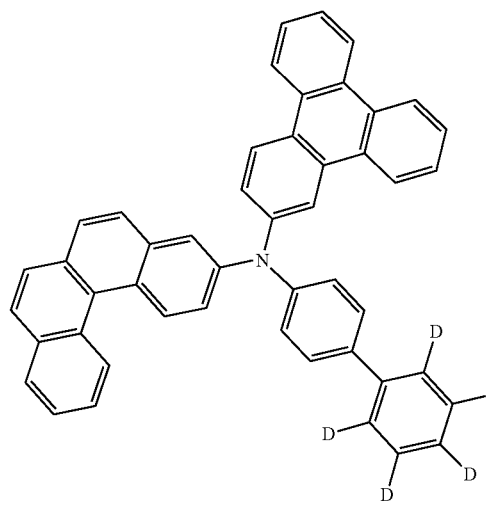

207
-continued
H-124
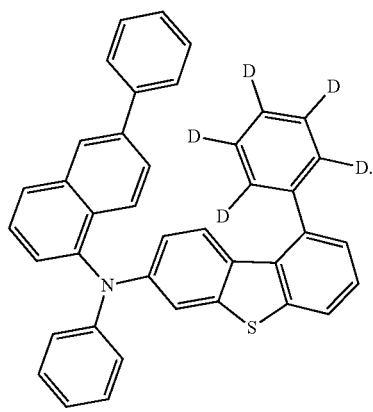
7. The composition for an organic electronic element according to claim 4, wherein the compound of Formula 5 is any one of Compounds S-1 to S-116:
S-1
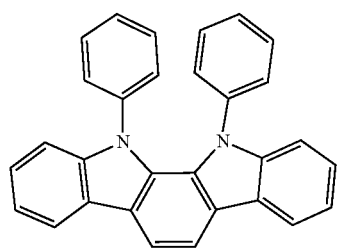
S-2
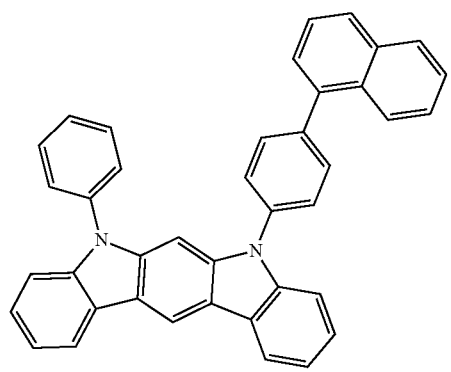
208
-continued
S-3
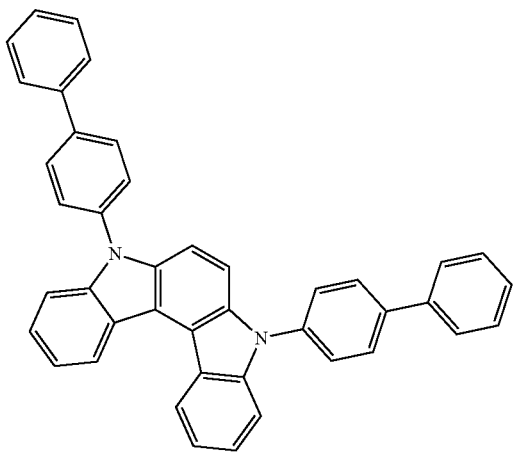
S-4
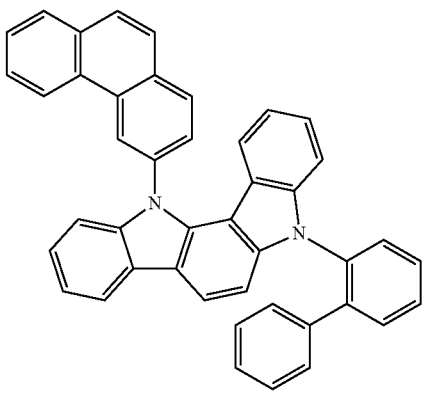
S-5
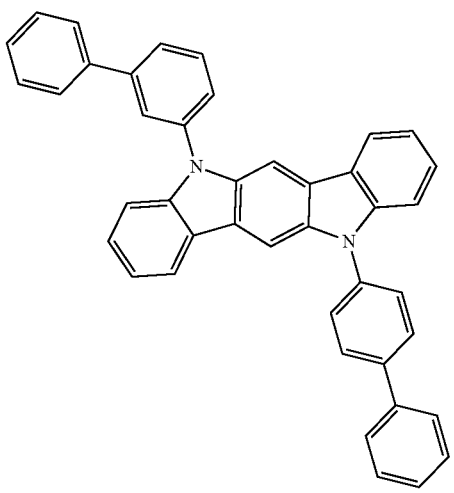

-continued
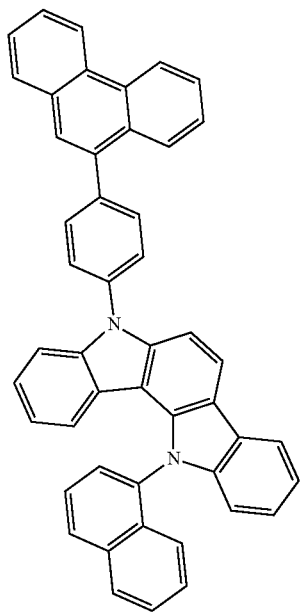
S-6
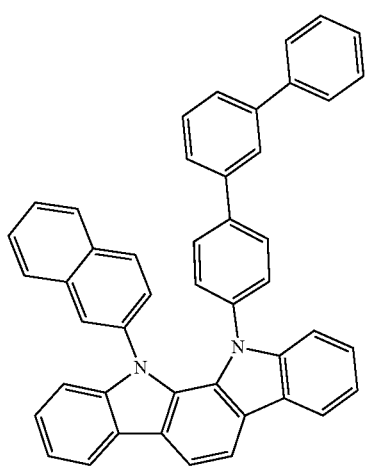
S-7
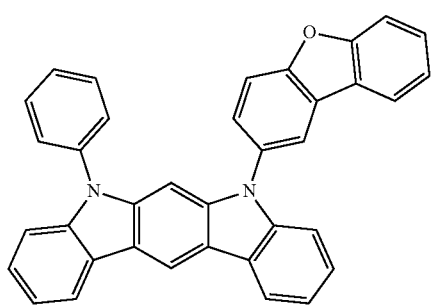
S-8
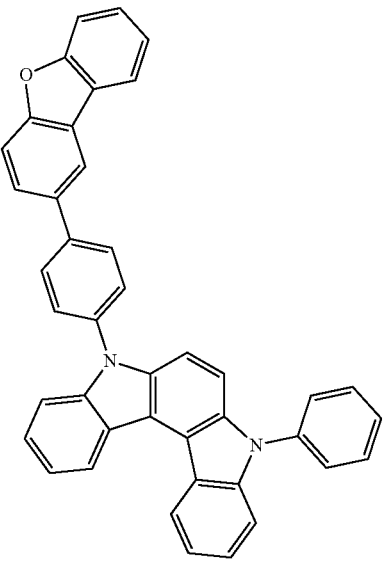
S-9
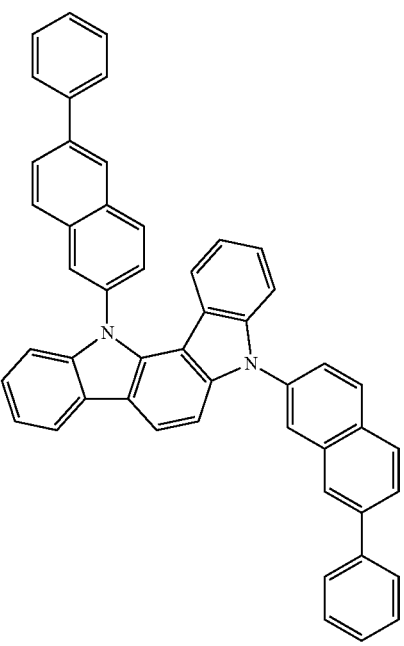
S-10

S-11
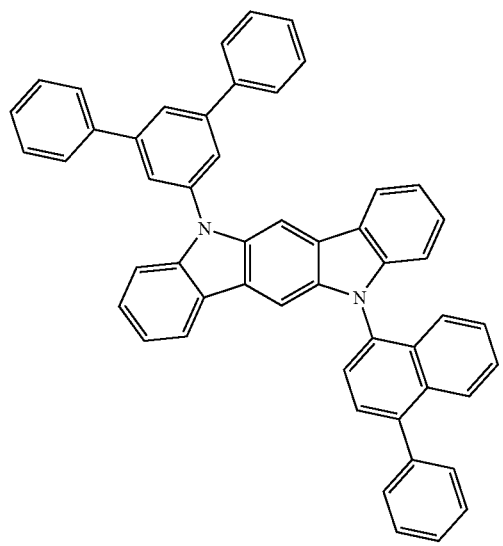
S-12
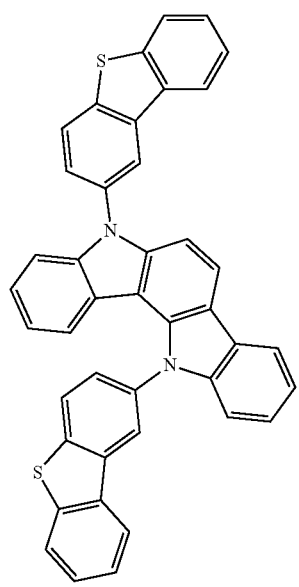
S-13
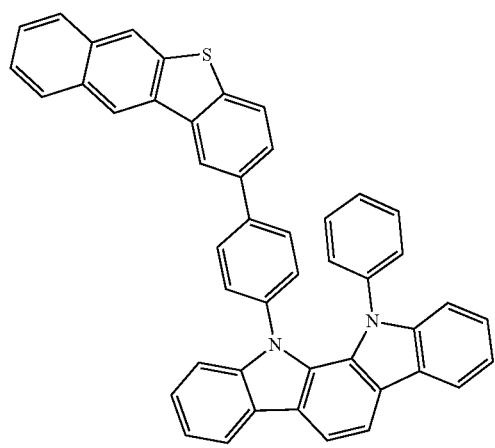
S-14
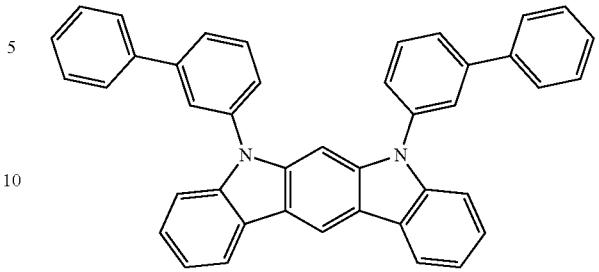
S-15
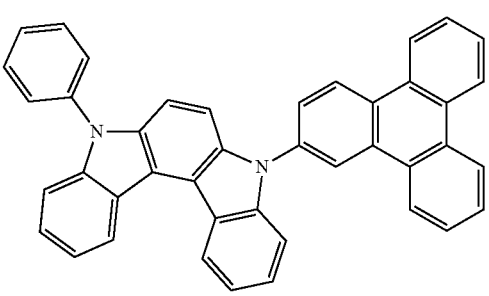
S-16
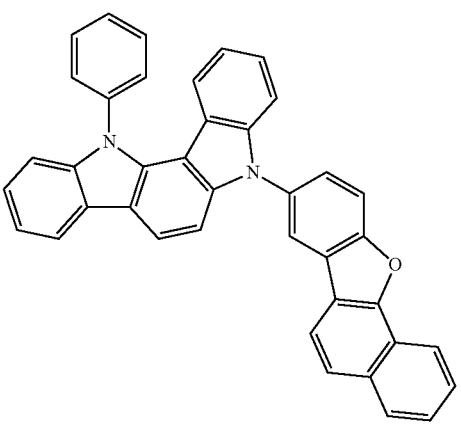
S-17
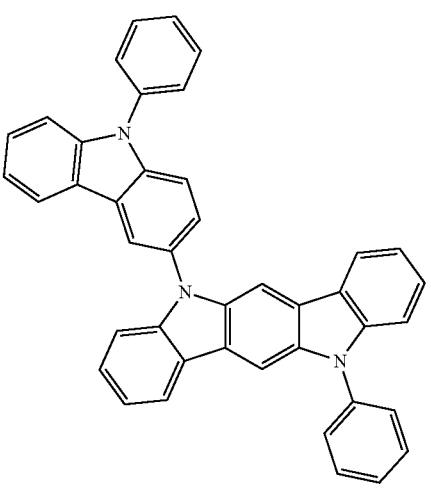

-continued
S-18
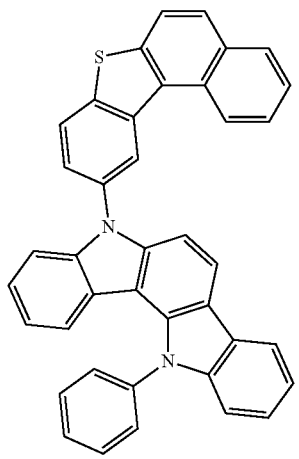
S-19
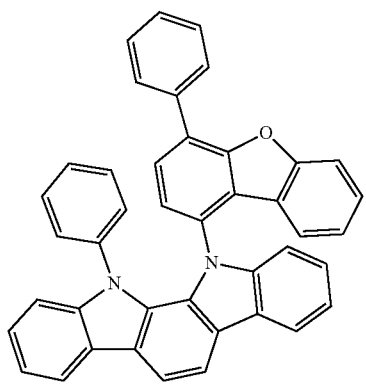
S-20
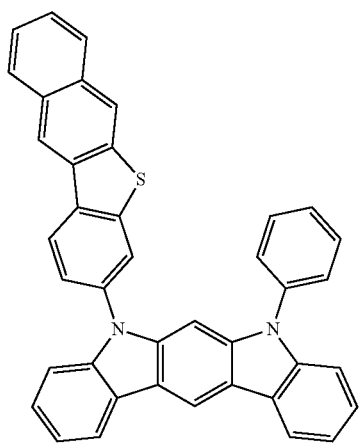
S-21
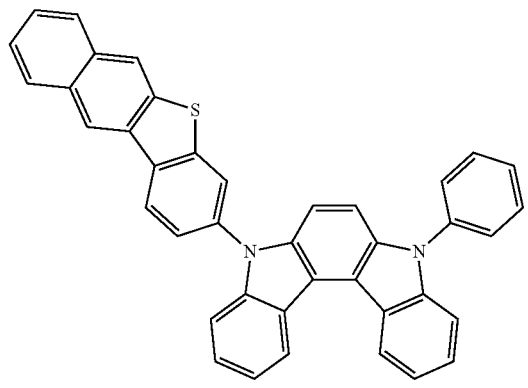
S-22
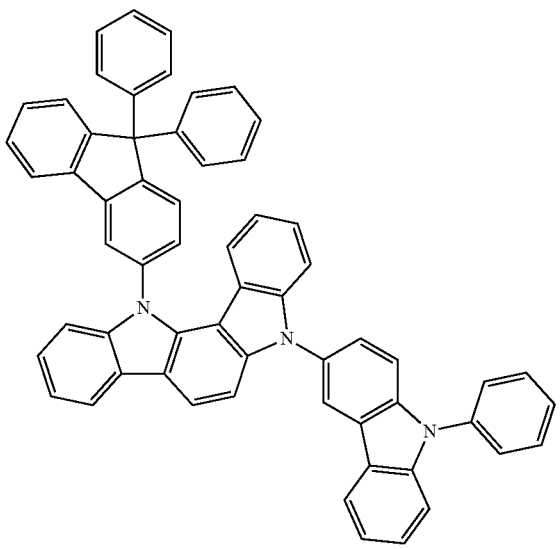
S-23
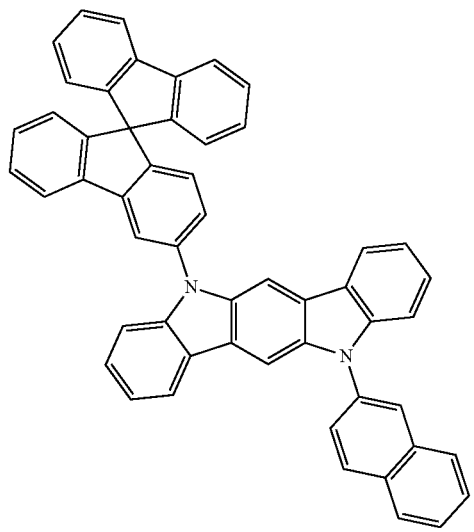

S-24
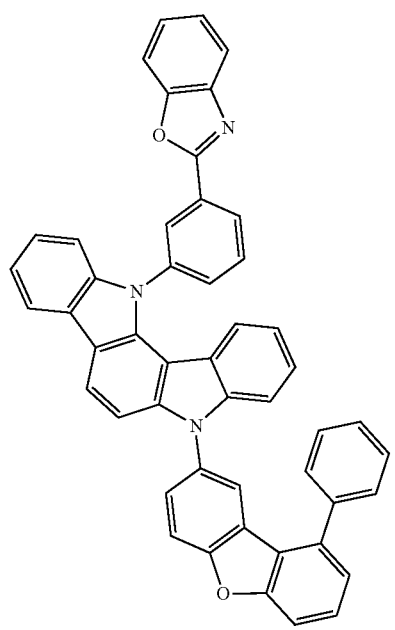
S-25
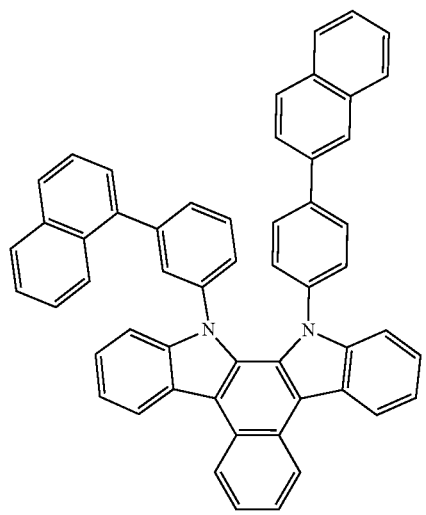
S-26
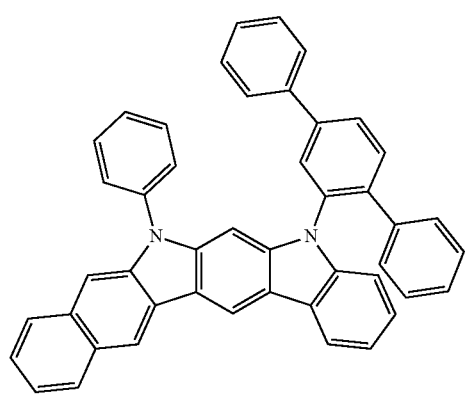
S-27
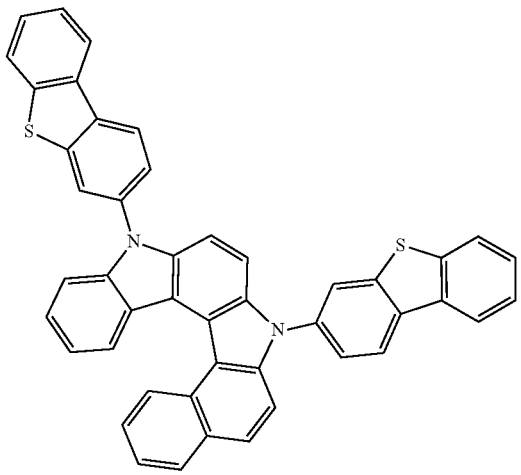
S-28
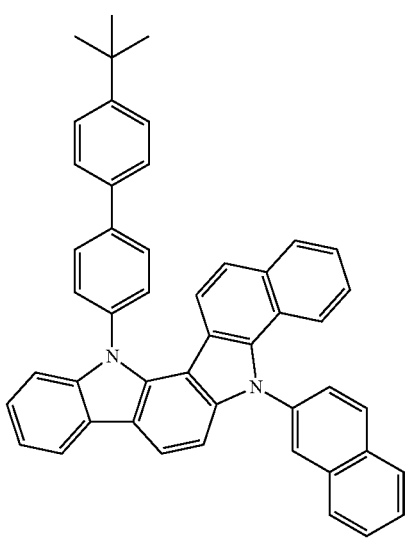
S-29
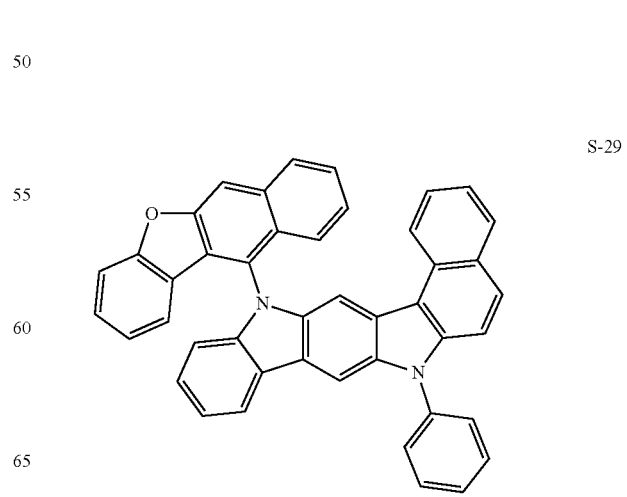

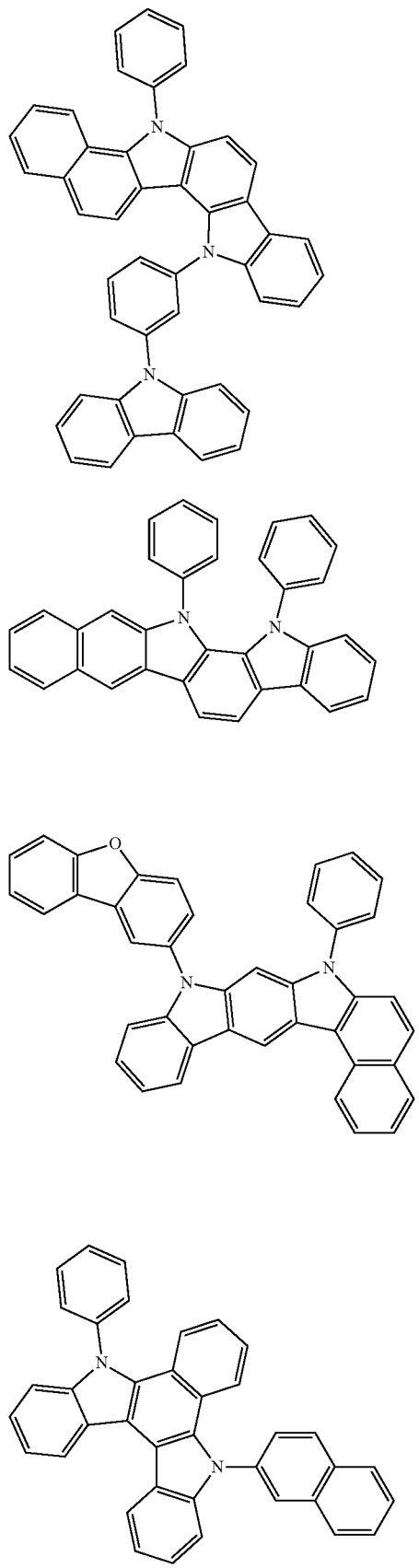
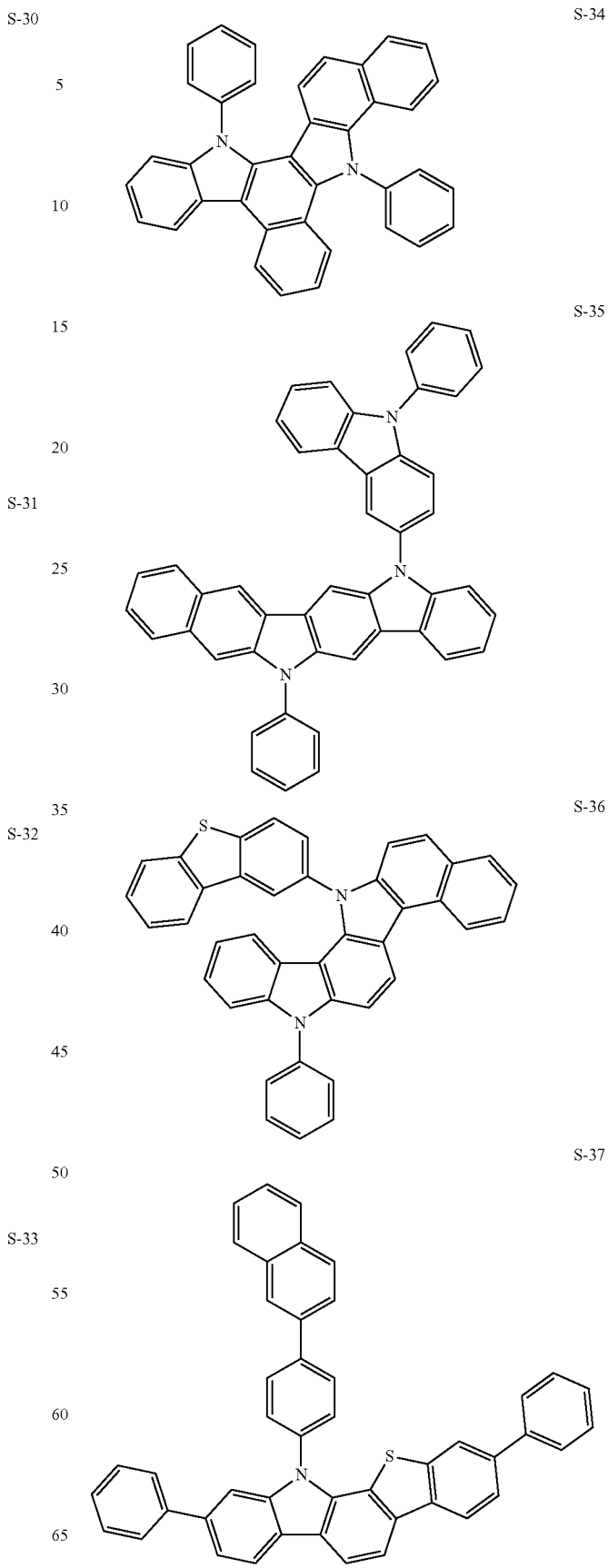

S-38
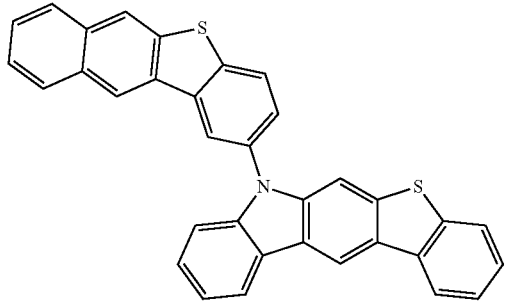
S-39
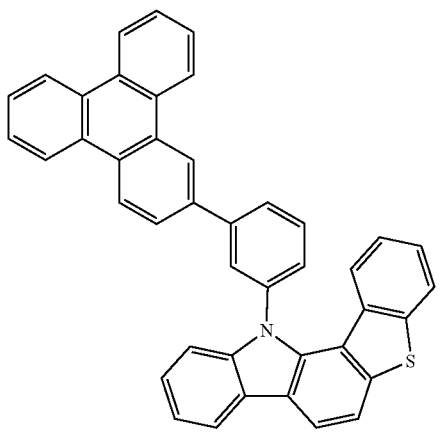
S-40
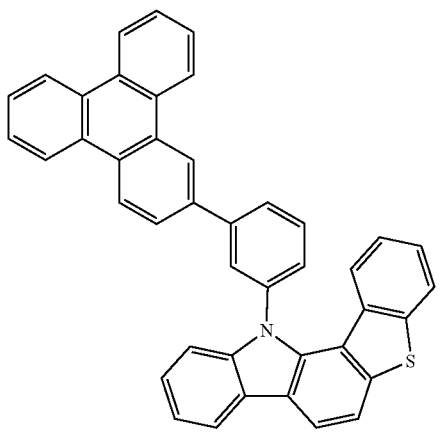
S-41
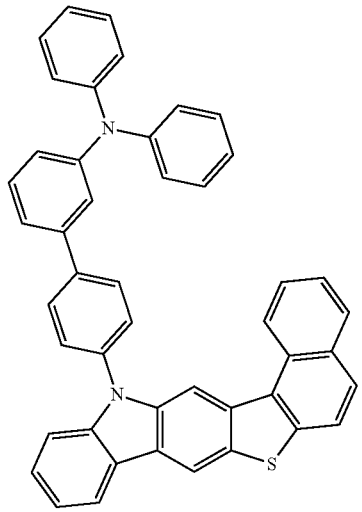
S-42
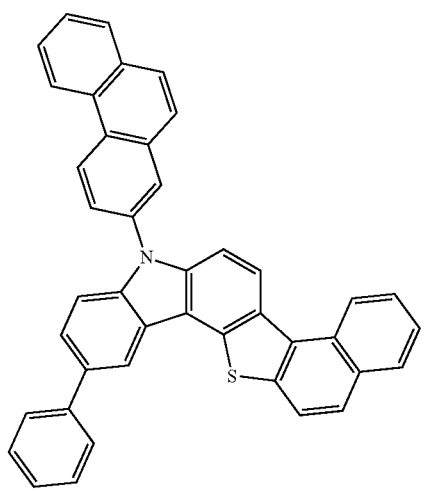
S-43
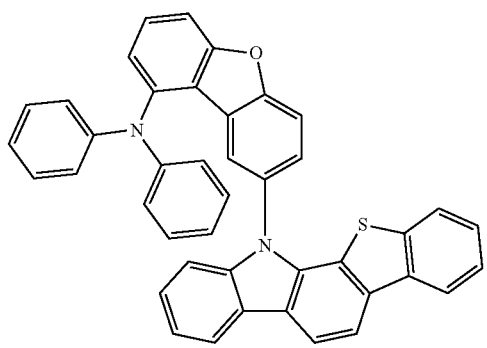

-continued
S-44
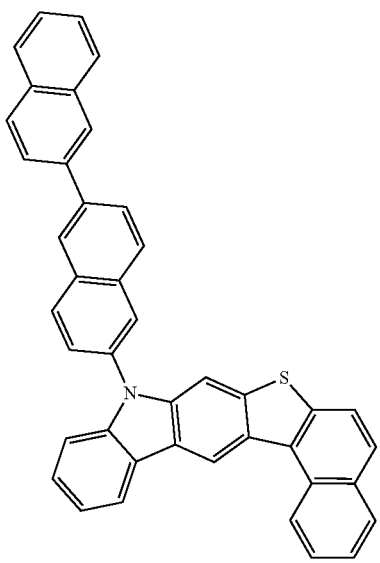
S-45
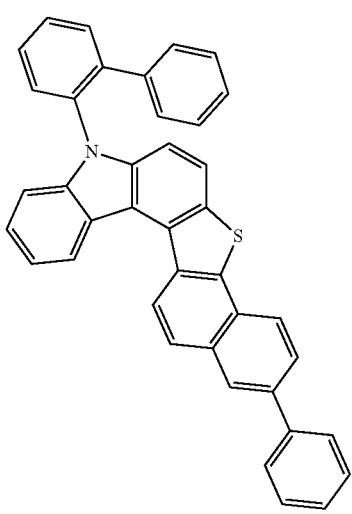
S-46
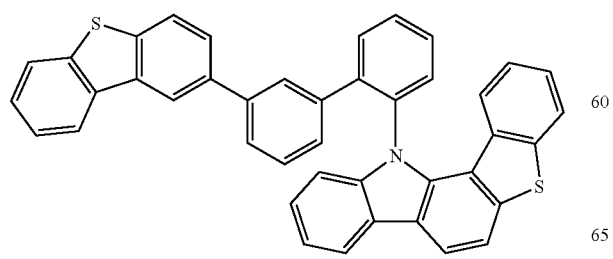
-continued
S-47
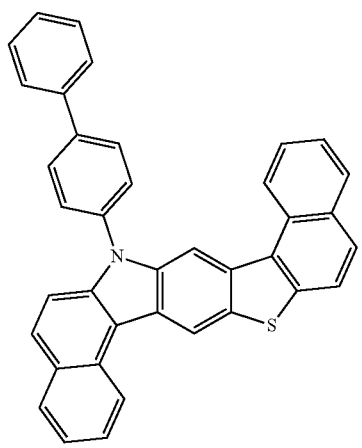
S-48
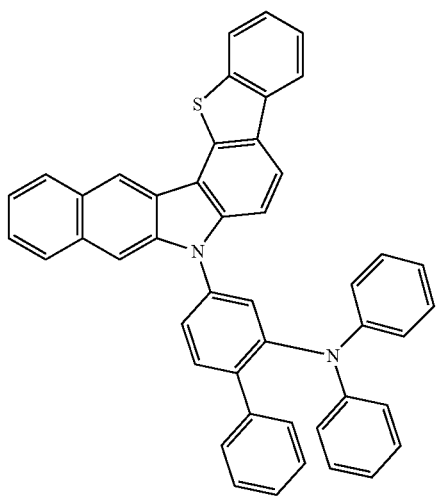
S-49
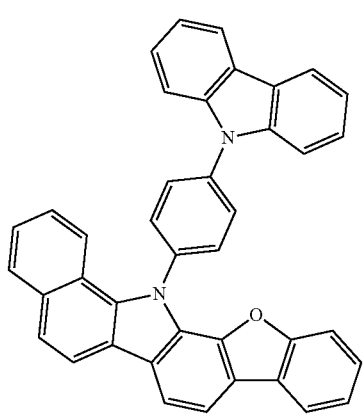

-continued
S-50
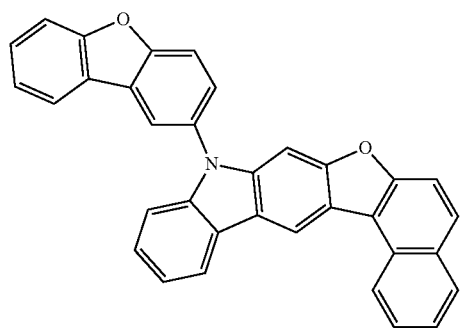
S-51
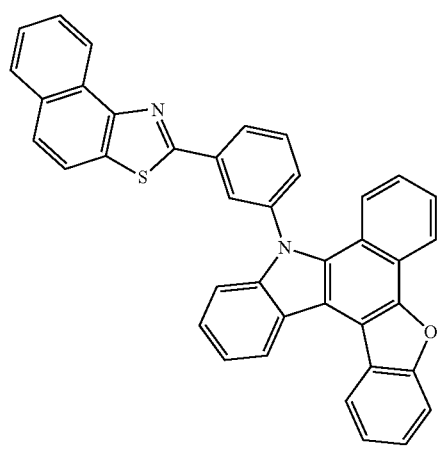
S-52
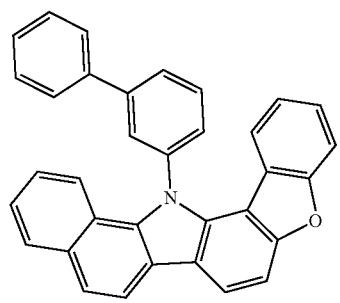
S-53
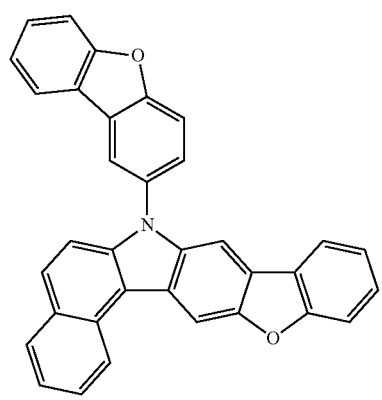
-continued
S-54
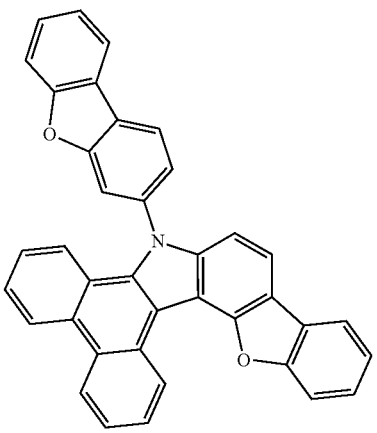
S-55
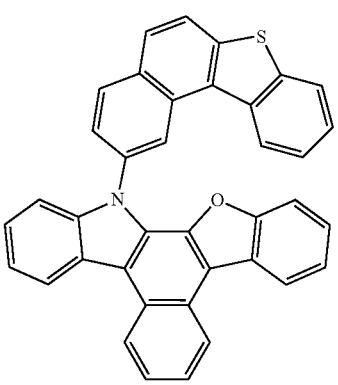
S-56
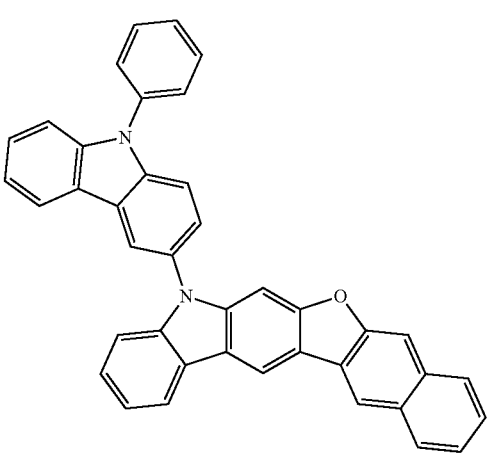
S-57
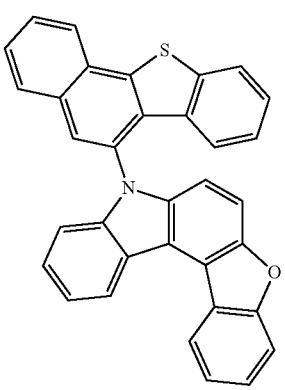

S-58
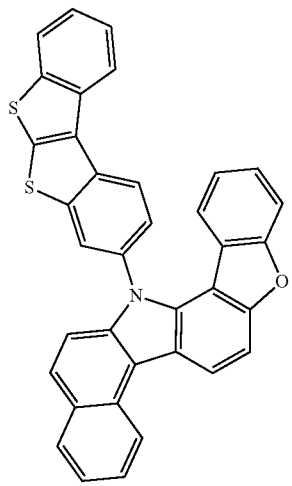
S-61
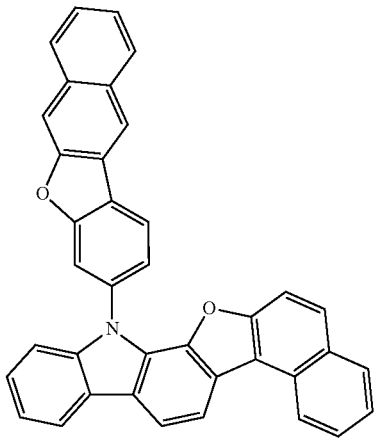
S-59
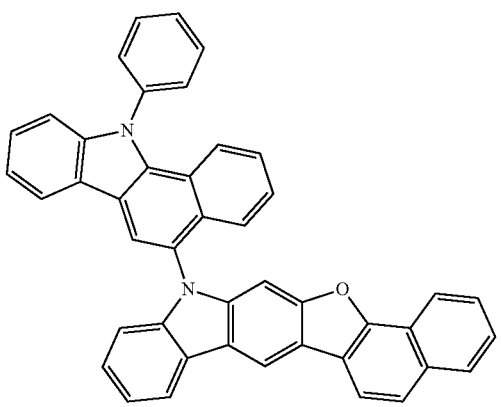
S-62
S-60
S-63
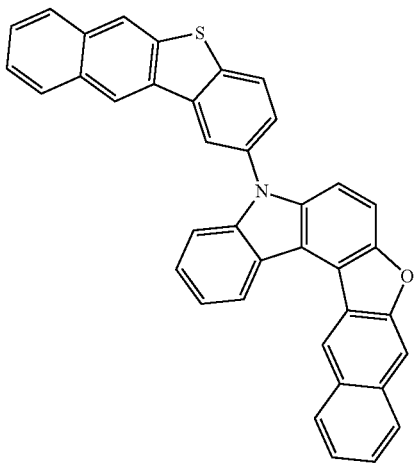

-continued
S-64
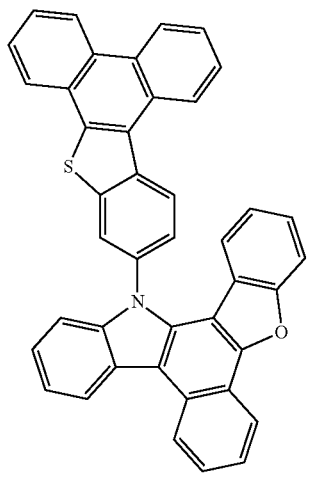
S-65
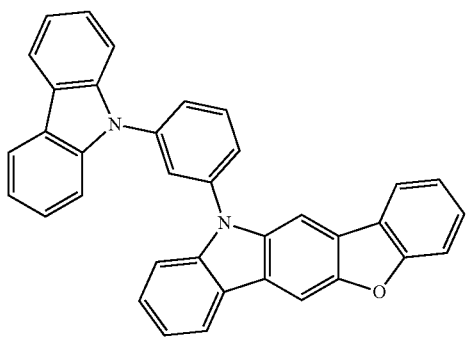
S-66
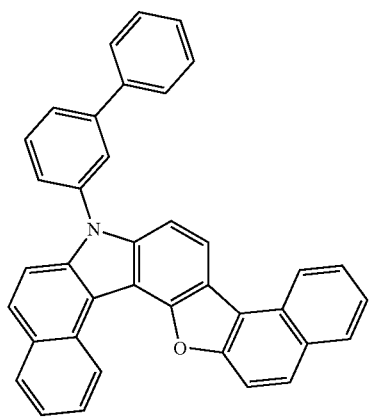
S-67
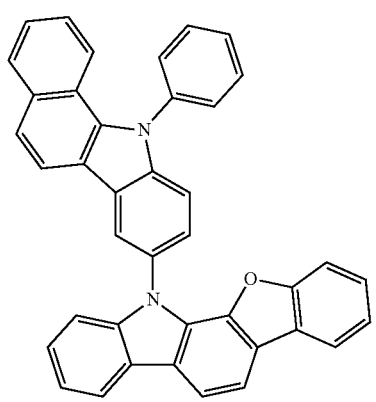
-continued
S-68
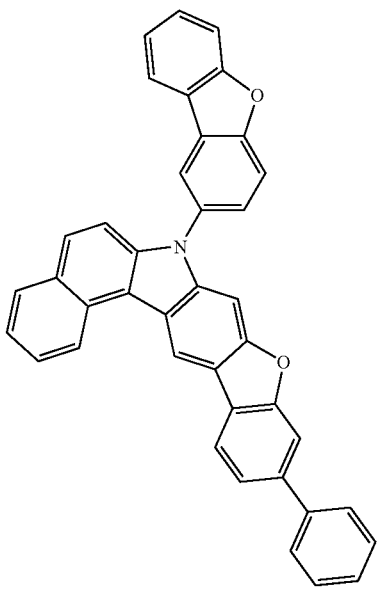
S-69
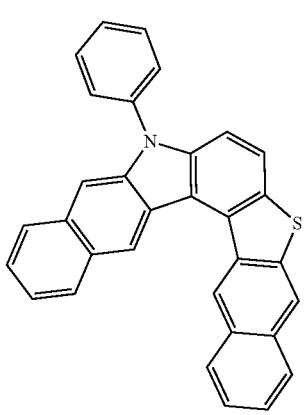
S-70
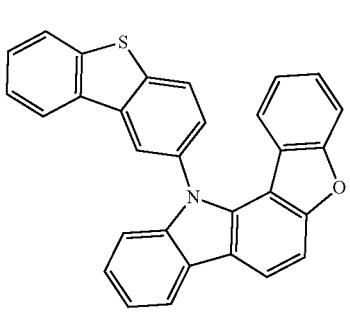

S-71
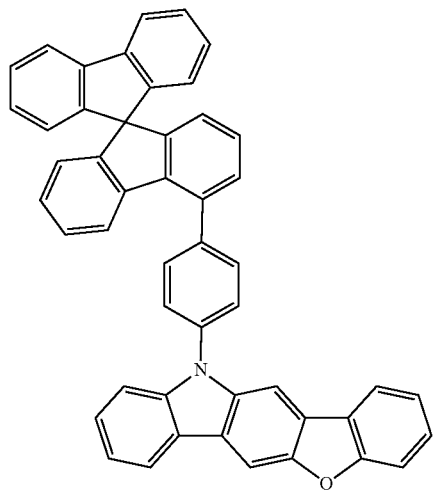
S-72
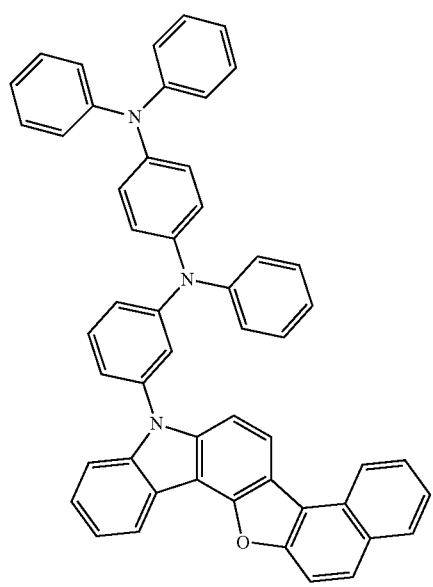
S-73
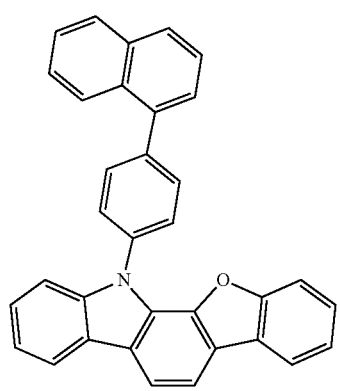
S-74
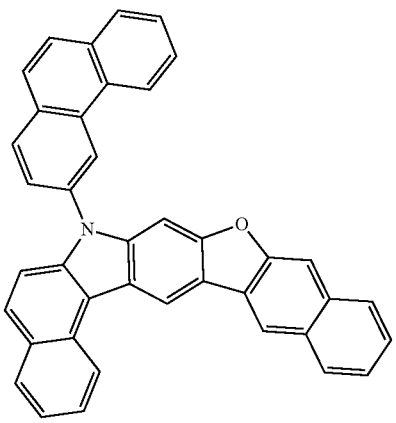
S-75
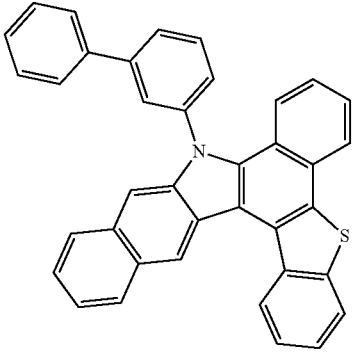
S-76
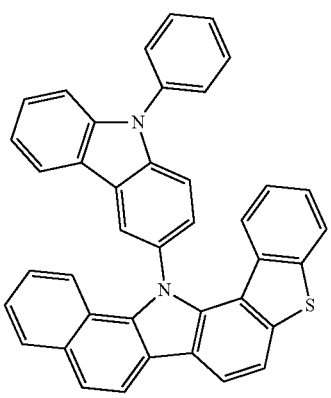
S-77
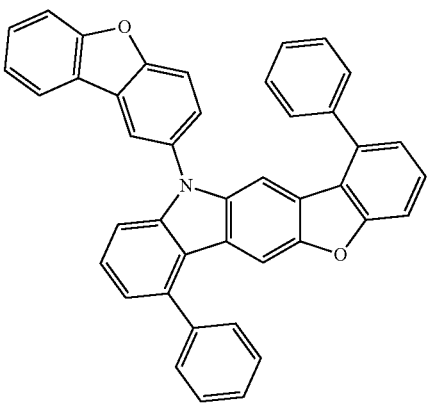

-continued
S-78
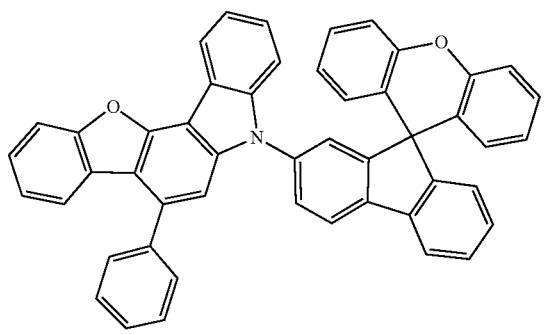
S-79
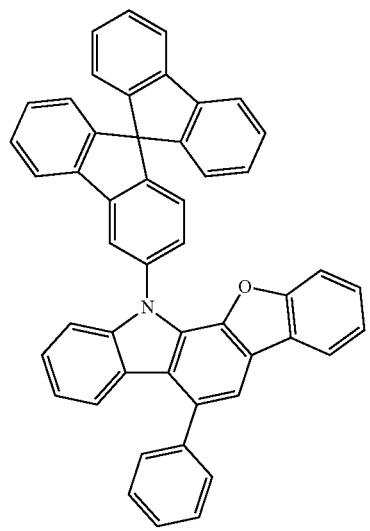
S-80
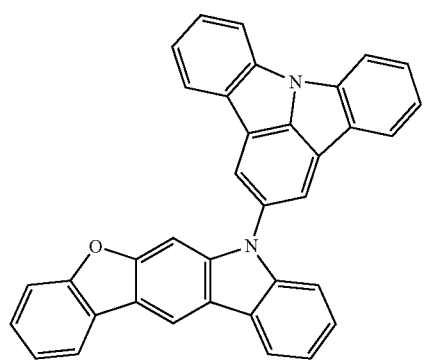
S-81
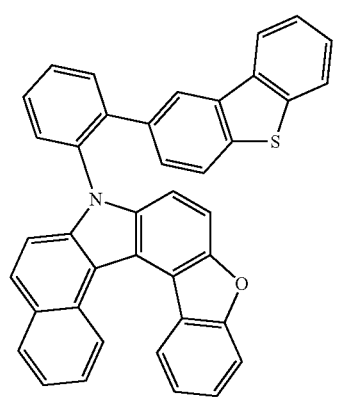
S-82
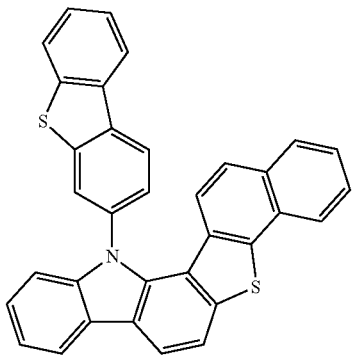
S-83
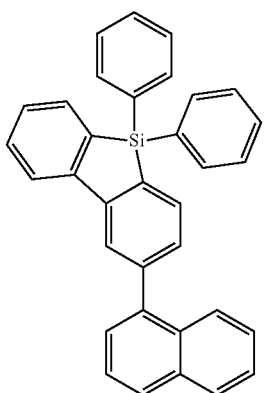
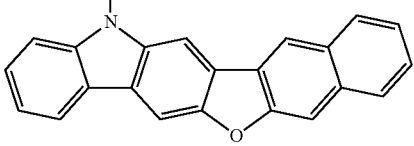
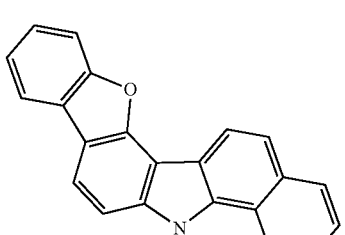
S-84
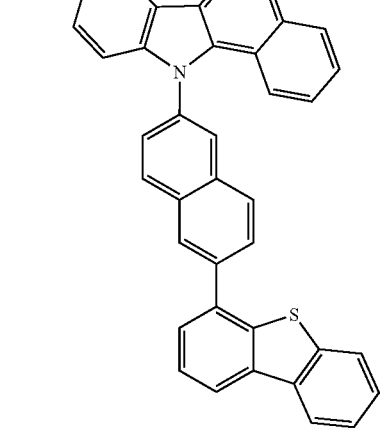

-continued
S-85
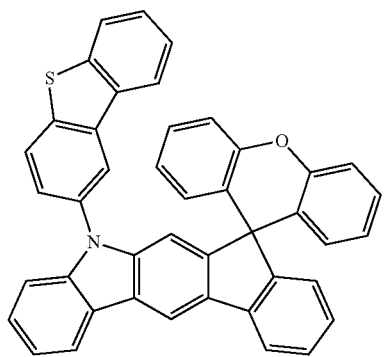
S-86
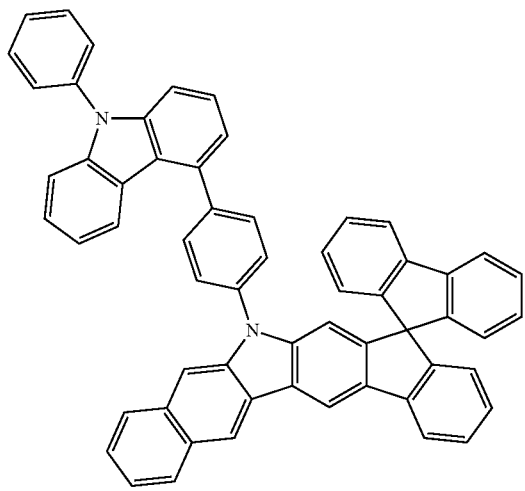
S-87
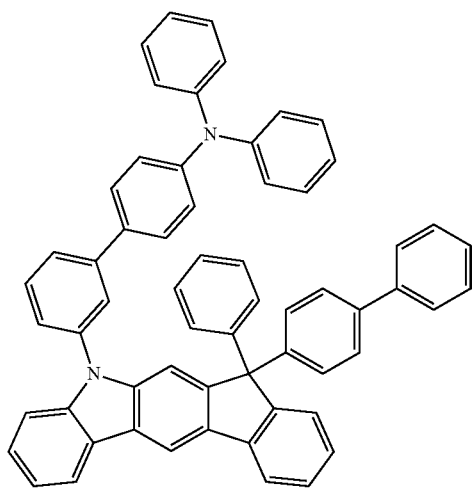
-continued
S-88
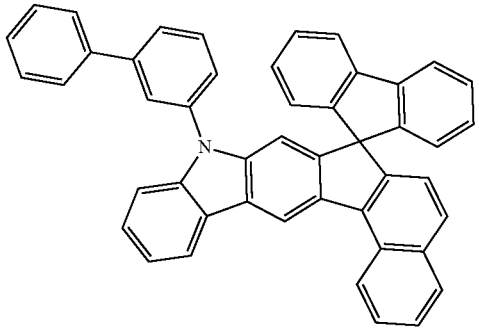
S-89
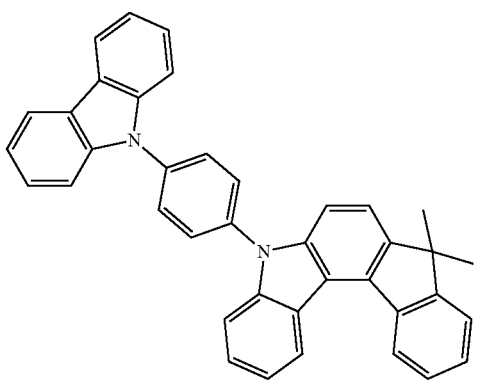
S-90
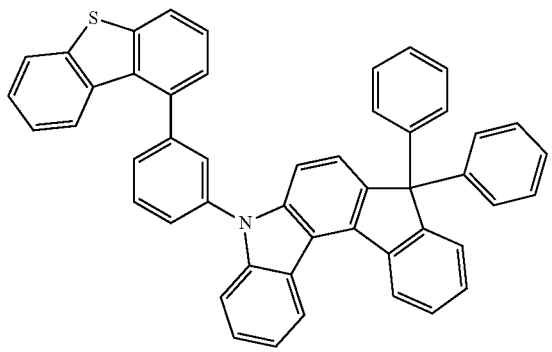
S-91
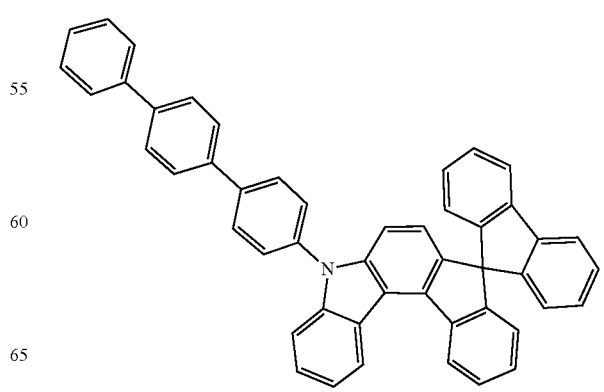

S-92
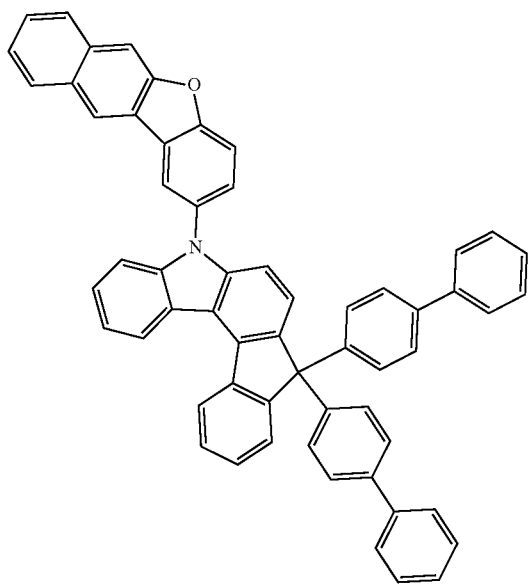
S-93
S-95
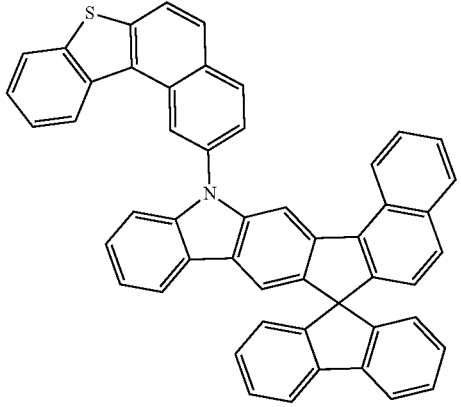
S-96
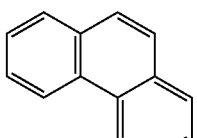
S-94
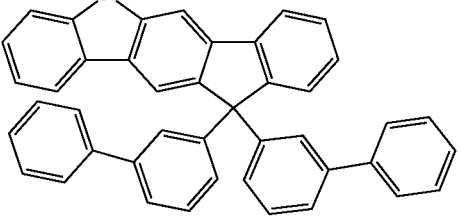
S-97
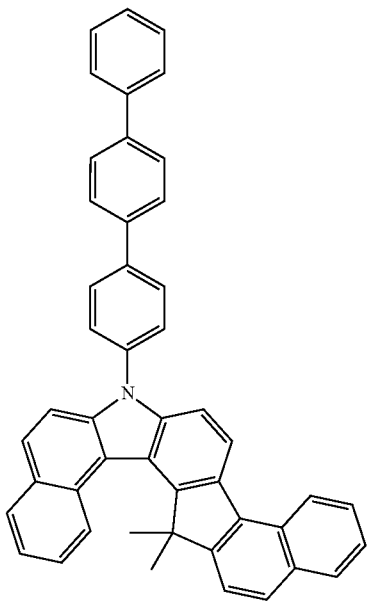

-continued
S-98
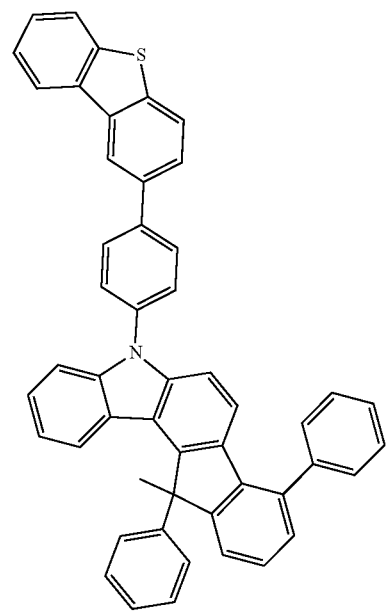
S-99
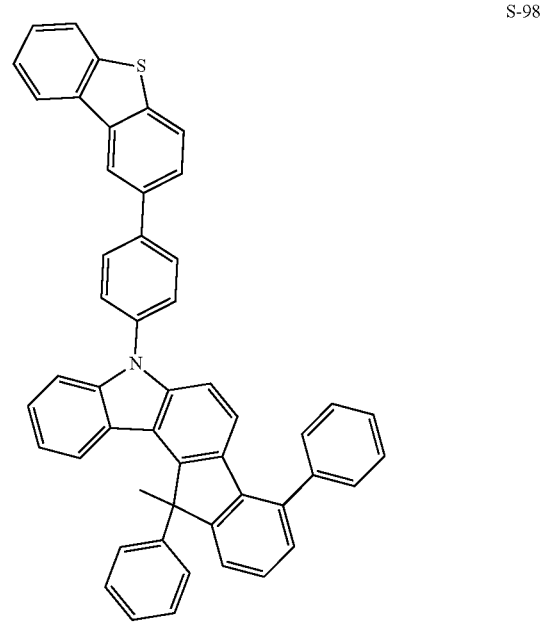
S-100
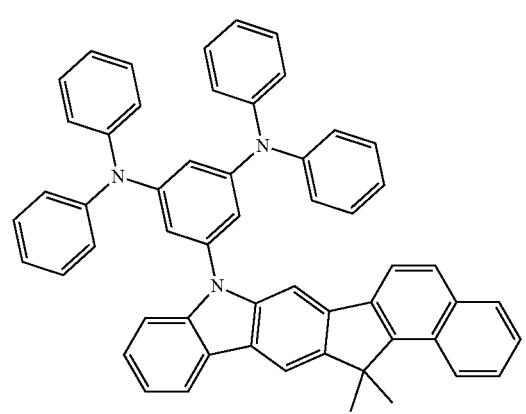
-continued
S-101
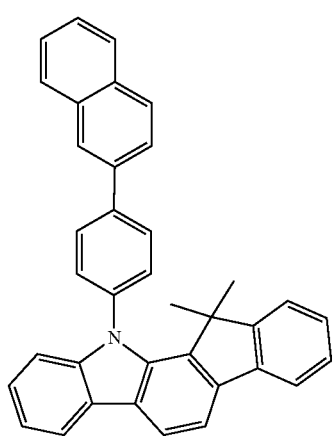
S-102
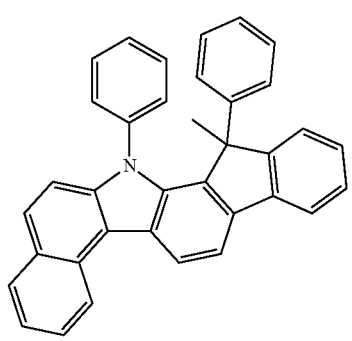
S-103
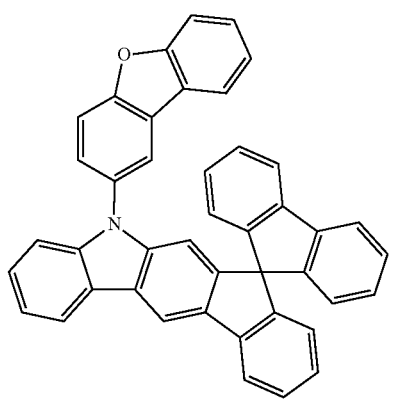
S-104
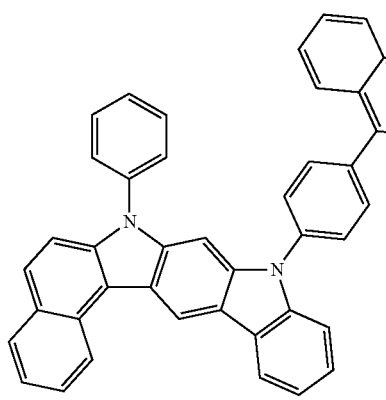

S-105
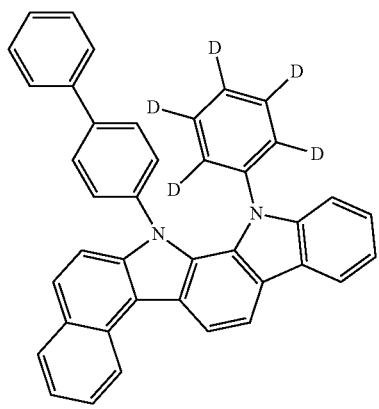
S-106
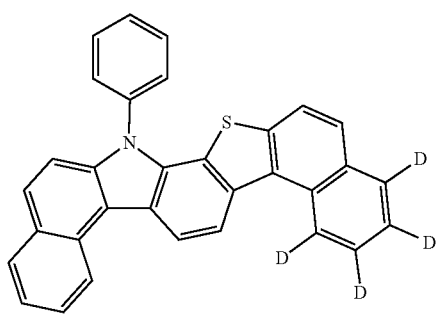
S-107
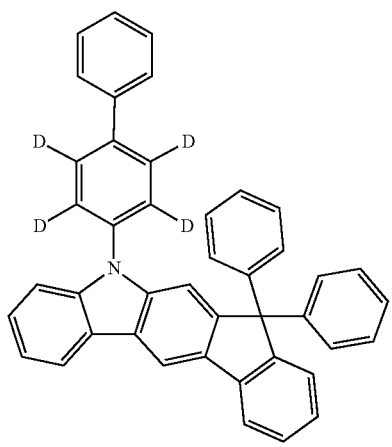
S-108
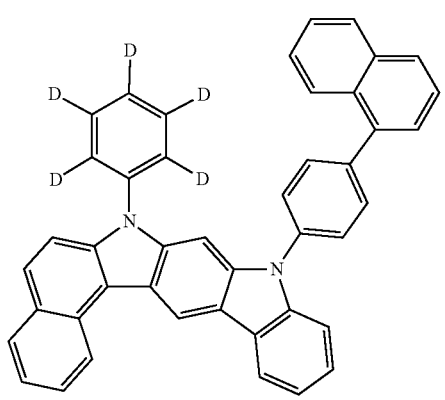
S-109
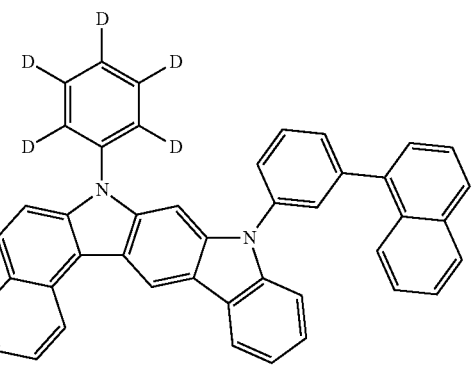
S-110
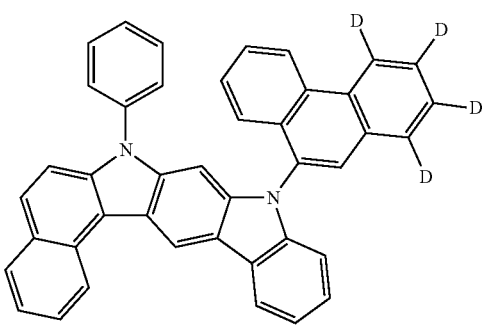
S-111
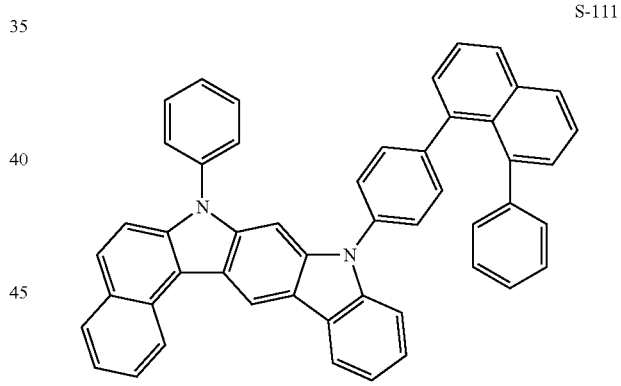
S-112
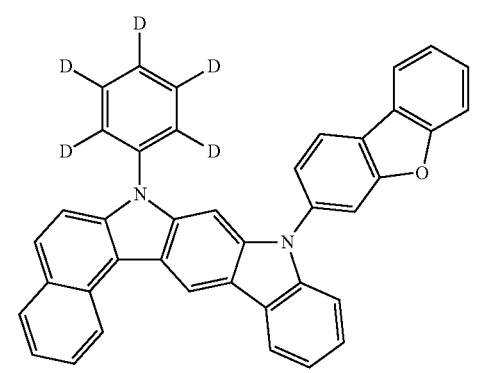

S-113

S-114

S-115

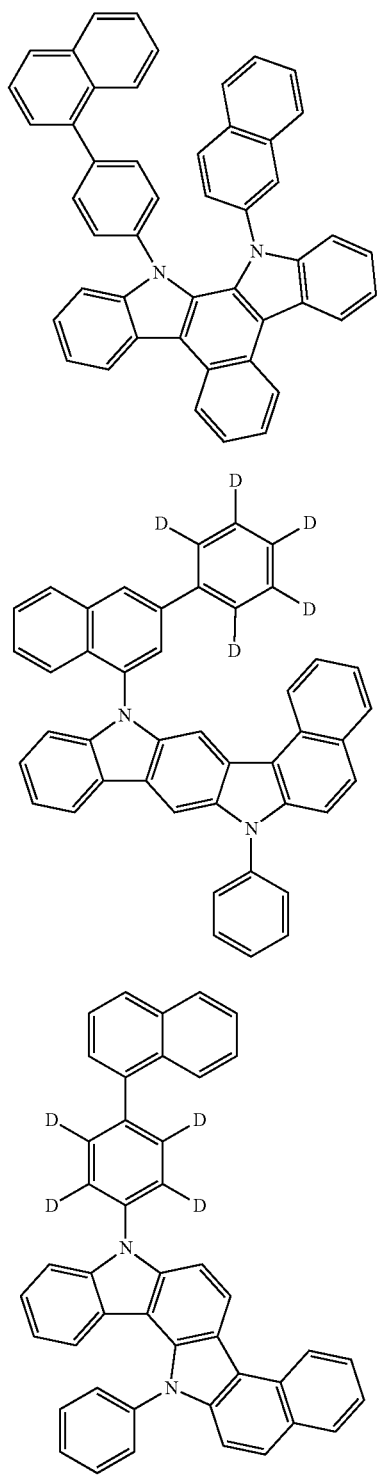

S-116

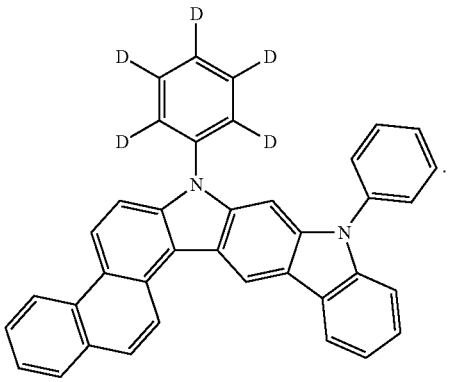

8. An organic electronic element comprising a first electrode; a second electrode; and an organic material layer formed between the first electrode and the second electrode; wherein the organic material layer comprises the compound represented by Formula (1) of claim 1 or the composition for an organic electronic element of claim 4.

9. The organic electronic element according to claim 8, further comprising a light efficiency enhancing layer formed on at least one surface of the first electrode and the second electrode, the surface being opposite to the organic material layer.

10. The organic electronic element according to claim 8, wherein the organic material layer comprises 2 or more stacks comprising a hole transport layer, an emitting layer and an electron transport layer sequentially formed on the first electrode.

11. The organic electronic element according to claim 10, the organic material layer further comprise a charge generation layer formed between the 2 or more stacks.

12. An electronic device comprising a display device comprising the organic electronic element of claim 8; and a control unit for driving the display device.

13. The electronic device according to claim 12, wherein the organic electronic element is at least one of an OLED, an organic solar cell, an organic photo conductor(OPC), organic transistor (organic TFT) and an element for monochromic or white illumination.

14. A method for reusing a compound of Formula (1) of claim 1 comprising:
  recovering a crude organic light emitting material comprising the compound of Formula (1) from a deposition apparatus used in a process for depositing the organic emitting material to prepare an organic light emitting device;
  removing impurities from the crude organic light emitting material;
  recovering the organic light emitting material after the impurities are removed; and
  purifying the recovered organic light emitting material to have a purity of 99.9% or higher.

\* \* \* \* \*